US006919329B2

(12) United States Patent
Thomas et al.

(10) Patent No.: US 6,919,329 B2
(45) Date of Patent: Jul. 19, 2005

(54) N-ARYL-2-OXAZOLIDINONE-5-CARBOXAMIDES AND THEIR DERIVATIVES

(75) Inventors: Richard Charles Thomas, Kalamazoo, MI (US); Toni-Jo Poel, Wayland, MI (US); Michael Robert Barbachyn, Kalamazoo, MI (US); Mikhail F. Gordeev, Castro Valley, CA (US); Gary W. Luehr, Hayward, CA (US); Adam Renslo, Oakland, CA (US); Upinder Singh, Freemont, CA (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/373,286

(22) Filed: Feb. 24, 2003

(65) Prior Publication Data

US 2004/0044052 A1 Mar. 4, 2004

Related U.S. Application Data

(60) Provisional application No. 60/359,495, filed on Feb. 25, 2002.

(51) Int. Cl.[7] ..................... A61K 31/55; C07D 223/02; A61P 31/00
(52) U.S. Cl. ................. 514/217.01; 514/248; 514/249; 514/252.05; 514/255.05; 514/259; 514/260; 514/266; 514/269; 514/273; 514/307; 514/310; 540/480; 540/603; 544/106
(58) Field of Search ........................... 544/106

(56) References Cited

U.S. PATENT DOCUMENTS

| | | | |
|---|---|---|---|
| 4,705,799 A | 11/1987 | Gregory ..................... 546/209 |
| 5,043,443 A | 8/1991 | Carlson et al. ............. 544/112 |
| 5,164,510 A | 11/1992 | Brickner .................... 548/231 |
| 5,182,403 A | 1/1993 | Brickner .................... 548/231 |
| 5,225,565 A | 7/1993 | Brickner .................... 548/229 |
| 5,231,188 A | 7/1993 | Brickner .................... 548/221 |
| 5,247,090 A | 9/1993 | Brickner ...................... 546/89 |
| 5,523,403 A | 6/1996 | Barbachyn ................. 544/137 |
| 5,529,998 A | 6/1996 | Habich et al. ............ 514/233.8 |
| 5,547,950 A | 8/1996 | Hutchinson et al. ........ 514/252 |
| 5,565,571 A | 10/1996 | Barbachyn et al. ......... 546/144 |
| 5,614,535 A | 3/1997 | Juraszyk et al. ............ 514/326 |
| 5,627,181 A | 5/1997 | Riedl et al. .............. 514/326.8 |
| 5,652,238 A | 7/1997 | Brickner et al. ......... 514/235.8 |
| 5,684,023 A | 11/1997 | Riedl et al. ................. 514/337 |
| 5,688,792 A | 11/1997 | Barbachyn et al. ...... 514/235.5 |
| 5,698,574 A | 12/1997 | Riedl et al. ................. 514/376 |
| 5,792,765 A | 8/1998 | Riedl et al. .............. 514/236.8 |
| 5,827,857 A | 10/1998 | Riedl et al. ................. 514/301 |
| 5,843,967 A | 12/1998 | Riedl et al. ................. 514/340 |
| 5,861,413 A | 1/1999 | Häbich et al. .............. 514/312 |
| 5,869,659 A | 2/1999 | Stolle et al. ................ 544/114 |
| 5,952,324 A | 9/1999 | Barbachyn et al. ......... 514/211 |
| 5,968,962 A | 10/1999 | Thomas et al. ............. 514/376 |
| 5,981,528 A | 11/1999 | Gravestock ................. 514/252 |
| 5,990,136 A | 11/1999 | Barbachyn et al. ......... 514/340 |
| 6,043,266 A | 3/2000 | Ennis et al. ................. 514/376 |
| 6,051,716 A | 4/2000 | Hutchinson et al. ........ 548/229 |
| 6,069,145 A | 5/2000 | Betts .......................... 514/252 |
| 6,069,160 A | 5/2000 | Stolle et al. ................ 514/367 |
| 6,110,936 A | 8/2000 | Gravestock ................. 514/315 |
| 6,166,056 A | 12/2000 | Thomas et al. ............. 514/376 |
| 6,194,441 B1 | 2/2001 | Roberts et al. ............. 514/340 |
| 6,239,152 B1 | 5/2001 | Gordeev et al. ............ 514/340 |
| 6,239,283 B1 | 5/2001 | Gage .......................... 548/225 |
| 6,271,383 B1 | 8/2001 | Gravestock ................. 546/209 |
| 6,313,307 B1 | 11/2001 | Ennis et al. ................. 548/229 |

FOREIGN PATENT DOCUMENTS

| | | | | |
|---|---|---|---|---|
| EP | 417044 | 8/1990 | ......... C07D/263/20 |
| EP | 697408 | 8/1995 | ......... C07D/263/20 |
| WO | WO94/01110 | 1/1994 | .......... A61K/31/42 |
| WO | WO95/07271 | 5/1995 | ......... C07D/263/20 |
| WO | WO95/25106 | 9/1995 | ......... C07D/413/10 |
| WO | WO96/13502 | 5/1996 | ......... C07D/413/10 |
| WO | WO96/15130 | 5/1996 | ....... C07D/491/048 |
| WO | WO96/23788 | 8/1996 | ......... C07D/413/10 |
| WO | WO96/35691 | 11/1996 | ......... C07D/487/04 |
| WO | WO97/09328 | 3/1997 | ......... C07D/413/10 |
| WO | WO97/30995 | 8/1997 | ......... C07D/413/10 |
| WO | WO98/54161 | 12/1998 | ......... C07D/263/20 |
| WO | WO99/03846 | 1/1999 | ......... C07D/263/24 |
| WO | WO99/29688 | 6/1999 | ......... C07D/413/10 |
| WO | WO99/37641 | 7/1999 | ......... C07D/413/04 |
| WO | WO99/37652 | 7/1999 | ......... C07D/498/04 |
| WO | WO99/40094 | 8/1999 | ......... C07D/498/04 |
| WO | WO99/64417 | 12/1999 | ......... C07D/413/14 |
| WO | WO00/21960 | 4/2000 | ......... C07D/413/14 |
| WO | WO00/44741 | 8/2000 | ......... C07D/335/00 |
| WO | WO00/73301 | 12/2000 | ......... C07D/413/04 |
| WO | WO01/40236 | 6/2001 | ............ C07F/9/09 |
| WO | WO01/46185 | 6/2001 | ......... C07D/417/10 |
| WO | WO01/81350 | 11/2001 | ......... C07D/491/10 |
| WO | WO02/059155 | 8/2002 | ........... C07K/16/28 |
| WO | WO02/096916 | 12/2002 | ............ C07F/9/09 |
| WO | WO03/006440 | 1/2003 | ......... C07D/263/00 |

OTHER PUBLICATIONS

Abdelaal, et. al., "Synthesis of 1-[3-Methyl]-2(3H)-benzazolon-5- or 6-yl-4-{4-[cis-2-(2, 4-dichlorophenyl)-2-(1H-imidazol-1-yl-methyl)-1, 3-dioxolan-4-yl]methyleneoxyphenyl}piperazines" Journal of Heterocyclic Chem., 29, 1069, (1992).

Barbachyn, et al. "Identification of a Novel Oxazolidinone(U–100480) with Potent Antimycobacterial Activity." Journal of Medicinal Chemistry. 1996, 39, 680–685.

(Continued)

*Primary Examiner*—Kamal Saeed
(74) *Attorney, Agent, or Firm*—Lucy X. Yang; Jonathan P. O'Brien

(57) ABSTRACT

The present invention provides antibacterial agents having the formulae I, II, and III described herein.

45 Claims, No Drawings

OTHER PUBLICATIONS

Blache, et. al. "*Application of the Mercuric Acetate–Edetic Acid Oxidation Method To The Synthesis of 11–Aza–1,2,3, 4,5,6,7,12bpOctahydroindolo[2,3–α]Quinolizines.*" Heterocycles, vol. 45, No. 1, pp. 57–69, 1997.

Bodor, Nicholas and J. Hillis Miller, "*Novel Approaches in Prodrug Design.*" Drugs of the Future vol. VI, No. 3, 1981, pp. 165–182.

Brickner, Steven J. "*Oxazolidinone Antibacterial Agents*" Current Pharmaceutical Design. 1996, 2, 175–194.

Brickner, et al. "*Synthesis and Antibacterial Activity of U–100592 and U–100766, Two Oxazolidinone Antibacterial Agents for the Potential Treatment of Multidrug–Resistant Gram–Positive Bacterial Infections.*" Journal of Medicinal Chemistry. 1996, 39, 673–679.

Bundgaard, Hans. "*Design of prodrugs: Bioreversible derivatives for various functional groups and chemical entities.*" Design of Prodrugs, Chapter 1, 1985.

Cava, Michael P. and Matthew I. Levinson. "*Thionation Reactions of Lawesson's Reagents.*" Tetrahedron vol. 41, No. 22, pp. 5061–5087, 1985.

Clark, Robert L. and Arsenio A. Pessolano. "*Synthesis of Some Substituted Benzoxazolones.*" Journal of the American Chemical Society vol. 80, pp. 1662, 1958.

Comins, et. al. "*Preparation of 2,6–Disubstituted 2,3–Dihydro–4–pyridones: Dehydrogenation of Trimethylsilyl Enol Ethers with Palladium (II)Acetate.*" Tetrahedron Letters, vol. 36, No. 52, pp. 9449–9452, 1995.

Comins, et. al. "*Regio– and Stereoselective Addition of Nucleophiles to 1– Phenoxycarbonyl–2,3–Dihydropyridium Salts.*" Heterocycles, vol. 37 No. 2, 1994.

Dehmlow, Eckehard, and Ralf Westerheide. "*Studies Towards 3,4–Dimethoxy–1–Methyl–1,2–Dihydropyridine, so–called Arecolidine, or its Tautomers.*" Heterocycles, vol. 37, No. 1, 1994.

Diez, et. al. "*Preparation of α New Chiral 5,6–Dihydropyridinium Synthon.*" Heterocycles, vol. 31, No. 3, 1990.

Dodd, Dharmpal and Allan Oehlschlager. "*Efficient Route to the Synthesis of C–2, C–3 Substituted 4–Piperidones.*" Tetrahedron Letters, vol. 32 No. 30, pp. 3643–3646, 1991.

Evans, et. al. "*Regioselective Preparation of α,B–Unsaturated Ketones via the Direct Dehydrogeantion of Triisopropylsilyl Enol Ethers.*" Tetrahedron Letters, vol. 36, No. 23, pp. 3985–3988, 1995.

Gage, et. al. "*Stereodivergent synthesis of sulfoxide–containing oxazolidinone antibiotic.*" Tetrahedron Letters, 41 (2000) 4301–4305.

Guerry, Philippe and Reinhard Neier, "*Photochemical Cycloadditions to 5,6–Dihydro–4–pyridones.*" Chimia 41 (1987) No. 10 (Oct.).

Guerry, Philippe and Reinhard Neier. "*Reduktion von 4–Pyridinonen.*" Synthesis, Jun. 1984 pp. 485–488.

Haider, et. al. "*140. Synthesis of 4–Oxo–1,2,3,4–tetrahydropyridine (2,3–Dihydro–4(1H)pyridinone).*" Helvetica Chimica Acta—vol. 58, Fasc. 5 (1975)—Nr. 139–140 pp. 1287–1292.

Herrinton, et. al. "*Iodination and Metal Halogen Exchange of Aromatic Compounds: An Improved Preparation of α Key Oxazolidinone Antibiotic Intermediate.*" Organic Process Research and Development 2001, 5, 80–83.

Ishii, et. al. "*Rhodium–Catalyzed Reaction of N–Acylpiperazines with CO and Ethylene, Carbonylation at α C–H Bond Directed by an Amido Group.*" Tetrahedron Letters, vol. 38, No. 43 pp. 7565–7568, 1997.

Kirschbaum, Stephen, and Herbert Waldmann. "*Construction of the Tricyclic Benzoquinolizine Ring System by Combination of α Tandem Mannich–Michael Reaction with α Heck Reaction.*" Tetrahedron Letters, vol. 38, No. 16, pp. 2829–2832, 1997.

Kirschbaum, Stepen, and Herbert waldmann. "*Three–Step Acces to the Tricyclic Benzo[α]quinolizine Ring System.*" Journal of Organic Chemistry. 1998, 63, 4936–4946.

Lock, Ralf, and Herbert Waldmann. "*Asymetric Synthesis of Highly Functionalized Tetracyclic Indole Bases Embodying the Basic Skeleton of Yohimbinep and Reserpine Type Alkaloids.*" Tetrahedron Letters, vol. 37, No. 16, pp. 2753–2756, 1996.

Lock, Ralf, and Herbert Waldmann. "*Enantioselective Construction of Highly Functionalized Indoloquinolizines Congeners to Polycylic Indole Alkaloids.*" Chem. Eur. J. 1997, 3, No. 1, pp. 143–151.

Mai, et. al. "*N–[4–(1,1'–Biphenylyl)Methyl]–4–(4–Thiomorpholinylmethyl) Benzenamines, αNew Class of Synthetic Antituberculosis Agents Active Against Mycobacterium Avium.*" Medicinal Chemistry Research, 9:3 (1999) 149–161.

Notari, Robert E., "*Theory and Practice of Prodrug Kinetics.*" Methods in Enzymology, vol. 112, 1985, pp. 309–323.

Reggelin, Michael, and Cornelia Zur, "*Sulfoximines; Structures, Properties and Synthetic Applications.*" Synthesis, 2000, No. 1, 1–64.

Roush, William R., and Bradley B. Brown. "*Enantioselective Syntehsis of 2–Alkyl–5–methylene–1, 3–dioxolan–4–ones and Exo–Selective Diels–Alder Reactions with Cyclopentadiene.*" Journal of Organic Chemistry. 1992, 57, 3380–3387.

Stutz, P, and PA Stadler, "*A Novel Approach to Cyclic β–Carbonyl–Enamines 7,8—Lysergic Acid Derivatives Via The Polonovski Reaction.*" Tetrahedron Letters No. 51, pp. 5095–5098, 1973.

Wagner, G. and S. Leistner, "*Darstellung von 4.6–Dinitrobenzoxazolinonen und deren Spaltung zu 3.5–Dinitro–2–aminophenolen.*" Pharmazie, 1971, 26, 280–282.

Waldmann, et. al. "*Asymmetric Synthesis of Indolo [2,3–α] quinolizidin–2—onesCongeners to Yohimbine–Type Alkaloids.*" Tetrahedron vol. 49, No. 2, 1993, pp. 397–416.

Yamamoto, Yutaka, and Akihiko Yanagi. "*Studies on Organometallic Compounds, II Facile and Convenient Method for the Synthesis of Iodoazines through Iododestannation of Trimethylstannylazines.*" Chem Pharm. Bull. 30(5) 1731–1737(1982).

N-ARYL-2-OXAZOLIDINONE-5-CARBOXAMIDES AND THEIR DERIVATIVES

CROSS REFERENCE TO RELATED APPLICATIONS

This application claims the benefit of U.S. Ser. No. 60/359,495 filed Feb. 25, 2002, under 35 USC 119(e)(i).

FIELD OF THE INVENTION

The present invention relates to novel N-Aryl-2-oxazolidinone-5-carboxamides, derivatives thereof, and their preparations. These compounds have potent antibacterial activity.

BACKGROUND OF THE INVENTION

The oxazolidinone antibacterial agents are a novel synthetic class of antimicrobials with potent activity against a number of human and veterinary pathogens, including gram-positive aerobic bacteria such as multiply-resistant staphylococci and streptococci, anaerobic organisms such as bacteroides and *clostridia* species, and acid-fast organisms such as *Mycobacterium tuberculosis* and *Mycobacterium avium*.

SUMMARY OF THE INVENTION

In one aspect, the invention provides compounds of formula I

B—C—A—C(=O)—NHR$_1$    I or a pharmaceutically acceptable salt thereof wherein:
A is a structure i, ii, or iii

[structure i]

[structure ii]

[structure iii]

C is aryl or heteroaryl, wherein each of the aryl and heteroaryl are optionally substituted with 1–3 of R$_2$;
B is selected from cycloalkyl, substituted cycloalkyl, cycloalkenyl, substituted cycloalkenyl, aryl, substituted aryl, het and substituted het, or B and one R$_2$, if present, together with the phenyl carbon atoms to which B and the one R$_2$ are bonded, form a het, the het optionally being a substituted het, provided that
when C is phenyl optionally substituted with R$_2$ that B is not

[structure]

where
Q is independently selected from H, C$_1$–C$_6$ alkyl, —O—C$_1$–C$_6$ alkyl, phenyl, benzyl, —OH, CF$_3$, CCl$_3$, —NR$_3$R$_3$, —C$_1$–C$_6$ alkylene-NR$_3$R$_3$, C$_1$–C$_6$ alkylene-(CH$_2$phenyl)-NR$_3$R$_3$, C$_1$–C$_6$ alkylene-(CH$_2$benzyl)-NR$_3$R$_3$, and

[phthalimide structure]

R$_1$ is selected from H, —OH, alkyl, cycloalkyl, alkoxy, alkenyl, amino, substituted alkyl, substituted alkoxy, and substituted alkenyl;
Each R$_2$ is independently selected from H, alkyl, amino, NO$_2$, —CN, halo, and substituted alkyl; and
Each R$_3$ is independently selected from H or C$_1$–C$_6$ alkyl.
Embodiments of this aspect of the invention may include one or more of the following features. Each R$_2$ is independently selected from H, F, Cl, Br, CN, NH$_2$, NO$_2$, CF$_3$, and CH$_3$. The structure of A is

[structure i]

[structure ii]

R$_1$ is H, —NH$_2$, —OH, C$_{1-4}$ alkyl, C$_{3-5}$ cycloalkyl, C$_{1-4}$ alkoxy, or C$_{2-4}$ alkenyl, the alkyl, alkoxy and alkenyl each optionally being substituted with one or more halo, —OH, —CN. R$_1$ is H, —OH, —CH$_2$—CH=CH$_2$, methyl, ethyl, propyl, —CH$_2$—CH$_2$F, —CH$_2$—CH$_2$OH, or methoxy. B is het or substituted het such as morpholinyl, piperazinyl, pyridyl, thiomorpholinyl, 3,6-dihydro-2H-thiopyranyl, tetrahydro-2H-thiopyranyl, 3,6-dihydro-2H-pyranyl, tetrahydro-2H-pyranyl, azetidinyl, 5,6-dihydro-4H-[1,3,4]thiadiazinyl, 2,5-dihydro-1H-pyrrolyl, 3,4-dihydro-1(2H)-pyridinyl, tetrahydropyridyl, 5,7-dihydro-6H-pyrrolo[3,4-b]pyridinyl, 2,3-dihydro-4H-1,4-thiazinyl, each of the morpholinyl, piperazinyl, pyridyl, thiomorpholinyl, 3,6-dihydro-2H-thiopyranyl, tetrahydro-2H-thiopyranyl, 3,6-dihydro-2H-pyranyl, tetrahydro-2H-pyranyl, azetidinyl, 5,6-dihydro-4H-[1,3,4]thiadiazinyl, 2,5-dihydro-1H-pyrrolyl, 3,4-dihydro-1(2H)-pyridinyl, tetrahydropyridyl, 5,7-dihydro-6H-pyrrolo[3,4-b]pyridinyl, 2,3-dihydro-4H-1,4- thiazinyl being optionally substituted with 1–4 groups selected from =O, alkyl, substituted alkyl, amino, substituted amino, —OH, =NOH, =NC$_{1-4}$ alkyl, and halo.

B is selected from

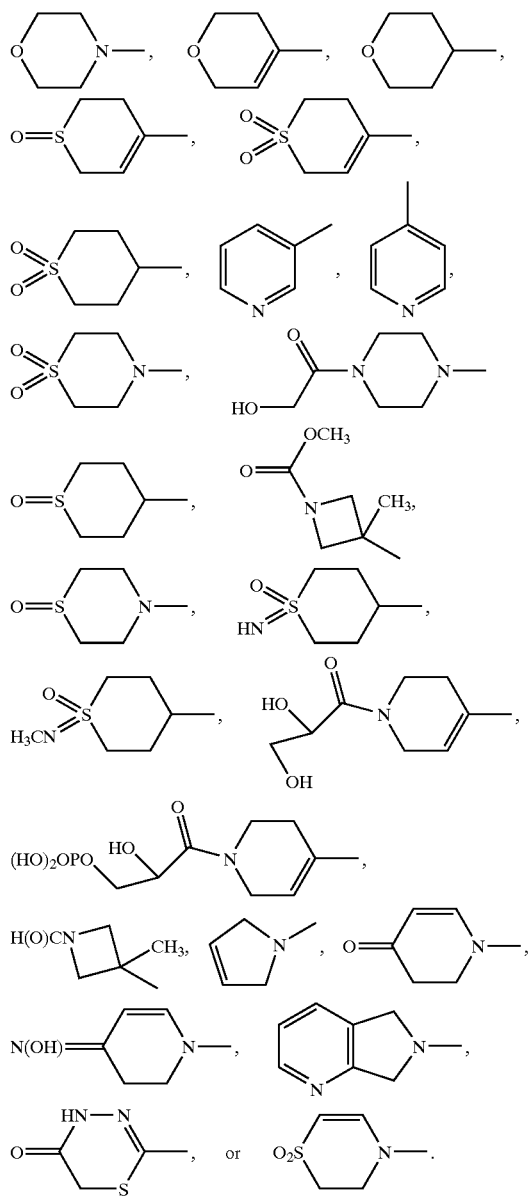

One R$_2$ is hydrogen and the other R$_2$ is F. Both R$_2$ substituents are F. One R$_2$ and B together form a het. R$_2$ and B form —S—C(O)—N(Q$_{50}$)-, —O—C(O)—N(Q$_{50}$)-, —N(Q$_{50}$)-HCQ$_{50}$-CH$_2$—, —NQ$_{50}$-C(O)—CH$_2$—O—, —NQ$_{50}$-C(O)—CF$_2$—O—, —NQ$_{50}$—C(O)—CH$_2$—S—, —NQ$_{50}$-C(O)—CF$_2$—S—, —NQ$_{50}$—C(S)—CH$_2$—S—, —NQ$_{50}$-C(O)—CH$_2$—CH$_2$—, —CH$_2$—CH$_2$—NQ$_{50}$-CH$_2$—CH$_2$—, or —CH$_2$—NQ$_{50}$-CH$_2$—CH$_2$—CH$_2$—, where Q$_{50}$ is H or C$_{1-4}$ alkyl optionally substituted with 1–3 of =O, or —OH. Q$_{50}$ is methyl, isopropyl, ethyl, formyl, acetyl, or —C(O)—CH$_2$OH.

In another aspect, the invention provides compounds of formula II

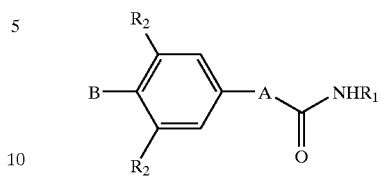

II or a pharmaceutically acceptable salt thereof wherein:
A is a structure i, ii, or iii

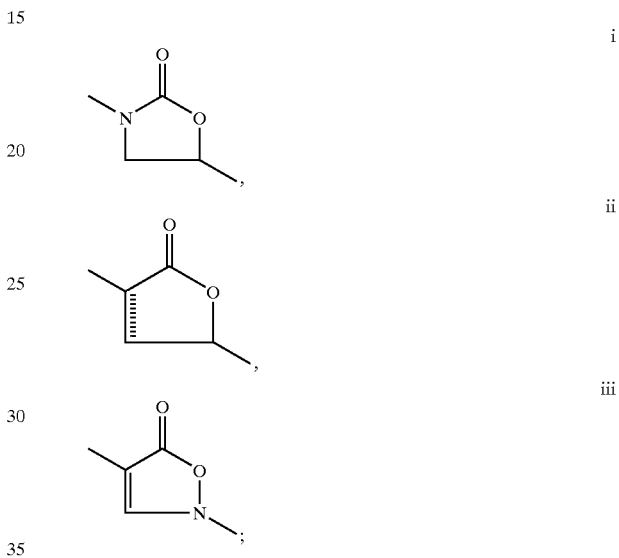

B is selected from cycloalkyl, substituted cycloalkyl, cycloalkenyl, substituted cycloalkenyl, aryl, substituted aryl, het, and substituted het, or B and one R$_2$ together, with the phenyl carbon atoms to which B and the one R$_2$ are bonded, form a het, the het optionally being a substituted het,
provided that
B is not

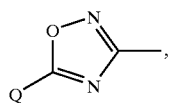

where
Q is independently selected from H, C$_1$–C$_6$ alkyl, —O—C$_1$–C$_6$ alkyl, phenyl, benzyl, —OH, CF$_3$, CCl$_3$, —NR$_3$R$_3$, —C$_1$–C$_6$ alkylene-NR$_3$R$_3$, C$_1$–C$_6$ alkylene-(CH$_2$phenyl)-NR$_3$R$_3$, C$_1$–C$_6$ alkylene-(CH$_2$benzyl)-NR$_3$R$_3$, and

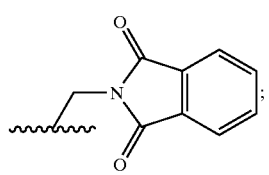

R$_1$ is selected from H, —OH, alkyl, cycloalkyl, alkoxy, alkenyl, amino, substituted alkyl, substituted alkoxy, and substituted alkenyl;

Each $R_2$ is independently selected from H, alkyl, amino, $NO_2$, —CN, halo, and substituted alkyl;

Each $R_3$ is independently selected from H or $C_1$–$C_6$ alkyl.

In another aspect the invention features a compound of formula III

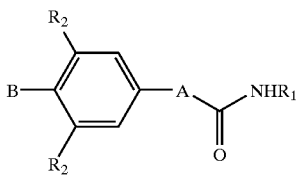
III or a pharmaceutically acceptable salt thereof wherein:

A is a structure i, ii, or iii

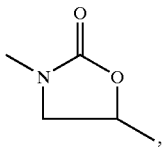
i

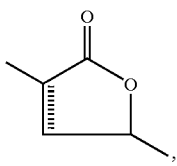
ii

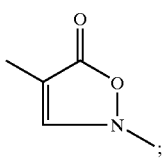
iii

B is a) 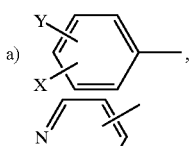

b) 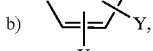

c) 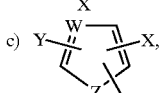

d) 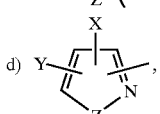

e) 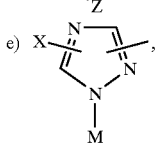

f) 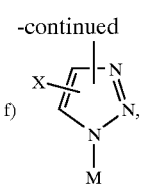

g) 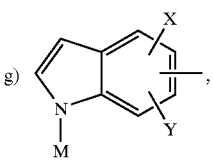

h) 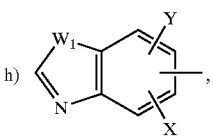

i) 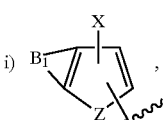

j) 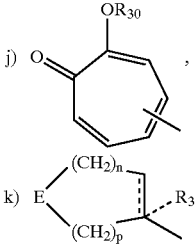

k) 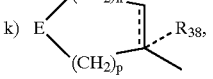

l) a diazinyl group optionally substituted with X and Y,
m) a triazinyl group optionally substituted with X and Y,
n) a quinolinyl group optionally substituted with X and Y,
o) a quinoxalinyl group optionally substituted with X and Y,
p) a naphthyridinyl group optionally substituted with X and Y, q) 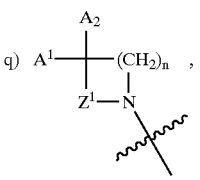

r) 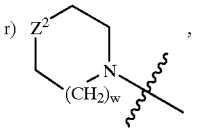

s) 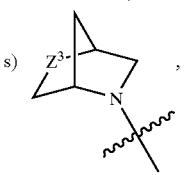

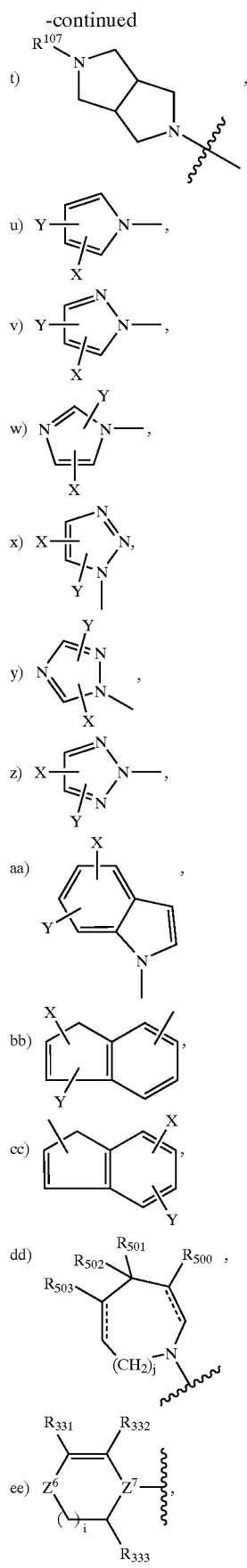
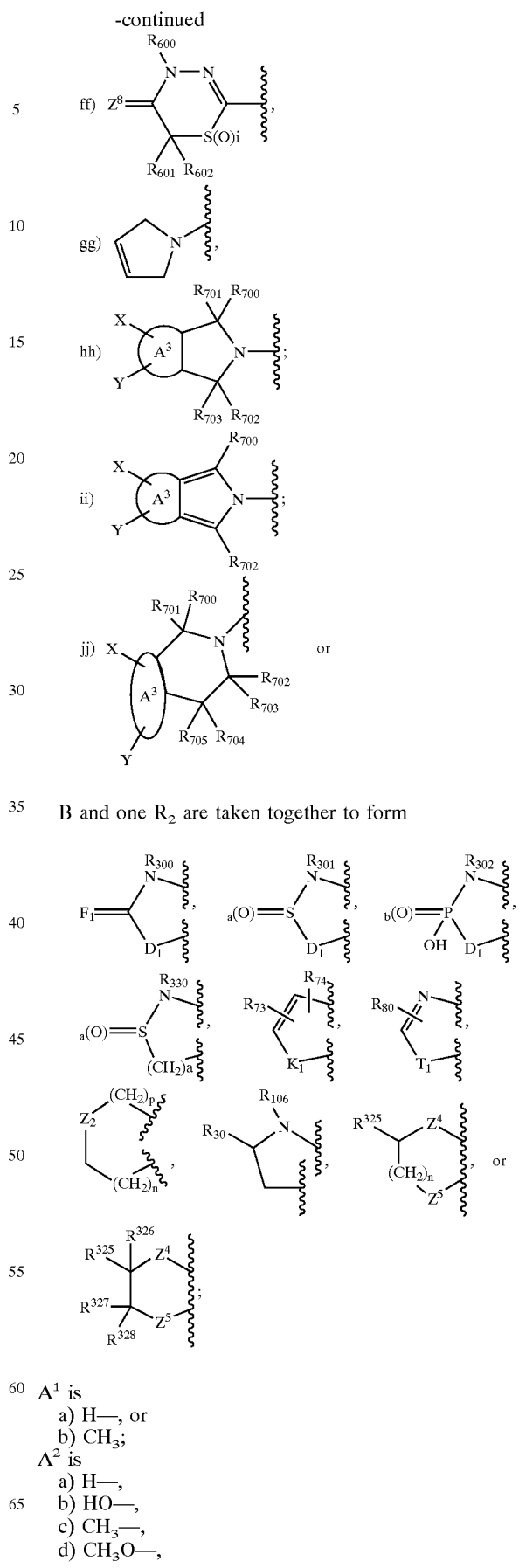
B and one $R_2$ are taken together to form
$A^1$ is
    a) H—, or
    b) $CH_3$;
$A^2$ is
    a) H—,
    b) HO—,
    c) $CH_3$—,
    d) $CH_3O$—, e) $R^{102}O\text{—}CH_2\text{—}C(O)\text{—}NH\text{—}$
f) $R^{103}O\text{—}C(O)\text{—}NH\text{—}$,
g) $(C_1\text{-}C_2)alkyl\text{-}O\text{—}C(O)\text{—}$,
h) $HO\text{—}CH_2\text{—}$,
i) $CH_3O\text{—}NH\text{—}$,
j) $(C_1\text{-}C_3)alkyl\text{-}O_2C\text{—}$,
k) $CH_3\text{—}C(O)\text{—}$,
l) $CH_3\text{—}C(O)\text{—}CH_2\text{—}$, m)
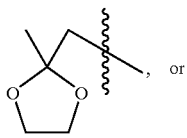
, or n)
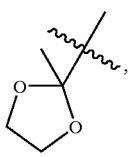
, $A^1$ and $A^2$ taken together are:

a)
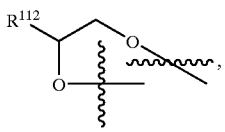
, b)
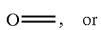
, or c)
;

$A^3$ represents any 5–10 membered aryl ring or aromatic het, the het having 1–4 heteroatoms selected from O, S, or N;

B, is
a) $\text{—}N\text{=}C(H)\text{—}C(H)\text{=}C(H)\text{—}$, or
b) $\text{—}C(H)\text{=}N\text{—}C(H)\text{=}C(H)\text{—}$;

$D_1$ is
a) O,
b) S, or
c) $\text{—}N(R_{304})\text{—}$;

E is
a) $NR_{39}$,
b) $\text{—}S(\text{=}O)_i$,
c) O, or
d) $\text{—}S(\text{=}O)(\text{=}NR_{315})$;

$F_1$ is
a) O,
b) S,
c) NH,
d) N—OH,
e) $N\text{—}O\text{—}C_{1\text{-}4}$ alkyl, or
f) $N\text{—}OC(O)\text{—}C_{1\text{-}4}$ alkyl;

$K_1$ is
a) O,
b) S, or
c) $\text{—}NR_{305}\text{—}$;

M is
a) H,
b) $C_{1\text{-}8}$ alkyl,
c) $C_{3\text{-}8}$ cycloalkyl,
d) $\text{—}(CH_2)_m OR_{13}$, or
e) $\text{—}(CH_2)_h\text{—}NR_{21}R_{22}$;

$T_1$ is
a) —O—,
b) $\text{—}NR_{306}\text{—}$
c) —S—, or
d) $\text{—}SO_2\text{—}$;

V is
a) O,
b) $CH_2$, or
c) $NR_{87}$;

W is
a) CH, or
b) N;

$W_1$ is
a) —NH—,
b) O, or
c) S;

X is
a) H,
b) —CN,
c) $\text{—}OR_{27}$,
d) halo,
e) $\text{—}NO_2$,
f) tetrazoyl,
g) —SH,
h) $\text{—}S(\text{=}O)_i R_4$,
i) $\text{—}SC(\text{=}O)R_7$,
j) $\text{—}C(\text{=}O)R_{25}$,
k) $\text{—}C(\text{=}O)NR_{27}R_{28}$,
l) $\text{—}C(\text{=}NR_{29})R_{25}$,
m) $\text{—}C(R_{25})(R_{28})\text{—}OR_{13}$,
n) $\text{—}C(R_{25})(R_{28})\text{—}OC(\text{=}O)R_{13}$,
o) $\text{—}C(R_{28})(OR_{13})\text{—}(CH_2)_h\text{—}NR_{27}R_{28}$,
p) $\text{—}NR_{27}R_{28}$,
q) $\text{—}N(R_{27})C(\text{=}O)R_7$,
r) $\text{—}N(R_{27})\text{—}S(\text{=}O)_i R_7$,
s) $\text{—}C(OR_{14})(OR_{15})R_{28}$,
t) $\text{—}C(R_{25})(R_{16})\text{—}NR_{27}R_{26}$, or
u) $C_{1\text{-}8}$ alkyl substituted with one or more halos, OH, =O other than at alpha position, $\text{—}S(\text{=}O)_i R_{17}$, $\text{—}NR_{27}R_{28}$, $C_{2\text{-}5}$ alkenyl, $C_{2\text{-}5}$ alkynyl, or $C_{3\text{-}8}$ cycloalkyl;

Y is
a) H,
b) F,
c) Cl,
d) Br,
e) $C_{1\text{-}3}$ alkyl, or
f) $NO_2$;

Z is
a) O,
b) S, or
c) NM;

$Z_1$ is
a) $\text{—}CH_2\text{—}$,
b) $\text{—}CH(R^{104})\text{—}CH_2\text{—}$,
c) —C(O)—, or
d) $\text{—}CH_2CH_2CH_2\text{—}$;

$Z^2$ is
a) $\text{—}S(O)_i\text{—}$,
b) —O—,
c) $\text{—}N(R^{107})\text{—}$, or
d) $\text{—}S(\text{=}O)(\text{=}NR^{315})\text{—}$;

$Z^3$ is
  a) —S(O)$_i$—, or
  b) —O—,
$Z^4$ is
  a) —S(=O)$_i$—, or
  b) —NR$^{303}$—;
$Z^5$ is
  a) —O—,
  b) —NH—,
  c) —CH$_2$—, or
  d) —S(=O)$_i$—;
$Z^6$ is
  a) S(=O)$_i$,
  b) S(=NR$^{315}$), or
  c) S(=NR$^{315}$)(=O);
$Z^7$ is
  a) N,
  b) CR$^{110}$,
  c) CR$^{115}$, or
  d) CR$^{116}$;
$Z^8$ is
  a) O, or
  b) S;
$R_1$ is
  a) H,
  b) —OH,
  c) C$_{1-6}$ alkyl optionally substituted with one or more halos, —OH, —CN, aryl, het, alkoxy, substituted aryl or substituted het,
  d) C$_{1-6}$ alkoxy optionally substituted with one or more halos, —OH, —CN, aryl, het, substituted aryl or substituted het,
  e) C$_{2-6}$ alkenyl optionally substituted with aryl, het, substituted aryl or substituted het,
  f) —NH$_2$, or
  g) C$_{3-5}$ cycloalkyl;
$R_2$ is
  a) H,
  b) C$_{1-2}$ alkyl optionally substituted with one or more halos,
  c) —NH$_2$,
  d) —NO$_2$,
  e) —CN, or
  f) halo;
$R_4$ is
  a) C$_{1-4}$ alkyl optionally substituted with one or more halos, OH, CN, NR$_{10}$R$_{11}$, or —CO$_2$R$_{13}$,
  b) C$_{2-4}$ alkenyl,
  c) —NR$_{16}$R$_{18}$,
  d) —NHC(=O)R$_7$,
  e) —NR$_{20}$C(=O)R$_7$,
  f) —N(R$_{17}$)$_2$,
  g) —NR$_{16}$R$_{17}$, or
  h) —NR$_{17}$R$_{20}$;
$R_5$ and $R_6$ at each occurrence are the same or different and are
  a) C$_{1-2}$ alkyl, or
  b) R$_5$ and R$_6$ taken together are —(CH$_2$)$_k$—;
$R_7$ is
  a) C$_{1-4}$ alkyl optionally substituted with one or more halos;
$R_{10}$ and $R_{11}$ at each occurrence are the same or different and are
  a) H,
  b) C$_{1-4}$ alkyl, or
  c) C$_{3-8}$ cycloalkyl;
$R_{13}$ is
  a) H, or
  b) C$_{1-4}$ alkyl;
$R_{14}$ and $R_{15}$ at each occurrence are the same or different and are
  a) C$_{1-4}$ alkyl, or
  b) R$_{14}$ and R$_{15}$ taken together are —(CH$_2$)$_l$—;
$R_{16}$ is
  a) H,
  b) C$_{1-4}$ alkyl, or
  c) C$_{3-8}$ cycloalkyl;
$R_{17}$ is
  a) C$_{1-4}$ alkyl, or
  b) C$_{3-8}$ cycloalkyl;
$R_{18}$ is
  a) H,
  b) C$_{1-4}$ alkyl,
  c) C$_{2-4}$ alkenyl,
  d) C$_{3-4}$ cycloalkyl,
  e) —OR$_{13}$ or
  f) —NR$_{21}$R$_{22}$;
$R_{20}$ is a physiologically acceptable cation, such as sodium, potassium, lithium, calcium or magnesium;
$R_{21}$ and $R_{22}$ at each occurrence are the same or different and are
  a) H,
  b) C$_{1-4}$ alkyl, or
  c) R$_{21}$ and R$_{22}$ taken together are —(CH$_2$)$_m$—;
$R_{25}$ is
  a) H,
  b) C$_{1-8}$ alkyl optionally substituted with one or more halos, C$_{3-8}$ cycloalkyl, C$_{1-4}$ alkyl substituted with one or more of —S(=O)$_i$R$_{17}$, —OR$_{13}$, or OC(=O)R$_{13}$, NR$_{27}$R$_{28}$, or
  c) C$_{2-5}$ alkenyl optionally substituted with —C(O)H, or CO$_2$R$_{13}$;
$R_{26}$ is
  a) R$_{28}$, or
  b) —NR$_{27}$N$_{28}$;
$R_{27}$ and $R_{28}$ at each occurrence are the same or different and are
  a) H,
  b) C$_{1-8}$ alkyl,
  c) C$_{3-8}$ cycloalkyl,
  d) —(CH$_2$)$_m$OR$_{13}$,
  e) —(CH$_2$)$_n$—NR$_{21}$R$_{22}$, or
  f) R$_{27}$ and R$_{28}$ taken together are —(CH$_2$)$_2$O(CH$_2$)$_2$—, —(CH$_2$)$_n$CH(COR$_7$)—, or —(CH$_2$)$_2$N(CH$_2$)$_2$(R$_7$);
$R_{29}$ is
  a) —NR$_{27}$R$_{28}$,
  b) —OR$_{27}$, or
  c) —NHC(=O)R$_{28}$;
$R_{30}$ is
  a) H, or
  b) C$_{1-4}$ alkyl optionally substituted with one or more halos, OH, C$_{1-4}$ alkoxy, CN, SH, NH$_2$, —OR$_{31}$, —NHR$_{31}$, —N(R$_{31}$)$_2$, or —S(O)iR$_{31}$;
$R_{31}$ is
  a) C$_{1-4}$ alkyl,
  b) —C(O)C$_{1-4}$ alkyl,
  c) —C(O)OC$_{1-4}$ alkyl,
  d) —C(O)NH$_2$,
  e) —C(O)NHC$_{1-4}$ alkyl, or
  f) —SO$_2$C$_{1-4}$ alkyl;
$R_{38}$ is
  a) H,
  b) C$_{1-6}$ alkyl, c) —(CH$_2$)$_q$-aryl, or
d) halo;

R$_{39}$ is
a) H,
b) C$_{1-6}$ alkyl optionally substituted with one or more OH, halo, or —CN,
c) —(CH$_2$)$_q$-aryl,
d) —CO$_2$R$_{40}$,
e) —COR$_{41}$,
f) —C(=O)—(CH$_2$)$_q$—C(=O)R$_{40}$,
g) —S(=O)$_2$—C$_{1-6}$ alkyl,
h) —S(=O)$_2$—(CH$_2$)$_q$-aryl, or
i) —(C=O)$_j$-Het;

R$_{40}$ is
a) H,
b) C$_{1-6}$ alkyl optionally substituted with one or more OH, halo, or —CN,
c) —(CH$_2$)$_q$-aryl, or
d) —(CH$_2$)$_q$—OR$_{42}$;

R$_{41}$ is
a) C$_{1-6}$ alkyl optionally substituted with one or more OH, halo, —OP(O)(OH)$_2$, —OP(OH)$_2$, or —CN,
b) —(CH$_2$)$_q$-aryl, or
c) —(CH$_2$)$_q$—OR$_{42}$;

R$_{42}$ is
a) H,
b) C$_{1-6}$ alkyl,
c) —(CH$_2$)$_q$-aryl, or
d) —C(=O)—C$_{1-6}$ alkyl;

R$_{49}$ and R$_{50}$ at each occurrence are the same or different and are
a) H,
b) C$_{1-4}$ alkyl,
c) C$_{5-6}$ cycloalkyl, or
d) R$_{49}$ and R$_{50}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, C$_{1-3}$ alkyl, or C$_{1-3}$ acyl;

R$_{51}$ is
a) carboxyl,
b) halo,
c) —CN,
d) mercapto,
e) formyl,
f) CF$_3$,
g) —NO$_2$,
h) C$_{1-6}$ alkoxy,
i) C$_{1-6}$ alkoxycarbonyl,
j) C$_{1-6}$ alkylthio,
k) C$_{1-6}$ acyl,
l) C$_{1-6}$ alkyl optionally substituted with OH, C$_{1-5}$ alkoxy, C$_{1-5}$ acyl, or —NR$_{49}$R$_{50}$,
m) phenyl,
n) —C(=O)NR$_{52}$R$_{53}$,
o) —NR$_{49}$R$_{50}$,
p) —N(R$_{52}$)(—SO$_2$R$_{54}$),
q) —SO$_2$—NR$_{52}$R$_{53}$, or
r) —S(=O)$_t$R$_{54}$;

R$_{52}$ and R$_{53}$ at each occurrence are the same or different and are
a) H,
b) C$_{1-6}$ alkyl, or
c) phenyl;

R$_{54}$ is
a) C$_{1-4}$ alkyl, or
b) phenyl optionally substituted with C$_{1-4}$ alkyl;

R$_{73}$ and R$_{74}$ at each occurrence are the same or different and are
a) H,
b) carboxyl,
c) halo,
d) —CN,
e) mercapto,
f) formyl,
g) CF$_3$,
h) —NO$_2$,
i) C$_{1-6}$ alkoxy,
j) C$_{1-6}$ alkoxycarbonyl,
k) C$_{1-6}$ alkylthio,
l) C$_{1-6}$ acyl,
m) —NR$_{78}$R$_{79}$,
n) C$_{1-6}$ alkyl optionally substituted with OH, C$_{1-5}$ alkoxy, C$_{1-5}$ acyl, —NR$_{78}$R$_{79}$, —N(phenyl)(CH$_2$—CH$_2$—OH), —O—CH(CH$_3$)(OCH$_2$CH$_3$), or —O-phenyl-[para-NHC(=O)CH$_3$],
o) C$_{2-8}$ alkenylphenyl optionally substituted with R$_{51}$,
p) phenyl optionally substituted with R$_{51}$, or
q) a 5-, or 6-membered saturated or unsaturated heterocyclic moiety having one to three atoms selected from the group consisting of S, N, and O, optionally substituted with R$_{51}$;

R$_{78}$ and R$_{79}$ at each occurrence are the same or different and are
a) H,
b) C$_{1-4}$ alkyl,
c) phenyl, or
d) R$_{78}$ and R$_{79}$ taken together with the nitrogen atom is a 5-, 6-membered saturated heterocyclic moiety which optionally has a further hetero atom selected from the group consisting of S, N, and O, and can in turn be optionally substituted with, including on the further nitrogen atom, C$_{1-3}$ alkyl, or C$_{1-3}$ acyl;

R$_{80}$ is
a) H,
b) formyl,
c) carboxyl,
d) C$_{1-6}$ alkoxycarbonyl,
e) C$_{1-8}$ alkyl,
f) C$_{2-8}$ alkenyl,
wherein the substituents (e) and (f) can be optionally substituted with OH, halo, C$_{1-6}$ alkoxy, C$_{1-6}$ acyl, C$_{1-6}$ alkylthio or C$_{1-6}$ alkoxycarbonyl, or phenyl optionally substituted with halo,
g) an aromatic moiety having 6 to 10 carbon atoms optionally substituted with carboxyl, halo, —CN, formyl, CF$_3$, —NO$_2$, C$_{1-6}$ alkyl, C$_{1-6}$ alkoxy, C$_{1-6}$ acyl, C$_{1-6}$ alkylthio, or C$_{1-6}$ alkoxycarbonyl;
h) —NR$_{81}$R$_{82}$,
i) —OR$_{90}$,
j) —S(=O)$_t$—R$_{91}$, or
k) —SO$_2$—N(R$_{92}$)(R$_{93}$);

R$_{81}$ and R$_{82}$ at each occurrence are the same or different and are
a) H,
b) C$_{3-6}$ cycloalkyl,
c) phenyl,
d) C$_{1-6}$ acyl,
e) C$_{1-8}$ alkyl optionally substituted with OH, C$_{1-6}$ alkoxy which can be substituted with OH, a 5-, or 6-membered aromatic heterocyclic moiety having one to three atoms selected from the group consisting of S, N, and O, phenyl optionally substituted with OH, CF$_3$, halo, —NO$_2$, C$_{1-4}$ alkoxy, —NR$_{83}$R$_{84}$, or

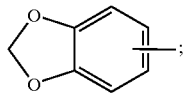

f)

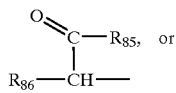

g)

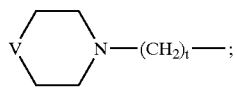

R$_{83}$ and R$_{84}$ at each occurrence are the same or different and are
  a) H, or
  b) C$_{1-4}$ alkyl;
R$_{85}$ is
  a) OH,
  b) C$_{1-4}$ alkoxy, or
  c) —NR$_{88}$R$_{89}$;
R$_{86}$ is
  a) H, or
  b) C$_{17}$ alkyl optionally substituted with indolyl, OH, mercaptyl, imidazoly, methylthio, amino, phenyl optionally substituted with OH, —C(=O)—NH$_2$, —CO$_2$H, or —C(=NH)—NH$_2$;
R$_{87}$ is
  a) H,
  b) phenyl, or
  c) C$_{1-6}$ alkyl optionally substituted by OH;
R$_{88}$ and R$_{89}$ at each occurrence are the same or different and are
  a) H,
  b) C$_{1-5}$ alkyl
  c) C$_{3-6}$ cycloalkyl, or
  d) phenyl;
R$_{90}$ is
  a) C$_{1-8}$ alkyl optionally substituted with C$_{1-6}$ alkoxy or C$_{1-6}$ hydroxy, C$_{3-6}$ cycloalkyl, a 6-membered aromatic optionally benzo-fused heterocyclic moiety having one to three nitrogen atoms, which can in turn be substituted with one or two —NO$_2$, CF$_3$, halo, —CN, OH, C$_{1-5}$ alkyl, C$_{1-5}$ alkoxy, or C$_{1-5}$ acyl;

b)

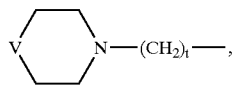

c) phenyl, or
  d) pyridyl;
R$_{91}$ is
  a) C$_{1-16}$ alkyl,
  b) C$_{2-16}$ alkenyl,
  wherein the substituents (a) and (b) can be optionally substituted with C$_{1-6}$ alkoxycarbonyl, or a 5-, 6-, 7-membered aromatic heterocyclic moiety having one to three atoms selected from the group consisting of S, N, and O,
  c) an aryl having 6 to 10 carbon atoms, or
  d) a 5-, 6-, 7-membered aromatic heterocyclic moiety having one to three atoms selected from the group consisting of S, N, and O, wherein the substituents (c) and (d) can be optionally substituted with carboxyl, halo, —CN, formyl, CF$_3$, —NO$_2$, C$_{1-6}$ alkyl, C$_{1-6}$ alkoxy, C$_{1-6}$ acyl, C$_{1-6}$ alkylthio, or C$_{1-6}$ alkoxycarbonyl;
R$_{92}$ and R$_{93}$ at each occurrence are the same or different and are
  a) H,
  b) phenyl,
  c) C$_{1-6}$ alkyl, or
  d) benzyl;
R$^{102}$ is
  a) H—,
  b) CH$_3$—,
  c) phenyl-CH$_2$—, or
  d) CH$_3$C(O)—;
R$^{103}$ is
  a) (C$_1$–C$_3$)alkyl-, or
  b) phenyl-;
R$^{104}$ is
  a) H—, or
  b) HO—;
R$^{106}$ is
  a) CH$_3$—C(O)—,
  b) H—C(O)—,
  c) Cl$_2$CH—C(O)—,
  d) HOCH$_2$—C(O)—,
  e) CH$_3$SO$_2$—, f)

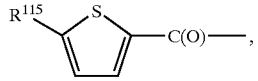

g) F$_2$CHC(O)—, h)

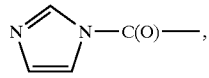

i) H$_3$C—C(O)—O—CH$_2$—C(O)—,
j) H—C(O)—O—CH$_2$—C(O)—, k)

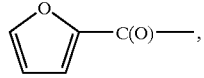

l) HC≡C—CH$_2$O—CH$_2$—C(O)—,
m) phenyl-CH$_2$—O—CH$_2$—C(O)—,
o) C$_{1-4}$alkyl-NH—C(S)—, or
p) C$_{1-4}$alkyl optionally substituted with one or more halo, CN, NO$_2$, OH, SH, or NH$_2$;
R$^{107}$ is
  a) R$^{102}$O—C(R$^{110}$)(R$^{111}$)—C(O)—,
  b) R$^{103}$O—C(O)—,
  c) R$^{108}$—C(O)—, d)

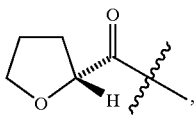

e)

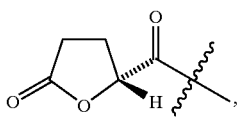

f) H$_3$C—C(O)—(CH$_2$)$_2$—C(O)—,
g) R$^{109}$—SO$_2$—, h)

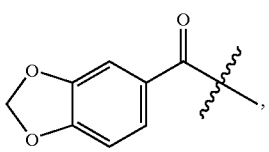

i) HO—CH$_2$—C(O)—,
j) R$^{116}$—(CH$_2$)$_2$—,
k) R$^{113}$—C(O)—O—CH$_2$—C(O)—,
l) (CH$_3$)$_2$N—CH$_2$—C(O)—NH—,
m) NC—CH$_2$—,
n) F$_2$—CH—CH$_2$—, or
o) R$^{150}$R$^{151}$NSO$_2$

R$^{108}$ is
  a) H—,
  b) (C$_1$–C$_4$)alkyl,
  c) aryl —(CH$_2$)$_n$,
  d) ClH$_2$C—,
  e) Cl$_2$HC—,
  f) FH$_2$C—,
  g) F$_2$HC—,
  h) (C$_3$—C$_6$)cycloalkyl, or
  i) CNCH$_2$—.

R$^{109}$ is
  a) C$_1$–C$_4$alkyl,
  b) —CH$_2$Cl
  c) —CH$_2$CH=CH$_2$,
  d) aryl, or
  e) —CH$_2$CN;

R$^{110}$ and R$^{111}$ are independently
  a) H—,
  b) CH$_3$—; or

R$^{112}$ is
  a) H—,
  b) CH$_3$O—CH$_2$O—CH$_2$—, or
  c) HOCH$_2$—;

R$^{113}$ is
  a) CH$_3$—,
  b) HOCH$_2$—,
  c) (CH$_3$)$_2$N-phenyl, or
  d) (CH$_3$)$_2$N—CH$_2$—;

R$^{114}$ is
  a) HO—,
  b) CH$_3$O—,
  c) H$_2$N—,
  d) CH$_3$O—C(O)—O—,
  e) CH$_3$—C(O)—O—CH$_2$—C(O)—O—,
  f) phenyl-CH$_2$—O—CH$_2$—C(O)—O—,
  g) HO—(CH$_2$)$_2$—O—,
  h) CH$_3$O—CH$_2$—O—(CH$_2$)$_2$—O—, or
  i) CH$_3$O—CH$_2$—O—;

R$^{115}$ is
  a) H—, or
  b) Cl—;

R$^{116}$ is
  a) HO—
  b) CH$_3$O—, or
  c) F;

R$^{150}$ and R$^{151}$ are each independently
  a) H,
  b) C$_1$–C$_4$alkyl, or
  c) R$^{150}$ and R$^{151}$ taken together with the nitrogen atom, to which R$^{150}$ and R$^{151}$ are attached, form a monocyclic heterocyclic ring having from 3 to 6 carbon atoms;

Each R$_{300}$, R$_{301}$, R$_{302}$, R$_{303}$, R$_{304}$, R$_{305}$, and R$_{306}$ is independently selected from
  a) H,
  b) C$_{3-6}$ cycloalkyl optionally substituted with =O,
  c) C$_{1-6}$ alkoxy,
  d) C$_{1-10}$ alkyl optionally substituted with one or more of R$_{310}$,
  e) C$_{2-10}$ alkenyl optionally substituted with one or more of R$_{310}$,
  f) benzyloxycarbonyl,
  g) aryl,
  h) het,
  i) —C(O)—NR$_{311}$R$_{312}$,
  j) —S(O)$_2$—NR$_{311}$R$_{312}$,
  k) —(O)$_i$SR$_{311}$,
  l) —C(O)—R$_{310}$,
  m) —C(S)—NR$_{311}$R$_{312}$,
  n) —C(O)—H, or
  o) —C(O)—C$_{1-4}$alkyl optionally substituted with one or more of R$_{310}$;

R$_{310}$ is
  a) —CN,
  b) —N$_3$,
  c) —CF$_3$,
  d) pyridyl,
  e) halo,
  f) —OH,
  g) —O(O)C$_1$–C$_6$alkyl,
  h) —C$_{1-6}$ alkyloxycarbonyl,
  i) —SH,
  j) —NH$_2$;

Each R$_{311}$ and R$_{312}$ is independently selected from
  a) H,
  b) C$_{1-4}$ alkyl,
  c) phenyl, or
  d) R$_{311}$ and R$_{312}$ together with the N-atom to which they are attached forms a 5- or 6-membered, saturated heterocyclic ring optionally having one or more O, S, or N atoms in the ring, the heterocyclic ring being optionally substituted with C$_{1-3}$ alkyl;

R$_{315}$ is
  a) H,
  b) C$_{1-4}$ alkyl optionally substituted with halo, —OH, C$_{1-8}$ alkoxy, amino, C$_{1-8}$ alkylamino, or C$_{1-8}$dialkylamino,
  c) aryl-S(O)$_2$—,
  d) C(=O)C$_{1-4}$alkyl,
  e) C(=O)OC$_{1-4}$alkyl,
  f) C(=O)NHR$_{320}$,
  g) C(=S)NHR$_{320}$,
  h) —OC(=O)C$_{1-4}$alkyl,
  i) —S(O)$_i$C$_{1-4}$alkyl, j) $C_{1-4}$ alkyl-O—$C_{1-4}$ alkyl, or
k) $C_{1-4}$ alkyl-S—$C_{1-4}$ alkyl;

$R_{320}$ is independently selected from
  a) H, or
  b) substituted alkyl;

Each $R_{325}$, $R_{326}$, $R_{327}$, and $R_{328}$ is independently selected from
  a) H,
  b) $C_1$–$C_6$alkyl,
  c) substituted alkyl,
  d) halo, or
  e) $R_{325}$ and $R_{326}$ or $R_{327}$ and $R_{328}$ together are =O or =S, or
  f) one of $R_{325}$ or $R_{326}$ and $R_{303}$, when Z4 is —N($R_{303}$)—, together with the carbon and nitrogen atoms to which they are bound form a 5–7 membered heterocyclic ring containing one or more heteroatoms selected from O, S, or N;

$R_{330}$ is
  a) H, or
  b) alkyl, or
  c) substituted alkyl;

$R_{331}$ is
  a) $R_{332}$,
  b) Cl,
  c) $NH_2$,
  d) OH,
  e) $NHC_1$–$C_4$alkyl, or
  f) $R_{315}$;

$R_{332}$ is
  a) H,
  b) $C_1$–$C_4$alkyl,
  c) $OC_1$–$C_4$alkyl,
  d) $SC_1$–$C_4$alkyl, or
  e) $NHC_1$–$C_4$alkyl;

$R_{333}$ is
  a) F, or
  b) $R_{332}$;

$R_{500}$ and $R_{503}$ are each and independently
  (a) H,
  (b) halo,
  (c) $C_1$–$C_8$ alkyl,
  (d) $C_3$–$C_6$ cycloalkyl,
  (e) —(CH$_2$)$_i$—OR$_{511}$, or
  (f) —C(=O)—$R_{541}$;

$R_{501}$ and $R_{502}$ are each and independently
  (a) hydrogen atom,
  (b) $C_1$–$C_8$ alkyl,
  (c) $C_1$–$C_8$ alkoxy,
  (d) $C_1$–$C_8$ alkylthio,
  (e) —(CH$_2$)$_i$—OR$_{551}$,
  (f) —O—(CH$_2$)$_i$—OR$_{551}$,
  (g) —NR$_{542}$R$_{552}$,
  (h) —C(=O)—NR$_{542}$R$_{552}$,
  (i) —(CH$_2$)$_i$—C(=O)—$R_{541}$,
  or $R_{501}$ and $R_{502}$ together form
  (j) =O,
  (k) =NR$_{543}$,
  (l) =S,
  (m) =CR$_{544}$R$_{554}$, or
  (n) an unsaturated or saturated 5- or 6-membered hetero ring having 1–3 hetero atoms selected from the group consisting of a nitrogen atom, an oxygen atom and a sulfur atom;

$R_{511}$ and $R_{512}$ are each and independently
  (a) hydrogen atom,
  (b) $C_1$–$C_8$ alkyl;

$R_{541}$ is
  (a) hydrogen atom,
  (b) —(CH$_2$)$_m$—OH,
  (c) $C_1$–$C_8$ alkyl,
  (d) $C_1$–$C_8$ alkoxy, or
  (e) —O—CH$_2$—O—C(=O)—$R_{511}$;

$R_{542}$ and $R_{552}$ are each and independently
  (a) hydrogen atom,
  (b) —(CH$_2$)$_i$—OH,
  (c) $C_1$–$C_8$ alkyl,
  (d) C(=O)—$R_{541}$,
  (e) —C(=O)—NR$_{511}$R$_{512}$,
  (f) —(CH$_2$)$_q$-phenyl, or
  or $R_{542}$ and $R_{552}$ together form a pyrrolidino group, a piperidino group, a piperazino group, a morpholino group, or a thiomorpholino group, each of which may be substituted by $C_1$–$C_8$ alkyl or —(CH$_2$)$_i$—OH;

$R_{543}$ is
  (a) H,
  (b) —OR$_{551}$,
  (c) $C_1$–$C_8$ alkyl,
  (d) $C_1$–$C_8$ alkoxy,
  (e) —(CH$_2$)$_q$-phenyl,
  (f) —NR$_{542}$R$_{552}$,
  (g) —NH—C(=NH)—$NH_2$, or
  (h) [1,2,4]triazol-4-yl;

$R_{544}$ and $R_{554}$ are each and independently
  (a) H,
  (b) $C_1$–$C_8$ alkyl,
  (c) —C(=O)—$R_{541}$, or
  (d) —(CH$_2$)$_q$-phenyl;

$R_{551}$ is
  (a) H,
  (b) $C_1$–$C_8$ alkyl,
  (c) $C_1$–$C_8$ alkyl substituted with 1–3 halo,
  (d) —(CH$_2$)$_i$—OR$_{511}$,
  (e) —(CH$_2$)$_i$—C(=O)—$R_{541}$, or
  (f) —C(=O)—(CH$_2$)$_i$—OR$_{544}$;

$R_{600}$ is
  a) H,
  b) $C_1$–$C_4$alkyl
  c) het,
  d) (CH$_2$)$_b$C(O)O$C_1$–$C_4$alkyl,
  e) (CH$_2$)$_b$C(O)$C_1$–$C_4$alkyl, or
  f) aryl;

$R_{601}$ and $R_{602}$ are each independently
  a) H,
  b) $C_1$–$C_4$alkyl,
  c) het,
  d) $C_3$–$C_6$cycloalkyl,
  e) aryl,
  f) $OC_1$–$C_4$alkyl,
  g) C(O)O$C_1$–$C_4$alkyl; or
  h) $R_{601}$ and $R_{602}$ taken together along with the carbon atom to which they attach form a $C_3$–$C_6$cycloalkyl;

Each $R_{700}$, $R_{701}$, $R_{702}$, $R_{703}$, $R_{704}$, and $R_{705}$ is independently selected from
  a) H,
  b) $C_{1-4}$ alkyl optionally substituted with 1–3 halo, =O, =S, —OH
  c) C(O)$NH_2$,
  d) —CN,
  e) aryl,
  f) substituted aryl,
  g) het,
  h) substituted het,
  i) C(O)OH,
  j) C(O)O$C_{1-4}$ alkyl, or k) $R_{700}$ and $R_{701}$ form =O or =S, or
l) $R_{702}$ and $R_{703}$ form =O or =S, or
m) $R_{704}$ and $R_{705}$ form =O or =S;

a is 1 or 2;
b is 0 or 1;
h is 1, 2, or 3;
i is 0, 1, or 2;
j is 0 or 1;
k is 3, 4, or 5;
l is 2 or 3;
m is 2, 3, 4 or 5;
n is 0, 1, 2, 3, 4, or 5;
p is 0, 1, 2, 3, 4, or 5; with the proviso that n and p together are 1, 2, 3, 4, or 5;
q is 1, 2, 3, or 4;
t is 0, 1, 2, 3, 4, 5, or 6; and
w is 0, 1, 2, or 3.

Embodiments of this aspect of the invention may include one or more of the following features. 21. $R_2$ is independently selected from H, F, Cl, Br, CN, $NH_2$, $NO_2$, $CF_3$, and $CH_3$. The structure of A is

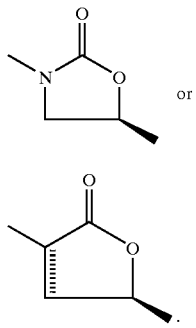

i or ii

The structure of A is

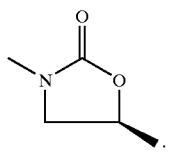

i $R_1$ is H, $-NH_2$, $-OH$, $C_{1-4}$alkyl, $C_{3-5}$ cycloalkyl, $C_{1-4}$ alkoxy, or $C_{2-4}$ alkenyl, the alkyl and alkoxy each optionally being substituted with one or more halo, $-OH$, $-CN$. $R_1$ is H, $-OH$, $-CH_2-CH=CH_2$, methyl, ethyl, propyl, $-CH_2-CH_2F$, $-CH_2-CH_2OH$, or methoxy. B is

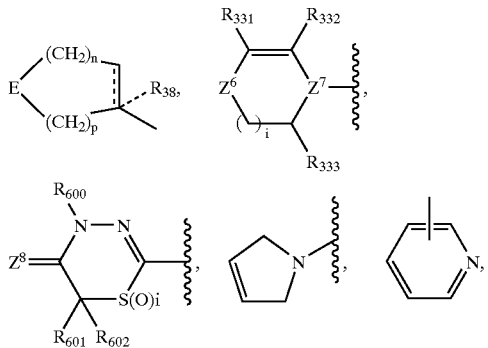

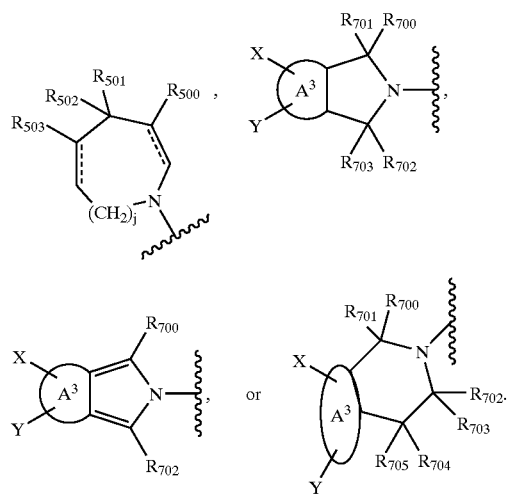

B is selected from

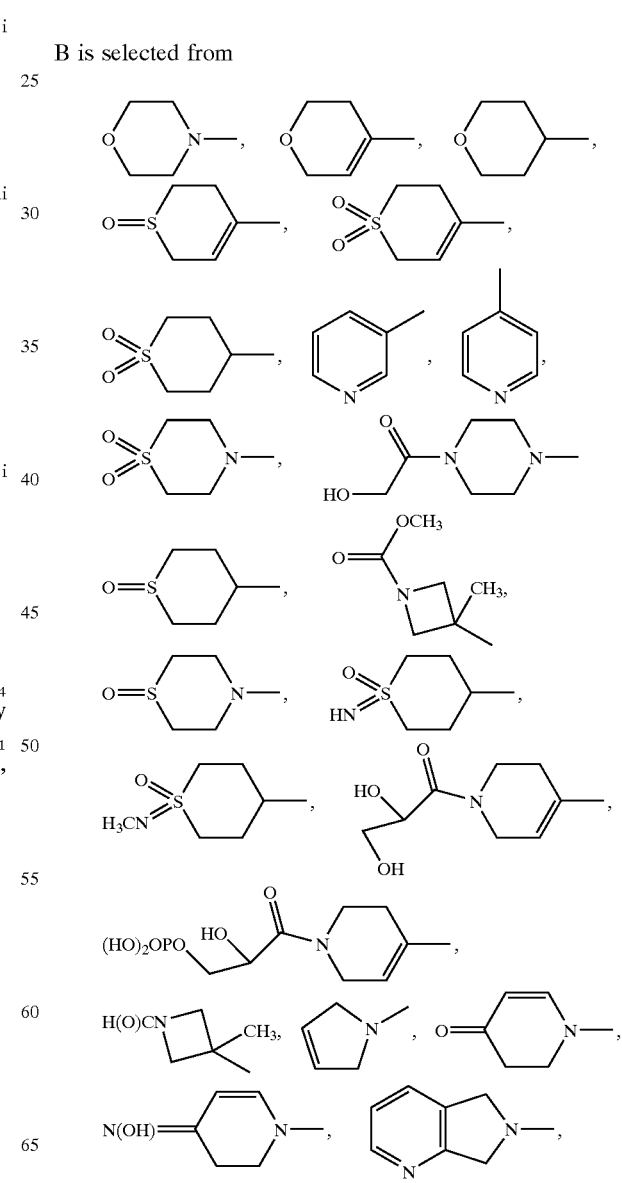

-continued

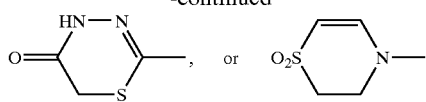

B and one $R_2$ from

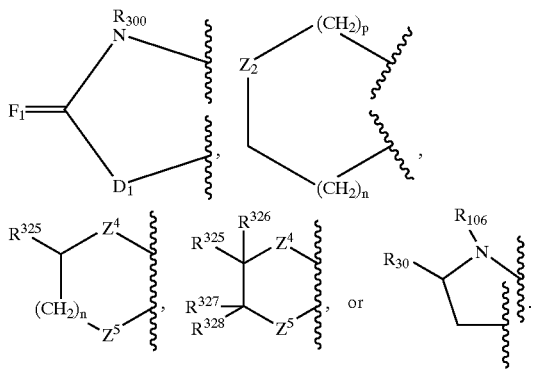

B and one $R_2$ form —S—C(O)—N($R_{300}$)—, —O—C(O)—N($R_{300}$)—, —N($R_{106}$)—HC$R_{30}$—CH$_2$—, —N$R_{300}$—C(O)—C($R_{327}R_{328}$)—O—, —N$R_{300}$—C(O)—C($R_{327}R_{328}$)—S—, —N$R_{300}$—C(S)—C($R_{327}R_{328}$)—S—, —N$R_{300}$—C(O)—C($R_{327}R_{328}$)—CH$_2$—, —CH$_2$—CH$_2$—N$R_{107}$—CH$_2$—CH$_2$—, or —CH$_2$—N$R_{107}$—CH$_2$—CH$_2$—CH$_2$—. $D_1$ is S. $D_1$ is O. $R_{300}$ is $C_{1-4}$ alkyl such as methyl, ethyl, or isopropyl. One $R_2$ is hydrogen and the other $R_2$ is F. Both $R_2$ substituents are F.

Other aspects of the invention include pharmaceutical compositions including a compound of formulae I, II, or III and a pharmaceutically acceptable carrier, and methods for treating microbial infections in mammals by administering an effective amount of a compound of formulae I, II, or III. The compound may be administered to the mammal orally, parenterally, transdermally, or topically in a pharmaceutical composition. The compound may be administered in an amount of from about 0.1 to about 100 mg/kg of body weight/day, such as in an amount of from about 1 to about 50 mg/kg of body weight/day.

Specific compounds of the invention include but are not limited to the following.

(5R)-(–)-3-[3-Fluoro-4-(4-morpholinyl)phenyl]-2-oxo-5-oxazolidinecarboxamide;
(5R)-(–)-3-[3-Fluoro-4-(4-morpholinyl)phenyl]-N-methyl-2-oxo-5-oxazolidinecarboxamide;
(5R)-(–)-3-[3-Fluoro-4-(4-morpholinyl)phenyl]-N-allyl-2-oxo-5-oxazolidinecarboxamide;
(5R)-(–)-3-[3-Fluoro-4-(4-morpholinyl)phenyl]-N-propyl-2-oxo-5-oxazolidinecarboxamide;
(5R)-(–)-3-[3-Fluoro-4-(4-morpholinyl)phenyl]-N-methoxy-2-oxo-5-oxazolidinecarboxamide;
(5R)-(–)-N-Methyl-3-[3,5-difluoro-4-(4-morpholinyl)phenyl]-2-oxo-5-oxazolidinecarboxamide;
(5R)-(–)-3-[3-Fluoro-4-(4-morpholinyl)phenyl]-N-hydroxy-2-oxo-5-oxazolidinecarboxamide;
(5R)-(–)-3-[3,5-Difluoro-4-(4-morpholinyl)phenyl]-2-oxo-5-oxazolidinecarboxamide;
(5R)-(–)-3-[4-(3-Pyridyl)-3-fluorophenyl]-2-oxo-5-oxazolidinecarboxamide;
(5R)-(–)-3-[4-(4-Pyridyl)-3-fluorophenyl]-2-oxo-5-oxazolidinecarboxamide;
(5R)-(–)-3-[4-(3,6-Dihydro-2H-pyran-4-yl)-3-fluorophenyl]-2-oxo-5-oxazolidinecarboxamide;
(5R)-(–)-3-[4-(Tetrahydro-2H-pyran-4-yl)-3-fluorophenyl]-2-oxo-5-oxazolidinecarboxamide;
(5R)-3-[4-(3,6-Dihydro-2H-thiopyran-4-yl)-3-fluorophenyl]-2-oxo-5-oxazolidinecarboxamide S-oxide;
(5R)-(–)-3-[4-(3,6-Dihydro-2H-thiopyran-4-yl)-3-fluorophenyl]-2-oxo-5-oxazolidinecarboxamide S,S-dioxide;
(5R)-(–)-3-[4-(Tetrahydro-2H-thiopyran-4-yl)-3-fluorophenyl]-2-oxo-5-oxazolidinecarboxamide S,S-dioxide;
(5R)-3-[3-Fluoro-4-(cis-tetrahydro-1-oxido-2H-thiopyran-4-yl)phenyl]-2-oxo-5-oxazolidinecarboxamide;
(5R)-3-[3-Fluoro-4-(trans-tetrahydro-1-oxido-2H-thiopyran-4-yl)phenyl]-2-oxo-5-oxazolidinecarboxamide;
(5R)-(–)-3-[4-(tetrahydro-2H-thiopyran-4-yl)phenyl]-2-oxo-5-oxazolidinecarboxamide S,S-dioxide;
(5R)-3-[4-(cis-tetrahydro-1-oxido-2H-thiopyran-4-yl)phenyl]-2-oxo-5-oxazolidinecarboxamide;
(5R)-3-[4-(trans-tetrahydro-1-oxido-2H-thiopyran-4-yl)phenyl]-2-oxo-5-oxazolidinecarboxamide;
(5R)-(–)-N-Methyl-3-[4-(Tetrahydro-2H-thiopyran-4-yl)-3-fluorophenyl]-2-oxo-5-oxazolidinecarboxamide S,S-dioxide;
(5R)-3-[3,5-Difluoro-4-(Tetrahydro-2H-thiopyran-4-yl)phenyl]-2-oxo-5-oxazolidinecarboxamide S,S-dioxide;
(5R)-(–)-3-[3,5-Difluoro-4-(cis-tetrahydro-1-oxido-2H-thiopyran-4-yl)phenyl]-2-oxo-5-oxazolidinecarboxamide;
(5R)-(–)-3-[3,5-Difluoro-4-(trans-tetrahydro-1-oxido-2H-thiopyran-4-yl)phenyl]-2-oxo-5-oxazolidinecarboxamide;
(5R)-N-Methyl-3-[3,5-difluoro-4-(trans-tetrahydro-1-oxido-2H-thiopyran-4-yl)phenyl]-2-oxo-5-oxazolidinecarboxamide;
(5R)-3-[4-(cis-1-(methylimino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(cis-1-imino-1-oxido-1,1,3,4,5,6-hexahydro-2H-thiopyran-4-yl)-3-fluorophenyl]-2-oxo-5-oxazolidinecarboxamide;
(5R)-3-[4-(cis-1-Imino-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(cis-1-(methylimino)-1-oxido-1,1,3,4,5,6-hexahydro-2H-thiopyran-4-yl)-3-fluorophenyl]-2-oxo-5-oxazolidinecarboxamide;
(5R)-3-[4-(trans-1-(imino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(trans-1-(imino)-1-oxido-1,1,3,4,5,6-hexahydro-2H-thiopyran-4-yl)-3-fluorophenyl]-2-oxo-5-oxazolidinecarboxamide;
(5R)-3-[4-(trans-1-(methylimino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(trans-1-(methylimino)-1-oxido-1,1,3,4,5,6-hexahydro-2H-thiopyran-4-yl)-3-fluorophenyl]-2-oxo-5-oxazolidinecarboxamide;
(5R)-3-[4-(3,6-Dihydro-2H-thiopyran-4-yl)-3,5-difluorophenyl]-N-methyl-2-oxo-5-oxazolidinecarboxamide S,S-dioxide;
(5R)-3-[4-(3,6-Dihydro-2H-thiopyran-4-yl)-3,5-difluorophenyl]-2-oxo-5-oxazolidinecarboxamide S,S-dioxide;
(5R)-N-Methyl-3-[3-fluoro-4-(trans-tetrahydro-1-oxido-2H-thiopyran-4-yl)phenyl]-2-oxo-5-oxazolidinecarboxamide;

(5R)-(−)-3-[3-Fluoro-4-[4-(hydroxyacetyl)-1-piperazinyl]phenyl]-2-oxo-5-oxazolidinecarboxamide;
(5R)-(−)-3-[4-(Thiomorpholin-4-yl)-3,5-difluorophenyl]-2-oxo-5-oxazolidinecarboxamide S,S-dioxide;
(5R)-(−)-3-[4-(Thiomorpholin-4-yl)phenyl]-2-oxo-5-oxazolidinecarboxamide S,S-dioxide;
(5R)-(−)-3-[3-Fluoro-4-(thiomorpholin-4-yl)phenyl]-2-oxo-5-oxazolidinecarboxamide S,S-dioxide;
(5R)-(−)-3-[3-Fluoro-4-(thiomorpholin-4-yl)phenyl]-2-oxo-5-oxazolidinecarboxamide S-oxide;
(5R)-3-[3-Fluoro-4-(1-imino-1-oxido-4-thiomorpholinyl)phenyl]-2-oxo-5-oxazolidinecarboxamide;
(5R)-N-Methyl-3-[3-Fluoro-4-(1-imino-1-oxido-4-thiomorpholinyl)phenyl]-2-oxo-5-oxazolidinecarboxamide;
(5R)-3-[3-Fluoro-4-(1-methylimino-1-oxido-4-thiomorpholinyl)phenyl]-2-oxo-5-oxazolidinecarboxamide;
(5R)-N-Methyl-3-[3-Fluoro-4-(1-methylimino-1-oxido-4-thiomorpholinyl)phenyl]-2-oxo-5-oxazolidinecarboxamide;
(5R)-3-[3,5-Difluoro-4-(1-imino-1-oxido-4-thiomorpholinyl)phenyl]-2-oxo-5-oxazolidinecarboxamide;
(5R)-3-[3,5-Difluoro-4-(1-imino-1-oxido-4-thiomorpholinyl)phenyl]-2-oxo-5
(5R)-N-Methyl-3-[3,5-Difluoro-4-(1-imino-1-oxido-4-thiomorpholinyl)phenyl]-2-oxo-5-oxazolidinecarboxamide;
(5R)-3-[3,5-Difluoro-4-(1-methylimino-1-oxido-4-thiomorpholinyl)phenyl]-2-oxo-5-oxazolidinecarboxamide;
(5R)-N-Methyl-3-[3,5-Difluoro-4-(1-methylimino-1-oxido-4-thiomorpholinyl)phenyl]-2-oxo-5-oxazolidinecarboxamide;
(5R)-(−)-3-[3,5-Difluoro-4-(thiomorpholin-4-yl)phenyl]-2-oxo-5-oxazolidinecarboxamide S-oxide;
(5R)-(−)-N-Methyl-3-[3,5-difluoro-4-(thiomorpholin-4-yl)phenyl]-2-oxo-5-oxazolidinecarboxamide s-oxide;
(5R)-(−)-N-Methyl-3-[3,5-difluoro-4-(thiomorpholin-4-yl)phenyl]-2-oxo-5-oxazolidinecarboxamide S,S-dioxide;
(5R)-(−)-3-(2,3-Dihydro-3-methyl-2-oxo-6-benzothiazolyl)-2-oxo-5-oxazolidinecarboxamide;
(5R)-(−)-3-(2,3-Dihydro-3-ethyl-2-oxo-6-benzothiazolyl)-2-oxo-5-oxazolidinecarboxamide;
(5R)-(−)-3-(2,3-Dihydro-3-isopropyl-2-oxo-6-benzothiazolyl)-2-oxo-5-oxazolidinecarboxamide;
(5R)-(−)-N-Methyl-3-(2,3-dihydro-3-methyl-2-oxo-6-benzothiazolyl)-2-oxo-5-oxazolidinecarboxamide;
(5R)-(−)-N-Ethyl-3-(2,3-dihydro-3-methyl-2-oxo-6-benzothiazolyl)-2-oxo-5-oxazolidinecarboxamide;
(5R)-(−)-N-(2-Hydroxyethyl)-3-(2,3-dihydro-3-methyl-2-oxo-6-benzothiazolyl)-2-oxo-5-oxazolidinecarboxamide;
(5R)-N-(2-Fluoroethyl)-3-(2,3-dihydro-3-methyl-2-oxo-6-benzothiazolyl)-2-oxo-5-oxazolidinecarboxamide;
(5R)-(−)-N-Methyl-3-(2,3-dihydro-3-ethyl-2-oxo-6-benzothiazolyl)-2-oxo-5-oxazolidinecarboxamide;
(5R)-(−)-N-Methyl-3-(2,3-dihydro-3-isopropyl-2-oxo-6-benzothiazolyl)-2-oxo-5-oxazolidinecarboxamide;
(5R)-3-(2,3-Dihydro-3-methyl-4-fluoro-2-oxo-6-benzothiazolyl)-2-oxo-5-oxazolidinecarboxamide;
(5R)-N-Methyl-3-(2,3-dihydro-3-methyl-4-fluoro-2-oxo-6-benzothiazolyl)-2-oxo-5-oxazolidinecarboxamide;
(5R)-3-(2,3-Dihydro-3-ethyl-4-fluoro-2-oxo-6-benzothiazolyl)-2-oxo-5-oxazolidinecarboxamide;
(5R)-N-Methyl-3-(2,3-dihydro-3-ethyl-4-fluoro-2-oxo-6-benzothiazolyl)-2-oxo-5-oxazolidinecarboxamide;
(5R)-3-(2,3-Dihydro-3-isopropyl-4-fluoro-2-oxo-6-benzothiazolyl)-2-oxo-5-oxazolidinecarboxamide;
(5R)-N-Methyl-3-(2,3-dihydro-3-isopropyl-4-fluoro-2-oxo-6-benzothiazolyl)-2-oxo-5-oxazolidinecarboxamide;
(5R)-(−)-3-(2,3-dihydro-3-methyl-2-oxo-6-benzoxazolyl)-2-oxo-5-oxazolidinecarboxamide;
(5R)-(−)-3-(2,3-Dihydro-3-ethyl-2-oxo-6-benzoxazolyl)-2-oxo-5-oxazolidinecarboxamide;
(5R)-(−)-3-(2,3-Dihydro-3-isopropyl-2-oxo-6-benzoxazolyl)-2-oxo-5-oxazolidinecarboxamide;
(5R)-(−)-N-Methyl-3-(2,3-dihydro-3-methyl-2-oxo-6-benzoxazolyl)-2-oxo-5-oxazolidinecarboxamide;
(5R)-(−)-N-Methyl-3-(2,3-dihydro-3-ethyl-2-oxo-6-benzoxazolyl)-2-oxo-5-oxazolidinecarboxamide;
(5R)-(−)-N-Methyl-3-(2,3-dihydro-3-isopropyl-2-oxo-6-benzoxazolyl)-2-oxo-5-oxazolidinecarboxamide;
(5R)-3-(2,3-dihydro-3-methyl-4-fluoro-2-oxo-6-benzoxazolyl)-2-oxo-5-oxazolidinecarboxamide;
(5R)-N-Methyl-3-(2,3-dihydro-3-methyl-4-fluoro-2-oxo-6-benzoxazolyl)-2-oxo-5-oxazolidinecarboxamide;
(5R)-3-(2,3-dihydro-3-ethyl-4-fluoro-2-oxo-6-benzoxazolyl)-2-oxo-5-oxazolidinecarboxamide;
(5R)-N-Methyl-3-(2,3-dihydro-3-ethyl-4-fluoro-2-oxo-6-benzoxazolyl)-2-oxo-5-oxazolidinecarboxamide;
(5R)-3-(2,3-Dihydro-3-isopropyl-4-fluoro-2-oxo-6-benzoxazolyl)-2-oxo-5-oxazolidinecarboxamide;
(5R)-N-Methyl-3-(2,3-dihydro-3-isopropyl-4-fluoro-2-oxo-6-benzoxazolyl)-2-oxo-5-oxazolidinecarboxamide;
(5R)-3-[(2R)-2,3-Dihydro-1-formyl-2-methyl-1H-indol-5-yl]-2-oxo-5-oxazolidinecarboxamide;
(5R)-3-[(2R)-2,3-Dihydro-1-(hydroxyacetyl)-2-methyl-1H-indol-5-yl]-2-oxo-5-oxazolidinecarboxamide;
(5R)-3-[4-(5,7-Dihydro-6H-pyrrolo[3,4-b]pyridin-6-yl)-3-fluorophenyl]-2-oxo-5-oxazolidinecarboxamide;
(5R)-N-Methyl-3-[4-(5,7-dihydro-6H-pyrrolo[3,4-b]pyridin-6-yl)-3-fluorophenyl]-2-oxo-5-oxazolidinecarboxamide;
(5R)-(−)-3-[3,5-Difluoro-4-(1-methoxycarbonyl-3-methylazetidin-3-yl)phenyl]-2-oxo-5-oxazolidinecarboxamide;
(5R)-3-[3,5-Difluoro-4-(1-formyl-3-methylazetidin-3-yl)phenyl]-2-oxo-5-oxazolidinecarboxamide;
(5R)-N-Methyl-3-[3,5-difluoro-4-(1-formyl-3-methylazetidin-3-yl)phenyl]-2-oxo-5-oxazolidinecarboxamide;
(5R)-3-[3-Fluoro-4-(1-formyl-3-methylazetidin-3-yl)phenyl]-2-oxo-5-oxazolidinecarboxamide;
(5R)-N-Methyl-3-[3-fluoro-4-(1-formyl-3-methylazetidin-3-yl)phenyl]-2-oxo-5-oxazolidinecarboxamide;
(5R)-(−)-N-Methyl-3-[3,5-difluoro-4-(1-methoxycarbonyl-3-methylazetidin-3-yl)phenyl]-2-oxo-5-oxazolidinecarboxamide;
(5R)-3-(3,4-Dihydro-4-methyl-3-oxo-2H-1,4-benzoxazin-7-yl)-2-oxo-5-oxazolidinecarboxamide;
(5R)-N-Methyl-3-(3,4-dihydro-4-methyl-3-oxo-2H-1,4-benzoxazin-7-yl)-2-oxo-5-oxazolidinecarboxamide;
(5R)-N-(2-Fluoroethyl)-3-(3,4-dihydro-4-methyl-3-oxo-2H-1,4-benzoxazin-7-yl)-2-oxo-5-oxazolidinecarboxamide;
(5R)-3-(3,4-Dihydro-4-methyl-3-oxo-2H-1,4-benzothiazin-7-yl)-2-oxo-5-oxazolidinecarboxamide;
(5R)-3-(1-Methyl-2-oxo-1,2,3,4-tetrahydroquinolin-6-yl)-2-oxo-5-oxazolidinecarboxamide;
(5R)-N-Methyl-3-(1-methyl-2-oxo-1,2,3,4-tetrahydroquinolin-6-yl)-2-oxo-5-oxazolidinecarboxamide;
(5R)-3-(2,2-Difluoro-4-methyl-3,4-dihydro-3-oxo-2H-1,4-benzoxazin-7-yl)-2-oxo-5-oxazolidinecarboxamide;

(5R)-N-Methyl-3-(2,2-difluoro-4-methyl-3,4-dihydro-3-oxo-2H-1,4-benzoxazin-7-yl)-2-oxo-5-oxazolidinecarboxamide;
(5R)-3-(8-Fluoro-1-methyl-2-oxo-1,2,3,4-tetrahydroquinolin-6-yl)-2-oxo-5-oxazolidinecarboxamide;
(5R)-N-Methyl-3-(8-fluoro-1-methyl-2-oxo-1,2,3,4-tetrahydroquinolin-6-yl)-2-oxo-5-oxazolidinecarboxamide;
(5R)-3-(4-Methyl-3-thioxo-3,4-dihydro-2H-1,4-benzothiazin-7-yl)-2-oxo-5-oxazolidinecarboxamide;
(5R)-N-Methyl-3-(3,4-dihydro-4-methyl-3-oxo-2H-1,4-benzothiazin-7-yl)-2-oxo-5-oxazolidinecarboxamide;
(5R)-3-(3,4-Dihydro-5-fluoro-4-methyl-3-oxo-2H-1,4-benzothiazin-7-yl)-2-oxo-5-oxazolidinecarboxamide;
(5R)-N-Methyl-3-(3,4-dihydro-5-fluoro-4-methyl-3-oxo-2H-1,4-benzothiazin-7-yl)-2-oxo-5-oxazolidinecarboxamide;
(5R)-3-(3,4-Dihydro-5-fluoro-4-methyl-3-oxo-2H-1,4-benzoxazin-7-yl)-2-oxo-5-oxazolidinecarboxamide;
(5R)-N-Methyl-3-(3,4-dihydro-5-fluoro-4-methyl-3-oxo-2H-1,4-benzoxazin-7-yl)-2-oxo-5-oxazolidinecarboxamide;
(5R)-3-[3-Fluoro-4-(5-oxo-5,6-dihydro-4H-[1,3,4]thiadiazin-2-yl)phenyl]-2-oxo-5-oxazolidinecarboxamide;
(5R)-3-[4-(1,1-dioxido-2,3-dihydro-4H-1,4-thiazin-4-yl)-3,5-difluorophenyl]-2-oxo-5-oxazolidinecarboxamide;
(5R)-3-[4-(2,5-Dihydro-1H-pyrrol-1-yl)-3,5-difluorophenyl]-2-oxo-2-oxo-5-oxazolidinecarboxamide;
(5R)-3-[4-(4-Oxo-3,4-dihydro-1(2H)-pyridinyl)-3-fluorophenyl]-2-oxo-5-oxazolidinecarboxamide;
(5R)-N-Methyl-3-[4-(4-oxo-3,4-dihydro-1(2H)-pyridinyl)-3-fluorophenyl]-2-oxo-5-oxazolidinecarboxamide;
(5R)-N-Ethyl-3-[4-(4-oxo-3,4-dihydro-1(2H)-pyridinyl)-3-fluorophenyl]-2-oxo-5-oxazolidinecarboxamide;
(5R)-3-[4-(4-Oxo-3,4-dihydro-1(2H)-pyridinyl)phenyl]-2-oxo-5-oxazolidinecarboxamide;
(5R)-N-Methyl-3-[4-(4-oxo-3,4-dihydro-1(2H)-pyridinyl)phenyl]-2-oxo-5-oxazolidinecarboxamide;
(5R)-N-Ethyl-3-[4-(4-oxo-3,4-dihydro-1(2H)-pyridinyl)phenyl]-2-oxo-5-oxazolidinecarboxamide;
(5R)-N-(2-Fluoroethyl)-3-[4-(4-oxo-3,4-dihydro-1(2H)-pyridinyl)phenyl]-2-oxo-5-oxazolidinecarboxamide;
(5R)-3-[4-(4-Oxo-3,4-dihydro-1(2H)-pyridinyl)-3,5-difluorophenyl]-2-oxo-5-oxazolidinecarboxamide;
(5R)-N-Methyl-3-[4-(4-oxo-3,4-dihydro-1(2H)-pyridinyl)-3,5-difluorophenyl]-2-oxo-5-oxazolidinecarboxamide;
(5R)-N-Ethyl-3-[4-(4-oxo-3,4-dihydro-1(2H)-pyridinyl)-3,5-difluorophenyl]-2-oxo-5-oxazolidinecarboxamide;
(5R)-3-[4-[3,4-Dihydro-4-(hydroxyimino)-1(2H)-pyridinyl]-3-fluorophenyl]-2-oxo-5-oxazolidinecarboxamide;
(5R)-3-(2-Formyl-2,3,4,5-tetrahydro-1H-2-benzazepin-7-yl)-2-oxo-5-oxazolidinecarboxamide;
(5R)-N-Methyl-3-(2-formyl-2,3,4,5-tetrahydro-1H-2-benzazepin-7-yl)-2-oxo-5-oxazolidinecarboxamide;
(5R)-3-[2-(Hydroxyacetyl)-2,3,4,5-tetrahydro-1H-2-benzazepin-7-yl]-2-oxo-5-oxazolidinecarboxamide;
(5R)-N-Methyl-3-[2-(hydroxyacetyl)-2,3,4,5-tetrahydro-1H-2-benzazepin-7-yl]-2-oxo-5-oxazolidinecarboxamide;
(5R)-3-(3-Formyl-2,3,4,5-tetrahydro-1H-3-benzazepin-7-yl)-2-oxo-5-oxazolidinecarboxamide;
(5R)-N-Methyl-3-(3-formyl-2,3,4,5-tetrahydro-1H-3-benzazepin-7-yl)-2-oxo-5-oxazolidinecarboxamide;
(5R)-3-[3-(Hydroxyacetyl)-2,3,4,5-tetrahydro-1H-3-benzazepin-7-yl]-2-oxo-5-oxazolidinecarboxamide;
(5R)-N-Methyl-3-[3-(hydroxyacetyl)-2,3,4,5-tetrahydro-1H-3-benzazepin-7-yl]-2-oxo-5-oxazolidinecarboxamide;
(5R)-3-[4-(1-(2(S)-Hydroxy-3-phosphorylpropanoyl)-1,2,5,6-tetrahydropyrid-4-yl)-3,5-difluorophenyl]-2-oxo-5-oxazolidinecarboxamide;
(5R)-N-Methyl-3-[4-(1-(2(S)-hydroxy-3-phosphorylpropanoyl)-1,2,5,6-tetrahydropyrid-4-yl)-3,5-difluorophenyl]-2-oxo-5-oxazolidinecarboxamide;
(5R)-3-[4-(1-(2(S),3-Dihydroxypropanoyl)-1,2,5,6-tetrahydropyrid-4-yl)-3,5-difluorophenyl]-2-oxo-5-oxazolidinecarboxamide;
(5R)-N-Methyl-3-[4-(1-(2(S),3-dihydroxypropanoyl)-1,2,5,6-tetrahydropyrid-4-yl)-3,5-difluorophenyl]-2-oxo-5-oxazolidinecarboxamide;
(5R)-3-[4-(1-(2(S)-Hydroxy-3-phosphorylpropanoyl)-1,2,5,6-tetrahydropyrid-4-yl)-3-fluorophenyl]-2-oxo-5-oxazolidinecarboxamide;
(5R)-N-Methyl-3-[4-(1-(2(S)-hydroxy-3-phosphorylpropanoyl)-1,2,5,6-tetrahydropyrid-4-yl)-3-fluorophenyl]-2-oxo-5-oxazolidinecarboxamide;
(5R)-3-[4-(1-(2(S),3-Dihydroxypropanoyl)-1,2,5,6-tetrahydropyrid-4-yl)-3-fluorophenyl]-2-oxo-5-oxazolidinecarboxamide;
(5R)-N-Methyl-3-[4-(1-(2(S),3-dihydroxypropanoyl)-1,2,5,6-tetrahydropyrid-4-yl)-3-fluorophenyl]-2-oxo-5-oxazolidinecarboxamide.

DETAILED DESCRIPTION OF THE INVENTION

The following definitions are used, unless otherwise described.

Variables including a letter followed by a numeric superscript are equivalent to the same letter followed by the same number as a subscript. For instance, $R^1$ and $R_1$ are equivalent and refer to the same variable.

The carbon atom content of various hydrocarbon-containing moieties may be indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to a halogen atom selected from Cl, Br, I, and F.

The term "alkyl" refers to both straight- and branched-chain moieties. Unless otherwise specifically stated, such as by a $C_{i-j}$ prefix, alkyl moieties include between 1 and 6 carbon atoms.

The term "alkenyl" refers to both straight- and branched-chain moieties containing at least one —C═C—. Unless otherwise specifically stated, such as by a $C_{i-j}$ prefix, alkenyl moieties include between 2 and 6 carbon atoms.

The term "alkynyl" refers to both straight- and branched-chain moieties containing at least one —C≡C—. Unless otherwise specifically stated, such as by a $C_{i-j}$ prefix, alkynyl moieties include between 2 and 6 carbon atoms.

The term "alkoxy" refers to —O-alkyl groups. Unless otherwise specifically stated, such as by a $C_{i-j}$ prefix, the alkyl portion of the —O-alkyl group includes between 1 and 6 carbon atoms.

The term "amino" refers to $NH_2$.

The term "cycloalkyl" refers to a cyclic alkyl moiety. Unless otherwise specifically stated, such as by a $C_{i-j}$ prefix, cycloalkyl moieties will include between 3 and 7 carbon atoms.

The term "cycloalkenyl" refers to a cyclic alkenyl moiety. Unless otherwise specifically stated, such as by a $C_{i-j}$ prefix, cycloalkenyl moieties will include between 3 and 7 carbon atoms and at least one —C=C— group within the cyclic ring.

The term "aryl" refers to phenyl and naphthyl.

The term "het" refers to mono- or bicyclic ring systems containing at least one heteroatom selected from O, S, and N. Each monocyclic ring may be aromatic, saturated, or partially unsaturated. A bicyclic ring system may include a monocyclic ring containing at least one heteroatom which is fused with a cycloalkyl or aryl group. A bicyclic ring system may also include a monocyclic ring containing at least one heteroatom fused with another het, monocyclic ring system.

Examples of "het" include, but are not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo[2.2.1]heptyl.

The term "heteroaryl" refers to an aromatic het, examples of which include, but are not limited to, pyridine and thiophene.

The term "substituted alkyl" refers to an alkyl moiety including 1–4 substituents selected from halo, het, cycloalkyl, cycloalkenyl, aryl, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOH)Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$OPO(OH)_2$, and —$SNQ_{10}Q_{10}$. Each of the het, cycloalkyl, cycloalkenyl, and aryl may be optionally substituted with 1–4 substituents independently selected from halo and $Q_{15}$.

The term "substituted aryl" refers to an aryl moiety having 1–3 substituents selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOH)Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

The term "substituted het" refers to a het moiety including 1–4 substituents selected from —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOH)Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The substituted het also may be substituted by one or more =O or =S substituents provided that the O or S are bound to ring atoms capable of supporting a double bond between the ring atom and O or S. The het, cycloalkyl, cycloalkenyl, and aryl may be optionally substituted with 1–3 substituents selected from halo and $Q_{15}$.

The term "substituted alkenyl" refers to a alkenyl moiety including 1–3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

The term "substituted alkoxy" refers to an alkoxy moiety including 1–3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

The term "substituted cycloalkenyl" refers to a cycloalkenyl moiety including 1–3 substituents —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$SC(O)Q_{10}$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, =O, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, —$NO_2$, —$SNQ_{10}Q_{10}$, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

The term "substituted amino" refers to an amino moiety in which one or both of the amino hydrogens are replaced with a group selected from —$OQ_{10}$, —$SQ_{10}$, —$S(O)_2Q_{10}$, —$S(O)Q_{10}$, —$OS(O)_2Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(O)C(Q_{16})_2OC(O)Q_{10}$, —CN, alkyl, substituted alkyl, het, halo, cycloalkyl, cycloalkenyl, and aryl. The het, cycloalkyl, cycloalkenyl, and aryl may be optionally substituted with 1–3 substituents selected from halo and $Q_{15}$.

Each $Q_{10}$ is independently selected from —H, alkyl, cycloalkyl, het, cycloalkenyl, and aryl. The het, cycloalkyl, cycloalkenyl, and aryl may be optionally substituted with 1–3 substituents selected from halo and $Q_{13}$.

Each $Q_{11}$ is independently selected from —H, halo, alkyl, aryl, cycloalkyl, and het. The alkyl, cycloalkyl, and het may be optionally substituted with 1–3 substituents independently selected from halo, —$NO_2$, —CN, =S, =O, and $Q_{14}$. The aryl may be optionally substituted with 1–3 substituents independently selected from halo, $-NO_2$, $-CN$, and $Q_{14}$.

Each $Q_{13}$ is independently selected from $Q_{11}$, $-OQ_{11}$, $-SQ_{11}$, $-S(O)_2Q_{11}$, $-S(O)Q_{11}$, $-OS(O)_2Q_{11}$, $-C(=NQ_{11})Q_{11}$, $-SC(O)Q_{11}$, $-NQ_{11}Q_{11}$, $-C(O)Q_{11}$, $-C(S)Q_{11}$, $-C(O)OQ_{11}$, $-OC(O)Q_{11}$, $-C(O)NQ_{11}Q_{11}$, $-C(O)C(Q_{16})_2OC(O)Q_{10}$, $-CN$, $=O$, $=S$, $-NQ_{11}C(O)Q_{11}$, $-NQ_{11}C(O)NQ_{11}Q_{11}$, $-S(O)_2NQ_{11}Q_{11}$, $-NQ_{11}S(O)_2Q_{11}$, $-NQ_{11}S(O)Q_{11}$, $-NQ_{11}SQ_{11}$, $-NO_2$, and $-SNQ_{11}Q_{11}$, provided that $Q_{13}$ is not $=O$ or $=S$ when $Q_{10}$ is aryl or a het lacking any atom capable of forming a double bond with O or S.

Each $Q_{14}$ is $-H$ or a substituent selected from alkyl, cycloalkyl, cycloalkenyl, phenyl, or naphthyl, each optionally substituted with 1–4 substituents independently selected from $-F$, $-Cl$, $-Br$, $-I$, $-OQ_{16}$, $-SQ_{16}$, $-S(O)_2Q_{16}$, $-S(O)Q_{16}$, $-OS(O)_2Q_{16}$, $-NQ_{16}Q_{16}$, $-C(O)Q_{16}$, $-C(S)Q_{16}$, $-C(O)OQ_{16}$, $-NO_2$, $-C(O)NQ_{16}Q_{16}$, $-CN$, $-NQ_{16}C(O)Q_{16}$, $-NQ_{16}C(O)NQ_{16}Q_{16}$, $-S(O)_2NQ_{16}Q_{16}$, and $-NQ_{16}S(O)_2Q_{16}$. The alkyl, cycloalkyl, and cycloalkenyl may be further substituted with $=O$ or $=S$.

Each $Q_{15}$ is alkyl, cycloalkyl, cycloalkenyl, het, phenyl, or naphthyl, each optionally substituted with 1–4 substituents independently selected from $-F$, $-Cl$, $-Br$, $-I$, $-OQ_{16}$, $-SQ_{16}$, $-S(O)_2Q_{16}$, $-S(O)Q_{16}$, $-OS(O)_2Q)_{16}$, $-C(=NQ_{16})Q_{16}$, $-SC(O)Q_{16}$, $-NQ_{16}Q_{16}$, $-C(O)Q_{16}$, $-C(S)Q_{16}$, $-C(O)OQ_{16}$, $-OC(O)Q_{16}$, $-C(O)NQ_{16}Q_{16}$, $-C(O)C(Q_{16})_2OC(O)Q_{16}$, $-CN$, $-NQ_{16}C(O)Q_{16}$, $-NQ_{16}C(O)NQ_{16}Q_{16}$, $-S(O)_2NQ_{16}Q_{16}$, $-NQ_{16}S(O)_2Q_{16}$, $-NQ_{16}S(O)Q_{16}$, $-NQ_{16}SQ_{16}$, $-NO_2$, and $-SNQ_{16}Q_{16}$. The alkyl, cycloalkyl, and cycloalkenyl may be further substituted with $=O$ or $=S$.

Each $Q_{16}$ is independently selected from $-H$, alkyl, and cycloalkyl. The alkyl and cycloalkyl may optionally include 1–3 halos.

Specific $R_2$ substituents include H, F, Cl, Br, $-CN$, $-NH_2$, $-NO_2$, $-CH_3$.

Specific structures of A include

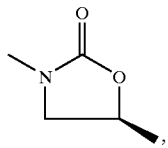

i

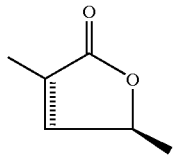

ii

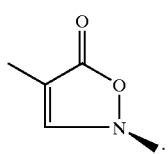

iii

Mammal refers to human or animals.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

It is to be understood that the present invention encompasses any racemic, optically-active, polymorphic, tautomeric, or stereoisomeric form, or mixture thereof, of a compound of the invention which possesses the useful properties described herein.

The compounds of the present invention can be converted to their salts, where appropriate, according to conventional methods.

In cases where compounds are sufficiently basic or acidic to form stable nontoxic acid or base salts, use of the compounds as pharmaceutically acceptable salts may be appropriate. Examples of pharmaceutically acceptable salts which are within the scope of the present invention include organic acid addition salts formed with acids which form a physiological acceptable anion and inorganic salts. Examples of pharmaceutically acceptable salts include, but are not limited to, the following acids: acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic and toluenesulfonic. Examples of pharmaceutically acceptable salts include, but are not limited to, the following bases: primary, secondary, and tertiary amines, substituted amines including naturally occurring substituted amines, cyclic amines, arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, hist isopropylamine, lysine, methylglucamine, morpholine, piperazine, piperidine, polyamine resins, procaine, purines, theobromine, triethylamine, trimethylamine, tripropylamine, and the like. The pharmaceutically acceptable salts may be in hydrated form.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of Formula I of this invention contain a chiral center, such as at C-5 of the oxazolidinone ring, and as such there exist two enantiomers or a racemic mixture of both. This invention relates to both the enantiomer that possesses the useful properties described herein, as well as to mixtures containing both of the isomers. In addition, depending on substituents, additional chiral centers and other isomeric forms may be present in any of A, B, or $R_1$ groups, and this invention embraces all possible stereoisomers and geometric forms in these groups.

The compounds of this invention are useful for treatment of microbial infections in humans and other warm blooded animals.

Dosages and Pharmaceutical Compositions

By the phrase "effective amount" of a compound as provided herein is meant a nontoxic but sufficient amount of one or more compounds of this invention to provide the desired effect. The desired effect may be to prevent, give relief from, or ameliorate microbial infections.

As pointed out below, the exact amount of the compound of this invention required to treat a microbial infection will vary from subject to subject, depending on the species, age, and general condition of the subject, the severity of the disease that is being treated, the particular compound(s) used, and the mode of administration, such as the route and frequency of administration, and the like. Thus, it is not possible to specify an exact "effective amount." However, an appropriate effective amount may be determined by one of ordinary skill in the art using only routine experimentation.

Pharmaceutical compositions of this invention may be prepared by combining the compounds of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound according to this invention.

The quantity of active component, that is the compound according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2–4 times per day.

A specific active agent may have more than one recommended dosage range, particularly for different routes of administration. Generally, an effective amount of dosage of compounds of this invention, either administered individually or in combination with other inhibitor compound(s), will be in the range of about 5 to about 2500 mg/day, more specifically about 10 to about 750 mg/day, and most conveniently from 50 to 500 mg per unit dosage form. It is to be understood that the dosages of active component(s) may vary depending upon the requirements of each subject being treated and the severity of the microbial infection.

Initial treatment of a patient suffering from microbial infection can begin with a dosage regimen as indicated above. Treatment is generally continued as necessary over a period of several days to several months until the condition or disorder has been controlled or eliminated. Patients undergoing treatment with a composition of the invention can be routinely monitored by any of the methods well known in the art to determine the effectiveness of therapy. Continuous analysis of data from such monitoring permits modification of the treatment regimen during therapy so that optimally effective amounts of drug are administered at any point in time, and so that the duration of treatment can be determined. In this way, the treatment regimen and dosing schedule can be rationally modified over the course of therapy so that the lowest amount of the compounds of this invention exhibiting satisfactory effectiveness is administered, and so that administration is continued only for so long as is necessary to successfully treat the condition or disorder.

In a combination therapy, the compound(s) of this invention and other inhibitor compound(s) can be administered simultaneously or at separate intervals. When administered simultaneously the compound(s) of this invention and the other inhibitor compound(s) can be incorporated into a single pharmaceutical composition or into separate compositions, e.g., compound(s) of this invention in one composition and the other inhibitor compound(s) in another composition. For instance, the compound(s) of this invention may be administered concurrently or concomitantly with the other inhibitor compound(s). The term "concurrently" means the subject being treated takes one drug within about 5 minutes of taking the other drug. The term "concomitantly" means the subject being treated takes one drug within the same treatment period of taking the other drug. The same treatment period is preferably within twelve hours and up to forty-eight hours.

When separately administered, therapeutically effective amounts of compound(s) of this invention and the other inhibitor compound(s) are administered on a different schedule. One may be administered before the other as long as the time between the two administrations falls within a therapeutically effective interval. A therapeutically effective interval is a period of time beginning when one of either (a) the compound(s) of this invention, or (b) the other inhibitor compound(s) is administered to a mammal and ending at the limit of the beneficial effect in the treatment of microbial infections of the combination of (a) and (b). The methods of administration of the compound(s) of this invention and the other inhibitor compound(s) may vary. Thus, one agent may be administered orally, while the other is administered by injection.

In addition to the compounds of this invention and other antimicrobial agents, the pharmaceutical composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

Routes of Administration

In therapeutic use for treating, or combating, infections in a mammal (i.e., humans and animals) the pharmaceutical composition can be administered orally, parenterally, topically, rectally, or intranasally.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Generally, the concentration of each of the compounds of this invention in a liquid composition, such as a lotion, will be from about 0.1 wt. % to about 20 wt. %, preferably from about 0.5 wt. % to about 10 wt. %. The solution may contain other ingredients, such as emulsifiers, antioxidants or buffers. The concentration in a semi-solid or solid composition, such as a gel or a powder, will be about 0.1 wt. % to about 5 wt. %, preferably about 0.5 wt. % to about 2.5 wt. %. When topically delivered, the pharmaceutical composition of the present invention being utilized to effect targeted treatment of a specific internal site, each of the compounds of this invention is preferably contained in the composition in an amount of from 0.05–10 wt. %, more preferably 0.5–5 wt. %.

Parenteral administrations include injections to generate a systemic effect or injections directly to the afflicted area. Examples of parenteral administrations are subcutaneous, intravenous, intramuscular, intradermal, intrathecal, intraocular, intravetricular, and general infusion techniques.

Topical administrations include the treatment of infectious areas or organs readily accessibly by local application, such as, for example, eyes, ears including external and middle ear infections, vaginal, open and sutured or closed wounds and skin. It also includes transdermal delivery to generate a systemic effect.

The rectal administration includes the form of suppositories.

The intranasally administration includes nasal aerosol or inhalation applications.

Pharmaceutical compositions including the compounds of this invention may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries that facilitate processing of the active compounds into preparations which can be used pharmaceutically. Proper formulation is dependent upon the route of administration chosen.

For oral administration, the compounds of this invention can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mnnitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identificatin or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may also be added in these formulations.

Liquid form compositions include solutions, suspensions and emulsions. For example, there may be provided solutions of pharmaceutical compositions with the compounds of this invention dissolved in water and water-propylene glycol and water-polyethylene glycol systems, optionally containing suitable conventional coloring agents, flavoring agents, stabilizers and thickening agents.

The compounds of this invention may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of this invention may be formulated in aqueous solution, preferably in physiologically compatible buffers or physiological saline buffer. Suitable buffering agents include tri-sodium orthophosphate, sodium bicarbonate, sodium citrate, N-methyl-glucamine, L(+)-lysine and L(+)-arginine.

The compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Other parenteral administrations also include aqueous solutions of a water soluble form, such as, without limitation, a salt, of the compounds of this invention.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the compounds of this invention may be in a powder form for constitution with a suitable vehicle (e.g., sterile, pyrogen-free water) before use.

For suppository administration, the pharmaceutical compositions may also be formulated by mixing the compounds of this invention with a suitable non-irritating excipient which is solid at room temperature but liquid at rectal temperature and therefore will melt in the rectum to release the drug. Such materials include cocoa butter, beeswax and other glycerides.

For administration by inhalation, the compounds of this invention can be conveniently delivered through an aerosol spray in the form of solution, dry powder, or cream. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative, such as benzylalkonium chloride. Alternatively, for ophthalmic uses, the pharmaceutical compositions may be formulated in an ointment, such as petrolatum.

In addition to the formulations described previously, the compounds of this invention may also be formulated as depot preparations. Such long acting formulations may be in the form of implants. The compounds of this invention may be formulated for this route of administration with suitable polymers, hydrophobic materials, or as a sparing soluble derivative such as, without limitation, a sparingly soluble salt.

Additionally, the compounds of this invention may be delivered using a sustained-release system. Various sustained-release materials have been established and are well known by those skilled in the art. Sustained-release capsules may, depending on their chemical nature, release the compounds for 24 hours up to several days. Depending on the chemical nature and the biological stability of the therapeutic reagent, additional strategies for protein stabilization may be employed. In certain embodiments, the compounds of this invention are applied topically. For topical applications, the pharmaceutical composition may be formulated in a suitable ointment containing the compounds of this invention suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

In some embodiments, the antibacterial compounds are prodrugs of the compounds of this invention. The expression "prodrug" denotes a derivative of a known direct acting drug, which is transformed into the active drug by an enzymatic or chemical process. Prodrugs of the compounds of this invention are prepared by modifying functional groups present on the compound in such a way that the modifications are cleaved, either in routine manipulation or in vivo, to the parent compound. Prodrugs include, but are not limited to, compounds wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

The antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA.

The following Charts describe the preparation of compounds of the present invention. The starting materials are prepared by procedures described in these charts or by procedures known to one of ordinary skill in the art.

CHART I

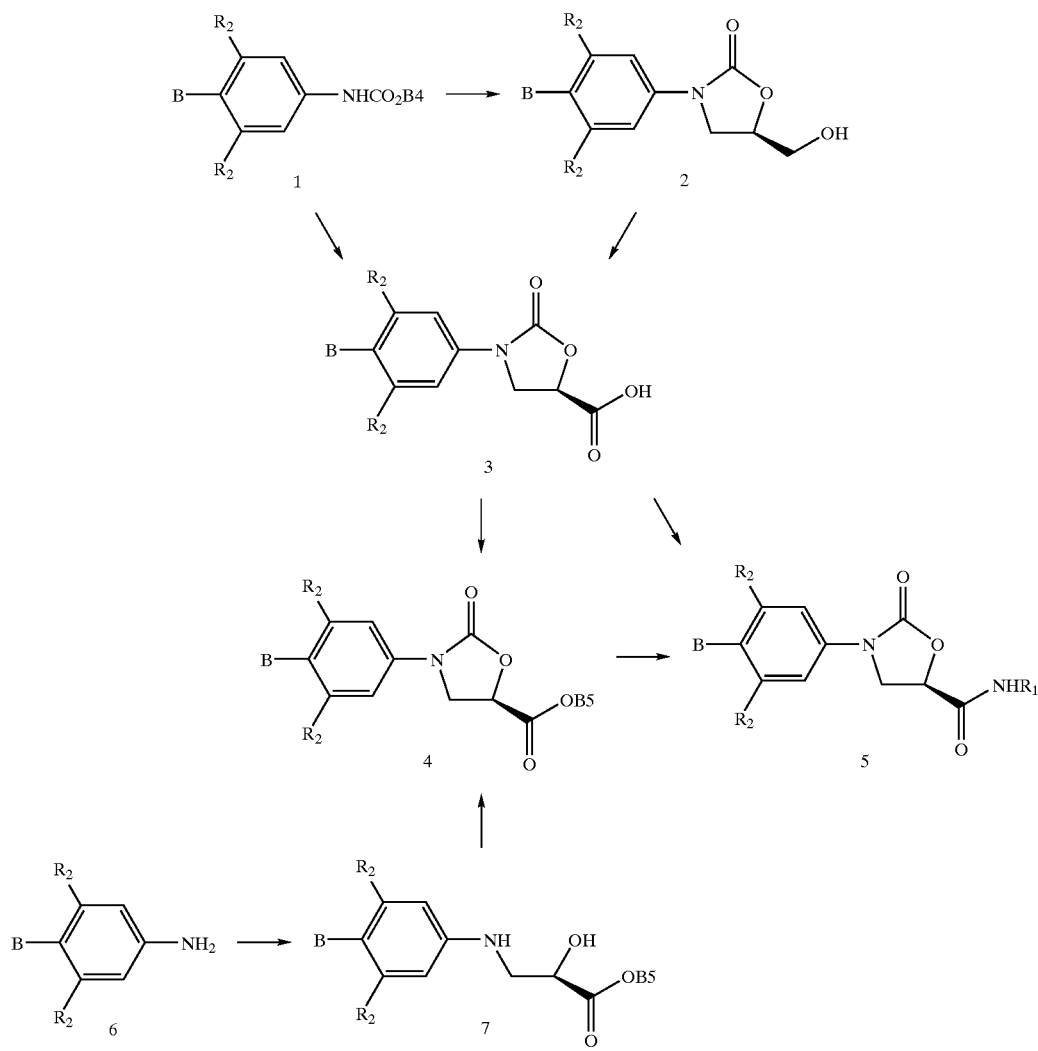

CHART I illustrates methods for preparing aryl oxazolidinone-5-carboxamides 5 and their N-substituted derivatives. In METHOD A, aryl carbamate derivatives 1 (B4=C(1–6)alkyl or benzyl) (known in the literature, prepared by known methods such as by derivatizing the aniline 6, or described in the charts to follow) can be deprotonated with a lithium base such as n-butyllithium in a suitable solvent such as THF at a suitable temperature, typically in a range of −78° C. to −40° C., to give a lithiated species which is directly treated with potassium (2R)-glycidate (*J. Org. Chem.* 1992, 57(12), 3380–3387). Warming to ambient temperature and stirring for a suitable period of time affords the aryl oxazolidinone-5(R)-carboxylic acids 3. The acids 3 can than be converted to the targeted structures 5 using methods known to those skilled in the art. For instance, treatment of the acids 3 with oxalyl chloride under an inert atmosphere affords the acid chloride intermediates which can be converted to the amides 5 ($R_1$=H or optionally substituted alkyl) upon treatment with ammonia or optionally substituted alkyl amines ($R_1NH_2$) or to the hydroxamates 5 ($R_1$=Oalkyl) upon treatment with O-alkylhydroxylamines. The hydroxamate derivatives can also be prepared directly from the acids 3 upon treatment with an O-alkylhydroxylamine (or its hydrochloride salt) in the presence of a coupling agent such as 1-(3-dimethylaminopropyl)-3-ethylcarbodiimide hydrochloride. When $R_1$ is O-benzyl, hydrogenolysis of 5 then affords the hydroxamic acid derivatives ($R_1$=OH). Alternatively, the acids 3 can be converted to the targeted structures 5 via the ester intermediates 4 (B5=methyl, ethyl, propyl, butyl, for example) using methods known to those skilled in the art. For example, the methyl esters 4 (B5=Me) can be prepared by treating methanolic solutions of the acids 3 with an acid catalyst such as sulfuric acid at ambient temperature. Subsequent treatment with amines $R_1NH_2$ in a suitable solvent such as methanol or acetonitrile then affords the amides 5 ($R_1$=H or optionally substituted alkyl). Similarly, treatment with hydrazine gives the hydrazides 5 ($R_1$=$NH_2$).

In METHOD B, (5R)-hydroxymethyl aryl oxazolidinones 2 can be oxidized using, for example, chromium(VI) oxide/sulfuric acid in a solvent system such as acetone/water (EP 91-417044, 13 Mar. 1991; Appl. EP 90-810654, 29 Aug. 1990) or ruthenium(III) chloride (cat.)/sodium periodate in the presence of sodium dihydrogenphosphate in a solvent system such as acetonitrile/methylene chloride/water (See U.S. Pat. No. 5,614,535, the entire contents of which are incorporated herein) to give the aryl oxazolidinone-5(R)-carboxylic acids 3 which can then be converted to the targeted structures 5 as described previously. The (5R)-hydroxymethyl aryl oxazolidinone starting materials 2 may be obtained by treating the aryl carbamates 1 with a lithium base such as n-butyllithium or lithium hexamethyldisilazide in a solvent such as THF at a suitable temperature, typically in a range from −78° C. to −40° C., to give a lithiated species which is directly treated with R-(−)-glycidyl butyrate. Warming to room temperature then affords the structures 2.

In METHOD C, anilines 6, which are known in the literature or produced by known methods (see also the charts to follow), can be converted to structures 7 upon treatment with an alkyl (2R)-epoxypropanoate and lithium triflate in a suitable solvent such as acetonitrile at a suitable temperature, typically in a range from 20° C. to 110° C. depending on the solvent. Amino alcohols 7 can then be ring closed to give the aryl oxazolidinones 4 using methods known to one skilled in the art. For instance, treatment of structures 7 with 1,1'-carbonyldiimidazole in a solvent such as acetonitrile or THF at an appropriate temperature, typically in a range of 20° C. to 60° C., or with phosgene in a solvent such as toluene or methylene chloride, or mixtures thereof, in the presence of a base such as triethylamine at an appropriate temperature, typically in a range from −10° C. to 25° C., affords the oxazolidinones 4. The structures 4 can then be converted to the targeted compounds 5 using the methods described previously.

CHART II

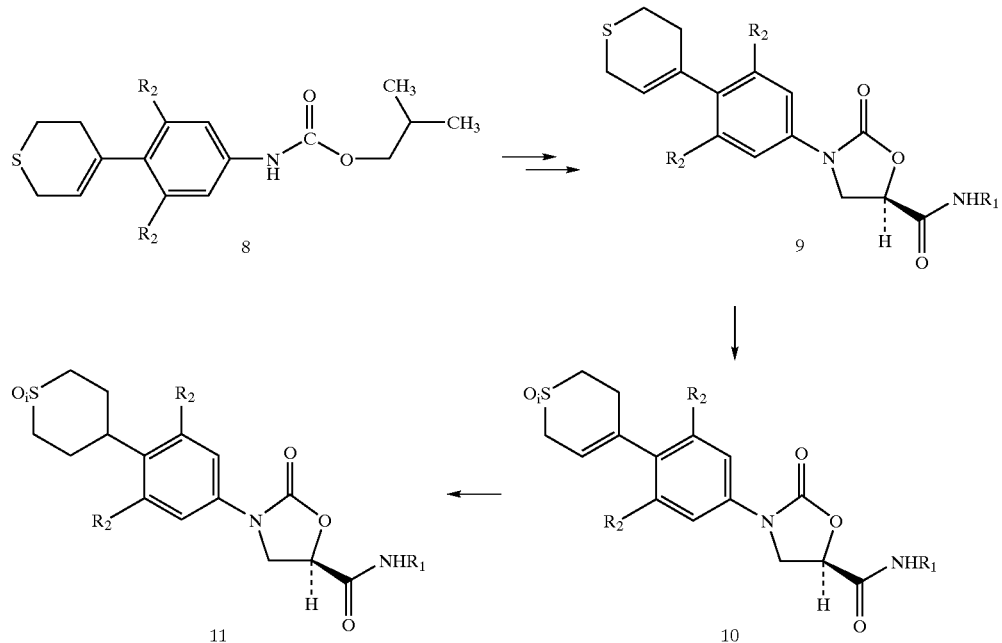

CHART II illustrates a preparation of the thiopyran-4-yl phenyl oxazolidinone-5-carboxamides 10 and 11. The (3,6-dihydro-2H-thiopyran-4-yl)phenyl carbamates 8 (See for example U.S. Pat. No. 6,239,283, the entire contents of which are incorporated herein; see also CHART VII and IX) can be converted to the oxazolidinone-5-carboxamide 9 using steps similar to those described in CHART I for the conversion of 1 to 5 using METHOD A. The sulfur group in structures 9 can then be oxidized with an appropriate oxidizing agent such as sodium periodate in an appropriate solvent such as mixtures of methanol and water or osmium tetroxide (cat.) and N-methylmorpholine N-oxide in an appropriate solvent such as mixtures of acetone and water to give the corresponding sulfoxide and sulfone derivatives 10 (i=1, 2). The double bond in structures 10 may be reduced by catalytic hydrogenation using an appropriate catalyst such as palladium-on-carbon in a suitable solvent such as methanol to give structures 11. See CHARTS VII, VIII and IX for alternate preparations of the thiopyran-4-yl phenyl oxazolidinone-5-carboxamides.

CHART III

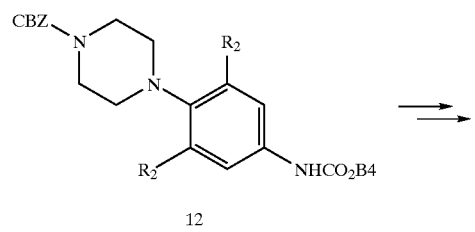

12

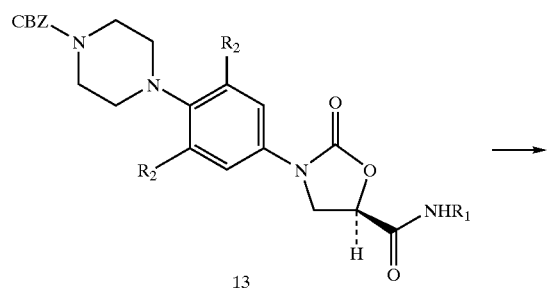

13

-continued

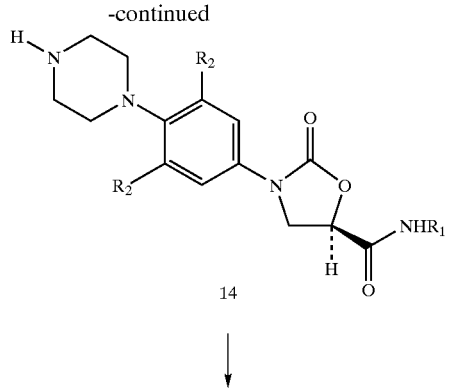

14

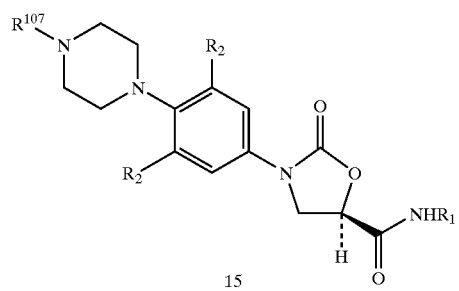

15

CHART III illustrates the preparation of the piperazinyl phenyl oxazolidinone-5-carboxamides 15. The piperizinylphenyl carbamates 12 (see for example *J. Med. Chem.* 1996, 39(3), 673–679) can be converted to the oxazolidinone-5-carboxamide 13 using steps similar to those described in CHART I for the conversion of 1 to 5 using METHOD A. The CBZ protecting group of 13 can be removed via hydrogenation in the presence of an appropriate catalyst such as palladium-on-carbon or Pearlman's catalyst in a solvent such as methanol, ethanol, ethyl acetate or mixtures thereof, and the piperazine ring of 14 can then be acylated or alkylated by methods well known to those skilled in the art to give the targeted structures 15. In the case where $R^{107}$ is benzyloxyacetyl, subsequent catalytic hydrogenation of 15 affords the hydroxyacetyl-substituted piperazinyl phenyl oxazolidinone-5-carboxamide 15 ($R^{107}$=C(=O)CH$_2$OH). Alternatively, structures 12 can be bis-deprotected using methods known to one skilled in the art to give the piperazinyl fluorobenzenamine intermediate which can then be converted to structures 15 using steps similar to those described in CHART XII for the conversion 68 to 70.

CHART IV

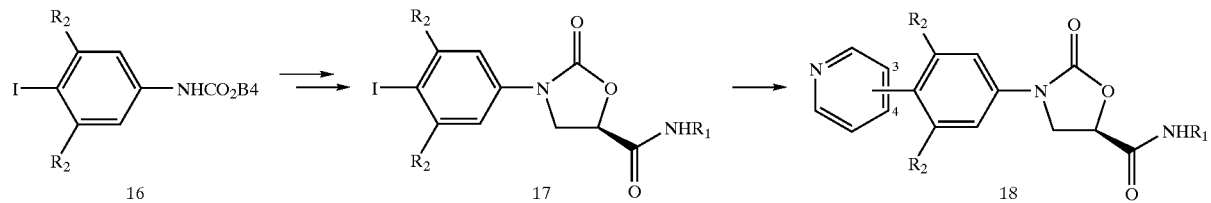

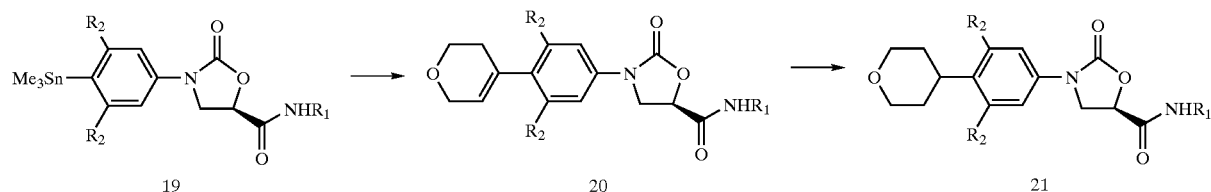

CHART IV illustrates the preparation of the 3- and 4-pyridyl and 4-pyranyl phenyl oxazolidinone-5-carboxamides 18, 20 and 21. The iodophenyl carbamates 16 (see for example *Org. Process Res. Dev.* 2001, 5(1), 80–83) can be converted to the 4-iodophenyl oxazolidinone-5-carboxamide 17 using steps similar to those described in CHART I for the conversion of 1 to 5 using METHOD B. The aryl iodide 17 can then be coupled with 3-(trimethylstannyl)pyridine (see EXAMPLE 7, step 4 below) or 4-(trimethylstannyl)pyridine (See U.S. Pat. No. 5,990,136, the entire contents of which are incorporated herein) using a palladium catalyst system such as tris(dibenzylideneacetone)dipalladium(0) and triphenylarsine in a solvent such as N-methyl-2-pyrrolidinone at an appropriate temperature, typically in a range of 50° C. to 100° C., to give structures 18. The aryl iodide 17 can also be converted to the aryl stannane 19 upon treatment with hexamethylditin in the presence of a palladium catalyst such as bis(triphenylphosphine)palladium(II) chloride in a solvent such as 1,4-dioxane at an appropriate temperature, typically in a range from 50° C. to 100° C. Coupling of this aryl stannane then with the vinyl triflate of tetrahydro-4H-pyran-4-one (See U.S. Pat. No. 5,968,962, the entire contents of which are incorporated herein.) at ambient temperature using a catalyst system similar to that used to prepare structures 18 affords the pyranyl phenyl oxazolidinone-5-carboxamide 20. Subsequent catalytic hydrogenation affords structures 21.

CHART V

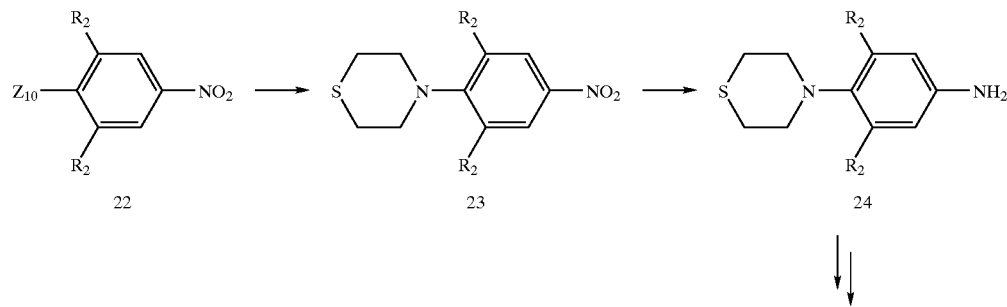

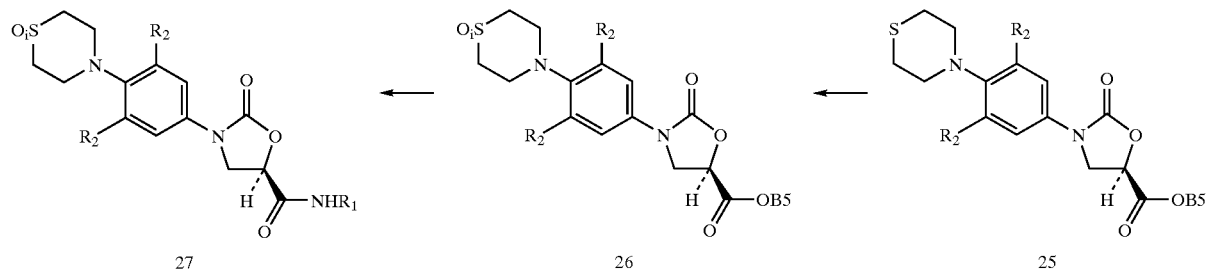

CHART V illustrates the preparation of the thiomorpholinyl phenyl and fluorophenyl oxazolidinone-5-carboxamides 27. Nitrobenzenes 22 ($Z_{10}$=F, Cl, OTf or other leaving group) can be converted to structures 23 upon treatment with thiomorpholine in the presence of a base such as N,N-diisopropylethylamine in a suitable solvent such as acetonitrile at a temperature typically in a range from 25–80° C. Reduction of the nitro group of 23 using, for example, catalytic hydrogenation with an appropriate catalyst such as Raney Nickel in a suitable solvent system such as a mixture of tetrahydrofuran and water gives the anilines 24 which can be converted to structures 25 using steps similar to those described in CHART I for the conversion of 6 to 4 by METHOD C. Oxidation of the sulfur atom in structures 25 using the methods described previously (see CHART II) affords the sulfoxide and sulfone derivatives 26 which are converted to the targeted structures 27 as described in CHART I.

CHART VI

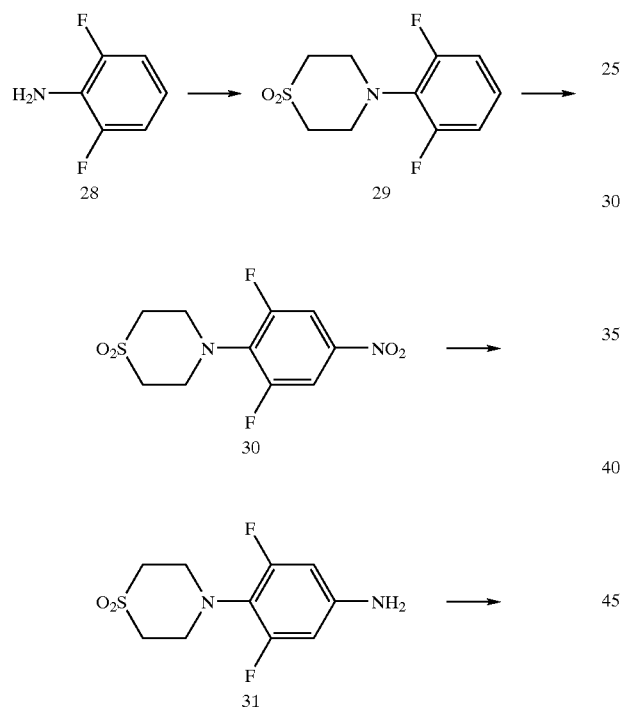

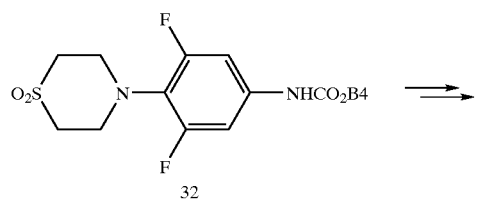

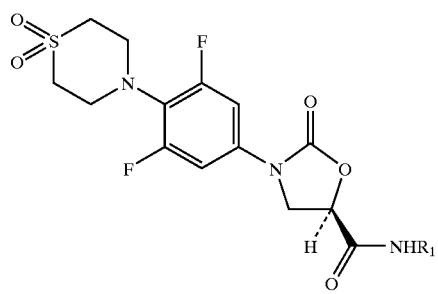

CHART VI illustrates an alternate preparation of the thiomorpholinyl difluorophenyl oxazolidinone-5-carboxamide 33. In this method, the phenyl thiomorpholine sulfone 29 is prepared by the treatment of 2,6-difluoroaniline 28 with vinyl sulfone in the presence of aluminum chloride in a suitable solvent such as chlorobenzene at an elevated temperature. Nitration of the phenyl ring of 29 with fuming nitric acid in acetic acid at ambient temperature then affords the nitrobenzene structure 30 which can then be converted to the aniline 31 as before under catalytic hydrogenation conditions using a suitable catalyst such as Raney Nickel. Treatment of the aniline 31 with an appropriate alkyl or benzyl chloroformate in the presence of a base such as sodium bicarbonate gives the carbamate structures 32 which can then be converted to the targeted structures 33 using steps similar to those described in CHART I for the conversion of 1 to 5 using METHOD A. Alternatively, the aniline 31 can be converted to 33 using steps similar to those described in CHART I for the conversion of 6 to 5 using METHOD C.

CHART VII

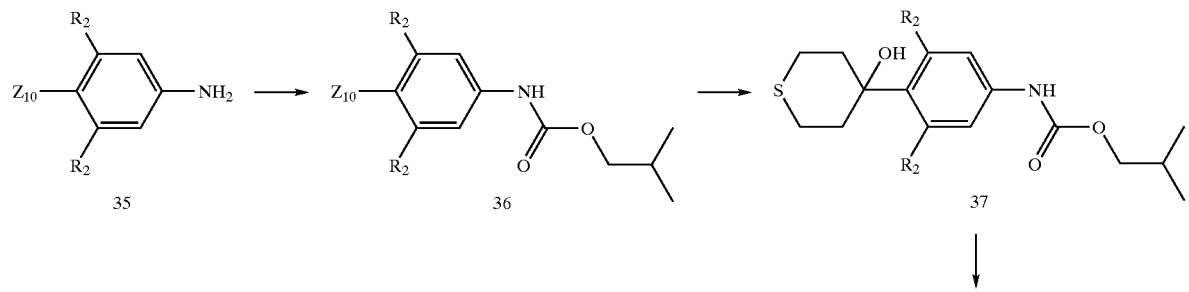

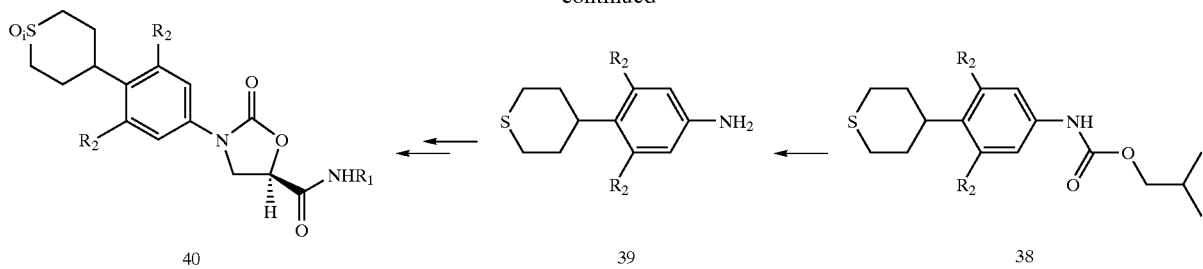

CHART VII illustrates an alternate preparation of the thiopyran-4-yl phenyl oxazolidinone-5-carboxamides 40. For structures 40 where $R_2$=H, 4-bromo- or 4-iodoaniline 35 ($Z_{10}$=Br, I) can be converted to its isobutyl carbamate derivative 36 ($Z_{10}$=Br, I) upon treatment with isobutyl chloroformate in the presence of an appropriate base such as sodium bicarbonate in a suitable solvent system. Treatment of 36 with two equivalents of n-butyllithium in a suitable solvent such as tetrahydrofuran at an appropriate temperature, typically in a range of −78 to −40° C., gives the dilithiated species resulting from deprotonation of the carbamate and metal-halogen exchange of the aryl halide. Subsequent treatment with tetrahydro-2H-thiopyran-4-one followed by warming to 0–25° C. affords the 4hydroxythiopyran-4-yl phenyl carbamate 37 which can then be reduced to the thiopyran-4-yl phenyl carbamate 38 using, for example, excess triethylsilane in trifluoroacetic acid at ambient temperature. The isobutyl carbamate group of 38 is readily cleaved upon treatment, for instance, with aqueous potassium hydroxide in ethylene glycol at an elevated temperature, 100° C. for example, to afford the aniline 39 which can then be converted to the targeted structures 40 ($R_2$=H, i=1,2) using steps similar to those outlined in CHART V for the conversion of 24 to 27. Alternatively, the sulfur atom of carbamate 38 can first be oxidized using the methods described previously (CHART II) to give the corresponding sulfoxide and sulfone derivatives. The carbamate is then cleaved as described above to give aniline 39 S-oxide or S,S-dioxide which can then be converted to the structures 40 using steps similar to those described in CHART I for the conversion of 6 to 5 using METHOD C. Note that the oxidations to give the sulfoxide products provide mixtures of cis and trans isomers which are separable by preparative HPLC. However selective oxidation methods exist for the formation of the trans isomer (see *Tetrahedron Lett.* 2000, 4301–4305, and references cited therein).

For structures 40 where one $R_2$=H and the other $R_2$=F, 3-fluoroaniline ($Z_{10}$=H) can be converted to the 4-hydroxythiopyran-4-yl phenyl carbamate 37 via the carbamate 36 ($Z_{10}$=I, Br), as described in *Org. Proc. Res. Dev.* 2001, 5, 80–83 and *Tetrahedron Lett.* 2000, 4301–4305. Carbamate 37 can then be converted to the targeted structures 40 ($R_2$, $R_2$=H, F; i=1, 2) using the methods described above.

For structures 40 where $R_2$=F, 3,5-difluoroaniline ($Z_{10}$= H) can be converted to its isobutyl carbamate derivative 36 as described above. Treatment of 36 with two equivalents of n-butyllithium in a suitable solvent such as tetrahydrofuran at a suitable temperature, typically in a range of −78 to −40° C., gives the dilithiated species resulting from deprotonation of the carbamate and metallation at the para position (adjacent to the two fluorine atoms) of the phenyl ring. A chelating additive such as N,N,N',N'-tetramethylethylenediamine (TMEDA) may be used in this reaction. Subsequent treatment with tetrahydro-2H-thiopyran-4-one followed by warming to 0–25° C. affords the 4-hydroxythiopyran-4-yl phenyl carbamate 37 which can then be reduced to the thiopyran-4-yl phenyl carbamate 38 upon treatment, for example, with excess triethylsilane in trifluoroacetic acid at an elevated temperature, typically from 40 to 75° C. Carbamate 38 can then be converted to the targeted structures 40 ($R_2$=F, i=1, 2) using the methods described above.

CHART VIII

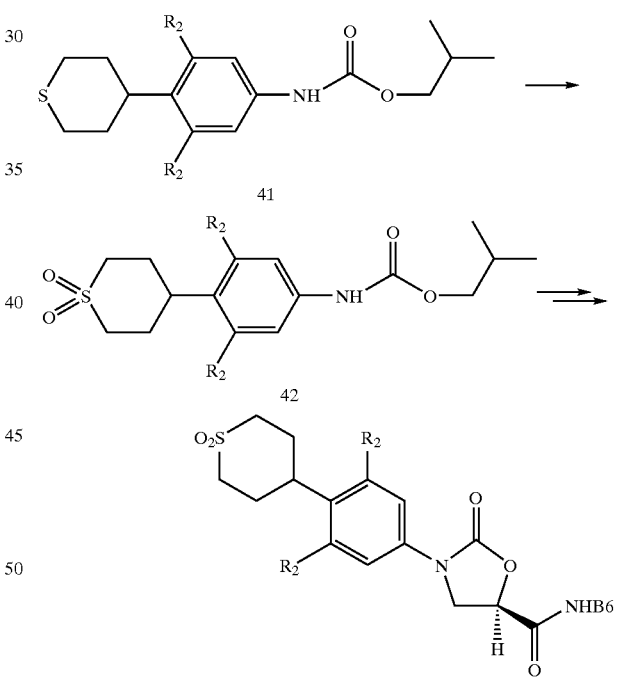

CHART VIII illustrates an additional method for the preparation of the thiopyran-4-yl phenyl oxazolidinone-5-carboxamide sulfones 43. The tetrahydrothiopyran ring of structures 41 (see CHART VII for the preparation) can be oxidized using methods described previously (CHART II) to give the corresponding sulfone structures 42. Carbamate 42 can then be converted to the targeted structures 43 using steps similar to those described in CHART I for the conversion of 1 to 5 through the 5-hydroxymethyl oxazolidinone intermediate 2 using METHOD B.

CHART IX

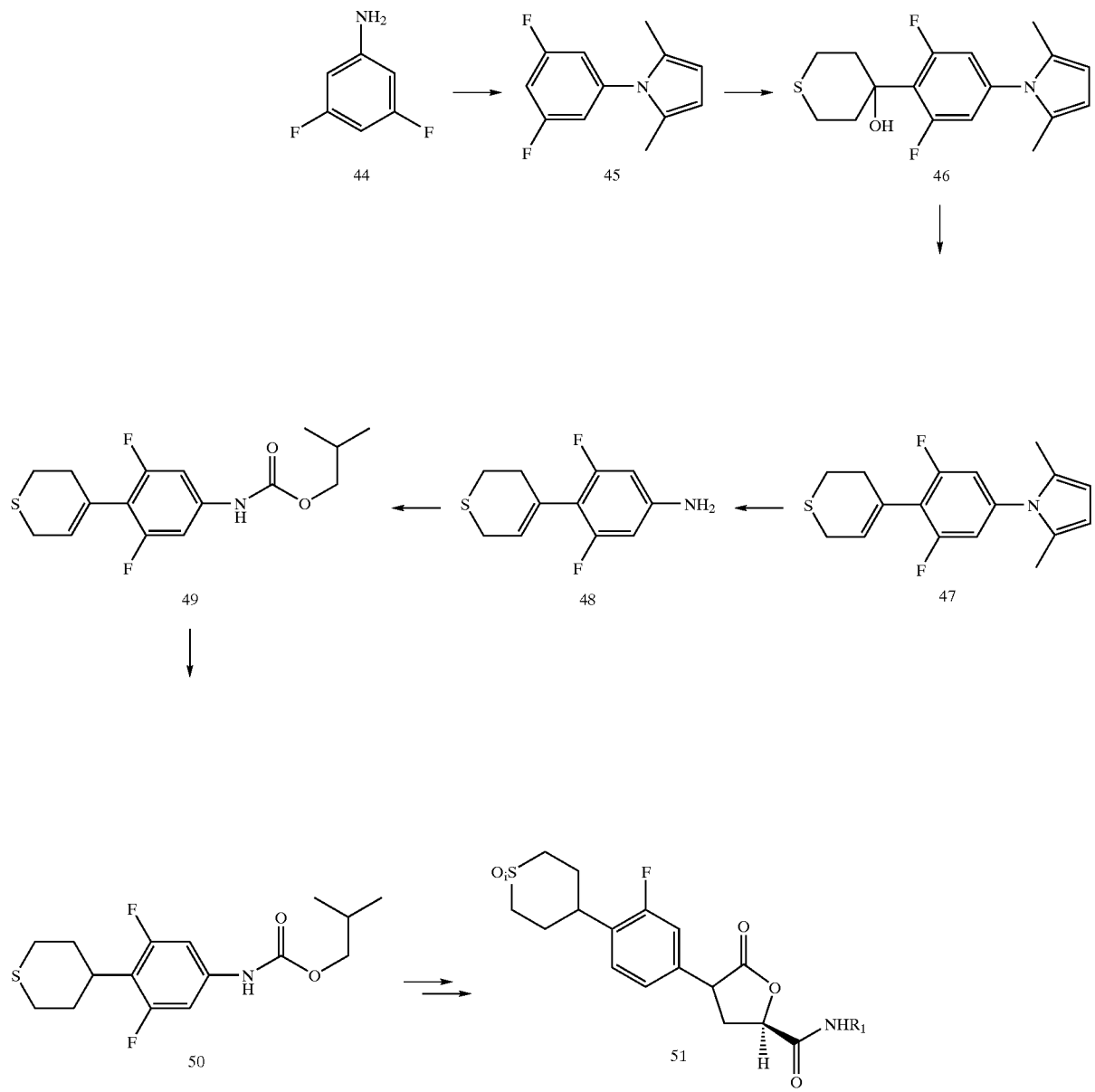

CHART IX illustrates an additional method for the preparation of the thiopyran-4-yl difluorophenyl oxazolidinone-5-carboxamides 51. 3,5-Difluoroaniline 44 can be protected as its 2,5-dimethylpyrrole derivative 45 upon treatment with acetonylacetone and catalytic amounts of p-toluenesulfonic acid in an appropriate solvent, such as mixtures of toluene and tetrahydrofuran, at an appropriate temperature, typically from 40° C. to reflux. Treatment of 45 with n-butyllithium in a solvent such as tetrahydrofuran at a suitable temperature, typically in a range of −78 to −40° C., gives the aryllithium species resulting from deprotonation at the para position (adjacent to the two fluorine atoms) of the phenyl ring. Subsequent treatment with tetrahydro-2H-thiopyran-4-one followed by warming to 0–25° C. affords the 4-hydroxythiopyran 46 which can be converted to the dihydrothiopyran 47 using, for example, catalytic amounts of p-toluenesulfonic acid in an appropriate solvent such as benzene at an elevated temperature, typically from 60–120° C. The pyrrole protecting group can then be removed upon treatment with excess hydroxylamine hydrochloride in the presence of an appropriate base, such as triethylamine, in a suitable solvent, such as mixtures of ethanol and tetrahydrofuran, at an appropriate temperature, typically 40–80° C., to give the aniline 48 which is reprotected as the carbamate 49 using methods described previously (CHART VI). The dihydrothiopyran ring of 49 can then be reduced upon treatment, for example, with excess triethylsilane in trifluoroacetic acid at an elevated temperature, typically from 40–80° C., to give the tetrahydrothiopyran 50 which can then be converted to the targeted structures 51 (i=1, 2) using the steps outlined in CHART VII for the conversion of 38 to 40.

CHART X

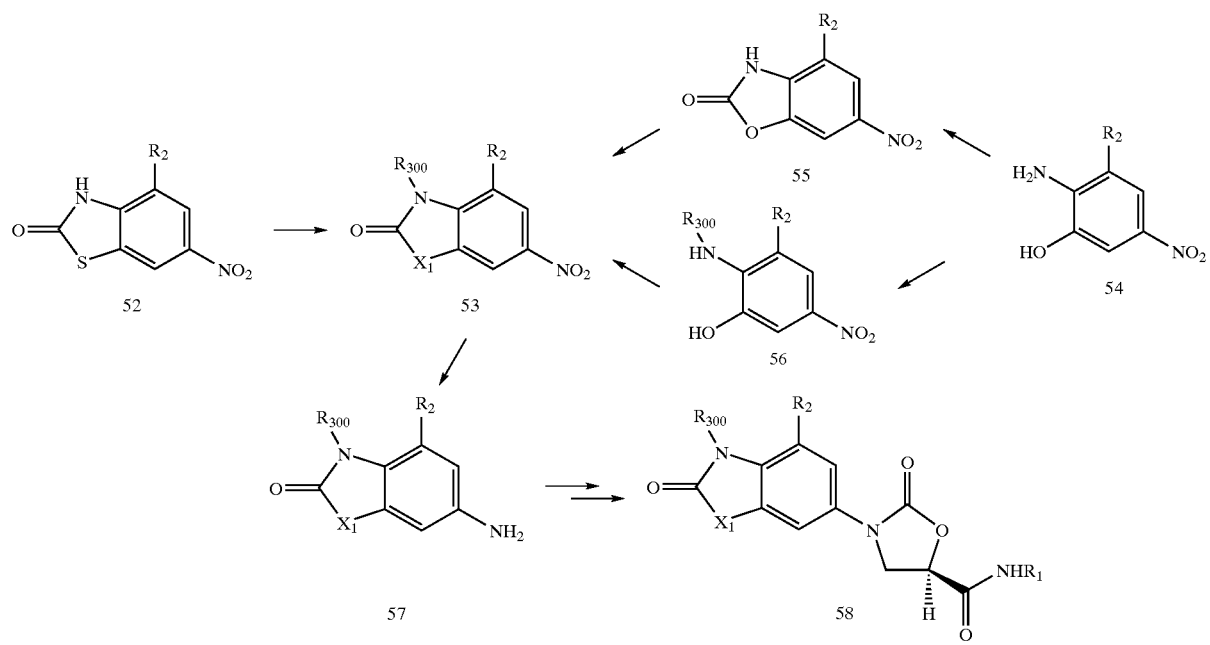

CHART X illustrates the preparation of the N-alkylated benzothiazolone and benzoxazolone oxazolidinone-5-carboxamides 58 ($X_1$=O, S; $R_{300}$=alkyl or substituted alkyl). For the benzothiazolones (X=S), 6-nitro-2-benzothiazolinones 52 (commercially available, known in the literature or prepared using methods known to one skilled in the art) can be N-alkylated under conditions known to those skilled in the art (see *J. Heterocyclic Chem.*, 1992, 29, 1069, and U.S. Pat. No. 6,069,160, the entire contents of which are incorporated herein, for specific examples of interest), including treatment with an alkylating agent such as iodomethane, dimethylsulfate, iodoethane, 2-iodopropane, bromoacetonitrile or 1-bromo-2-fluoroethane in the presence of a base such as sodium hydride, 1,8-diazobicyclo[5.4.0]undec-7-ene (DBU), or potassium carbonate in an suitable solvent such as dimethylformamide, tetrahydrofuran, acetonitrile or acetone at an appropriate temperature, typically from 0° C. to 100° C., to give structures 53 ($X_1$=S). For the benzoxazolones ($X_1$=O), 6-nitro-2-benzoxazolones 55 (prepared, for example, from 2-amino-5-nitrophenol 54 according to *J. Heterocyclic Chem.*, 1992, 29, 1069) can be N-alkylated to give 53 ($X_1$=O) under conditions described above for the benzothiazolinone 52 (see *J. Heterocyclic Chem.*, 1992, 29, 1069; also see *Pharmazie*, 1971, 26, 280, and *J. Am. Chem. Soc.*, 1958, 80, 1662, for alternate routes to structures 53 ($X_1$=O)). Alternatively, 2-amino-5-nitrophenols 54 can be reductively alkylated with simple aldehydes or ketones, acetone for example, in the presence of an appropriate reducing agent such as sodium cyanoborohydride in a suitable solvent such as ethanol to give structures 56 which can then be converted to structures 53 ($X_1$=O) upon treatment, for example, with 1,1'-carbonyldiimidazole under conditions similar to those used for the preparation of 55 from 54. Reduction of the nitro group of 53 using methods known to one skilled in the art, by catalytic hydrogenation, for instance, over an appropriate catalyst such as palladium-on-carbon or platinum oxide in a suitable solvent system such as mixtures of tetrahydrofuran and methanol (see *J. Heterocyclic Chem.*, 1992, 29, 1069, for example), gives the aniline 57 which can then be converted to structures 58 ($X_1$=O, S) using steps similar to those described in CHART I for the conversion of 6 to 5 by METHOD C.

CHART XI

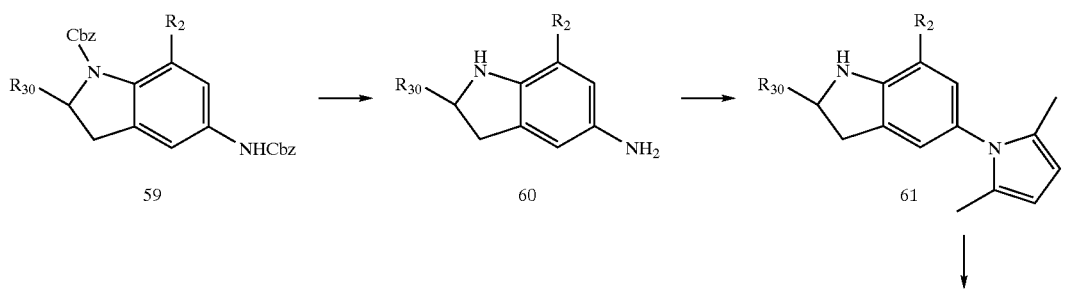

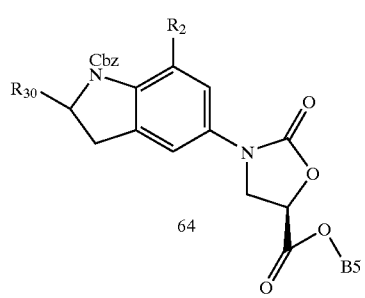
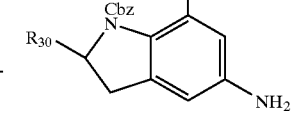
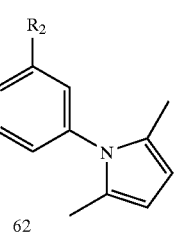

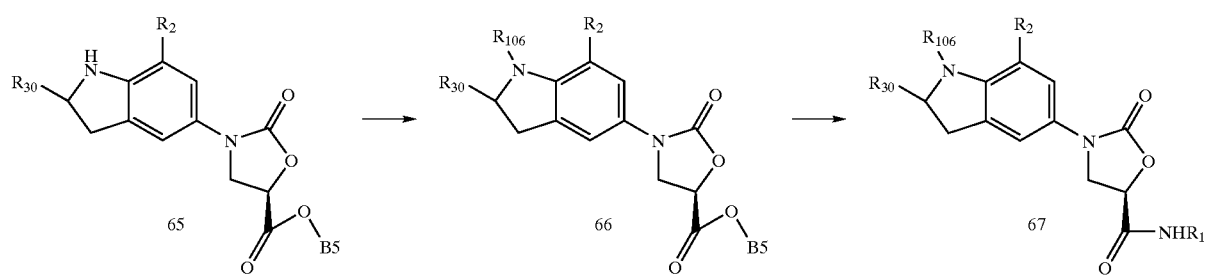

CHART XI illustrates the preparation of the indolinyl oxazolidinone-5-carboxamides 67. Double deprotection of the aminoindoline 59 (for the (2R)-methyl derivative, see PCT/US00/08224; WO00/73301) using methods known to one skilled in the art, for example catalytic hydrogenation over an appropriate catalyst such as palladium-on-carbon or Pearlman's catalyst in a suitable solvent, affords the aminoindoline 60. The 5-amino group is reprotected as its 2,5-dimethyl-1H-pyrrole derivative 61 using the methods described in CHART IX for the conversion of 44 to 45, and the indoline nitrogen is reprotected as its benzyl carbamate using methods known to one skilled in the art to give structures 62. The pyrrole protecting group can then be removed using the methods described in CHART IX for the conversion of 47 to 48 to give the aminoindoline 63 which is then converted to structures 64 using the steps outlined in CHART I for the conversion of 6 to 4 by METHOD C. The CBZ protecting group is then removed and the indoline nitrogen acylated or alkylated using methods known to one skilled in the art to give 66 using steps similar to those described in CHART III for the conversion 13 to 15, and 66 is then converted to the target structures 67 as described in CHART I for the conversion of 4 to 5. Alternatively, the aminoindoline 59 can be converted to the target structures 67 using steps similar to those described in CHART III for the conversion of 12 to 15.

CHART XII

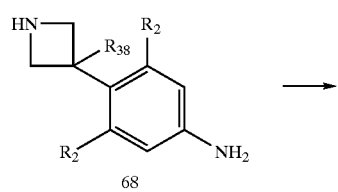

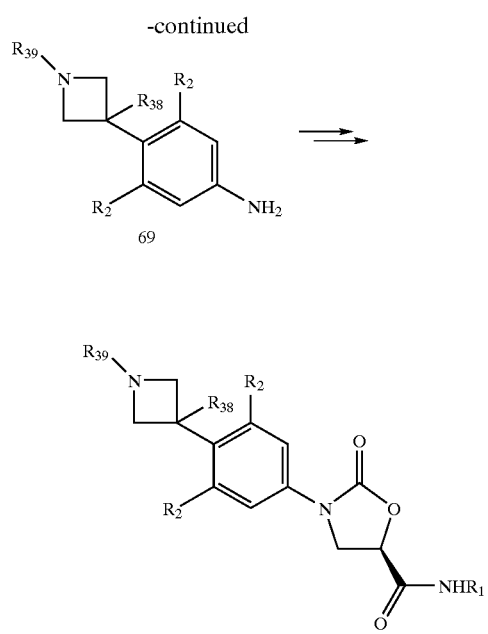

CHART XII illustrates the preparation of the azetidinyl oxazolidinone-5-carboxamides 70. The azetidines 68 (prepared using steps similar to those described in PCT/US96/12766) can be acylated selectively on the ring nitrogen using methods known to those skilled in the art to give structures 69 which can then be converted to the targeted structures 70 using steps similar to those described in CHART I for the conversion of 6 to 5.

CHART XIII

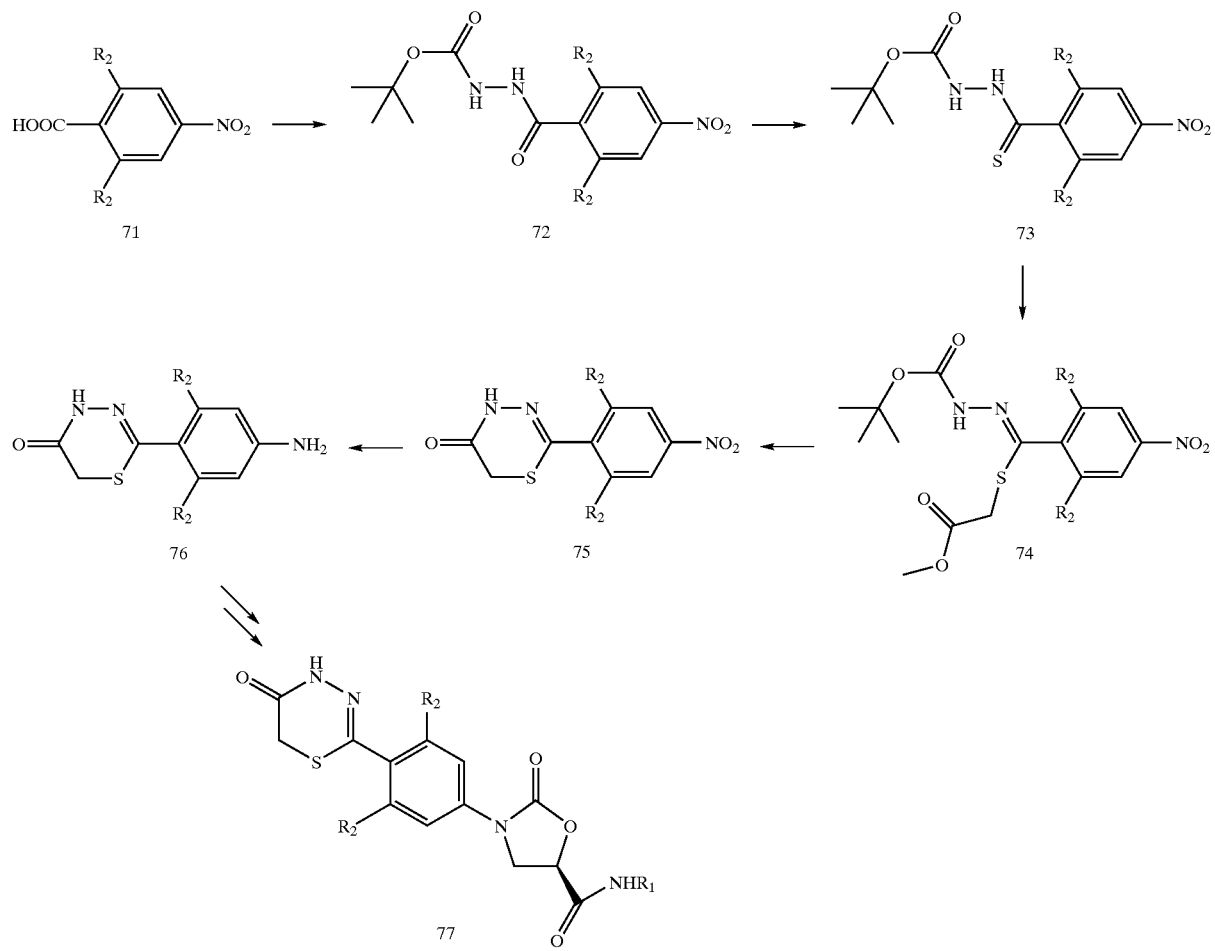

CHART XIII illustrates a general synthesis of the thiadiazinone oxazolidinone-5-carboxamides 77. First, a nitrobenzene carboxylic acid 71 is coupled with a suitable N-protected hydrazine reagent, such as N-(tert-butoxycarbonyl)hydrazine. This reaction can be performed with any number of known coupling reagents, such as HATU or carboduimides. The coupling reaction is typically performed in a polar aprotic solvent, such as dimethylformamide, acetonitrile, or mixtures thereof, in presence of an organic base, such as triethylamine or (N,N-diisopropyl)ethylamine (DIEA). The process is typically carried out between about 0° C. to about 50° C. Next, the hydrazide is converted into the thiohydrazide 73 with a Lawesson's reagent under conditions well precedented in the chemical literature. This conversion may be conducted in suitable organic solvent, such as dioxane or tetrahydrofuran, and is typically performed at temperatures in a range of from about 25° C. to about 100° C. By way of example, Lawesson's chemistry is reviewed by Cava et al. in Tetrahedron, 1985, vol. 41, pp. 5061–5087. The next step involves an alkylation of the resulting protected thiohydrazide reagent with a suitable alpha-substituted ester reagent (such as methyl or ethyl ester) to give structures 74. The ester bears a good leaving group in a position alpha to the ester functionality, e.g., bromo, iodo, nitrobenzenesulfonyloxy, mesyloxy (OMs), or a like group. The reaction is typically performed in a polar organic solvent such as acetonitrile, tetrahydrofuran, or dimethylformamide in the presence of an organic or inorganic base, such as potassium carbonate, pyridine, or triethylamine. A typical range of temperatures for this transformation is from about 0° C. to about 50° C. The following step involves deprotection of an acid-sensitive thiohydrazide protective group (exemplified by Boc in this case). Under reaction conditions, the acid-induced N-deprotection is immediately followed by a high-yielding heterocyclization into the desired thiadiazinone derivative 75. This transformation is conveniently performed in the presence of organic or inorganic acids, such as trifluoroacetic acid or hydrogen chloride. The reaction is carried out in organic solvent, such as dichloromethane, dichloroethane, dioxane, or tetrahydrofuran, at temperatures in a range from about 10° C. to about 60° C. The nitro group is then reduced using methods known to one skilled in the art to give the aniline 76. This reduction can be accomplished by reacting the nitro intermediate with iron metal. The reaction is carried out at temperatures between 60° C. and 90° C. in mixtures of water and alcohol (methanol, ethanol, etc.) as solvent, and in the presence of ammonium chloride to buffer the reaction mixture. The aniline is then converted to the targeted structures 77 using steps similar to those described in CHART I for the conversion of 6 to 5.

CHART XIV

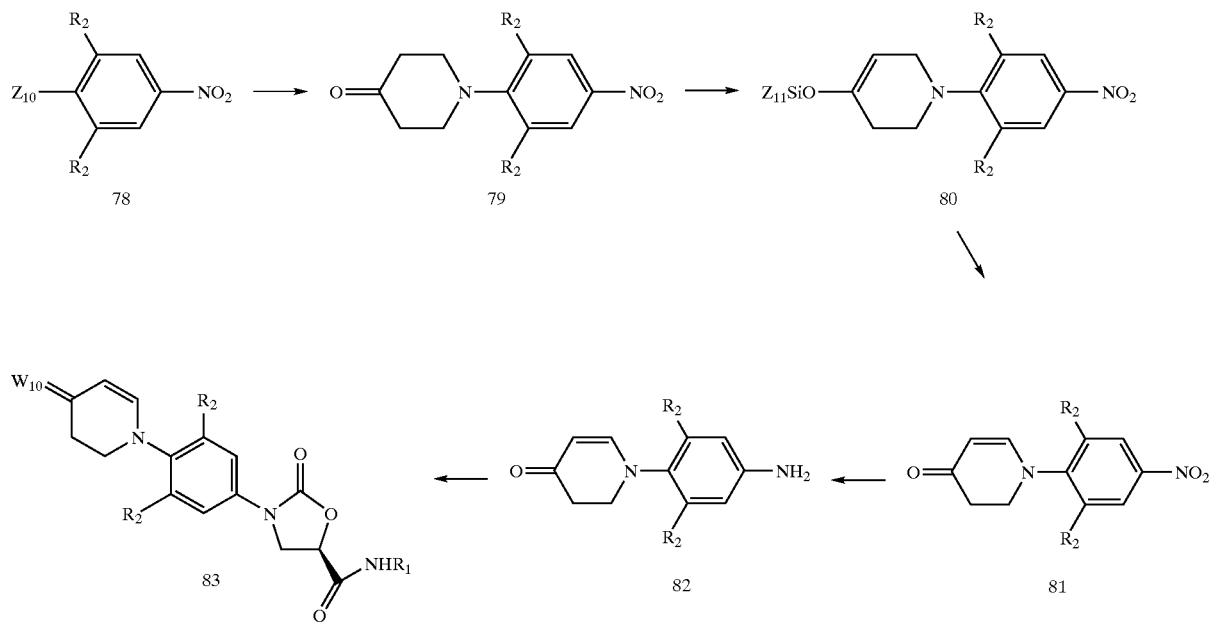

Syntheses of dihydropyridones are well precedented in the prior art. Thus, dihydropyridone compounds can be made by variations of oxidative transformations of piperidone derivatives exemplified by the following references: Stutz et al. in Tetrahedron Lett., 1973, pp. 5095–5098; Dodd et al., Tetrahedron Lett., 1991, pp. 3643–3646; Evans et al., Tetrahedron Lett., 1995, pp. 3985–3988; Blache et al., Heterocycles, 1997, pp. 57–69; and Ishii et al., Tetrahedron Lett., 1997, pp. 7565–7568. In another embodiment, dihydropyridone compounds can be synthesized by variations of hetero Diels-Alder transformations of imine derivatives exemplified by the following publications: Diez et al., Heterocycles, 1990, p. 485; Waldmann et al., Tetrahedron, 1993, pp. 397–416; Lock et al., Tetrahedron lett., 1996, pp. 2753–2756; Kirschbaum et al., Tetrahedron Lett., 1997, pp. 2829–2832; Kirschbaum et al., Chem. Eur. J., 1997, pp. 143–151; and Kirschbaum et al., J. Org. Chem, 1998, pp. 4936–4946. In yet another embodiment, dihydropyridone compounds can be prepared by reductive transformations of pyridine and pyridone derivatives, see, e.g. references: Haider, et. al., Helv. Chim. Acta, 1975, p.1287; Guerry et al., Synthesis, 1984, p. 485; Guerry et al., Chimia, 1987, p. 341; Comins et al., Heterocycles, 1994, pp. 1121–1140; and Dehmlow et al., Heterocycles, 1994, pp. 355–366.

CHART XIV illustrates one general method for the preparation of the dihydropyridone oxazolidinone-5-carboxamides from nitrobenzene and piperidine derivatives. Step 1 involves a nucleophilic aromatic substitution reaction of a suitable nitrobenzene 78 ($Z_{10}$=F, Cl, OTf or other leaving group) with a piperidine derivative, such as 4-piperidone, to give structures 79. This reaction is performed in aprotic polar solvent such as dimethylformamide, acetonitrile, or dimethylsulfoxide in the presence of an organic or inorganic base, such as pyridine, triethylamine, or potassium carbonate. Temperatures in the range of about 20° C. to about 80° C. are generally suitable for this reaction. The next step involves formation of a silyl enolate 80 from the 1-arylpiperidone intermediate 79 and a silylating agent, such as triisopropylsilyl chloride, trialkylsilyl triflate, or a similar reagent. This reaction is typically conducted in the presence of an organic base, such as triethylamine, pyridine, or imidazole at temperatures from about 0° C. to about 60° C. Step 3 of this synthesis involves an oxidation of the silyl enolate intermediates to the dihydropyridone compounds 81 with a suitable inorganic oxidant, such as ceric ammonium nitrate (CAN; described by Evans et al. in Tetrahedron Lett., 1995, vol. 36, pp. 3985–3988) or palladium acetate (as described by Comins et al. in Tetrahedron Lett., 1995, vol. 36, pp. 9449–9452). The nitro group of 81 can then be reduced using methods known to one skilled in the art, for example through an iron metal reduction (see CHART XIII) or through catalytic hydrogenation over palladium/$CaCO_3$ in the presence of acetic acid, to give the aniline 82 which is then converted to the targeted structures 83 ($W_{10}$=O) using steps similar to those described in CHART I for the conversion of 6 to 5. Oxime derivatives of 83 can then be prepared using methods known to one skilled in the art. The simple oxime ($W_{10}$=N(OH)) can be prepared from 83 upon treatment hydroxylamine hydrochloride in the presence of an appropriate base such as pyridine which can also be used as the solvent or as part of a solvent mixture.

CHART XV

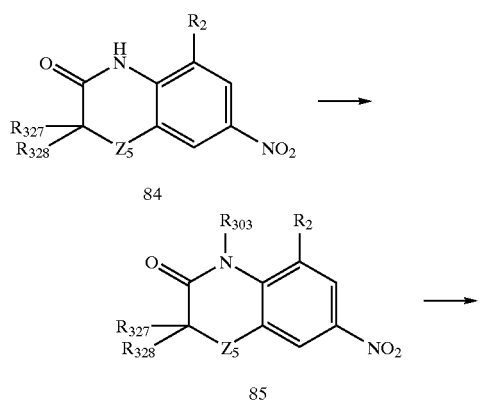

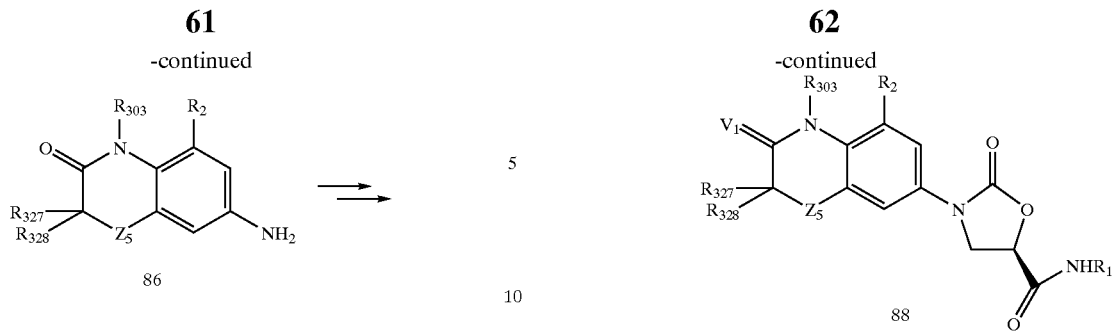

CHART XV illustrates the preparation of the benzoxazin-3-one, benzothiazin-3-one and tetrahydroquinolin-2-one oxazolidinone-5-carboxamides 88. Structures 84 ($Z_5$=O, S, $CH_2$, etc.), which are known in the literature (see WO99/37641 and WO99/40094 and references cited therein for specific examples) or can be prepared using known methods (such as nitration of the parent bicyclic ring system), can be alkylated using methods described previously (see CHART X) to give 85. The nitro group is then reduced using methods known to one skilled in the art, for example through an iron metal reduction (see CHART XIII) or through catalytic hydrogenation, to give the aniline 86 which can then be converted to the target structures 88 ($V_1$=O) using steps similar to those described in CHART I for the conversion of 6 to 5. In addition, the thioxo derivatives ($V_1$=S) can be prepared from intermediate structures 87 ($V_1$=O). Treatment of 87 ($V_1$=O) with Lawesson's reagent under conditions well precedented in the literature (see CHART XIII) affords the thioxo intermediates 87 ($V_1$=S) which can then be converted to the target structures 88 ($V_1$=S) as described previously.

CHART XVI

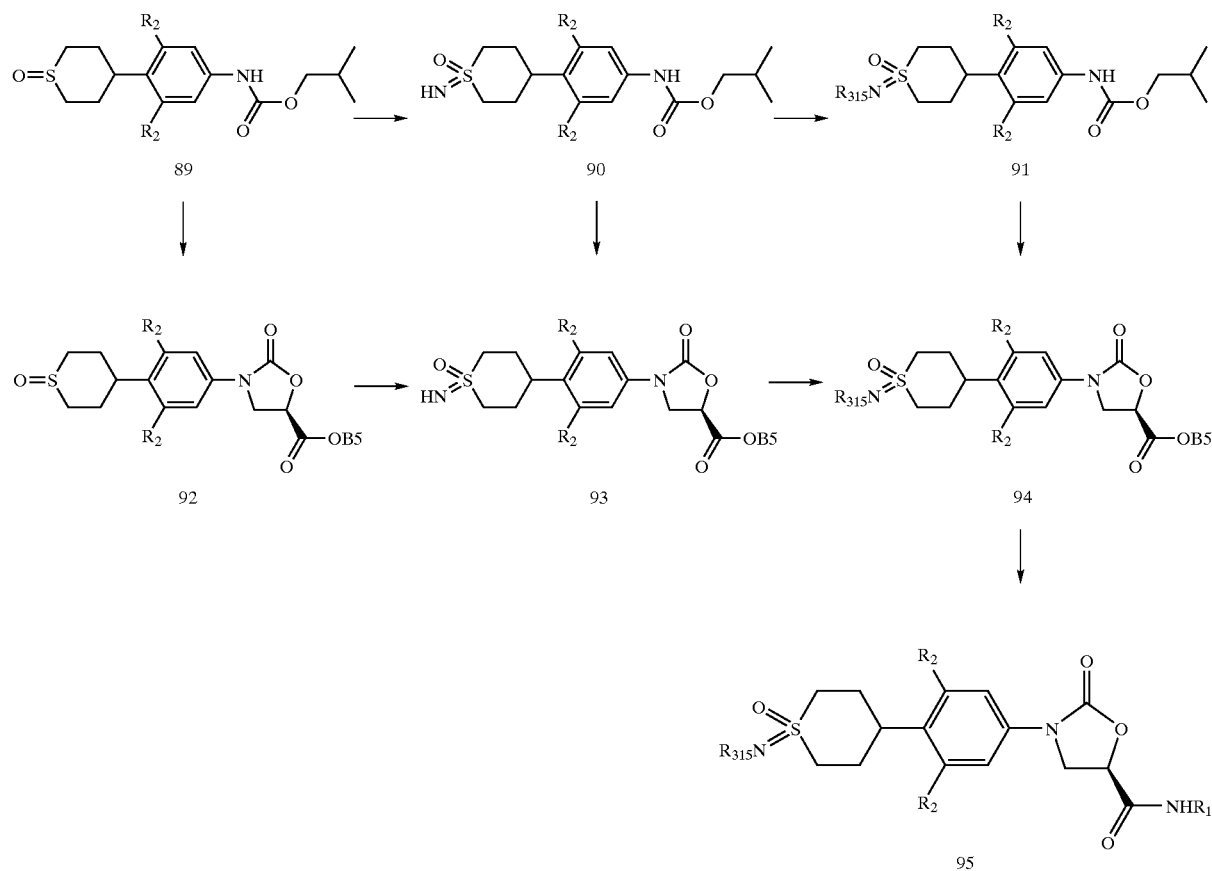

CHART XVI illustrates general methods for the preparation of the thiopyran sulfoximine oxazolidinone-5-carboxamides 95. Sulfoxide structures 89 in either the cis or trans configuration (prepared as outlined in CHART VII or using methods similar to those described in U.S. Pat. No. 6,239,283) can be converted to the sulfoximines 90 with retention of the sulfoxide stereochemistry using amination methods known to one skilled in the art, for example through treatment with O-mesitylene sulfonylhydroxylamine (MSH) in a suitable solvent such as methylene chloride generally at or near ambient temperature (see also WO01/46185 and *Synthesis*, 2000, 1, 1). Sulfoximines 90 can then be converted to the targeted structures 95 ($R_{315}$=H) using steps similar to those described in CHART VII for the conversion of 38 to 39 followed by those in CHART I for the conversion of 6 to 5. The sulfoximines 90 can also be alkylated to give structures 91 (where $R_{315}$ is alkyl or substituted alkyl), for example through reaction with an aldehyde or ketone, triethylsilane and trifluoroacetic acid in a suitable solvent such as acetonitrile at a temperature, depending on the solvent, in the range of 10–120° C. or through reaction with an aldehyde or ketone and formic acid using Leuckart-Wallach or Eschweiler-Clarke conditions. Para-formaldehyde is a convenient source of formaldehyde for this reaction to afford the N-methyl derivatives (see WO01/46185 for additional methods for the functionalization of the sulfoximine group). The substituted sulfoximines 91 can then be converted to the target structures 95 as described previously.

Alternatively, the alkylation can be carried out as the last step in the sequence using structures 95 ($R_{315}$=H).

The amination can also be carried out at a later stage in the synthesis starting from the sulfoxide structures 92. These structures can be prepared from the carbamates 89 as described previously or using the methods outlined in CHART VII. Amination of 92 under the conditions described previously affords the sulfoximines 93 which can then be converted to the target structures 95 ($R_{315}$=H) as before. The sulfoximine group can also be functionalized as described above.

The corresponding thiomorpholine sulfoximine derivatives where the thiopyran ring in 95 is replaced with a thiomorpholine ring can be prepared using steps similar to those described above. However, the amination is generally carried out using sodium azide in polyphosphoric acid at a temperature generally in a range from about 40° C. to about 70° C.

CHART XVII

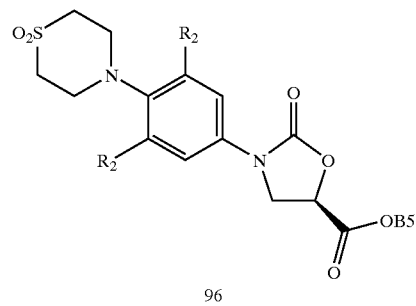

96

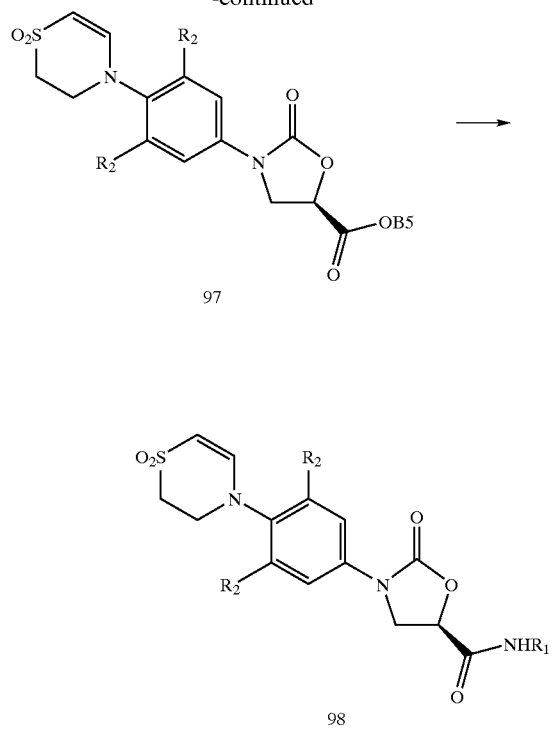

CHART XVII illustrates one method for the preparation of the dihydrothiazinyl sulfone oxazolidinone-5-carboxamides 98. The thiomorpholine S,S-dioxide oxazolidinone-5-carboxamides 96 (see CHART V) can be converted to the dihydrothiazine derivatives 97 upon treatment with a suitable organic oxidant such as 2,3-dichloro-5,6-dicyanobenzoquinone (DDQ) or chloranil. This transformation is typically performed in a polar organic solvent, such as dioxane, tetrahydrofuran or dimethylacetamide, at a temperature in the range of about 60° C. to about 110° C. Structures 97 can then be converted to the targeted structures as described previously in CHART I.

CHART XVIII

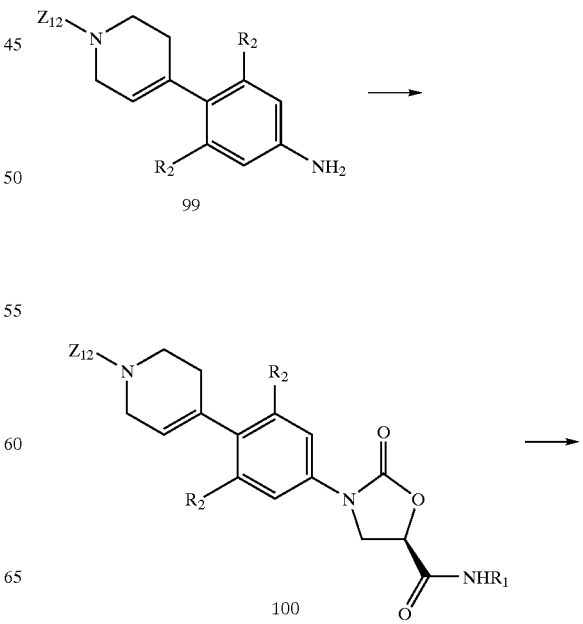

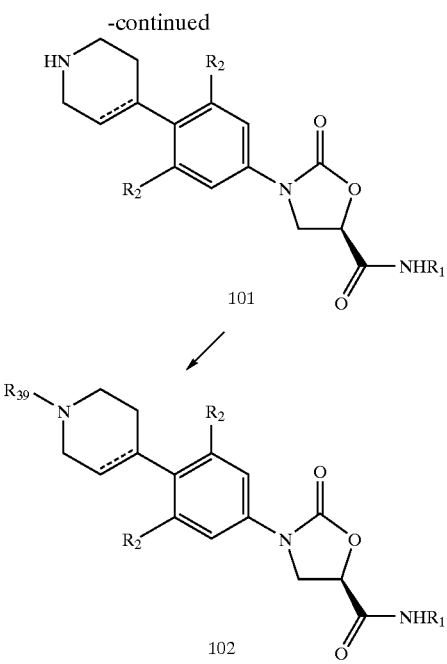

CHART XVIII illustrates one method for the preparation of the tetrahydropyridyl or piperidinyl oxazolidinone-5-carboxamides 102. The tetrahydropyridyl aniline derivatives 99 (See WO 97/09328 or WO 99/64417) can be converted to the tetrahydropyridyl oxazolidinone derivatives 100 via Method C described above with respect to Chart I. Removing the protecting group ($Z_{12}$=Cbz, BOC, or Bn) using known methods affords the deprotected derivatives 101. Conservation of the double bond in the tetrahydropyridyl group may be accomplished by removing the Cbz with a treatment of TMSI followed by methanol, BOC with a treatment of TFA, or Bn with a treatment of α-chloroethyl chloroformate followed by MeOH. For $Z_{12}$=Bn or Cbz, cleavage of the protecting group under catalytic hydrogenation conditions results in reduction of the double bond to give the piperidinyl structure 101. Functionalization of the tetrahydropyridyl or piperidinyl nitrogen may be performed by known methods, such as by alkylation and acylation. (See also WO 99/64417, WO02/096916, and WO01/40236)

Suitable intermediates useful in preparating compounds of this invention and additional synthetic methods to assist in producing the compounds may be found, for example, in the following publications, each of which is hereby incorporated by reference.

U.S. Pat. Nos. 5,225,565; 5,182,403; 5,164,510; 5,247,090; 5,231,188; 5,565,571; 5,547,950; 5,529,998; 5,627,181; 5,843,967; 5,861,413; 5,827,857; 5,869,659; 5,952,324; 5,968,962; 5,688,792; 6,069,160; 6,239,152; 5,792,765; 4,705,799; 5,043,443; 5,652,238; 5,827,857; 5,529,998; 5,684,023; 5,627,181; 5,698,574; 6,166,056; 6,194,441; 6,110,936; 6,069,145; 6,271,383; 5,981,528; 6,051,716; 6,043,266; 6,313,307; 5,614,535; 6,239,283; 5,990,136; and 5,523,403.

PCT Application and publications PCT/US93/04850, WO94/01110; PCT/US94/08904, WO95/07271; PCT/US95/02972, WO95/25106; PCT/US95/10992, WO96/13502; PCT/US96/05202, WO96/35691; PCT/US96/12766; PCT/US96/13726; PCT/US96/14135; PCT/US96/17120; PCT/US96/19149; PCT/US97/01970; PCT/US95/12751; WO96/15130, PCT/US96/00718, WO96/23788, WO98/54161, WO99/29688, WO99/03846, WO99/37641, WO99/37652, WO99/40094, WO97/30995, WO97/09328, WO01/81350, WO01/40236, WO00/21960 WO01/04022, WO00/73301, WO01/46185, WO99/64417, WO02/59155, WO02/096916 and WO95/07271.

In some embodiments, the antibacterial compounds are prodrugs of the compounds of formulae I, II, and III. The expression "prodrug" denotes a derivative of a known direct acting drug, which is transformed into the active drug by an enzymatic or chemical process. Prodrugs of the compounds of formulea I, II, and III are prepared by modifying functional groups present on the compound in such a way that the modifications are cleaved, either in routine manipulation or in vivo, to the parent compound. Prodrugs include, but are not limited to, compounds of structure I, II, and III wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups. See Notari, R. E., "Theory and Practice of Prodrug Kinetics," Methods in Enzymology, 112:309–323 (1985); Bodor, N., "Novel Approaches in Prodrug Design," Drugs of the Future, 6(3): 165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding-disclosure in any way whatsoever. Those skilled in the art will promptly recognize appropriate variations from the procedures both as to reactants and as to reaction conditions and techniques.

Example 1

(5R)-(−)-3-[3-Fluoro-4-(4-morpholinyl)phenyl]-2-oxo-5-oxazolidinecarboxamide—Method A

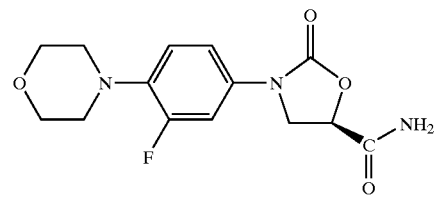

Step 1: Preparation of (5R)-(−)-3-[3-fluoro-4-(4-morpholinyl)phenyl]-2-oxo-5-oxazolidinecarboxylic acid A solution of benzyl 3-fluoro-4-(4-morpholinyl) phenylcarbamate (J. Med. Chem. 1996, 39(3), 673–679, 2.50 g, 7.57 mmol) in dry tetrahydrofuran (37.8 mL) at −78° C. under nitrogen is treated with n-butyllithium (1.6M in hexanes, 4.82 mL, 7.72 mmol) dropwise and stirred at −78° C. for 30 minutes. The cooling bath is removed and the mixture is allowed to slowly warm to −40° C., at which point potassium (2R)-glycidate (J. Org. Chem. 1992, 57(12), 3380–3387, 974 mg, 7.72 mmol) is added. After subsequent warming to ambient temperature, the resulting mixture is vigorously stirred for 2.75 days and then quenched with saturated aqueous ammonium chloride (20 mL), diluted with water (20 mL) and extracted with ethyl acetate (2×75 mL) to remove the remaining starting. The aqueous phase is adjusted to pH 2 with 1M aqueous hydrochloric acid, saturated with sodium chloride and extracted with methylene chloride (5×100 mL), and this combined organic phase is dried over anhydrous sodium sulfate and concentrated under reduced pressure to give the crude product. The product mixture is then chromatographed on a Flash 40M silica gel (90 g, 32–63 μm) cartridge, eluting with a gradient of acetonitrile/methylene chloride (10/90–40/60) containing 1% formic acid, and those fractions with an $R_f$=0.15 by TLC (acetonitrile/methylene chloride, 50/50+1% formic acid) are pooled and concentrated to give the title compound, $^1$H NMR (400 MHz, DMSO-d$_6$) δ 13.7 (bs, 1H), 7.48 (dd, 1H), 7.23 (m, 1H), 7.05 (t, 1H), 5.17 (dd, 1H), 4.30 (t, 1H), 4.06 (dd, 1H), 3.73 (m, 4H), 2.96 (m, 4H); MS (ESI+) for $C_{14}H_{15}FN_2O_5$ m/z 311 (M+H)$^+$; $[α]^{25}_D$=−38° (c 0.94, DMSO).

Step 2: Preparation of (5R)-(−)-3-[3-fluoro-4-(4-morpholinyl)phenyl]-2-oxo-5-oxazolidinecarboxamide To a flame-dried flask containing (5R)-(−)-3-[3-fluoro-4-(4-morpholinyl)phenyl]-2-oxo-5-oxazolidinecarboxylic acid (Step 1, 250 mg, 0.806 mmol) under nitrogen is added oxalyl chloride (4 mL) with stirring. The flask is capped with a drying tube, and the mixture is stirred at ambient temperature for 15 h and then concentrated under reduced pressure to give the acid chloride intermediate [MS (ESI+) m/z 325 (M+H)$^+$ observed for the methyl ester obtained by reaction of the acid chloride with methanol] which is used without further purification. This intermediate is then taken up in anhydrous tetrahydrofuran (8 mL) under nitrogen, cooled to 0° C., and ammonia (g) is bubbled in for 5 minutes. The resulting mixture is capped with a drying tube, stirred at ambient temperature for 1 h, and then diluted with water (20 mL) and extracted with methanol/chloroform (10/90, 2×30 mL). The combined organic phase is dried over anhydrous sodium sulfate and concentrated under reduced pressure, and the product mixture is recrystallized from ethyl acetate/hexane to give the title compound, mp 185–187° C. (decomp.); MS (ESI+) for $C_{14}H_{16}FN_3O_4$ m/z 310 (M+H)$^+$; $[α]^{25}_D$=−23° (c 0.89, DMSO).

Example 2

(5R)-(−)-3-[3-Fluoro-4-(4-morpholinyl)phenyl]-N-methyl-2-oxo-5-oxazolidinecarboxamide

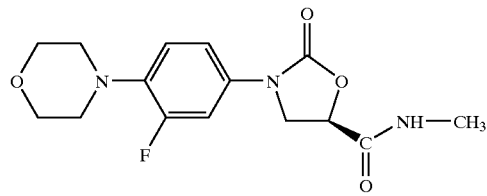

Following the general procedure of EXAMPLE 1, Step 2, and making non-critical variations but substituting methylamine for ammonia, the title compound is obtained, mp 182–183° C. (decomp.); MS (ESI+) for $C_{15}H_{18}FN_3O_4$ m/z 324 (M+H)$^+$; $[α]^{25}_D$=−39(c0.92, DMSO).

Example 3

(5R)-(−)-3-[3-Fluoro-4-(4-morpholinyl)phenyl]-N-allyl-2-oxo-5-oxazolidinecarboxamide

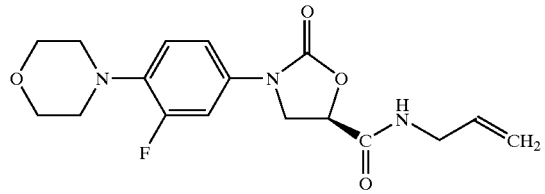

To a flame-dried flask under nitrogen is added allylamine (0.60 mL, 8.05 mmol). The flask is cooled in an ice bath, and a solution of (5R)-3-[3-fluoro-4-(4-morpholinyl)phenyl]-2-oxo-5-oxazolidinecarbonyl chloride (EXAMPLE 1, Step 2, 0.805 mmol theory) in anhydrous tetrahydrofuran (8.0 mL) is added. The resulting mixture is stirred under nitrogen for 2 h, allowing the cooling bath to slowly expire, and is then diluted with water (10 mL) and extracted with methylene chloride (20 mL). The organic phase is washed with water (10 mL) and saline (10 mL), dried over anhydrous sodium sulfate and concentrated under reduced pressure, and the crude product is chromatographed on a Flash 40S silica gel (40 g, 32–63 μm) cartridge, eluting with a gradient of methanol/methylene chloride (0.5/99.5–2/98). Pooling and concentration of those fractions with an $R_f$=0.44 by TLC (methanol/chloroform, 5/95) provides the title compound, mp 167–169° C.; MS (ESI+) for $C_{17}H_{20}FN_3O_4$ m/z 350 (M+H)$^+$; $[α]^{25}_D$=−44° (c 0.94, DMSO).

Example 4

(5R)-(−)-3-[3-Fluoro-4-(4-morpholinyl)phenyl]-N-propyl-2-oxo-5-oxazolidinecarboxamide

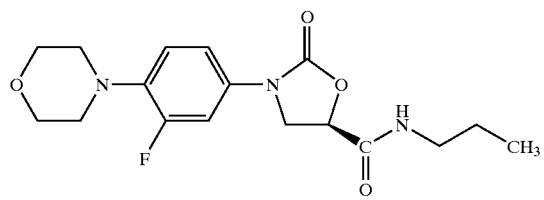

Following the general procedure of EXAMPLE 3, and making non-critical variations but substituting propylamine for allylamine and triturating and filtering the final product from methanol/diethyl ether, the title compound is obtained, mp 165–167° C.; MS (ESI+) for $C_{17}H_{22}FN_3O_4$ m/z 352 (M+H)$^+$; $[α]^{25}_D$=−43° (c. 1.02, DMSO).

Example 5

(5R)-(−)-3-[3-Fluoro-4-(4-morpholinyl)phenyl]-N-methoxy-2-oxo-5-oxazolidinecarboxamide

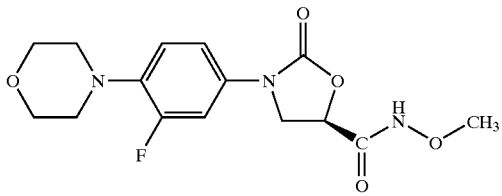

A mixture of (5R)-(−)-3-[3-fluoro-4-(4-morpholinyl)phenyl]-2-oxo-5-oxazolidinecarboxylic acid (EXAMPLE 1, Step 1, 150 mg, 0.483 mmol) and O-methylhydroxylamine hydrochloride (61 mg, 0.724 mmol) in tetrahydrofuran/water (1/1, 4.8 mL) is treated with 1-(3-dimethylaminopropyl)-3-ethylcarbodiimide hydrochloride (278 mg, 1.45 mmol), and the resulting mixture is stirred at ambient temperature for 30 minutes and is then diluted with water (10 mL) and extracted with ethyl acetate (2×20 mL). The combined organic phase is washed with water (10 mL) and saline (10 mL), dried over anhydrous sodium sulfate and concentrated under reduced pressure, and the crude product is chromatographed on a Flash 40S silica gel (40 g, 32–63 μm) cartridge, eluting with methanol/methylene chloride (2.5/97.5). Pooling and concentration of those fractions with an $R_f$=0.53 by TLC (methanol/chloroform, 10/90) gives the title compound, mp 206–208° C. (decomp.); MS (ESI+) for $C_{15}H_{18}FN_3O_5$ m/z 340 (M+H)$^+$; $[\alpha]^{25}_D$=−56° (c 0.92, DMSO).

Example 6

(5R)-(−)-3-[3-Fluoro-4-(4-morpholinyl)phenyl]-N-hydroxy-2-oxo-5-oxazolidinecarboxamide

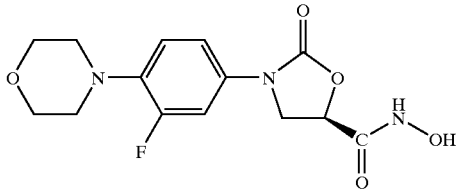

Step 1: Preparation of (5R)-(−)-3-[3-fluoro-4-(4-morpholinyl)phenyl]-N-benzyloxy-2-oxo-5-oxazolidinecarboxamide Following the general procedure of EXAMPLE 5, and making non-critical variations but substituting O-benzylhydroxylamine hydrochloride for O-methylhydroxylamine hydrochloride, the title compound is obtained, mp 191–193° C. (decomp.); MS (ESI+) for $C_{21}H_{22}FN_3O_5$ m/z 416 (M+H)$^+$; $[\alpha]^{25}_D$=−46° (c 0.93, DMSO).

Step 2: Preparation of (5R)-(−)-3-[3-fluoro-4-(4-morpholinyl)phenyl]-N-hydroxy-2-oxo-5-oxazolidinecarboxamide To a mixture of (5R)-(−)-3-[3-fluoro-4-(4-morpholinyl)phenyl]-N-benzyloxy-2-oxo-5-oxazolidinecarboxamide (Step 1, 300 mg, 0.722 mmol) in methanol (28.8 mL) is added 5% palladium-on-carbon (77 mg) under nitrogen. The resulting mixture is degassed and stirred under a hydrogen atmosphere (balloon) for 1 h. The catalyst is then removed by filtration through Celite, rinsing with methanol (60 mL), and the filtrate is concentrated under reduced pressure. Trituration of this residue with (5% methanol/methylene chloride)/diethyl ether gives the title compound, mp 141–143° C.; MS (ESI+) for $C_{14}H_{16}FN_3O_5$ m/z 326 (M+H)$^+$; $[\alpha]^{25}_D$=−70° (c 0.99, DMSO).

Example 7

(5R)-(−)-3-[4-(3-Pyridyl)-3-fluorophenyl]-2-oxo-5-oxazolidinecarboxamide

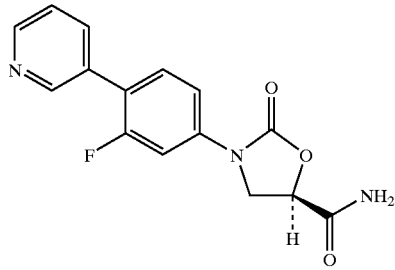

Step 1: Preparation of (5R)-(−)-3-[3-fluoro-4-iodophenyl]-5-hydroxymethyl-2-oxazolidinone A solution of isobutyl 3-fluoro-4-iodophenylcarbamate (Org. Process Res. Dev. 2001, 5(1), 80–83,5.00 g, 14.83 mmol) in dry tetrahydrofuran (59 mL) at −78° C. under nitrogen is treated with lithium hexamethyldisilazide (1.0M in tetrahydrofuran, 15.6 mL, 15.57 mmol) dropwise and stirred at −78° C. for 45 minutes. Then, (R)-glycidyl butyrate (2.21 mL, 15.57 mmol) is added dropwise, and the resulting mixture is stirred at −78° C. for 1 h and at ambient temperature for 2.75 days. The reaction mixture is then quenched with saturated aqueous ammonium chloride (20 mL), diluted with water (20 mL) and the layers are separated. The aqueous phase is extracted with ethyl acetate (25 mL), and the combined organic phase is washed with water (25 mL) and saline (25 mL), dried over anhydrous magnesium sulfate and concentrated under reduced pressure. The product mixture is then chromatographed on a Flash 40M silica gel (90 g, 32–63 μm) cartridge, eluting with a gradient of methanol/methylene chloride (1/99–2/98), and those fractions with an $R_f$=0.25 by TLC (methanol/chloroform, 5/95) are pooled and concentrated to give the title compound, mp 116–117° C.; MS (ESI+) for $C_{10}H_9FINO_3$ m/z 338 (M+H)$^+$; $[\alpha]^{25}_D$=−41 (c 0.98, DMSO).

Step 2: Preparation of (−)-methyl (5R)-3-[3-fluoro-4-iodophenyl]-2-oxo-5-oxazolidinecarboxylate A solution of (5R)-(−)-3-[3-fluoro-4-iodophenyl]-5-hydroxymethyl-2-oxazolidinone (Step 1, 7.61 g, 22.58 mmol) in acetone (150 mL) at —10° C. is treated with a mixture of $CrO_3$ (6.21 g, 62.1 mmol) in sulfuric acid (6M, 16.9 mL, 101 mmol) dropwise over 15 minutes. The resulting mixture is allowed to slowly warm to ambient temperature with vigorous stirring (slight exotherm to 35° C.) and is stirred for an additional 16 h. The mixture is then treated with isopropanol (35 mL), diluted with saline (150 mL) and diethyl ether (150 mL), stirred until all solids are dissolved, and the layers are separated. The aqueous phase is extracted with diethyl ether (100 mL), and the combined organic phase is dried over anhydrous magnesium sulfate and concentrated under reduced pressure to give the crude carboxylic acid intermediate which is taken up in methanol (225 mL) and treated with concentrated sulfuric acid (8 drops). The resulting homogeneous mixture is stirred at ambient temperature for 20 h and is then concentrated under reduced pressure to give the crude methyl ester product which is chromatographed on two Flash 40M 90 g silica gel (32–63 μm) cartridges, eluting with a gradient of ethyl acetate/heptane (20/80–40/60). Pooling and concentration of those fractions with an $R_f$=0.36 by TLC (ethyl acetate/hexane, 50/50) gives the title compound, mp 106–109° C.; MS (ESI+) for $C_{11}H_9FINO_4$ m/z 366 (M+H)$^+$; $[\alpha]^{25}_D$=–30 (c 0.93, DMSO).

Step 3: Preparation of (5R)-(–)-3-[3-fluoro-4-iodophenyl]-2-oxo-5-oxazolidinecarboxamide A solution of (–)-methyl (5R)-3-[3-fluoro-4-iodophenyl]-2-oxo-5-oxazolidinecarboxylate (Step 2, 6.23 g, 17.1 mmol) in acetonitrile (85 mL) is treated with concentrated ammonium hydroxide (85 mL), and the resulting mixture is stirred at ambient temperature for 1 h. The mixture is then diluted with saline (100 mL) and extracted with methylene chloride (3×100 mL), and the combined organic phase is washed with saline (100 mL), dried over anhydrous sodium sulfate and concentrated under reduced pressure. The crude product is diluted with hot ethyl acetate (200 mL) and filtered to remove inorganic residue, and the filtrate is diluted with hexanes (300 mL). The resulting precipitate is isolated by filtration to give the title compound, mp 176–178° C.; MS (ESI+) for $C_{10}H_8FIN_2O_3$ m/z 351 (M+H)$^+$; $[\alpha]^{25}_D$=–19 (c 0.97, DMSO).

Step 4: Preparation of 3-(trimethylstannyl)pyridine

A mixture of hexamethylditin (654 mg, 1.99 mmol), 3-bromopyridine (300 mg, 1.90 mmol) and bis(triphenylphosphine)palladium(II) chloride (40 mg, 0.057 mmol) in 1,4-dioxane (9.5 ml) is degassed, heated up to 90° C. under nitrogen, stirred at this temperature for 2.5 h and at ambient temperature overnight, and is then concentrated under reduced pressure. The product mixture is chromatographed on a Flash 40S 40 g silica gel (32–63 μm) cartridge, eluting with ethyl acetate/heptane (20/80), and those fractions with an $R_f$=0.47 by TLC (ethyl acetate/hexane, 50/50) are pooled and concentrated to give the title compound (see *Chem. Pharm. Bull.* 1982, 30(5), 1731–1737 for characterization).

Step 5: Preparation of (5R)-(–)-3-[4-(3-pyridyl)-3-fluorophenyl]-2-oxo-5-oxazolidinecarboxamide A mixture of (5R)-(–)-3-[3-fluoro-4-iodophenyl]-2-oxo-5-oxazolidinecarboxamide (Step 3, 422 mg, 1.21 mmol), 3-(trimethylstannyl)pyridine (Step 4, 350 mg, 1.45 mmol), tris(dibenzylideneacetone)dipalladium(0) (22 mg, 0.0242 mmol), triphenylarsine (59 mg, 0.194 mmol) and copper(I) iodide (9 mg, 0.0484 mmol) in N-methyl-2-pyrrolidinone (4.8 mL) under nitrogen is degassed, heated up to 50° C. and stirred at this temperature for 2 days, during which additional tris(dibenzylideneacetone)dipalladium(0) (22 mg, 0.0242 mmol), triphenylarsine (59 mg, 0.194 mmol) and copper(I) iodide (9 mg, 0.0484 mmol) are added. The resulting mixture is diluted with water (15 mL) and extracted with methylene chloride (3×20 mL), and the combined organic phase is dried over anhydrous sodium sulfate and concentrated under reduced pressure. The resulting oil is diluted with ethyl acetate (25 mL) and extracted with aqueous hydrochloric acid (1M, 25 mL), and the aqueous phase is neutralized with sodium hydroxide (s), saturated with sodium chloride and extracted with methylene chloride (3×25 mL) containing a small amount of methanol. This combined organic phase is dried over anhydrous sodium sulfate and concentrated under reduced pressure, and the residue is recrystallized from ethyl acetate/hexane to give the title compound, mp 240–242° C. (dec.); MS (ESI+) for $C_{15}H_{12}FN_3O_3$ m/z 302 (M+H)$^+$; $[\alpha]^{25}_D$=–25 (c 0.94, DMSO).

Example 8

(5R)-(–)-3-[4-(4-Pyridyl)-3-fluorophenyl]-2-oxo-5-oxazolidinecarboxamide

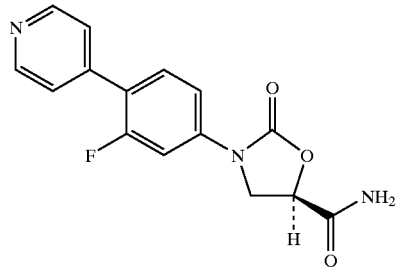

Following the general procedure of EXAMPLE 7, Step 5, and making non-critical variations but substituting 4-(trimethylstannyl)pyridine (U.S. Pat. No. 5,990,136; Nov. 23, 1999) for 3-(trimethylstannyl)pyridine, the title compound is obtained, mp 256–259° C. (dec.); MS (ESI+) for $C_{15}H_{12}FN_3O_3$ m/z 302 (M+H)$^+$; $[\alpha]^{25}_D$=–27 (c 0.94, DMSO).

Example 9

(5R)-(–)-3-[4-(3,6-Dihydro-2H-pyran-4-yl)-3-fluorophenyl]-2-oxo-5-oxazolidinecarboxamide

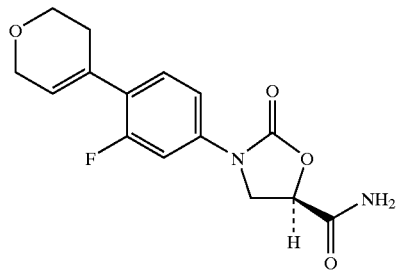

Step 1: Preparation of (5R)-3-[4-(trimethylstannyl)-3-fluorophenyl]-2-oxo-5-oxazolidinecarboxamide A mixture of (5R)-(–)-3-[3-fluoro-4-iodophenyl]-2-oxo-5-oxazolidinecarboxamide (EXAMPLE 7, Step 3, 3.50 g, 10.0 mmol), hexamethylditin (3.44 g, 10.5 mmol) and bis(triphenylphosphine)palladium(II) chloride (140 mg, 0.200 mmol) in 1,4-dioxane (50 mL) under nitrogen is degassed, heated up to 90° C. and stirred at 90° C. for 2 h and at ambient temperature overnight. The resulting mixture is concentrated under reduced pressure to remove dioxane, diluted with methylene chloride (75 mL), washed with saline (25 mL), dried over anhydrous sodium sulfate and concentrated under reduced pressure. The residue is chromatographed on a Flash 40M 90 g silica gel (32–63 μm) cartridge, eluting with a gradient of methanol/methylene chloride (1/99–2/98), and those fractions with an $R_f$=0.26 by TLC (methanol/chloroform, 5/95) are pooled and concentrated to give the title compound, $^1$H NMR (400 MHz, CDCl$_3$) δ 7.38 (m, 2H), 7.20 (m, 1H), 6.65 (s, 1H), 5.82 (s, 1H), 5.00 (dd, 1H), 4.26 (m, 2H), 0.35 (m, 9H).

Step 2: Preparation of (5R)-(−)-3-[4-(3,6-dihydro-2H-pyran-4-yl)-3-fluorophenyl]-2-oxo-5-oxazolidinecarboxamide A mixture of 3,6-dihydro-2H-pyran-4-yl trifluoromethanesulfonic acid ester (U.S. Pat. No. 5,968,962, Oct. 19, 1999, 682 mg, 2.94 mmol), tris(dibenzylideneacetone)dipalladium(0) (54 mg, 0.0588 mmol) and triphenylarsine (144 mg, 0.470 mmol) in N-methyl-2-pyrrolidinone (14.7 mL) is degassed and stirred under nitrogen for 5 minutes. (5R)-3-[4-(Trimethylstannyl)-3-fluorophenyl]-2-oxo-5-oxazolidinecarboxamide (Step 1, 1.14 g, 2.94 mmol) is then added, and the resulting mixture is stirred at ambient temperature for 5 days. The reaction mixture is then diluted with water (25 mL) and extracted with ethyl acetate (3×30 mL), and the combined organic phase is washed with water (3×30 mL) and saline (20 mL), dried over anhydrous magnesium sulfate and concentrated under reduced pressure. The crude product mixture is chromatographed on a Flash 40M 90 g silica gel (32–63 μm) cartridge, eluting with a gradient of methanol/methylene chloride (1/99–2.5/97.5), and those fractions with an $R_f$=0.40 by TLC (methanol/chloroform, 2×5/95) are pooled and concentrated to give the title compound, mp 164–169° C.; MS (ESI−) for $C_{15}H_{15}N_2O_4F$ m/z 305 (M−H)$^−$; $[\alpha]^{25}_D$=−23 (c 0.96, DMSO).

Example 10

(5R)-(−)-3-[4-(Tetrahydro-2H-pyran-4-yl)-3-fluorophenyl]-2-oxo-5-oxazolidinecarboxamide

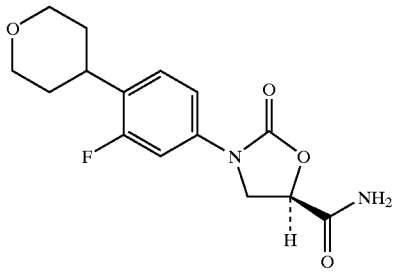

A mixture of (5R)-(−)-3-[4-(3,6-dihydro-2H-pyran-4-yl)-3-fluorophenyl]-2-oxo-5-oxazolidinecarboxamide (EXAMPLE 9, Step 2, 200 mg, 0.653 mmol) and 10% palladium-on-carbon (139 mg, 0.131 mmol) in methanol (26 mL) is shaken under a 40 psi hydrogen atmosphere on a Parr apparatus for 5 h. The catalyst is then removed by filtration through a pad of Celite, and the filtrate is concentrated under reduced pressure and chromatographed on a Flash 40S 40 g silica gel (32–63 μm) cartridge, eluting with a gradient of methanol/methylene chloride (2/98–3/97). Pooling and concentration of those fractions with an $R_f$=0.37 by TLC (methanol/chloroform, 2×5/95) gives the title compound, mp 153–156° C.; MS (ESI−) for $C_{15}H_{17}N_2O_4F$ m/z 307 (M−H)$^+$; $[\alpha]^{25}_D$=−21 (c 0.87, DMSO).

Example 11

(5R)-3-[4-(3,6-Dihydro-2H-thiopyran-4-yl)-3-fluorophenyl]-2-oxo-5-oxazolidinecarboxamide S-oxide

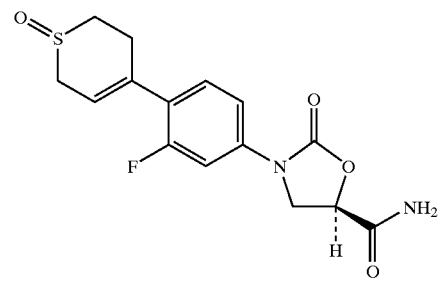

Step 1: Preparation of (−)-methyl (5R)-3-[4-(3,6-dihydro-2H-thiopyran-4-yl)-3-fluorophenyl]-2-oxo-5-oxazolidinecarboxylate Following the general procedure of EXAMPLE 1, Step 1, and making non-critical variations but substituting isobutyl 4-(3,6-dihydro-2H-thiopyran-4-yl)-3-fluorophenylcarbamate (WO 00/44741, Aug. 3, 2000) for benzyl 3-fluoro-4-(4-morpholinyl)phenylcarbamate, the crude (5R)-3-[4-(3,6-dihydro-2H-thiopyran-4-yl)-3-fluorophenyl]-2-oxo-5-oxazolidinecarboxylic acid intermediate is obtained and is used without further purification. This intermediate (540 mg crude) is taken up in methanol (16 mL), a drop of concentrated sulfuric acid is added, and the mixture is stirred at ambient temperature for 21 h. Then, the reaction mixture is concentrated under reduced pressure and chromatographed on a Flash 40S 40 g silica gel (32–63 μm) cartridge, eluting with ethyl acetate/heptane (25/75). Pooling and concentration of those fractions with an $R_f$=0.25 by TLC (ethyl acetate/hexs, 50/50) give the title compound, mp 106–110° C.; MS (ESI+) for $C_{16}H_{16}NO_4FS$ m/z 338 (M+H)$^+$; $[\alpha]^{25}_D$=−36 (c 0.99, DMSO).

Step 2: Preparation of (5R)-(−)-3-[4-(3,6-dihydro-2H-thiopyran-4-yl)-3-fluorophenyl]-2-oxo-5-oxazolidinecarboxamide Following the general procedure of EXAMPLE 7, Step 3, and making non-critical variations but substituting (−)-methyl (5R)-3-[4-(3,6-dihydro-2H-thiopyran-4-yl)-3-fluorophenyl]-2-oxo-5-oxazolidinecarboxylate (Step 1) for (−)-methyl (5R)-3-[3-fluoro-4-iodophenyl]-2-oxo-5-oxazolidinecarboxylate and purifying the product by recrystallization from methanol/diethyl ether, the title compound is obtained, mp 182–184° C. (dec.); MS (ESI−) for $C_{15}H_{15}FN_2O_3S$ m/z 321 (M−H)$^−$; $[\alpha]^{25}_D$=−24 (c 0.93, DMSO).

Step 3: Preparation of (5R)-3-[4-(3,6-dihydro-2H-thiopyran-4-yl)-3-fluorophenyl]-2-oxo-5-oxazolidinecarboxamide S-oxide A mixture of (5R)-(−)-3-[4-(3,6-dihydro-2H-thiopyran-4-yl)-3-fluorophenyl]-2-oxo-5-oxazolidinecarboxamide (Step 2, 294 mg, 0.912 mmol) in methanol (18 mL) is treated with sodium periodate (205 mg, 0.958 mmol) in water (3.8 mL), and the mixture is stirred at ambient temperature for 44 h. The resulting mixture is diluted with water (25 mL) and extracted with methylene chloride (5×30 mL), and the combined organic phase is dried over anhydrous sodium sulfate and concentrated under reduced pressure. The crude product mixture is triturated with acetone/diethyl ether and then filtered to give the title compound as a mixture of two diastereomers, $^1$H NMR (400 MHz, DMSO-d$_6$) δ 7.87 (s, 1H), 7.63 (s, 1H), 7.52 (d, 1H), 7.39 (m, 2H), 5.83 (m, 1H), 5.04 (dd, 1H), 4.29 (t, 1H), 4.02 (dd, 1H), 3.65 (m, 1H), 3.39 (m, 1H), 3.10 (m, 1H), 2.92 (m, 2H), 2.54 (m, 1H); MS (ESI+) for $C_{15}H_{15}FN_2O_4S$ m/z 339 (M+H)$^+$.

Example 12

(5R)-(−)-3-[4-(3,6-Dihydro-2H-thiopyran-4-yl)-3-fluorophenyl]-2-oxo-5-oxazolidinecarboxamide S,S-dioxide

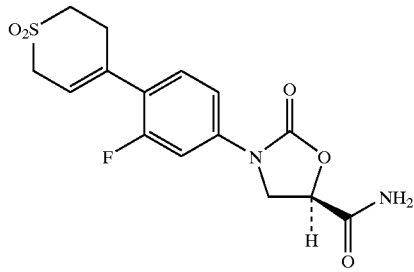

A solution of (5R)-(−)-3-[4-(3,6-dihydro-2H-thiopyran-4-yl)-3-fluorophenyl]-2-oxo-5-oxazolidinecarboxamide (EXAMPLE 11, Step 2, 209 mg, 0.648 mmol) in water/acetone (25/75, 13 mL) under nitrogen is treated with N-methylmorpholine N-oxide (190 mg, 1.62 mmol) and osmium tetroxide (2.5 wt % in tBuOH, 0.41 mL, 0.0324 mmol), and the mixture is stirred at ambient temperature for 43 h. The reaction is then treated with ½-saturated aqueous sodium bisulfite (25 mL) and extracted with methylene chloride (3×25 mL), and the combined organic phase is dried over anhydrous sodium sulfate and concentrated under reduced pressure. The residue is chromatographed on a Flash 40S 40 g silica gel (32–63 μm) cartridge, eluting with a gradient of methanol/methylene chloride (2.5/97.5–4/96), and those fractions with an R$_f$=0.48 by TLC (methanol/chloroform, 10/90) are pooled and concentrated to give the title compound, mp 206–208° C.; MS (ESI−) for $C_{15}H_{15}FN_2O_5S$ m/z 353 (M−H)$^−$; $[\alpha]^{25}_D$=−20 (c 0.98, DMSO).

Example 13

(5R)-(−)-3-[4-(Tetrahydro-2H-thiopyran-4-yl)-3-fluorophenyl]-2-oxo-5-oxazolidinecarboxamide S,S-dioxide

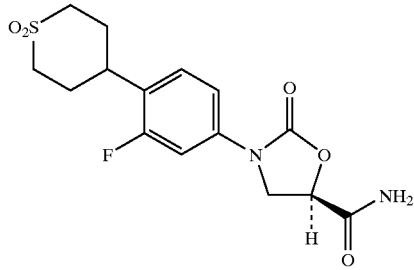

A mixture of (5R)-(−)-3-[4-(3,6-dihydro-2H-thiopyran-4-yl)-3-fluorophenyl]-2-oxo-5-oxazolidinecarboxamide S,S-dioxide (EXAMPLE 12, 73 mg, 0.206 mmol) and 10% palladium-on-carbon (44 mg, 0.0412 mmol) in methanol (21 mL) is shaken under a 40 psi hydrogen atmosphere on a Parr apparatus for 16 h. The catalyst is then removed by filtration through a pad of Celite, rinsing with methanol and tetrahydrofuran, and the filtrate is concentrated under reduced pressure and triturated with (5% methanol/methylene chloride)/diethyl ether. Filtration then provides the title compound, mp 229–231° C. (dec.); MS (ESI−) for $C_{15}H_{17}FN_2O_5S$ m/z 355 (M−H)$^−$; $[\alpha]^{25}_D$=−20 (c 0.83, DMSO).

Example 14

(5R)-(−)-3-[3-Fluoro-4-[4-(hydroxyacetyl)-1-piperazinyl]phenyl]-2-oxo-5-oxazolidinecarboxamide

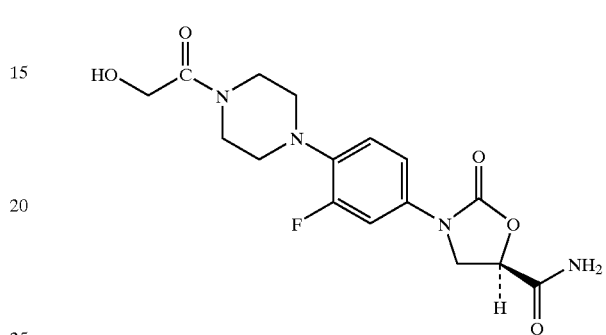

Step 1: Preparation of (−)-phenylmethyl 4-[4-[(5R)-5-(aminocarbonyl)-2-oxo-3-oxazolidinyl]-2-fluorophenyl]-1-piperazinecarboxylate Following the general procedure of EXAMPLE 1, Step 1, and making non-critical variations but substituting benzyl 4-(4-{[benzyloxycarbonyl]amino}-2-fluorophenyl)-1-piperazinecarboxylate (*J. Med. Chem.* 1996, 39(3), 673–679) for benzyl 3-fluoro-4-(4-morpholinyl) phenylcarbamate, the crude 1-(phenylmethyl)-4-[4-[(5R)-5-carboxy-2-oxo-3-oxazolidinyl]-2-fluorophenyl]-1-piperazinecarboxylate intermediate is obtained [MS (ESI−) for $C_{22}H_{22}N_3O_6F$ m/z 442 (M−H)$^−$] and is used without further purification. This intermediate (1.66 g crude) is taken up in methanol (75 mL), 4 drops of concentrated sulfuric acid are added, and the mixture is stirred at ambient temperature for 19 h. Then, the reaction mixture is concentrated under reduced pressure and chromatographed twice on a Flash 40M 90 g silica gel (32–63 μm) cartridge, eluting with a gradient of methanol/methylene chloride (1/99–2/98). Pooling and concentration of those fractions with an R$_f$=0.64 by TLC (methanol/chloroform, 5/95) provides 740 mg of the phenylmethyl 4-[2-fluoro-4-[(5R)-5-(methoxycarbonyl)-2-oxo-3-oxazolidinyl]phenyl]-1-piperazinecarboxylate intermediate [MS (ESI+) for $C_{23}H_{24}N_3O_6F$ m/z 458 (M+H)$^+$; 75–80% purity] which is used without further purification. This intermediate is taken up in 2M ammonia in methanol (13 mL), and the resulting mixture is stirred at ambient temperature for 3 h and then concentrated under reduced pressure. The residue is chromatographed on a Flash 40M 90 g silica gel (32–63 μm) cartridge, eluting with a gradient of methanol/methylene chloride (1/99–3/97), and those fractions with an R$_f$=0.20 by TLC (methanol/chloroform, 5/95) are pooled and concentrated to give the title compound, mp 172–175° C.; MS (ESI+) for $C_{22}H_{23}N_4O_5F$ m/z 443 (M+H)$^+$; $[\alpha]^{25}_D$=−17 (c 1.04, DMSO).

Step 2: Preparation of (5R)-3-[3-fluoro-4-[4-[(phenylmethoxy)acetyl]-1-piperazinyl]phenyl]-2-oxo-5-oxazolidinecarboxamide A mixture of (−)-phenylmethyl 4-[4-[(5R)-5-(aminocarbonyl)-2-oxo-3-oxazolidinyl]-2-fluorophenyl]-1-piperazinecarboxylate (Step 1, 415 mg, 0.938 mmol) and 10% palladium-on-carbon (100 mg, 0.0938 mmol) in methanol (45 mL) is shaken under a 45 psi hydrogen atmosphere on a Parr apparatus for 4 h. The catalyst is then removed by filtration through a pad of Celite, and the filtrate is concentrated under reduced pressure to give 290 mg (100%) of the (5R)-3-[(3-fluoro-4-piperazinyl)phenyl]-2-oxo-5-oxazolidinecarboxamide intermediate [MS (ESI+) for $C_{14}H_{17}N_4O_3F$ m/z 309 (M+H)$^+$] which is used without further purification. A mixture of this intermediate (240 mg, 0.778 mmol) in methylene chloride (7.8 mL) under nitrogen is treated with triethylamine (163 μL, 1.17 mmol) followed by benzyloxyacetyl chloride (135 μL, 0.856 mmol), and the resulting homogeneous mixture is stirred at ambient temperature for 3 h. The reaction mixture is then diluted with water (20 mL) and methylene chloride (20 mL), the layers are separated, and the organic phase is washed with saline (10 mL), dried over anhydrous sodium sulfate and concentrated under reduced pressure to give the crude product which is then chromatographed on a Flash 40M 90 g silica gel (32–63 μm) cartridge, eluting with methanol/methylene chloride (2.5/97.5). Pooling and concentration of those fractions with an $R_f$=0.50 by TLC (methanol/chloroform, 10/90) provides the title compound,
$^1$H NMR (400 MHz, DMSO-d$_6$) δ 7.85 (s, 1H), 7.61 (s, 1H), 7.52 (dd, 1H), 7.36 (m, 4H), 7.31 (m, 1H), 7.24 (m, 1H), 7.06 (m, 1H), 5.01 (dd, 1H), 4.53 (s, 2H), 4.25 (m, 3H), 3.97 (dd, 1H), 3.58 (m, 4H), 2.96 (m, 4H); MS (ESI+) for $C_{23}H_{25}FN_4O_5$ m/z 457 (M+H)$^+$.

Step 3: Preparation of (5R)-(−)-3-[3-fluoro-4-[4-(hydroxyacetyl)-1-piperazinyl]phenyl]-2-oxo-5-oxazolidinecarboxamide A mixture of (5R)-3-[3-fluoro-4-[4-[(phenylmethoxy)acetyl]-1-piperazinyl]phenyl]-2-oxo-5-oxazolidinecarboxamide (Step 2, 260 mg, 0.570 mmol) and 10% palladium-on-carbon (61 mg, 0.0570 mmol) in a mixture of methanol (5 mL) and EtOH (23 mL) is shaken under a 40 psi hydrogen atmosphere on a Parr apparatus for 22 h. The catalyst is then removed by filtration through a pad of Celite, rinsing with tetrahydrofuran (200 mL), and the filtrate is concentrated under reduced pressure and triturated with methanol/diethyl ether. Filtration then provides the title compound, mp 232–235° C. (dec.); MS (ESI+) for $C_{16}H_{19}FN_4O_5$ m/z 367 (M+H)$^+$; $[α]^{25}_D$=−20 (c 0.98, DMSO).

Example 15

(5R)-(−)-3-[4-(Thiomorpholin-4-yl)-3,5-difluorophenyl]-2-oxo-5-oxazolidinecarboxamide S,S-dioxide

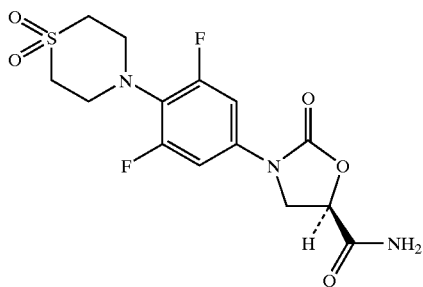

Step 1: Preparation of 4-(2,6-difluorophenyl)thiomorpholine 1,1-dioxide

Aluminum chloride (310 g, 2.3 mol) is added to chlorobenzene (2.5 L) to give a cloudy green suspension. Vinyl sulfone (230 mL, 2.3 mol) is added via funnel, followed by 2,6-difluoroaniline (250 mL, 2.3 mol). The light brown solution is heated to 110° C. Upon completion of the reaction, the heat is removed and the black solution is self-cooled to 70° C. The reaction mixture is then quenched in methylene chloride (4 L) and ice water (5 L), the aqueous phase is extracted with methylene chloride (3 L, 2 L, 2 L, 2 L) and the combined organic layers are concentrated, rediluted with branched octane (3 L), and then cooled to 0° C. for 30 minutes. The solids are filtered and washed with branched octane (2×500 mL) and are then dissolved in methylene chloride (3 L) and loaded onto a silica gel plug (1.8 kg). The column is eluted with dichloromethane (16 L) until clear. The methylene chloride solution is concentrated, and the solids are dissolved in hot ethyl acetate (3 L) followed by the addition of hexanes (900 mL). The black solution is self-cooled to room temperature overnight, and the resulting light amber crystal needles are filtered and washed with hexanes (4×250 mL). The solids are dried under reduced pressure at 50° C. overnight to give the title compound, $^1$H NMR (CDCl$_3$) δ 7.08 (m, 1H), 6.91 (m, 2H), 3.67 (m, 4H), 3.18 (m, 4H).

Step 2: Preparation of 4-(2,6-difluoro-4-nitrophenyl)thiomorpholine 1,1-dioxide

To a suspension of 4-(2,6-difluorophenyl)thiomorpholine 1,1-dioxide (Step 1, 300 g, 1.21 mol) in 3 L of acetic acid, nitric acid (255 mL, ca. 6 mol, fuming, 90%) is added over 30 minutes at ambient temperature. A yellow precipitate forms within minutes and increases over time. The reaction is kept at room temperature for 18 h and is then poured into 6 L of water. After stirring for 2 h, the yellow suspension is filtered. The precipitate is washed with water (1.5 L×3) and ethanol (0.5 L×2) and dried at 50° C. overnight to give the title compound, $^1$H NMR (DMSO-d$_6$) δ 8.05 (m, 2H), 3.69 (m, 4H), 3.26 (m, 4H).

Step 3: Preparation of 4-(1,1-dioxido-4-thiomorpholinyl)-3,5-difluoroaniline

To an autoclave is added 4-(2,6-difluoro-4-nitrophenyl)thiomorpholine 1,1-dioxide (Step 2, 7.0 kg, 24 moles, 1.0 eq). Raney Nickel (1.4 kg) is activated and suspended in tetrahydrofuran (4 L), and the slurry is added to the autoclave followed by additional tetrahydrofuran (66 L). The mixture is heated at 40° C. under a 40 psi hydrogen atmosphere until the reaction is complete. The mixture is then filtered, and the filtrate is directly used in the next step. A small portion of the filtrate can be concentrated and recrystallized in isopropanol to give the title compound in pure form, $^1$H NMR (DMSO-d$_6$) δ 6.17 (m, 2H), 5.35 (s, 2H), 3.32 (m, 4H), 3.15 (m, 4H).

Step 4: Preparation of isobutyl 4-(1,1-dioxido-4-thiomorpholinyl)-3,5-difluorophenylcarbamate To a 400 L glass-lined reactor containing the 4-(1,1-dioxido-4-thiomorpholinyl)-3,5-difluoroaniline/tetrahydrofuran solutions (Step 3, 12.6 kg, 48 moles, 1.0 moles, 1.0 eq) is added a 47% potassium carbonate solution (14.1 kg, 48 moles, 1.0 eq). The mixture is heated to approximately 45° C., and isobutyl chloroformate (7.2 kg, 53 moles, 1.1 eq) is added while maintaining a reaction temperature between 45° C. and 55° C. The reaction is stirred at 45°–55° C. Once complete, the reaction is quenched by slowly adding water (45 L) over 15 minutes. The reaction mixture is cooled to 25° C. and the phases are separated. The tetrahydrofuran solution is swapped to an isopropanol (150 L)/water (50 L) suspension, and the slurry is slowly cooled to 5° C. The yellow slurry is then filtered and the cake washed with cold isopropanol (2×30 L). The yellow solids are dried with 60° C. nitrogen to give the title compound, ¹H NMR (CDCl₃) δ 7.02 (m, 2H), 6.81 (s, 1H), 3.95 (d, 2H), 3.60 (m, 4H), 3.17 (m, 4H), 1.97 (m, 1H), 0.94 (d, 6H).

Step 5: Preparation of (5R)-(−)-3-[4-(thiomorpholin-4-yl)-3,5-difluorophenyl]-2-oxo-5-oxazolidinecarboxamide S,S-dioxide Following the general procedure of EXAMPLE 14, Step 1, and making non-critical variations but substituting isobutyl 4-(1,1-dioxido-4-thiomorpholinyl)-3,5-difluorophenylcarbamate (Step 4) for benzyl 4-(4-{[benzyloxycarbonyl]amino}-2-fluorophenyl)-1-piperazinecarboxylate and purifying the final product by trituration and filtration from (10% methanol/chloroform)/ diethyl ether, the title compound is obtained, mp 245–248° C. (dec.); MS (ESI+) for $C_{14}H_{15}F_2N_3O_5S$ m/z 376 (M+H)⁺; $[\alpha]^{25}_D = -22$ (c 1.00, DMSO).

Example 16

(5R)-(−)-3-[3-Fluoro-4-(4-morpholinyl)phenyl]-2-oxo-5-oxazolidinecarboxamide-Method C

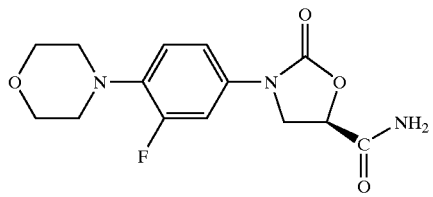

Step 1: Preparation of ethyl (5R)-3-[3-fluoro-4-(4-morpholinyl)phenyl]-2-oxo-5-oxazolidinecarboxylate A solution of 3-fluoro-4-morpholinoaniline (*J. Med. Chem.* 1996, 39(3), 673–679, 0.796 g, 4.0 mmol), ethyl 2(R)-epoxypropanoate (0.696 g, 6.0 mmol) and lithium triflate (0.97 g, 6.2 mmol) in acetonitrile (12 mL) is stirred at 50–60° C. overnight. Solvent and excess epoxide is removed under reduced pressure, and the crude amino alcohol is redissolved in dry acetonitrile (40 mL) and 1,1'-carbonyldiimidazole (1.46 g, 9.0 mmol) is added. The mixture is stirred at ambient temperature overnight, and then the solvent is removed under reduced pressure. The residue is partitioned between ethyl acetate (70 mL) and 3% aqueous citric acid (100 mL), the layers are separated, and the organic phase is washed with 3% aqueous citric acid (3×100 mL), water and saline, dried over anhydrous magnesium sulfate and concentrated under reduced pressure. The product mixture is then purified by silica gel chromatography, eluting with ethanol/methylene chloride (2/98), and the appropriate fractions are pooled and concentrated to give the title compound, MS (ESI+) for $C_{16}H_{19}N_2O_5F$ m/z 339 (M+H)⁺.

Step 2: Preparation of (5R)-(−)-3-[3-fluoro-4-(4-morpholinyl)phenyl]-2-oxo-5-oxazolidinecarboxamide A mixture of of ethyl (5R)-3-[3-fluoro-4-(4-morpholinyl)phenyl]-2-oxo-5-oxazolidinecarboxylate (Step 1, 0.22 g, 0.65 mmol) in 2M ammonia in methanol (5–6 mL) is heated in a closed vial at 60° C. for approximately 1 h. The resulting mixture is cooled to ambient temperature and concentrated under reduced pressure, and the crude product is recrystallized from methanol to give the title compound, MS (ESI+) for $C_{14}H_{16}N_3O_4F$ m/z 310 (M+H)⁺.

Example 17

(5R)-(−)-3-[3,5-Difluoro-4-(4-morpholinyl)phenyl]-2-oxo-5-oxazolidinecarboxamide

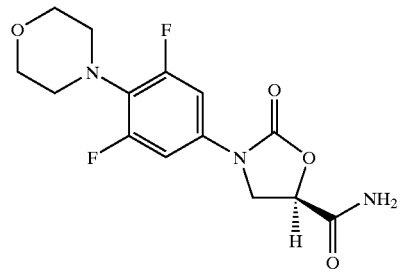

Step 1: Preparation of butyl (5R)-3-[3,5-difluoro-4-(4-morpholinyl)phenyl]-2-oxo-5-oxazolidinecarboxylate A solution of 3,5-difluoro-4-(4-morpholinyl)aniline (See U.S. Pat. No. 5,688,792, 2.00 g, 9.34 mmol), butyl 2(R)-glycidate (2.02 g, 14.0 mmol) and lithium triflate (2.18 g, 14.0 mmol) in acetonitrile (37 mL) is stirred at 60° C. under N₂ for 48 h. Solvent is removed under reduced pressure, and the residue is taken up in MeOH/CH₂Cl₂ (5/95, 100 mL), washed with water (2×25 mL) and saline (25 mL), dried over anhydrous sodium sulfate and concentrated under reduced pressure. The residue is flushed through a Flash 40M 90 g silica gel cartridge with EtOAc/CH₂Cl₂ (10/90), and the appropriate fractions are pooled and concentrated to give the amino alcohol intermediate [$R_f$=0.10 by TLC, EtOAc/hexanes (25/75)] which is contaminated with residual starting material. This intermediate (2.5 g in two lots) is then dissolved in acetonitrile (total of 70 mL) and treated with 1,1'-carbonyldiimidazole (total of 1.69 g, 10.4 mmol, 1.5 equiv.), and the reaction mixtures are stirred at ambient temperature for 6 days and then concentrated under reduced pressure. The product mixtures are each taken up in CH₂Cl₂ (50 mL), washed with 0.1M hydrochloric acid (2×20 mL) and saline (10 mL), dried over anhydrous sodium sulfate, concentrated under reduced pressure and chromatographed on a Flash 40M 90 g silica gel cartridge with EtOAc/CH₂Cl₂ (5/95). Those fractions with an $R_f$=0.16 by TLC (EtOAc/hexanes, 25/75) are pooled and concentrated to give the title compound, mp 99–100° C.; MS (ESI+) for $C_{18}H_{22}N_2O_5F_2$ m/z 385 (M+H)⁺.

Step 2: Preparation of (5R)-(−)-3-[3,5-difluoro-4-(4-morpholinyl)phenyl]-2-oxo-5-oxazolidinecarboxamide The butyl (5R)-3-[3,5-difluoro-4-(4-morpholinyl)phenyl]-2-oxo-5-oxazolidinecarboxylate (Step 1, 350 mg, 0.910 mmol) is treated with 7N ammonia in methanol (9.1 mL) under N₂, and the mixture is stirred at ambient temperature for 30 mins. The reaction mixture is then concentrated under reduced pressure, and the residue is recrystalized from EtOAc/hexanes to give the title compound, mp 181–183° C.; MS (ESI+) for $C_{14}H_{15}N_3O_4F_2$ m/z 328 (M+H)⁺; $[\alpha]^{25}_D$ −23 (c 0.94, DMSO).

Example 18

(5R)-(−)-3-[4-(Thiomorpholin-4-yl)phenyl]-2-oxo-5-oxazolidinecarboxamide S,S-dioxide

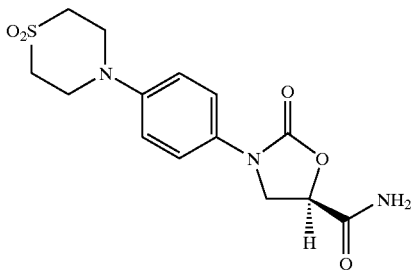

Step 1: Preparation of butyl (5R)-3-[4-(thiomorpholin-4-yl)phenyl]-2-oxo-5-oxazolidinecarboxylate A solution of 4-(4-thiomorpholinyl)aniline (See *Med. Chem. Res.* 1999, 9(3), 149–161, 2.60 g, 13.4 mmol), butyl 2(R)-glycidate (2.89 g, 20.1 mmol) and lithium triflate (3.13 g, 20.1 mmol) in acetonitrile (54 mL) is stirred at 60° C. under $N_2$ for 36 hrs. Solvent is removed under reduced pressure, and the residue is taken up in $MeOH/CH_2Cl_2$ (5/95, 100 mL), washed with water (50 mL) and saline (20 mL), dried over anhydrous sodium sulfate and concentrated under reduced pressure. The residue is flushed through a Flash 40M 90 g silica gel cartridge with $EtOAc/CH_2Cl_2$ (15/85), and the appropriate fractions are pooled and concentrated to give the amino alcohol intermediate [$R_f$=0.19 by TLC, EtOAc/hexanes (25/75)] which is contaminated with the dialkylated by-product. This intermediate (4.25 g) is then dissolved in acetonitrile (125 mL) and treated with 1,1'-carbonyldiimidazole (3.05 g, 18.8 mmol, 1.5 equiv.), and the reaction mixture is stirred at ambient temperature for approximately 3 days and then concentrated under reduced pressure. The product mixture is taken up in $CH_2Cl_2$ (100 mL), washed with 0.1M hydrochloric acid (3×25 mL) and saline (25 mL), dried over anhydrous sodium sulfate, concentrated under reduced pressure and chromatographed on a Flash 40M 90 g silica gel cartridge with $EtOAc/CH_2Cl_2$ (15/85). Those fractions with an $R_f$=0.57 by TLC (EtOAc/hexanes, 50/50) are pooled and concentrated to give the title compound, mp 95.5–98° C.; MS (ESI+) for $C_{18}H_{24}N_2O_4S$ m/z 365 $(M+H)^+$.

Step 2: Preparation of butyl (5R)-3-[4-(thiomorpholin-4-yl)phenyl]-2-oxo-5-oxazolidinecarboxylate S,S-dioxide A solution of butyl (5R)-3-[4-(thiomorpholin-4-yl)phenyl]-2-oxo-5-oxazolidinecarboxylate (Step 1, 600 mg, 1.65 mmol) in water/acetone (25/75, 32 mL) under $N_2$ is treated with N-methylmorpholine N-oxide (483 mg, 4.12 mmol) and osmium tetroxide (2.5 wt % in tBuOH, 1.03 mL, 0.0825 mmol), and the mixture is stirred at ambient temperature for 18 h. The reaction is then treated with ½-saturated aqueous sodium bisulfite (20 mL), diluted with water (20 mL) and extracted with $CH_2Cl_2$ (2×50 mL). The combined organic phase is washed with saline (20 mL), dried over anhydrous sodium sulfate and concentrated under reduced pressure, and the product mixture is chromatographed on a Flash 40S 40 g silica gel cartridge with $MeOH/CH_2Cl_2$ (1/99). Pooling and concentration of those fractions with an $R_f$=0.5 by TLC ($MeOH/CHCl_3$, 5/95) followed by recrystallization from EtOAc/hexanes gives the title compound, mp 100–102° C.; MS (ESI+) for $C_{18}H_{24}N_2O_6S$ m/z 397 $(M+H)^+$.

Step 3: Preparation of (5R)-(−)-3-[4-(thiomorpholin-4-yl)phenyl]-2-oxo-5-oxazolidinecarboxamide S,S-dioxide The butyl (5R)-3-[4-(thiomorpholin-4-yl)phenyl]-2-oxo-5-oxazolidinecarboxylate S,S-dioxide (Step 2, 400 mg, 1.01 mmol) is treated with 7N ammonia in methanol (10.1 mL) under $N_2$, and the mixture is stirred at ambient temperature for 25 mins. The resulting slurry is then diluted with diethyl ether (5 mL) and filtered to give the title compound, mp 226–228° C.; MS (ESI−) for $C_{14}H_{17}N_3O_5S$ m/z 338 $(M-H)^-$; $[\alpha]^{25}_D$ −22 (c 0.94, DMSO).

Example 20

(5R)-(−)-3-[3-Fluoro-4-(thiomorpholin-4-yl)phenyl]-2-oxo-5-oxazolidinecarboxamide S,S-dioxide

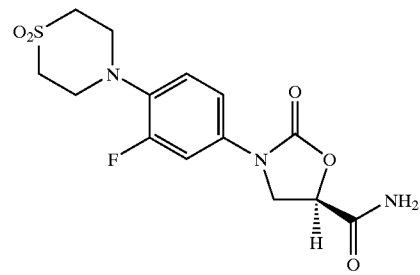

Step 1: Preparation of butyl (5R)-3-[3-fluoro-4-(thiomorpholin-4-yl)phenyl]-2-oxo-5-oxazolidinecarboxylate Following the general procedure of EXAMPLE 18, Step 1, and making non-critical variations but substituting 3-fluoro-4-(4-thiomorpholinyl)aniline (See *J. Med. Chem.* 1996, 39(3), 680–685) for 4-(4-thiomorpholinyl)aniline, the title compound is obtained, mp 128–130° C.; MS (ESI+) for $C_{18}H_{23}N_2O_4FS$ m/z 383 $(M+H)^+$.

Step 2: Preparation of butyl (5R)-3-[3-fluoro-4-(thiomorpholin-4-yl)phenyl]-2-oxo-5-oxazolidinecarboxylate S,S-dioxide Following the general procedure of EXAMPLE 18, Step 2, and making non-critical variations but substituting butyl (5R)-3-[3-fluoro-4-(thiomorpholin-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate, the title compound is obtained, mp 169–171° C. (dec.); MS (ESI+) for $C_{18}H_{23}N_2O_6FS$ m/z 415 $(M+H)^+$.

Step 3: Preparation of (5R)-(−)-3-[3-fluoro-4-(thiomorpholin-4-yl)phenyl]-2-oxo-5-oxazolidinecarboxamide S,S-dioxide Following the general procedure of EXAMPLE 18, Step 3, and making non-critical variations but substituting butyl (5R)-3-[3-fluoro-4-(thiomorpholin-4-yl)phenyl]-2-oxo-5-oxazolidinecarboxylate S,S-dioxide (Step 2) for butyl (5R)-3-[4-(thiomorpholin-4-yl)phenyl]-2-oxo-5-oxazolidinecarboxylate S,S-dioxide, the title compound is obtained, mp 245–247° C. (dec.); MS (ESI+) for $C_{14}H_{16}N_3O_5FS$ m/z 358 $(M+H)^+$; $[\alpha]^{25}_D$ −22 (c 0.92, DMSO).

Example 21

(5R)-(−)-3-[3-Fluoro-4-(thiomorpholin-4-yl)phenyl]-2-oxo-5-oxazolidinecarboxamide S-oxide

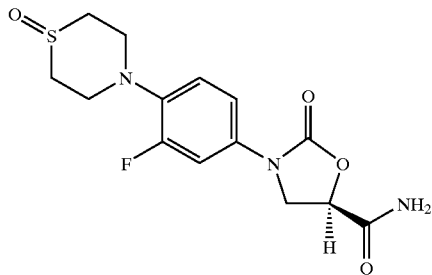

Step 1: Preparation of butyl (5R)-3-[3-fluoro-4-(thiomorpholin-4-yl)phenyl]-2-oxo-5-oxazolidinecarboxylate S-oxide A solution of sodium periodate (265 mg, 1.24 mmol) in water (5 mL) is treated with a slurry of butyl (5R)-3-[3-fluoro-4-(thiomorpholin-4-yl)phenyl]-2-oxo-5-oxazolidinecarboxylate (EXAMPLE 20, Step 1, 450 mg, 1.18 mmol) in methanol (24 mL), and the mixture is stirred at ambient temperature for 23 h. The resulting mixture is diluted with water (20 mL) and saline (20 mL) and extracted with $CH_2Cl_2$ (2×40 mL), and the combined organic phase is dried over anhydrous sodium sulfate and concentrated under reduced pressure. The residue is chromatographed on a Flash 40S 40 g silica gel cartridge, eluting with a gradient of $MeOH/CH_2Cl_2$ (1/99–2/98), and those fractions with an $R_f$=0.37 by TLC ($MeOH/CHCl_3$, 5/95) are pooled and concentrated and the residue recrystallized from EtOAc/hexanes to give the title compound, mp 128–129° C.; MS (ESI+) for $C_{18}H_{23}N_2O_5FS$ m/z 399 $(M+H)^+$.

Step 2: Preparation of (5R)-(−)-3-[3-fluoro-4-(thiomorpholin-4-yl)phenyl]-2-oxo-5-oxazolidinecarboxamide S-oxide Following the general procedure of EXAMPLE 18, Step 3, and making non-critical variations, but substituting (5R)-3-[3-fluoro-4-(thiomorpholin-4-yl)phenyl]-2-oxo-5-oxazolidinecarboxamide S-oxide (Step 1) for butyl (5R)-3-[4-(thiomorpholin-4-yl)phenyl]-2-oxo-5-oxazolidinecarboxylate S,S-dioxide and purifying the product by trituration and filtration from hot acetonitrile, the title compound is obtained, mp 264–266° C. (dec.); MS (ESI+) for $C_{14}H_{16}N_3O_4FS$ m/z 342 $(M+H)^+$; $[\alpha]^{25}_D$ −22 (c 0.39, DMSO).

Example 22

(5R)-(−)-3-[3,5-Difluoro-4-(thiomorpholin-4-yl)phenyl]-2-oxo-5-oxazolidinecarboxamide S-oxide

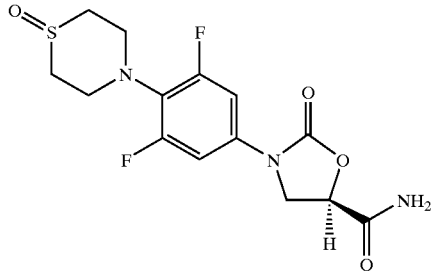

Step 1: Preparation of 4-(2,6-difluoro-4-nitrophenyl)thiomorpholine

A solution of 3,4,5-trifluoronitrobenzene (5.00 g, 28.24 mmol) in acetonitrile (60 mL) is cooled to 0° C. and treated with N,N-diisopropylethylamine (7.38 mL, 42.35 mmol) followed by thiomorpholine (2.98 mL, 29.65 mmol). The ice bath is removed and the reaction mixture stirred at room temperature under nitrogen for approximately 24 h, during which additional thiomorpholine (0.1 eq) is added. The solvent is removed under reduced pressure, and the residue is diluted with ethyl acetate, washed with 1N hydrochloric acid (until the washings are acidic), saturated aqueous sodium bicarbonate and saline, dried over anhydrous sodium sulfate, and concentrated under reduced pressure to give the title compound, mp 104–105° C.

Step 2: Preparation of 3,5-difluoro-4-(4-thiomorpholinyl)aniline

A solution of 4-(2,6-difluoro-4-nitrophenyl)thiomorpholine (3.00 g, 11.5 mmol) in tetrahydrofuran (60 mL) is added to a Parr bottle containing a mixture of Raney nickel (1 g) in water (15 mL) under $N_2$, and the reaction mixture is shaken on a Parr apparatus under a hydrogen atmosphere at 40 psi for 24 hrs. The catalyst is removed by filtration through Celite, rinsing with tetrahydrofuran and water, the filtrate is diluted with water (50 mL) and EtOAc (50 mL), and the layers are separated. The organic phase is washed with saline (25 mL), dried over anhydrous magnesium sulfate and concentrated under reduced pressure, and the resulting oil is chromatogtaphed on a Flash 40M 90 g silica gel cartridge eluting with EtOAc/heptane (15/85). Pooling and concentration of those fractions with an $R_f$=0.19 by TLC (EtOAc/hexanes, 25/75) gives the title compound, mp 85–86° C.; MS (ESI+) for $C_{10}H_{12}N_2F_2S$ m/z 231 $(M+H)^+$.

Step 3: Preparation of butyl (5R)-3-[3,5-difluoro-4-(thiomorpholin-4-yl)phenyl]-2-oxo-5-oxazolidinecarboxylate Following the general procedure of EXAMPLE 18, Step 1, and making non-critical variations but substituting 3,5-difluoro-4-(4-thiomorpholinyl)aniline (Step 2) for 4-(4-thiomorpholinyl)aniline, the title compound is obtained, mp 102–103° C.; MS (ESI+) for $C_{18}H_{22}N_2O_4F_2S$ m/z 401 $(M+H)^+$.

Step 4: Preparation of butyl (5R)-3-[3,5-difluoro-4-(thiomorpholin-4-yl)phenyl]-2-oxo-5-oxazolidinecarboxylate S-oxide Following the general procedure of EXAMPLE 21, Step 1, and making non-critical variations but substituting butyl (5R)-3-[3,5-difluoro-4-(thiomorpholin-4-yl)phenyl]-2-oxo-5-oxazolidinecarboxylate (Step 3) for butyl (5R)-3-[4-(thiomorpholin-4-yl)phenyl]-2-oxo-5-oxazolidinecarboxylate, the title compound is obtained, mp 114–116° C.; MS (ESI+) for $C_{18}H_{22}N_2O_5F_2S$ m/z 417 $(M+H)^+$.

Step 5: Preparation of (5R)-(−)-3-[3,5-difluoro-4-(thiomorpholin-4-yl)phenyl]-2-oxo-5-oxazolidinecarboxamide S-oxide Following the general procedure of EXAMPLE 18, Step 3, and making non-critical variations, but substituting (5R)-3-[3,5-difluoro-4-(thiomorpholin-4-yl)phenyl]-2-oxo-5-oxazolidinecarboxamide S-oxide (Step 4) for butyl (5R)-3-[4-(thiomorpholin-4-yl)phenyl]-2-oxo-5-oxazolidinecarboxylate S,S-dioxide, the title compound is obtained, mp 273–276° C. (dec.); MS (ESI+) for $C_{14}H_{15}N_3O_4F_2S$ m/z 360 $(M+H)^+$; $[\alpha]^{25}_D$ −24 (c 0.96, DMSO).

Example 23

(5R)-3-[3-Fluoro-4-(cis-tetrahydro-1-oxido-2H-thiopyran-4-yl)phenyl]-2-oxo-5-oxazolidinecarboxamide

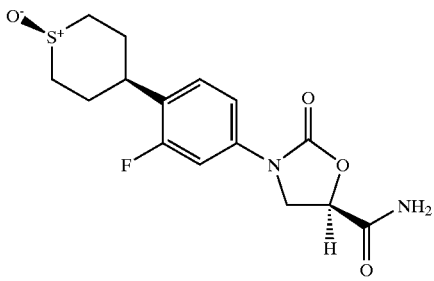

Step 1: Preparation of 2-methylpropyl [3-fluoro-4-(tetrahydro-2H-thiopyran-4-yl)phenyl]carbamate A solution of 2-methylpropyl [3-fluoro-4-hydroxy-2H-thiopyran-4-yl)phenyl]carbamate (See *Org. Proc. Res. Dev.* 2001, 5, 80–83, 4.00 g, 12.2 mmol) in trifluoroacetic acid (19 mL, 244 mmol) under $N_2$ is treated with triethylsilane (5.85 mL, 36.6 mmol) dropwise, stirred for 1 h, and then added dropwise to saturated aqueous potassium carbonate (250 mL) with vigorous stirring. The mixture is extracted with diethyl ether (200 mL), and the organic phase is washed with water (2×50 mL) and saline (50 mL), dried over anhydrous magnesium sulfate and concentrated under reduced pressure. Trituration and filtration from diethyl ether/hexanes or ethyl acetate/hexanes gives the title compound, $^1$H NMR (CDCl$_3$, 400 MHz) δ 7.26 (m, 1H), 7.11 (t, 1H), 6.97 (m, 1H), 6.59 (bs, 1H), 3.95 (d, 2H), 2.85 (m, 3H), 2.68 (m, 2H), 2.09 (m, 2H), 1.98 (m, 1H), 1.84 (m, 2H), 0.96 (d, 6H).

Step 2: Preparation of 3-fluoro-4-(tetrahydro-2H-thiopyran-4-yl)benzenamine

A mixture of 2-methylpropyl [3-fluoro-4-(tetrahydro-2H-thiopyran-4-yl)phenyl]carbamate (Step 1, 2.12 g, 6.81 mmol) in ethylene glycol (25 mL) is treated with aqueous potassium hydroxide (45%, 25.5 g, 204 mmol) with vigorous stirring, and the mixture is heated to 95° C. and stirred at this temperature for 18 h. The reaction is then cooled to ambient temperature and diluted with water (50 mL) and $CH_2Cl_2$ (100 mL), the layers are separated, and the organic phase is washed with water (50 mL) and saline (20 mL), dried over anhydrous sodium sulfate and concentrated under reduced pressure. The crude product is chromatographed on a Flash 40M 90 g silica gel cartridge with a gradient of EtOAc/heptane (15/85–25/75), and those fractions with an $R_f$=0.32 by TLC (EtOAc/hexanes, 25/75) are pooled and concentrated to give the title compound, mp 96–98° C.; MS (ESI+) for $C_{11}H_{14}NFS$ m/z 212 (M+H)$^+$.

Step 3: Preparation of butyl (5R)-3-[3-fluoro-4-(tetrahydro-2H-thiopyran-4-yl)phenyl]-2-oxo-5-oxazolidinecarboxylate Following the general procedure of EXAMPLE 18, Step 1, and making non-critical variations but substituting 3-fluoro-4-(tetrahydro-2H-thiopyran-4-yl)benzenamine (Step 2) for 4-(4-thiomorpholinyl)aniline, the title compound is obtained, mp 98–100° C.; MS (ESI+) for $C_{19}H_{24}NO_4FS$ m/z 382 (M+H)$^+$.

Step 4: Preparation of butyl (5R)-3-[3-fluoro-4-(cis-tetrahydro-1-oxido-2H-thiopyran-4-yl)phenyl]-2-oxo-5-oxazolidinecarboxylate Following the general procedure of EXAMPLE 21, Step 1, and making non-critical variations but substituting butyl (5R)-3-[3-fluoro-4-(tetrahydro-2H-thiopyran-4-yl)phenyl]-2-oxo-5-oxazolidinecarboxylate (Step 3) for butyl (5R)-3-[4-(thiomorpholin-4-yl)phenyl]-2-oxo-5-oxazolidinecarboxylate, a mixture of the cis and trans sulfoxide products in approximately a 2:1 ratio is obtained. Subsequent purification by preparative HPLC (Chiralcel OD column, EtOH eluent) followed by recrystallization from EtOAc/hexanes provides the title compound, mp 142–145° C.; MS (ESI+) for $C_{19}H_{24}NO_5FS$ m/z 398 (M+H)$^+$.

Step 5: Preparation of (5R)-3-[3-fluoro-4-(cis-tetrahydro-1-oxido-2H-thiopyran-4-yl)phenyl]-2-oxo-5-oxazolidinecarboxamide Following the general procedure of EXAMPLE 18, Step 3, and making non-critical variations, but substituting butyl (5R)-3-[3-fluoro-4-(cis-tetrahydro-1-oxido-2H-thiopyran-4-yl)phenyl]-2-oxo-5-oxazolidinecarboxylate (Step 4) for butyl (5R)-3-[4-(thiomorpholin-4-yl)phenyl]-2-oxo-5-oxazolidinecarboxylate S,S-dioxide and purifying the product by trituration and filtration from hot methanol and acetonitrile, the title compound is obtained, mp 279–281° C. (dec.); MS (ESI+) for $C_{15}H_{17}N_2O_4FS$ m/z 341 (M+H)$^+$.

Example 24

(5R)-3-[3-Fluoro-4-(trans-tetrahydro-1-oxido-2H-thiopyran-4-yl)phenyl]-2-oxo-5-oxazolidinecarboxamide

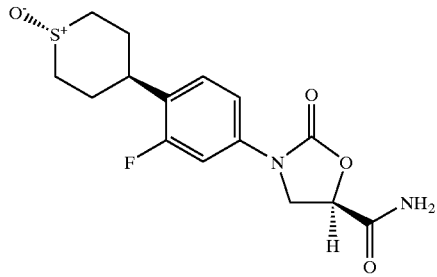

Step 1: Preparation of butyl (5R)-3-[3-fluoro-4-(trans-tetrahydro-1-oxido-2H-thiopyran-4-yl)phenyl]-2-oxo-5-oxazolidine Following the general procedure of EXAMPLE 21, Step 1, and making non-critical variations but substituting butyl (5R)-3-[3-fluoro-4-(tetrahydro-2H-thiopyran-4-yl)phenyl]-2-oxo-5-oxazolidinecarboxylate (EXAMPLE 23, Step 3) for butyl (5R)-3-[4-(thiomorpholin-4-yl)phenyl]-2-oxo-5-oxazolidinecarboxylate, a mixture of the cis and trans sulfoxide products in approximately a 2:1 ratio is obtained. Subsequent purification by preparative HPLC (Chiralcel OD column, EtOH eluent) followed by recrystallization from EtOAc/hexanes provides the title compound, mp 133–136° C.; MS (ESI+) for $C_{19}H_{24}NO_5FS$ m/z 398 (M+H)$^+$.

Step 2: Preparation of (5R)-3-[3-fluoro-4-(trans-tetrahydro-1-oxido-2H-thiopyran-4-yl)phenyl]-2-oxo-5-oxazolidinecarboxamide Following the general procedure of EXAMPLE 18, Step 3, and making non-critical variations, but substituting butyl (5R)-3-[3-fluoro-4-(trans-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound is obtained, mp 201–203° C.; MS (ESI+) for $C_{15}H_{17}N_2O_4FS$ m/z 341 (M+H)$^+$.

Example 25

(5R)-(−)-3-[4-(tetrahydro-2H-thiopyran-4-yl)phenyl]-2-oxo-5-oxazolidinecarboxamide S,S-dioxide

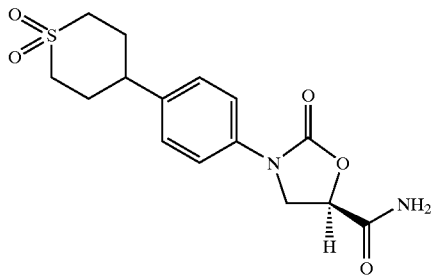

Step 1: Preparation of 2-methylpropyl 4-bromophenylcarbamate

A solution of 4-bromoaniline (10.0 g, 58.1 mmol) in tetrahydrofuran (230 mL) is treated with sodium bicarbonate (9.77 g, 116.2 mmol) and water (100 mL) followed by isobutyl chloroformate (8.3 mL, 63.9 mmol), and the mixture is stirred at ambient temperature for 2 h. The mixture is then diluted with water (100 mL) and EtOAc (100 mL), the layers are separated, and the organic phase is washed with water (50 mL) and saline (50 mL), dried over anhydrous magnesium sulfate and concentrated under reduced pressure. Recrystallization of the resulting solid from EtOAc/hexanes provides the title compound, mp 95–96° C.; MS (ESI−) for $C_{11}H_{14}NO_2Br$ m/z 270 (M−H)$^-$.

Step 2: Preparation of 2-methylpropyl [4-(tetrahydro-4-hydroxy-2H-thiopyran-4-yl)phenyl]carbamate A solution of 2-methylpropyl 4-bromophenylcarbamate (Step 1, 10.0 g, 36.7 mmol) in anhydrous tetrahydrofuran (184 mL) at −78° C. under $N_2$ is treated n-butyllithium (1.6M in hexanes, 48.2 mL, 77.1 mmol) dropwise over 20 mins, and the mixture is stirred at −78° C. for 45 mins. The resulting slurry is then treated with a solution of tetrahydro-2H-thiopyran-4-one (4.48 g, 38.5 mmol) in anhydrous tetrahydrofuran (38 mL) dropwise over 5 mins to give an opaque mixture which is allowed to slowly warm to 0° C. with stirring over approximately 2.5 h. The mixture is then quenched by the slow addition of saturated aqueous ammonium chloride (75 mL), water (75 mL) is added, and the layers are separated. The organic phase is washed with water (50 mL) and saline (50 mL), dried over anhydrous magnesium sulfate and concentrated under reduced pressure, and the crude product is recrystallized from EtOAc/hexanes to give the title compound, mp 150–151° C.; MS (ESI−) for $C_{16}H_{23}NO_3S$ m/z 308 (M−H)$^-$.

Step 3: Preparation of 2-methylpropyl [4-(tetrahydro-2H-thiopyran-4-yl)phenyl]carbamate Following the general procedure of EXAMPLE 23, Step 1, and making non-critical variations but substituting 2-methylpropyl [4-(tetrahydro-4-hydroxy-2H-thiopyran-4-yl)phenyl]carbamate (Step 2) for 2-methylpropyl [3-fluoro-4-(tetrahydro-4-hydroxy-2H-thiopyran-4-yl)phenyl]carbamate and purifying the product by recrystallization from EtOAc/hexanes, the title compound is obtained, mp 126–128° C.; MS (ESI−) for $C_{16}H_{23}NO_2S$ m/z 292 (M−H)$^-$.

Step 4: Preparation of 4-(tetrahydro-2H-thiopyran-4-yl)benzenamine

Following the general procedure of EXAMPLE 23, Step 2, and making non-critical variations but substituting 2-methylpropyl [4-(tetrahydro-2H-thiopyran-4-yl)phenyl]carbamate (Step 3) for 2-methylpropyl [3-fluoro-4-(tetrahydro-2H-thiopyran-4-yl)phenyl]carbamate, the title compound (ESI+) for $C_{11}H_{15}NS$ m/z 194 (M+H)$^+$.

Step 5: Preparation of butyl (5R)-3-[4-(tetrahydro-2H-thiopyran-4-yl)phenyl]-2-oxo-5-oxazolidinecarboxylate Following the general procedure of EXAMPLE 18, Step 1, and making non-critical variations but substituting 4-(tetrahydro-2H-thiopyran-4-yl)benzenamine (Step 4) for 4-(4-thiomorpholinyl)aniline, the title compound is obtained, mp 94–96° C.; MS (ESI+) for $C_{19}H_{25}NO_4S$ m/z 364 (M+H)$^+$.

Step 6: Preparation of butyl (5R)-3-[4-(tetrahydro-2H-thiopyran-4-yl)phenyl]-2-oxo-5-oxazolidinecarboxylate S,S-dioxide Following the general procedure of EXAMPLE 18, Step 2, and making non-critical variations but substituting butyl (5R)-3-[4-(tetrahydro-2H-thiopyran-4-yl)phenyl]-2-oxo-5-oxazolidinecarboxylate (Step 5) for butyl (5R)-3-[4-(thiomorpholin-4-yl)phenyl]-2-oxo-5-oxazolidinecarboxylate, the title compound is obtained, mp 176–179° C.; MS (ESI+) for $C_{19}H_{25}NO_6S$ m/z 396 (M+H)$^+$.

Step 7: Preparation of (5R)-(−)-3-[4-(tetrahydro-2H-thiopyran-4-yl)phenyl]-2-oxo-5-oxazolidinecarboxamide S,S-dioxide Following the general procedure of EXAMPLE 18, Step 3, and making non-critical variations, but substituting butyl (5R)-3-[4-(tetrahydro-2H-thiopyran-4-yl)phenyl]-2-oxo-5-oxazolidinecarboxylate S,S-dioxide (Step 6) for butyl (5R)-3-[4-(thiomorpholin-4-yl)phenyl]-2-oxo-5-oxazolidinecarboxylate S,S-dioxide, the title compound is obtained, mp 211–212° C.; MS (ESI−) for $C_{15}H_{18}N_2O_5S$ m/z 337 (M−H)$^-$; $[\alpha]^{25}_D$ −19 (c 0.95, DMSO).

Example 26

(5R)-3-[4-(cis-tetrahydro-1-oxido-2H-thiopyran-4-yl)phenyl]-2-oxo-5-oxazolidinecarboxamide

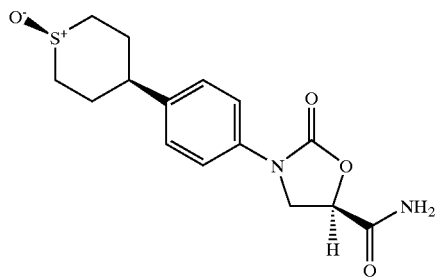

Step 1: Preparation of butyl (5R)-3-[4-(cis-tetrahydro-1-oxido-2H-thiopyran-4-yl)phenyl]-2-oxo-5-oxazolidinecarboxylate Following the general procedure of EXAMPLE 21, Step 1, and making non-critical variations but substituting butyl (5R)-3-[4-(tetrahydro-2H-thiopyran-4-yl)phenyl]-2-oxo-5-oxazolidinecarboxylate (EXAMPLE 25, Step 5) for butyl (5R)-3-[4-(thiomorpholin-4-yl)phenyl]-2-oxo-5-oxazolidinecarboxylate, a mixture of the cis and trans sulfoxide products in approximately a 2:1 ratio is obtained. Subsequent purification by preparative HPLC (Chiralcel OD column, EtOH eluent) followed by recrystallization from EtOAc/hexanes provides the title compound, mp 127–130° C.; MS (ESI+) for $C_{19}H_{25}NO_5S$ m/z 380 (M+H)$^+$.

Step 2: Preparation of (5R)-3-[4-(cis-tetrahydro-1-oxido-2H-thiopyran-4-yl)phenyl]-2-oxo-5-oxazolidinecarboxamide Following the general procedure of EXAMPLE 18, Step 3, and making non-critical variations, but substituting butyl (5R)-3-[4-(cis-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound is obtained, mp 269–273° C. (dec.); MS (ESI–) for $C_{15}H_{18}N_2O_4S$ m/z 321 (M–H)–.

Example 27

(5R)-3-[4-(trans-Tetrahydro-1-oxido-2H-thiopyran-4-yl)phenyl]-2-oxo-5-oxazolidinecarboxamide

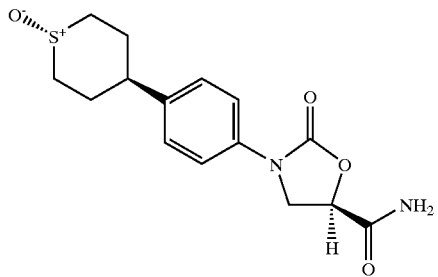

Step 1: Preparation of butyl (5R)-3-[4-(trans-tetrahydro-1-oxido-2H-thiopyran-4-yl)phenyl]-2-oxo-5-oxazolidinecarboxylate Following the general procedure of EXAMPLE 21, Step 1, and making non-critical variations but substituting butyl (5R)-3-[4-(tetrahydro-2H-thiopyran-4-yl)phenyl]-2-oxo-5-oxazolidinecarboxylate (EXAMPLE 25, Step 5) for butyl (5R)-3-[4-(thiomorpholin-4-yl)phenyl]-2-oxo-5-oxazolidinecarboxylate, a mixture of the cis and trans sulfoxide products in approximately a 2:1 ratio is obtained. Subsequent purification by preparative HPLC (Chiralcel OD column, EtOH eluent) followed by recrystallization from EtOAc/hexanes provides the title compound, mp 115–117° C.; MS (ESI+) for $C_{19}H_{25}NO_5S$ m/z 380 (M+H)+.

Step 2: Preparation of (5R)-3-[4-(trans-tetrahydro-1-oxido-2H-thiopyran-4-yl)phenyl]-2-oxo-5-oxazolidinecarboxamide Following the general procedure of EXAMPLE 18, Step 3, and making non-critical variations, but substituting butyl (5R)-3-[4-(trans-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound is obtained, mp 174–175° C.; MS (ESI–) for $C_{15}H_{18}N_2O_4S$ M/z 321 (M–H)–.

Example 28

(5R)-3-[4-(Tetrahydro-2H-thiopyran-4-yl)-3-fluorophenyl]-2-oxo-5-oxazolidinecarboxamide S,S-dioxide—Method B

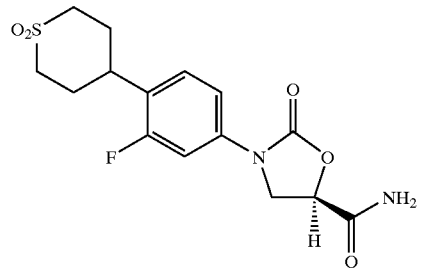

Step 1: Preparation of 2-methylpropyl [4-(tetrahydro-1,1-dioxido-2H-thiopyran-4-yl)-3-fluorophenyl]carbamate Following the general procedure of EXAMPLE 18, Step 2, and making non-critical variations but substituting 2-methylpropyl [4-(tetrahydro-2H-thiopyran-4-yl)-3-fluorophenyl]carbamate (EXAMPLE 23, Step 1) for butyl (5R)-3-[4-(thiomorpholin-4-yl)phenyl]-2-oxo-5-oxazolidinecarboxylate, the title compound is obtained, $^1$H NMR (CDCl$_3$) (δ) 7.36 (bd, 1H), 7.14 (t, 1H), 6.99 (m, 1H), 6.70 (bs, 1H), 3.95 (d, 2H), 3.14 (m, 4H), 3.07 (m, 1H), 2.38 (m, 2H), 2.18 (m, 2H), 1.95 (m, 1H), 0.96 (d, 6H).

Step 2: Preparation of (5R)-3-[4-(tetrahydro-2H-thiopyran-4-yl)-3-fluorophenyl]-5-hydroxymethyl-2-oxazolidinone S,S-dioxide A solution of 2-methylpropyl [4-(tetrahydro-1,1-dioxido-2H-thiopyran-4-yl)-3-fluorophenyl]carbamate (Step 1, 2.00 g, 5.82 mmol) in dry tetrahydrofuran at –78° C. under N$_2$ is treated with n-butyllithium (1.6M in hexanes, 3.82 mL, 6.11 mmol) dropwise and stirred at –78° C. for 45 mins. Then, (R)-glycidyl butyrate (0.86 mL, 6.11 mmol) is added dropwise, and the resulting mixture is stirred at –78° C. for 30 mins and at ambient temperature for 2.75 days. The reaction mixture is then quenched with saturated aqueous ammonium chloride (15 mL), diluted with water (15 mL) and EtOAc (25 mL), and the layers are separated. The organic phase is diluted with small amounts of methylene chloride, methanol and tetrahydrofuran in an attempt to dissolve a precipitate that had formed and is then washed with water (20 mL) and saline (20 mL), dried over anhydrous sodium sulfate and concentrated under reduced pressure. The resulting solid is then diluted with hot methanol/EtOAc (1:5, 100 mL), followed by hexanes (150 mL), and filtered to give the title compound, $^1$H NMR (DMSO) δ 7.51 (dd, 1H), 7.37 (t, 1H), 7.30 (m, 1H), 5.21 (t, 1H), 4.70 (m, 1H), 4.07 (t, 1H), 3.81 (dd, 1H), 3.65 (m, 1H), 3.55 (m, 1H), 3.37 (m, 2H), 3.20 (m, 1H), 3.10 (m, 2H), 2.15 (m, 2H), 2.03 (m, 2H).

Step 3: Preparation of methyl (5R)-3-[4-(tetrahydro-2H-thiopyran-4-yl)-3-fluorophenyl]-2-oxo-5-oxazolidinecarboxylate S,S-dioxide A mixture of ruthenium(III) trichloride (29 mg, 0.139 mmol, 4 mol %), sodium periodate (3.21 g, 15.0 mmol), and sodium dihydrogen phosphate monohydrate (2.60 g, 18.8 mmol) in water/methylene chloride (10:1, 21 mL) is treated with a suspension of (5R)-3-[4-(tetrahydro-2H-thiopyran-4-yl)-3-fluorophenyl]-5-hydroxymethyl-2-oxazolidinone S,S-dioxide (Step 2, 1.20 g, 3.49 mmol) in acetonitrile (35 mL), and the resulting mixture is stirred at ambient temperature for 24 h and is then adjusted to pH 2 with aqueous hydrochloric acid (1M) and extracted with methylene chloride (3×100 mL). The combined organic phase is dried over anhydrous sodium sulfate and concentrated under reduced pressure, and the residue is flushed through a Flash 40M 90 g silica gel cartridge with a gradient of $CH_3CN/CH_2Cl_2$ (20/80–40/60) containing 1% formic acid. Those fractions containing the carboxylic acid intermediate (920 mg total) are pooled and concentrated, and the white solid is dissolved in methanol (25 mL) and treated with 3 to 4 drops of concentrated sulfuric acid. The resulting mixture is stirred at ambient temperature for 4 h and is then concentrated under reduced pressure and chromatographed on a Flash 40S 40 g silica gel cartridge, eluting with a gradient of MeOH/ $CH_2Cl_2$ (1/99–2/98). Pooling and concentration of those fractions with an $R_f$=0.53 by TLC (MeOH/$CH_2Cl_2$, 5/95) provides the title compound as an amorphous solid, $^1H$ NMR (CDCl$_3$) δ 7.50 (dd, 1H), 7.25 (t, 1H), 7.15 (m, 1H), 5.09 (dd, 1H), 4.27 (t, 1H), 4.13 (dd, 1H), 3.88 (s, 3H), 3.15 (m, 4H), 3.11 (m, 1H), 2.40 (m, 2H), 2.19 (m, 2H).

Step 4: Preparation of (5R)-3-[4-(tetrahydro-2H-thiopyran-4-yl)-3-fluorophenyl]-2-oxo-5-oxazolidinecarboxamide S,S-dioxide Following the general procedure of EXAMPLE 18, Step 3, and making non-critical variations but substituting methyl (5R)-3-[4-(tetrahydro-2H-thiopyran-4-yl)-3-fluorophenyl]-2-oxo-5-oxazolidinecarboxylate S,S-dioxide (Step 3) for butyl (5R)-3-[4-(thiomorpholin-4-yl)phenyl]-2-oxo-5-oxazolidinecarboxylate S,S-dioxide and purifying the product by trituration and filtration from (5% MeOH/$CH_2Cl_2$)/ $Et_2O$, the title compound is obtained, mp 231–234° C. (dec.); MS (ESI−) for $C_{15}H_{17}FN_2O_5S$ m/z 355 (M−H)$^-$.

Example 29

(5R)-(−)-3-(2,3-Dihydro-3-methyl-2-oxo-6-benzothiazolyl)-2-oxo-5-oxazolidinecarboxamide

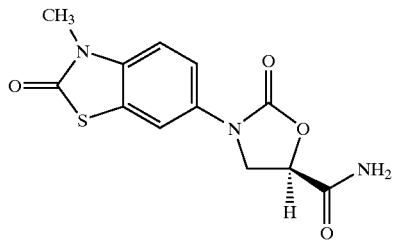

Step 1: Preparation of 6-amino-3-methyl-2(3H)-benzothiazolone

A mixture of 6-nitro-3-methyl-2-benzothiazolinone (*J. Heterocyclic Chem.* 1992, 29, 1069–1076, 4.85 g, 23.1 mmol) and 10% palladium-on-carbon (491 mg, 0.461 mmol) in a mixture of MeOH (45 mL) and tetrahydrofuran (45 mL) is shaken under a 40 psi hydrogen atmosphere on a Parr apparatus for 17 h. The catalyst is removed by filtration through a pad of Celite, and the filtrate is concentrated under reduced pressure and triturated with ethyl acetate/hexanes. Filtration then provides the title compound, mp 188–190° C.; MS (ESI+) for $C_8H_8N_2OS$ m/z 181 (M+H)$^+$.

Step 2: Preparation of butyl (5R)-3-(2,3-dihydro-3-methyl-2-oxo-6-benzothiazolyl)-2-oxo-5-oxazolidinecarboxylate Following the general procedure of EXAMPLE 18, Step 1, and making non-critical variations but substituting 6-amino-3-methyl-2(3H)-benzothiazolone (Step 1) for 4-(4-thiomorpholinyl)aniline, the title compound is obtained, mp 85–87° C.; MS (ESI+) for $C_{16}H_{18}N_2O_5S$ m/z 351 (M+H)$^+$.

Step 3: Preparation of (5R)-(−)-3-(2,3-dihydro-3-methyl-2-oxo-6-benzothiazolyl)-2-oxo-5-oxazolidinecarboxamide The butyl (5R)-3-(2,3-dihydro-3-methyl-2-oxo-6-benzothiazolyl)-2-oxo-5-oxazolidinecarboxylate (Step 2, 685 mg, 1.95 mmol) is treated with 7N ammonia in MeOH (19 mL) with vigorous stirring, and the mixture is diluted with additional MeOH (20 mL) and tetrahydrofuran (20 mL) and stirred at ambient temperature for 1 h. The resulting slurry is concentrated under reduced pressure and then triturated and filtered from acetone to give the title compound, mp 274–276° C. (dec.); MS (ESI−) for $C_{12}H_{11}N_3O_4S$ m/z 292 (M−H)$^-$; [α]$^{25}_D$−27 (c 0.98, DMSO).

Example 30

(5R)-(−)-3-(2,3-Dihydro-3-ethyl-2-oxo-6-benzothiazolyl)-2-oxo-5-oxazolidinecarboxamide

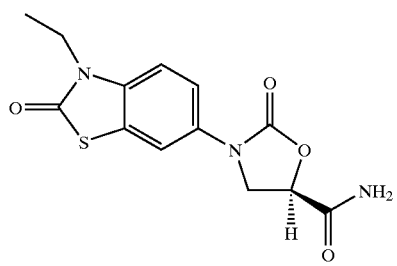

Step 1: Preparation of 6-nitro-3-ethyl-2(3H)-benzothiazolone

A solution of 6-nitro-2-benzothiazolinone (2.5 g, 12.7 mmol) in anhydrous N,N-dimethylformamide (25 mL) under $N_2$ is treated with 1,8-diazabicyclo[5.4.0]undec-7-ene (2.48 mL, 16.6 mmol) dropwise followed by iodoethane (1.22 mL, 15.3 mmol). Following a slight exotherm, the reaction mixture is stirred at ambient temperature for 21 h, diluted with water (20 mL) and filtered to give the title compound, mp 200–203° C.

Step 2: Preparation of 6-amino-3-ethyl-2(3H)-benzothiazolone

Following the general procedure of EXAMPLE 29, Step 1, and making non-critical variations but substituting 6-nitro-3-ethyl-2(3H)-benzothiazolone (Step 1) for 6-nitro-3-methyl-2(3H)-benzothiazolone, the title compound is obtained, mp 132–133° C.; MS (ESI+) for $C_9H_{10}N_2OS$ m/z 195 (M+H)$^+$.

Step 3: Preparation of butyl (5R)-3-(2,3-dihydro-3-ethyl-2-oxo-6-benzothiazolyl)-2-oxo-5-oxazolidinecarboxylate A solution of 6-amino-3-ethyl-2(3H)-benzothiazolone (Step 2, 790 mg, 4.07 mmol), butyl (2R)-glycidate (0.880 g, 6.10 mmol) and lithium triflate (0.952 g, 6.10 mmol) in acetonitrile (16 mL) is stirred at 60° C. under $N_2$ for 18 h. Solvent is removed under reduced pressure, and the residue is taken up in MeOH/$CH_2Cl_2$ (5/95, 50 mL), washed with water (50 mL) and saline (20 mL), dried over anhydrous sodium sulfate and concentrated under reduced pressure to give the crude amino alcohol intermediate [$R_f$=0.37 by TLC, EtOAc/hexanes (50/50)] which is carried forward without further purification. This intermediate is then dissolved in acetonitrile (41 mL) and treated with 1,1'-carbonyldiimidazole (0.989 g, 6.10 mmol), and the reaction mixture is stirred at ambient temperature for approximately 3 days and then concentrated under reduced pressure. The product mixture is taken up in MeOH/$CH_2Cl_2$ (10/90, 50 mL), washed with 0.1M hydrochloric acid (2×30 mL) and saline (20 mL), dried over anhydrous sodium sulfate, concentrated under reduced pressure and chromatographed on a Flash 40M 90 g silica gel cartridge with a gradient of EtOAc/hexanes (25/75–50/50). Those fractions with an $R_f=0.35$ by TLC (EtOAc/hexanes, 50/50) are pooled and concentrated to give the title compound, mp 99–102° C.; MS (ESI+) for $C_{17}H_{20}N_2O_5S$ m/z 365 (M+H)$^+$.

Step 4: Preparation of (5R)-(−)-3-(2,3-dihydro-3-ethyl-2-oxo-6-benzothiazolyl)-2-oxo-5-oxazolidinecarboxamide The butyl (5R)-3-(2,3-dihydro-3-ethyl-2-oxo-6-benzothiazolyl)-2-oxo-5-oxazolidinecarboxylate (Step 3, 500 mg, 1.37 mmol) is treated with 7N ammonia in MeOH (14 mL) with vigorous stirring, and the mixture is diluted with additional MeOH (20 mL) and stirred at ambient temperature for 30 mins. The resulting slurry is filtered to give the title compound, mp 211–212.5° C.; MS (ESI+) for $C_{13}H_{13}N_3O_4S$ m/z 308 (M+H)$^+$; $[\alpha]^{25}_D$ −25 (c 0.92, DMSO).

Example 31

(5R)-(−)-3-(2,3-Dihydro-3-isopropyl-2-oxo-6-benzothiazolyl)-2-oxo-5-oxazolidinecarboxamide

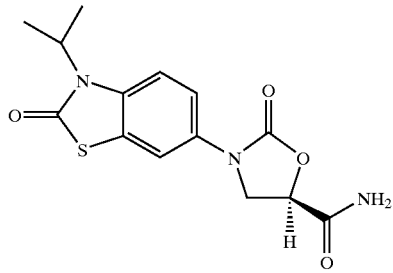

Step 1: Preparation of 6-nitro-3-isopropyl-2(3H)-benzothiazolone

A stirred solution of 6-nitro-2-benzothiazolinone (5.0 g, 25.5 mmol) in anhydrous N,N-dimethylformamide (51 mL) under $N_2$ is treated with 1,8-diazabicyclo[5.4.0]undec-7-ene (4.96 mL, 33.1 mmol) dropwise. Following a slight exotherm, the reaction mixture is heated up to 50° C. and treated with 2-iodopropane (12.7 mL, 127 mmol). The resulting mixture is quickly heated up to 75° C., stirred at this temperature for 40 mins, cooled to ambient temperature and diluted with ice (100 mL) and water (100 mL). The precipitate is isolated by filtration and recrystallized from ethyl acetate/hexanes to give the title compound, mp 138–142° C.

Step 2: Preparation of 6-amino-3-isopropyl-2(3H)-benzothiazolone

Following the general procedure of EXAMPLE 29, Step 1, and making non-critical variations but substituting 6-nitro-3-isopropyl-2(3H)-benzothiazolone (Step 1) for 6-nitro-3-methyl-2(3H)-benzothiazolone, the title compound is obtained, mp 146–148° C.

Step 3: Preparation of methyl (5R)-3-(2,3-dihydro-3-isopropyl-2-oxo-6-benzothiazolyl)-2-oxo-5-oxazolidinecarboxylate A vigorously stirred slurry of 6-amino-3-isopropyl-2(3H)-benzothiazolone (Step 2, 2.90 g, 13.9 mmol) and methyl (2R)-glycidate (1.49 g, 14.6 mmol) in anhydrous acetonitrile (7 mL) under $N_2$ is heated up to 70° C., lithium triflate (2.28 g, 14.6 mmol) is added, and the resulting homogeneous mixture is heated up to rapid reflux (95–100° C. heating bath) and monitored by HPLC. After 1 h, solvent is removed under reduced pressure, and the residue is taken up in MeOH/CH$_2$Cl$_2$ (5/95, 50 mL), washed with water (50 mL) and saline (25 mL), dried over anhydrous sodium sulfate and concentrated under reduced pressure to give the crude amino alcohol intermediate. This intermediate is then dissolved in acetonitrile (70 mL) and treated with 1,1'-carbonyldiimidazole (3.38 g, 20.9 mmol), and the reaction mixture is stirred at ambient temperature overnight and then concentrated under reduced pressure. The residue is taken up in CH$_2$Cl$_2$ (100 mL), washed with 0.1M hydrochloric acid (2×50 mL) and saline (50 mL), dried over anhydrous sodium sulfate and concentrated under reduced pressure. Trituration and filtration from MeOH then affords the title compound, mp 161–162° C.; MS (ESI+) for $C_{15}H_{16}N_2O_5S$ m/z 337 (M+H)$^+$.

Step 4: Preparation of (5R)-(−)-3-(2,3-dihydro-3-isopropyl-2-oxo-6-benzothiazolyl)-2-oxo-5-oxazolidinecarboxamide Following the general procedure of EXAMPLE 18, Step 3, and making non-critical variations but substituting methyl (5R)-3-(2,3-dihydro-3-isopropyl-2-oxo-6-benzothiazolyl)-2-oxo-5-oxazolidinecarboxylate (Step 3) for butyl (5R)-3-[4-(thiomorpholin-4-yl)phenyl]-2-oxo-5-oxazolidinecarboxylate S,S-dioxide, the title compound is obtained, mp 183–184.5° C.; MS (ESI+) for $C_{14}H_{15}N_3O_4S$ m/z 322 (M+H)$^+$; $[\alpha]^{25}_D$ −25 (c 0.90, DMSO).

Example 32

(5R)-(−)-N-Methyl-3-(2,3-dihydro-3-methyl-2-oxo-6-benzothiazolyl)-2-oxo-5-oxazolidinecarboxamide

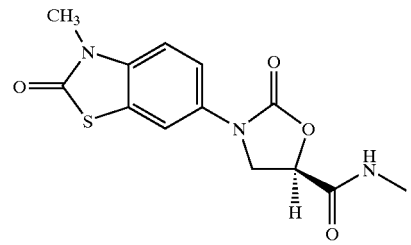

The butyl (5R)-3-(2,3-dihydro-3-methyl-2-oxo-6-benzothiazolyl)-2-oxo-5-oxazolidinecarboxylate (EXAMPLE 29, Step 2, 300 mg, 0.856 mmol) is treated with 2N methylamine in MeOH (8.6 mL) with vigorous stirring, and the mixture is diluted with additional MeOH (10 mL) and stirred at ambient temperature for 1 h. The resulting slurry is filtered to give the title compound, mp 264–267° C.; MS (ESI+) for $C_{13}H_{13}N_3O_4S$ m/z 308 (M+H)$^+$; $[\alpha]^{25}_D$ −44 (c 0.92, DMSO).

Example 33

(5R)-(−)-N-Ethyl-3-(2,3-dihydro-3-methyl-2-oxo-6-benzothiazolyl)-2-oxo-5-oxazolidinecarboxamide

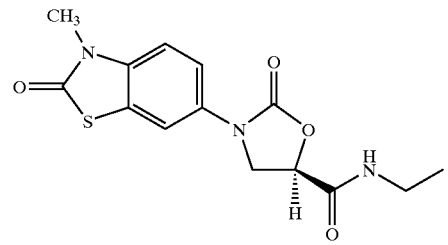

Following the general procedure of EXAMPLE 32 and making non-critical variations but substituting 2M ethylamine in MeOH for 2M methylamine in MeOH, the title compound is obtained, mp 224.5–226° C.; MS (ESI−) for $C_{14}H_{15}N_3O_4S$ m/z 320 (M−H)$^+$; $[\alpha]^{25}_D$ −46 (c 0.89, DMSO).

Example 34

(5R)-(−)-N-(2-Hydroxyethyl)-3-(2,3-dihydro-3-methyl-2-oxo-6-benzothiazolyl)-2-oxo-5-oxazolidinecarboxamide

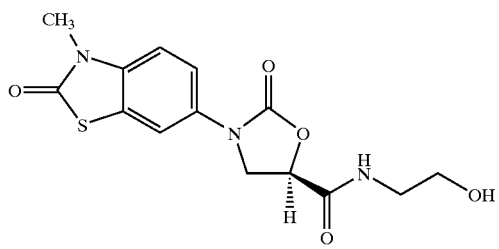

A solution of butyl (5R)-3-(2,3-dihydro-3-methyl-2-oxo-6-benzothiazolyl)-2-oxo-5-oxazolidinecarboxylate (EXAMPLE 29, Step 2, 300 mg, 0.856 mmol) in acetonitrile (3.4 mL) is treated with ethanolamine (103 μL, 1.71 mmol) and stirred at ambient temperature for 18 h. Solvent is removed under reduced pressure, and the crude product is triturated and filtered from hot ethyl acetate to give the title compound, mp 217–219° C.; MS (ESI+) for $C_{14}H_{15}N_3O_5S$ m/z 338 (M+H)+; $[\alpha]^{25}_D$ −43 (c 0.99, DMSO).

Example 35

(5R)-N-(2-Fluoroethyl)-3-(2,3-dihydro-3-methyl-2-oxo-6-benzothiazolyl)-2-oxo-5-oxazolidinecarboxamide

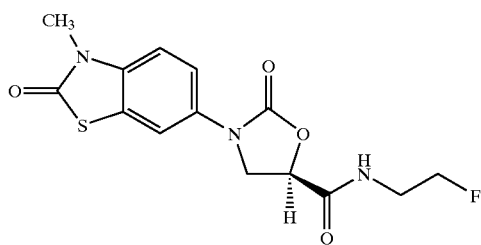

A solution of butyl (5R)-3-(2,3-dihydro-3-methyl-2-oxo-6-benzothiazolyl)-2-oxo-5-oxazolidinecarboxylate (EXAMPLE 29, Step 2, 985 mg, 2.81 mmol) in pyridine (5.5 mL) in a thick-walled, screw-cap vial is treated with fluoroethylamine hydrochloride (2.20 g, 22.1 mmol), and the stirred reaction mixture is placed in an oil bath maintained at 90° C. for 24 h. The mixture is then cooled to ambient temperature, diluted with $CH_2Cl_2$ (50 mL), washed with 0.2 M hydrochloric acid (25 mL portions, until the washings are at pH<2) and saline (25 mL), dried over anhydrous sodium sulfate and concentrated under reduced pressure, and the residue is chromatographed on a Flash 40M 90 g silica gel cartridge with $MeOH/CH_2Cl_2$ (1/99–2.5/97.5). Those fractions with an $R_f$=0.32 by TLC ($MeOH/CHCl_3$, 5/95) are pooled and concentrated and the residue triturated and filtered from MeOH to give the title compound, mp 201–203° C.; MS (ESI−) for $C_{14}H_{14}N_3O_4FS$ m/z 338 (M−H)−.

Example 36

(5R)-(−)-N-Methyl-3-(2,3-dihydro-3-ethyl-2-oxo-6-benzothiazolyl)-2-oxo-5-oxazolidinecarboxamide

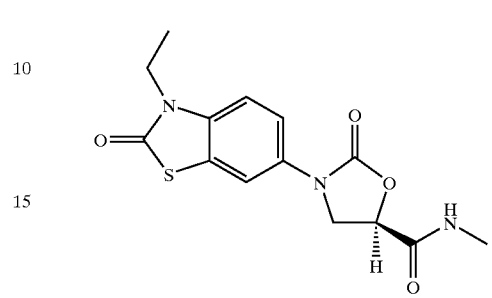

The butyl (5R)-3-(2,3-dihydro-3-ethyl-2-oxo-6-benzothiazolyl)-2-oxo-5-oxazolidinecarboxylate (EXAMPLE 30, Step 3, 300 mg, 0.823 mmol) is treated with 2N methylamine in MeOH (8.2 mL), and the mixture is stirred at ambient temperature for 1 h. The resulting slurry is diluted with $Et_2O$ (10 mL) and filtered to give the title compound, mp 227–229° C.; MS (ESI+) for $C_{14}H_{15}N_3O_4S$ m/z 322 (M+H)+; $[\alpha]^{25}_D$ −43 (c 0.93, DMSO).

Example 37

(5R)-(−)-N-Methyl-3-(2,3-dihydro-3-isopropyl-2-oxo-6-benzothiazolyl)-2-oxo-5-oxazolidinecarboxamide

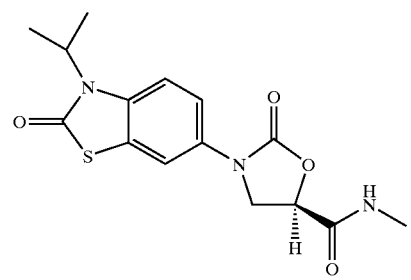

The methyl (5R)-3-(2,3-dihydro-3-isopropyl-2-oxo-6-benzothiazolyl)-2-oxo-5-oxazolidinecarboxylate (EXAMPLE 31, Step 3, 2.89 g, 8.59 mmol) is treated with 2N methylamine in MeOH (8.2 mL), and the mixture is stirred at ambient temperature for 45 mins and then filtered to give the title compound, mp 172–173.5° C.; MS (ESI+) for $C_{15}H_{17}N_3O_4S$ m/z 336 (M+H)+; $[\alpha]^{25}_D$ −43 (c 0.98, DMSO).

Example 38

(5R)-(−)-3-(2,3-Dihydro-3-methyl-2-oxo-6-benzoxazolyl)-2-oxo-5-oxazolidinecarboxamide

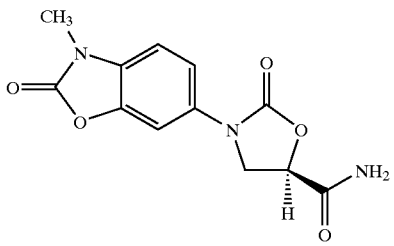

Step 1: Preparation of 6-nitro-3-methyl-2(3H)-benzoxazolone

Following the general procedure of EXAMPLE 30, Step 1, and making non-critical variations but substituting 6-nitro-2(3H)-benzoxazolone (*J. Heterocyclic Chem.* 1992, 29, 1069–1076) for 6-nitro-2-benzothiazolinone and iodomethane for iodoethane, the title compound is obtained, mp 183–185° C.

Step 2: Preparation of 6-amino-3-methyl-2(3H)-benzoxazolone

Following the general procedure of EXAMPLE 29, Step 1, and making non-critical variations but substituting 6-nitro-3-methyl-2(3H)-benzoxazolone (Step 1) for 6-nitro-3-methyl-2(3H)-benzothiazolone and using a 2- to 3-hour reaction time, the title compound is obtained, mp 151–153° C.; MS (ESI+) for $C_8H_8N_2O_2$ M/z 165 (M+H)$^+$.

Step 3: Preparation of butyl (5R)-3-(2,3-dihydro-3-methyl-2-oxo-6-benzoxazolyl)-2-oxo-5-oxazolidinecarboxylate A solution of 6-amino-3-methyl-2(3H)-benzoxazolone (Step 2, 1.00 g, 6.09 mmol), butyl 2(R)-glycidate (1.32 g, 9.14 mmol) and lithium triflate (1.43 g, 9.14 mmol) in acetonitrile (24 mL) is stirred at 65° C. under $N_2$ for 6 h and then at ambient temperature over the weekend. Solvent is removed under reduced pressure, and the residue is taken up in MeOH/CH$_2$Cl$_2$ (5/95, 50 mL), washed with water (20 mL) and saline, dried over anhydrous sodium sulfate and concentrated under reduced pressure to give the crude amino alcohol intermediate [MS (ESI+) for $C_{15}H_{20}N_2O_5$ m/z 309 (M+H)$^+$]. This intermediate is then dissolved in acetonitrile (61 mL) and treated with 1,1'-carbonyldiimidazole (1.48 g, 9.13 mmol), and the reaction mixture is stirred at ambient temperature for 18 h and then concentrated under reduced pressure. The product mixture is taken up in CH$_2$Cl$_2$ (50 mL), washed with 0.1M hydrochloric acid (2×30 mL) and saline (20 mL), dried over anhydrous sodium sulfate, concentrated under reduced pressure and chromatographed on a Flash 40M 90 g silica gel cartridge with EtOAc/CH$_2$Cl$_2$ (10/90). Those fractions with an R$_f$=0.67 by TLC (EtOAc/CH$_2$Cl$_2$, 25/75) are pooled and concentrated to give the title compound, mp 182–184° C.; MS (ESI+) for $C_{16}H_{18}N_2O_6$ m/z 335 (M+H)$^+$.

Step 4: Preparation of (5R)-(−)-3-(2,3-dihydro-3-methyl-2-oxo-6-benzoxazolyl)-2-oxo-5-oxazolidinecarboxamide Following the general procedure of EXAMPLE 30, Step 4, and making non-critical variations but substituting butyl (5R)-3-(2,3-dihydro-3-methyl-2-oxo-6-benzoxazolyl)-2-oxo-5-oxazolidinecarboxylate for butyl (5R)-3-(2,3-dihydro-3-ethyl-2-oxo-6-benzothiazolyl)-2-oxo-5-oxazolidinecarboxylate, the title compound is obtained, mp >260° C.; MS (ESI−) for $C_{12}H_{11}N_3O_5$ m/z 276 (M−H)$^−$; $[\alpha]^{25}_D$ −25 (c 0.94, DMSO).

Example 39

(5R)-(−)-3-(2,3-Dihydro-3-ethyl-2-oxo-6-benzoxazolyl)-2-oxo-5-oxazolidinecarboxamide

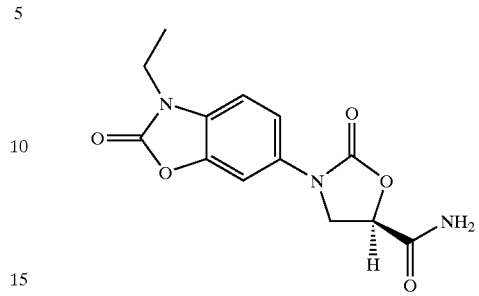

Step 1: Preparation of 6-nitro-3-ethyl-2(3H)-benzoxazolone

Following the general procedure of EXAMPLE 30, Step 1, and making non-critical variations but substituting 6-nitro-2(3H)-benzoxazolone (*J. Heterocyclic Chem.* 1992, 29, 1069–1076) for 6-nitro-2-benzothiazolinone, the title compound is obtained, mp 133–135° C.

Step 2: Preparation of 6-amino-3-ethyl-2(3H)-benzoxazolone

Following the general procedure of EXAMPLE 29, Step 1, and making non-critical variations but substituting 6-nitro-3-ethyl-2(3H)-benzoxazolone (Step 1) for 6-nitro-3-methyl-2(3H)-benzothiazolone and using a 2- to 3-hour reaction time, the title compound is obtained, mp 72–74° C.; MS (ESI+) for $C_9H_{10}N_2O_2$ m/z 179 (M+H)$^+$.

Step 3: Preparation of butyl (5R)-3-(2,3-dihydro-3-ethyl-2-oxo-6-benzoxazolyl)-2-oxo-5-oxazolidinecarboxylate Following the general procedure of EXAMPLE 38, Step 3, and making non-critical variations but substituting 6-amino-3-ethyl-2(3H)-benzoxazolone (Step 2) for 6-amino-3-methyl-2(3H)-benzoxazolone, the title compound is obtained, mp 155–157° C.; MS (ESI+) for $C_{17}H_{20}N_2O_6$ m/z 349 (M+H)$^+$.

Step 4: Preparation of (5R)-(−)-3-(2,3-dihydro-3-ethyl-2-oxo-6-benzoxazolyl)-2-oxo-5-oxazolidinecarboxamide Following the general procedure of EXAMPLE 30, Step 4, and making non-critical variations but substituting butyl (5R)-3-(2,3-dihydro-3-ethyl-2-oxo-6-benzoxazolyl)-2-oxo-5-oxazolidinecarboxylate for butyl (5R)-3-(2,3-dihydro-3-ethyl-2-oxo-6-benzothiazolyl)-2-oxo-5-oxazolidinecarboxylate, the title compound is obtained, mp 234–236° C.; MS (ESI+) for $C_{13}H_{13}N_3O_5$ m/z 292 (M+H)$^+$; $[\alpha]^{25}_D$ −23 (c 0.91, DMSO).

Example 40

(5R)-(−)-3-(2,3-Dihydro-3-isopropyl-2-oxo-6-benzoxazolyl)-2-oxo-5-oxazolidinecarboxamide

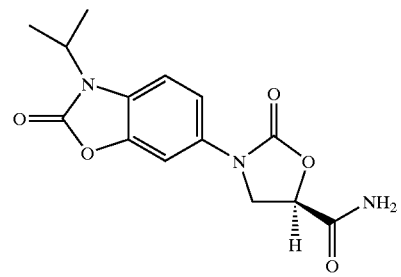

Step 1: Preparation of 2-(isopropylamino)-5-nitrophenol

A solution of 2-amino-5-nitrophenol (2.00 g, 13.0 mmol) in absolute EtOH (52 mL) and acetone (14.3 mL, 195 mmol, 15 equiv.) is treated with sodium cyanoborohydride (408 mg, 6.49 mmol), the pH is adjusted to 4.5–5.0 with glacial AcOH, and the mixture is stirred at ambient temperature for 4 days, during which time additional acetone (2×14.3 mL), sodium cyanoborohydride (3×408 mg) and glacial AcOH is added. The reaction mixture is then readjusted to pH 6, concentrated under reduced pressure, diluted with water (50 mL) and $CH_2Cl_2$ (75 mL), and the layers are separated. The organic phase is washed with saline (25 mL), dried over anhydrous sodium sulfate and concentrated under reduced pressure, and the residue is chromatographed on a Flash 40M 90 g silica gel cartridge with EtOAc/heptane (20/80). Pooling and concentration of those fractions with an $R_f$=0.59 by TLC (EtOAc/hexanes, 50/50) gives the title compound, mp 108–110° C.; MS (ESI+) for $C_9H_{12}N_2O_3$ m/z 197 $(M+H)^+$.

Step 2: Preparation of 6-nitro-3-isopropyl-2(3H)-benzoxazolone

Method A: A homogeneous mixture of 2-(isopropylamino)-5-nitrophenol (Step 1, 1.86 g, 9.48 mmol) and 1,1'-carbonyldiimidazole (2.31 g, 14.2 mmol) in anhydrous THF under $N_2$ is heated up to 60° C. and stirred at this temperature for 18 h. Solvent is then removed under reduced pressure, and the residue is taken up in $CH_2Cl_2$ (50 mL), washed with 0.1 M hydrochloric acid (2×50 mL) and saline (25 mL), dried over anhydrous sodium sulfate and concentrated under reduced pressure. Trituration and filtration from MeOH gives the title compound, mp 175–176.5° C.

Method B: Following the general procedure of EXAMPLE 31, Step 1, and making non-critical variations but substituting 6-nitro-2(3H)-benzoxazolone (*J. Heterocyclic Chem.* 1992, 29, 1069–1076) for 6-nitro-2-benzothiazolinone, the title compound is obtained.

Step 3: Preparation of 6-amino-3-isopropyl-2(3H)-benzoxazolone

Following the general procedure of EXAMPLE 29, Step 1, and making non-critical variations but substituting 6-nitro-3-isopropyl-2(3H)-benzoxazolone (Step 2) for 6-nitro-3-methyl-2(3H)-benzothiazolone and using a 2- to 3-hour reaction time, the title compound is obtained, MS (ESI+) for $C_{10}H_{12}N_2O_2$ m/z 193 $(M+H)^+$.

Step 4: Preparation of butyl (5R)-3-(2,3-dihydro-3-isopropyl-2-oxo-6-benzoxazolyl)-2-oxo-5-oxazolidinecarboxylate Following the general procedure of EXAMPLE 38, Step 3, and making non-critical variations but substituting 6-amino-3-isopropyl-2(3H)-benzoxazolone (Step 3) for 6-amino-3-methyl-2(3H)-benzoxazolone, the title compound is obtained, mp 86–89° C.; MS (ESI+) for $C_{18}H_{22}N_2O_6$ m/z 363 $(M+H)^+$.

Step 5: Preparation of (5R)-(−)-3-(2,3-dihydro-3-isopropyl-2-oxo-6-benzoxazolyl)-2-oxo-5-oxazolidinecarboxamide Following the general procedure of EXAMPLE 18, Step 3, and making non-critical variations but substituting butyl (5R)-3-(2,3-dihydro-3-isopropyl-2-oxo-6-benzoxazolyl)-2-oxo-5-oxazolidinecarboxylate (Step 4) for butyl (5R)-3-[4-(thiomorpholin-4-yl)phenyl]-2-oxo-5-oxazolidinecarboxylate S,S-dioxide, the title compound is obtained, mp 182.5–184° C.; MS (ESI+) for $C_{14}H_{15}N_3O_5$ m/z 306 $(M+H)^+$.

Example 41

(5R)-(−)-N-Methyl-3-[4-(Tetrahydro-2H-thiopyran-4-yl)-3-fluorophenyl]-2-oxo-5-oxazolidinecarboxamide S,S-dioxide

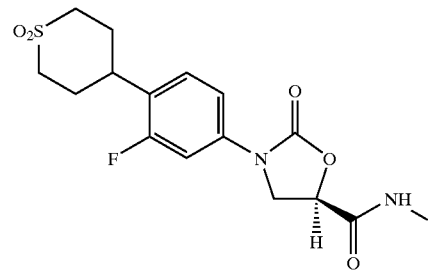

Following the general procedure of EXAMPLE 36 and making non-critical variations but substituting methyl (5R)-3-[4-(tetrahydro-2H-thiopyran-4-yl)-3-fluorophenyl]-2-oxo-5-oxazolidinecarboxylate S,S-dioxide (EXAMPLE 28, Step 3) for butyl (5R)-3-(2,3-dihydro-3-ethyl-2-oxo-6-benzothiazolyl)-2-oxo-5-oxazolidinecarboxylate, the title compound is obtained, mp 180.5–182° C.; MS (ESI+) for $C_{16}H_{19}N_2O_5FS$ m/z 371 $(M+H)^+$; $[\alpha]^{25}_D$ −34 (c 0.94, DMSO).

Example 42

(5R)-(−)-N-Methyl-3-[3,5-difluoro-4-(4-morpholinyl)phenyl]-2-oxo-5-oxazolidinecarboxamide

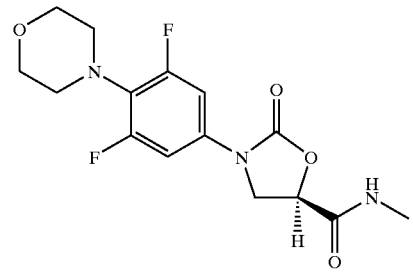

The butyl (5R)-3-[3,5-difluoro-4-(4-morpholinyl)phenyl]-2-oxo-5-oxazolidinecarboxylate (EXAMPLE 17, Step 1) is treated with 2M methylamine in MeOH (0.1 M in starting material), and the reaction mixture is stirred at ambient temperature for 30 mins and then concentrated under reduced pressure. The residue is purified by radial chromatography [4000 micron silica gel rotor; MeOH/$CH_2Cl_2$ (3/97) eluent] to give the title compound, mp 179–181° C.; MS (ESI+) for $C_{15}H_{17}N_3O_4F_2$ m/z 342 $(M+H)^+$; $[\alpha]^{25}_D$ −40 (c 0.95, DMSO).

Example 43

(5R)-(–)-N-Methyl-3-[3,5-difluoro-4-(thiomorpholin-4-yl)phenyl]-2-oxo-5-oxazolidinecarboxamide S-oxide

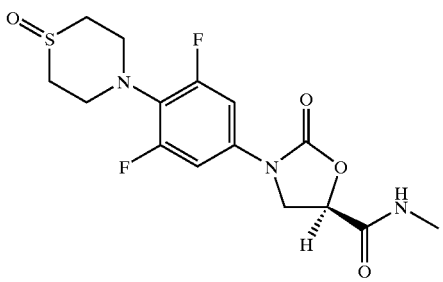

Step 1: Preparation of methyl (5R)-3-[3,5-difluoro-4-(thiomorpholin-4-yl)phenyl]-2-oxo-5-oxazolidinecarboxylate A vigorously stirred slurry of 3,5-difluoro-4-(4-thiomorpholinyl)aniline (EXAMPLE 22, Step 2, 10.2 mmol) and methyl (2R)-glycidate (1.14 g, 11.2 mmol) in anhydrous acetonitrile (5 mL) under $N_2$ is heated up to 75° C., lithium triflate (1.74 g, 11.2 mmol) is added, and the resulting homogeneous mixture is heated up to rapid reflux (95–100° C. heating bath) and monitored by HPLC. After 2 h, solvent is removed under reduced pressure, and the residue is taken up in MeOH/$CH_2Cl_2$ (10/90, 60 mL), washed with water (30 mL) and saline (20 mL), dried over anhydrous sodium sulfate and concentrated under reduced pressure to give the crude amino alcohol intermediate which is then purified by silica gel chromatography [Flash 40M 90 g cartridge; EtOAc/$CH_2Cl_2$ (5/95–10/90) eluent]. This intermediate is dissolved in acetonitrile (47 mL) and treated with 1,1'-carbonyldiimidazole (1.16 g, 7.12 mmol, 1.5 eq.), and the reaction mixture is stirred at ambient temperature overnight and then concentrated down to 10–15 mL under reduced pressure and stirred for an additional 5 days. Solvent is removed under reduced pressure, and the residue is taken up in $CH_2Cl_2$ (100 mL), washed with 0.1M hydrochloric acid (2×25 mL) and saline (25 mL), dried over anhydrous sodium sulfate and concentrated under reduced pressure. The crude product is then chromatographed on a Flash 40M 90 g silica gel cartridge, eluting with EtOAc/$CH_2Cl_2$ (5/95), and those fractions with an $R_f$=0.53 by TLC (EtOAc/hexanes, 50/50) are pooled and concentrated to afford the title compound, mp 99–101° C.; MS (ESI+) for $C_{15}H_{16}N_2O_4F_2S$ m/z 359 (M+H)$^+$.

Step 2: Preparation of methyl (5R)-3-[3,5-difluoro-4-(thiomorpholin-4-yl)phenyl]-2-oxo-5-oxazolidinecarboxylate S-oxide Following the general procedure of EXAMPLE 21, Step 1, and making non-critical variations but substituting methyl (5R)-3-[3,5-difluoro-4-(thiomorpholin-4-yl)phenyl]-2-oxo-5-oxazolidinecarboxylate (Step 1) for butyl (5R)-3-[3-fluoro-4-(thiomorpholin-4-yl)phenyl]-2-oxo-5-oxazolidinecarboxylate and purifying the crude product mixture by recrystallization from EtOAc/hexanes, the title compound is obtained, mp 123.5–125° C.; MS (ESI+) for $C_{15}H_{16}N_2O_5F_2S$ m/z 375 (M+H)$^+$.

Step 3: Preparation of (5R)-(–)-N-methyl-3-[3,5-difluoro-4-(thiomorpholin-4-yl)phenyl]-2-oxo-5-oxazolidinecarboxamide S-oxide Following the general procedure of EXAMPLE 36 and making non-critical variations but substituting methyl (5R)-3-[3,5-difluoro-4-(thiomorpholin-4-yl)phenyl]-2-oxo-5-oxazolidinecarboxylate S-oxide (Step 2) for butyl (5R)-3-(2,3-dihydro-3-ethyl-2-oxo-6-benzothiazolyl)-2-oxo-5-oxazolidinecarboxylate, the title compound is obtained, mp 237–241° C.; MS (ESI+) for $C_{15}H_{17}N_3O_4F_2S$ m/z 374 (M+H)$^+$; $[\alpha]^{25}_D$ –38 (c 0.94, DMSO).

Example 44

(5R)-(–)-N-Methyl-3-[3,5-difluoro-4-(thiomorpholin-4-yl)phenyl]-2-oxo-5-oxazolidinecarboxamide S,S-dioxide

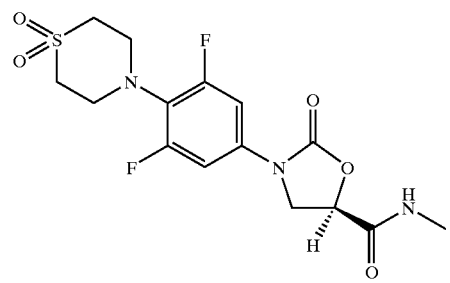

Step 1: Preparation of methyl (5R)-3-[3,5-difluoro-4-(thiomorpholin-4-yl)phenyl]-2-oxo-5-oxazolidinecarboxylate S,S-dioxide Following the general procedure of EXAMPLE 18, Step 2, and making non-critical variations but substituting methyl (5R)-3-[3,5-difluoro-4-(thiomorpholin-4-yl)phenyl]-2-oxo-5-oxazolidinecarboxylate (EXAMPLE 43, Step 1) for butyl (5R)-3-[4-(thiomorpholin-4-yl)phenyl]-2-oxo-5-oxazolidinecarboxylate and purifying the crude product mixture by recrystallization from EtOAc/hexanes, the title compound is obtained, mp 158.5–161° C.; MS (ESI+) for $C_{15}H_{16}N_2O_6F_2S$ m/z 391 (M+H)$^+$.

Step 2: Preparation of (5R)-(–)-N-methyl-3-[3,5-difluoro-4-(thiomorpholin-4-yl)phenyl]-2-oxo-5-oxazolidinecarboxamide S,S-dioxide Following the general procedure of EXAMPLE 36 and making non-critical variations but substituting methyl (5R)-3-[3,5-difluoro-4-(thiomorpholin-4-yl)phenyl]-2-oxo-5-oxazolidinecarboxylate S,S-dioxide (Step 1) for butyl (5R)-3-(2,3-dihydro-3-ethyl-2-oxo-6-benzothiazolyl)-2-oxo-5-oxazolidinecarboxylate, the title compound is obtained, mp 243–246° C.; MS (ESI–) for $C_{15}H_{17}N_3O_5F_2S$ m/z 388 (M–H)$^+$; $[\alpha]^{25}_D$ –37 (c 1.01, DMSO).

Example 45

(5R)-3-[3,5-Difluoro-4-(Tetrahydro-2H-thiopyran-4-yl)phenyl]-2-oxo-5-oxazolidinecarboxamide S,S-dioxide

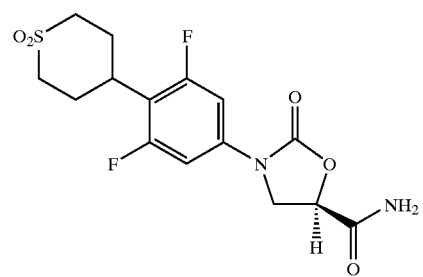

Step 1: Preparation of 1-(3,5-difluorophenyl)-2,5-dimethyl-1H-pyrrole

To the solution of 3,5-difluoroaniline (3.53 g, 26.8 mmol) in toluene/THF (1:1, 60 mL) is added acetonylacetone (3.24 mL, 26.8 mmol) and p-toluenesulfonic acid monohydrate (0.168 g). The reaction mixture is heated at reflux for 3 h, concentrated under reduced pressure, diluted with $CH_2Cl_2$ (60 mL), washed with water (3×10 mL) and saline (2×20 mL), dried over anhydrous sodium sulfate and concentrated under reduced pressure. Purification by chromatography on a Biotage Flash 40M 90 g silica gel cartridge eluting with EtOAc/Hexanes (5/95–10/90) affords the title compound, mp 55–56° C.

Step 2: Preparation of 4-[4-(2,5-dimethyl-1H-pyrrol-1-yl)-2,6-difluorophenyl]tetrahydro-2H-thiopyran-4-ol To the solution of 1-(3,5-difluorophenyl)-2,5-dimethyl-1H-pyrrole (Step 1, 16.7 g, 80.6 mmol) in anhydrous THF (161 mL) at −78° C. under $N_2$ is added n-BuLi (1.6 M in hexanes, 51.8 mL, 82.9 mmol) dropwise. After stirring at −78° C. for 1 h, the reaction mixture is treated with tetrahydrothiopyran-4-one (5.35 g, 46.1 mmol) in anhydrous THF (46 mL) dropwise and then stirred at −78° C. for 2 h and at 0° C. for 3 h. The reaction is then quenched by the slow addition of saturated aqueous ammonium chloride (50 mL), diluted with $H_2O$ (50 mL) and $Et_2O$ (50 mL) and the layers are separated. The organic phase is washed with $H_2O$ (50 mL) and saline (50 mL), dried over anhydrous magnesium sulfate, and concentrated under reduced pressure, and the residue is purified by silica gel chromatography (650 mL, 10–20% EtOAc/Hexanes eluent) to give the title compound, mp 125–126° C.; MS (ESI+) for $C_{17}H_{19}F_2NOS$ m/z 324 (M+H)$^+$.

Step 3: Preparation of 1-[4-(3,6-dihydro-2H-thiopyran-4-yl)-3,5-difluorophenyl]-2,5-dimethyl-1H-pyrrole A stirred solution of 4-[4-(2,5-dimethyl-1H-pyrrol-1-yl)-2,6-difluorophenyl]tetrahydro-2H-thiopyran-4-ol (Step 2, 1.617 g, 5.00 mmol) and p-toluenesulfonic acid monohydrate (0.107 g) in benzene (20 mL) is heated at reflux using a Dean-Stark trap for 5 h, during which additional p-toluenesulfonic acid monohydrate (0.342 g) is added. Solvent is then removed under reduced pressure, and the residue is taken up in $CH_2Cl_2$ (60 mL), washed with saturated aqueous $NaHCO_3$ (2×20 mL) and water (3×20 mL), dried over anhydrous sodium sulfate and concentrated under reduced pressure. Purification by chromatography on a Biotage Flash 40M 90 g silica gel cartridge, eluting with 2–5% EtOAc/Hexanes, affords the title compound, mp 118–119° C.; MS (ESI+) for $C_{17}H_{17}F_2NS$ m/z 306 (M+H)$^+$.

Step 4: Preparation of 4-(3,6-dihydro-2H-thiopyran-4-yl)-3,5-difluorobenzenamine To a stirred solution of 1-[4-(3,6-dihydro-2H-thiopyran-4-yl)-3,5-difluorophenyl]-2,5-dimethyl-1H-pyrrole (0.828 g, 2.71 mmol) in 95% ethanol/THF (10:1, 55 mL) is added hydroxylamine hydrochloride (3.77 g, 54.2 mmol) and triethylamine (3.8 mL, 27.1 mmol). The reaction mixture is heated at reflux for 2 days and then concentrated under reduced pressure, diluted with $CH_2Cl_2$ (60 mL), washed with water (3×20 mL), dried over anhydrous sodium sulfate, and concentrated under reduced pressure. Purification by chromatography on a Biotage Flash 40M 90 g silica gel cartridge, eluting with 10–20% EtOAC/Hexanes, affords the title compound, MS (ESI+) for $C_{11}H_{11}F_2NS$ m/z 228 (M+H)$^+$; $^1$H NMR (CDCl$_3$, 400 MHz) δ 6.22 (m, 2 H), 5.91 (m, 1 H), 3.83 (m, 2 H), 3.33 (m, 2 H), 2.86 (t, 2 H), 2.53 (m, 2 H).

Step 5: Preparation of isobutyl [4-(3,6-dihydro-2H-thiopyran-4-yl)-3,5-difluorophenyl]carbamate To a stirred, biphasic mixture of 4-(3,6-dihydro-2H-thiopyran-4-yl)-3,5-difluorobenzenamine (Step 4, 3.90 g, 17.2 mmol) in THF/water (2:1, 103 mL) is added sodium bicarbonate (2.88 g, 34.3 mmol) followed by isobutyl carbamate (2.45 mL, 18.9 mmol) dropwise. The reaction mixture is stirred at ambient temperature for 7 h and is then concentrated under reduced pressure, diluted with EtOAc (100 mL) and $H_2O$ (50 mL), and the layers are separated. The organic phase is washed with $H_2O$ (25 mL) and saline (25 mL), dried over anhydrous magnesium sulfate, and concentrated under reduced pressure. Purification of the residue by chromatography on a Biotage Flash 40M 90 g silica gel cartridge, eluting with 5–10% EtOAc/Hexanes, affords the title compound, mp 136–137° C.; MS (ESI-) for $C_{16}H_{19}F_2NO_2S$ m/z 326 (M-H)$^-$.

Step 6: Preparation of isobutyl [4-(tetrahydro-2H-thiopyran-4-yl)-3,5-difluorophenyl]carbamate Method A: To a stirred solution of isobutyl [4-(3,6-dihydro-2H-thiopyran-4-yl)-3,5-difluorophenyl]carbamate (Step 5, 5.62 g, 17.2 mmol) in TFA (26.5 mL, 343 mmol) is added triethylsilane (8.23 mL, 51.5 mmol), and the mixture is stirred at 70° C. for 2.2 days, during which additional triethylsilane (2×2.74 mL) is added, and at 40° C. for 2.6 days. The reaction is then cooled to ambient temperature, added slowly to saturated aqueous sodium bicarbonate (300 mL), and extracted with $Et_2O$ (200 mL). The organic layer is washed with $H_2O$ (2×50 mL) and saline (50 mL), dried over anhydrous magnesium sulfate, and concentrated under reduced pressure, and the residue is recrystallized from EtOAc/hexanes to give the title compound, mp 147–149° C.; MS (ESI-) for $C_{16}H_{21}F_2NO_2S$ m/z 328 (M-H)$^-$.

Method B: Step A: Preparation of isobutyl 3,5-difluorophenylcarbamate

Following the general procedure of Step 5, and making non-critical variations but substituting 3,5-difluoroaniline for 4-(3,6-dihydro-2H-thiopyran-4-yl)-3,5-difluoroaniline, the title compound is obtained, mp 71–74° C.; MS (ESI-) for $C_{11}H_{13}NO_2F_2$ m/z 228 (M-H)$^-$.

Step B: Preparation of isobutyl [4-(tetrahydro-4-hydroxy-2H-thiopyran-4-yl)-3,5-difluorophenyl]carbamate A stirred solution of isobutyl 3,5-difluorophenylcarbamate (Step A, 10.0 g, 43.6 mmol) and N,N,N',N'-tetramethylethylenediamine (13.7 mL, 87.3 mmol) in anhydrous THF (87 mL) at −78° C. under $N_2$ is treated n-butyllithium (1.6M in hexanes, 35.8 mL, 89.4 mmol) dropwise over 35 mins. The mixture is stirred at −78° C. for 20 mins and is then treated with a solution of tetrahydro-2H-thiopyran-4-one (5.32 g, 45.8 mmol) in anhydrous THF (15 mL) dropwise over 10 mins. After 45 mins at −78° C., the cooling bath is removed and the mixture is allowed to warm to ambient temperature and is then quenched by the slow addition of saturated aqueous ammonium chloride (50 mL). Water (50 mL) and EtOAc (100 mL) are added, the layers are separated, and the organic phase is washed with water (100 mL) and saline (50 mL), dried over anhydrous magnesium sulfate and concentrated under reduced pressure. The crude product is triturated and filtered from EtOAc (approx. 25 mL) to remove an insoluble impurity, and the filtrate is chromatographed on two Flash 40M 90 g silica gel cartridges, eluting with EtOAc/heptane (20/80). Pooling and concentration of those fractions with an R$_f$=0.26 by TLC (EtOAc/hexanes, 25/75) gives the title compound, mp 103–104° C.

Step C: Preparation of isobutyl [4-(tetrahydro-2H-thiopyran-4-yl)-3,5-difluorophenyl]carbamate Following the general procedure of Step 6, Method A, and making non-critical variations but substituting isobutyl [4-(tetrahydro-4-hydroxy-2H-thiopyran-4-yl)-3,5-difluorophenyl]carbamate (Step B) for isobutyl [4-(3,6-dihydro-2H-thiopyran-4-yl)-3,5-difluorophenyl]carbamate, the title compound is obtained.

Step 7: Preparation of 3,5-difluoro-4-(tetrahydro-2H-thiopyran-4-yl)benzeneamine Following the general procedure of EXAMPLE 23, step 2, and making non-critical variations but substituting of isobutyl [4-(tetrahydro-2H-thiopyran-4-yl)-3,5-difluorophenyl]carbamate (Step 6) for 2-methylpropyl [3-fluoro-4-(tetrahydro-2H-thiopyran-4-yl)phenyl]carbamate, the title compound is obtained, mp118–119° C.; MS (ESI–) for $C_{11}H_{13}NF_2S$ m/z 228 (M–H)⁻.

Step 8: Preparation of butyl (5R)-3-[3,5-difluoro-4-(tetrahydro-2H-thiopyran-4-yl)phenyl]-2-oxo-5-oxazolidinecarboxylate Following the general procedure of EXAMPLE 17, Step 1, and making non-critical variations but substituting 3,5-difluoro-4-(tetrahydro-2H-thiopyran-4-yl)benzenamine (Step 7) for 3,5-difluoro-4-(4-morpholinyl)aniline, the title compound is obtained, mp 86–89° C.; MS (ESI+) for $C_{19}H_{23}NO_4F_2S$ m/z 400 (M+H)⁺.

Step 9: Preparation of butyl (5R)-3-[3,5-difluoro-4-(tetrahydro-2H-thiopyran-4-yl)phenyl]-2-oxo-5-oxazolidinecarboxylate S,S-dioxide Following the general procedure of EXAMPLE 18, Step 2, and making non-critical variations but substituting butyl (5R)-3-[3,5-difluoro-4-(tetrahydro-2H-thiopyran-4-yl)phenyl]-2-oxo-5-oxazolidinecarboxylate (Step 8) for butyl (5R)-3-[4-(thiomorpholin-4-yl)phenyl]-2-oxo-5-oxazolidinecarboxylate, the title compound is obtained, mp 218–220° C.; MS (ESI+) for $C_{19}H_{23}NO_6F_2S$ m/z 432 (M+H)⁺.

Step 10: Preparation of (5R)-3-[3,5-difluoro-4-(tetrahydro-2H-thiopyran-4-yl)phenyl]-2-oxo-5-oxazolidinecarboxamide S,S-dioxide Following the general procedure of EXAMPLE 18, Step 3, and making non-critical variations but substituting butyl (5R)-3-[3,5-difluoro-4-(tetrahydro-2H-thiopyran-4-yl)phenyl]-2-oxo-5-oxazolidinecarboxamide S,S-dioxide (Step 9) for butyl (5R)-3-[4-(thiomorpholin-4-yl)phenyl]-2-oxo-5-oxazolidinecarboxylate S,S-dioxide, the title compound is obtained, mp 243–245° C.; MS (ESI–) for $C_{15}H_{16}N_2O_5F_2S$ m/z 373 (M–H)⁺.

Example 46

(5R)-(–)-3-[3,5-Difluoro-4-(cis-tetrahydro-1-oxido-2H-thiopyran-4-yl)phenyl]-2-oxo-5-oxazolidinecarboxamide

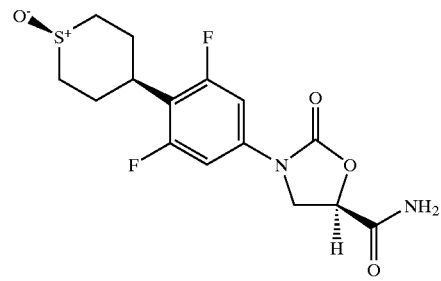

Step 1: Preparation of butyl (5R)-3-[3,5-difluoro-4-(cis-tetrahydro-1-oxido-2H-thiopyran-4-yl)phenyl]-2-oxo-5-oxazolidinecarboxylate Following the general procedure of EXAMPLE 21, Step 1, and making non-critical variations but substituting butyl (5R)-3-[3,5-difluoro-4-(tetrahydro-2H-thiopyran-4-yl)phenyl]-2-oxo-5-oxazolidinecarbonxylate (EXAMPLE 45, Step 8) for butyl (5R)-3-[4-(thiomorpholin-4-yl)phenyl]-2-oxo-5-oxazolidinecarboxylate, a mixture of the cis and trans sulfoxide products in approximately a 1:1 ratio is obtained. Subsequent purification by preparative HPLC (Chiralcel OD column, EtOH eluent) provides the title compound, MS (ESI+) for $C_{19}H_{23}NO_5F_2S$ m/z 416 (M+H)⁺;

¹H NMR (DMSO-$d_6$, 400 MHz) δ 7.33 (m, 2H), 5.34 (m, 1H), 4.35 (m, 1H), 4.16 (m, 3H), 3.18 (m, 1H), 2.92 (m, 2H), 2.81 (m, 2H), 2.62 (m, 2H), 1.61 (m, 4H), 1.35 (sext, 2H), 0.89 (t, 3H).

Step 2: Preparation of (5R)-(–)-3-[3,5-difluoro-4-(cis-tetrahydro-1-oxido-2H-thiopyran-4-yl)phenyl]-2-oxo-5-oxazolidinecarboxamide Following the general procedure of EXAMPLE 18, Step 3, and making non-critical variations, but substituting butyl (5R)-3-[3,5-difluoro-4-(cis-tetrahydro-1-oxido-2H-thiopyran-4-yl)phenyl]-2-oxo-5-oxazolidinecarboxylate (Step 1) for butyl (5R)-3-[4-(thiomorpholin-4-yl)phenyl]-2-oxo-5-oxazolidinecarboxylate S,S-dioxide, the title compound is obtained, mp 283–285° C. (dec.); MS (ESI+) for $C_{15}H_{16}N_2O_4F_2S$ m/z 359 (M+H)⁺; $[\alpha]^{25}_D$ –20 (c 0.94, DMSO).

Example 47

(5R)-(–)-3-[3,5-Difluoro-4-(trans-tetrahydro-1-oxido-2H-thiopyran-4-yl)phenyl]-2-oxo-5-oxazolidinecarboxamide

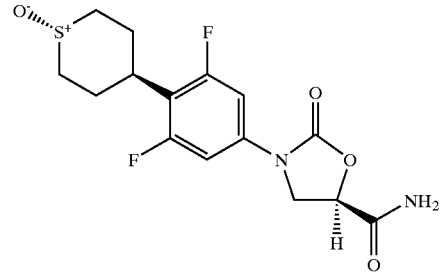

Step 1: Preparation of butyl (5R)-3-[3,5-difluoro-4-(trans-tetrahydro-1-oxido-2H-thiopyran-4-yl)phenyl]-2-oxo-5-oxazolidinecarboxylate Following the general procedure of EXAMPLE 21, Step 1, and making non-critical variations but substituting butyl (5R)-3-[3,5-difluoro-4-(tetrahydro-2H-thiopyran-4-yl)phenyl]-2-oxo-5-oxazolidinecarboxylate (EXAMPLE 45, Step 8) for butyl (5R)-3-[4-(thiomorpholin-4-yl)phenyl]-2-oxo-5-oxazolidinecarboxylate, a mixture of the cis and trans sulfoxide products in approximately a 1:1 ratio is obtained. Subsequent purification by preparative HPLC (Chiralcel OD column, EtOH eluent) provides the title compound, MS (ESI+) for $C_{19}H_{23}NO_5F_2S$ m/z 416 (M+H)$^+$;

$^1$H NMR (DMSO-d$_6$, 400 MHz) δ 7.31 (m, 2H), 5.34 (m, 1H), 4.33 (m, 1H), 4.13 (m, 3H), 3.36 (m, 2H), 3.19 (m, 1H), 2.82 (m, 2H), 2.01 (m, 4H), 1.60 (m, 2H), 1.33 (sext, 2H), 0.89 (t, 3H).

Step 2: Preparation of (5R)-(–)-3-[3,5-difluoro-4-(trans-tetrahydro-1-oxido-2H-thiopyran-4-yl)phenyl]-2-oxo-5-oxazolidinecarboxamide Following the general procedure of EXAMPLE 17, Step 2, and making non-critical variations but substituting butyl (5R)-3-[3,5-difluoro-4-(trans-tetrahydro-1-oxido-2H-thiopyran-4-yl)phenyl]-2-oxo-5-oxazolidinecarboxylate (Step 1) for butyl (5R)-3-[3,5-difluoro-4-(4-morpholinyl)phenyl]-2-oxo-5-oxazolidinecarboxylate and purifying the product by silica gel chromatography (2–5% MeOH/CH$_2$Cl$_2$ eluent), the title compound is obtained, MS (ESI+) for $C_{15}H_{16}N_2O_4F_2S$ m/z 359 (M+H)$^+$; $^1$H NMR (DMSO-d$_6$, 400 MHz) δ 7.87 (bs, 1H), 7.63 (bs, 1H), 7.33 (m, 2H), 5.04 (dd, 1H), 4.24 (t, 1H), 4.00 (dd, 1H), 3.36 (m, 2H), 3.19 (m, 1H), 2.82 (m, 2H), 2.05 (m, 4H); $[\alpha]^{25}_D$ –21 (c 0.96, DMSO).

Example 48

(5R)-N-Methyl-3-[3,5-difluoro-4-(trans-tetrahydro-1-oxido-2H-thiopyran-4-yl)phenyl]-2-oxo-5-oxazolidinecarboxamide

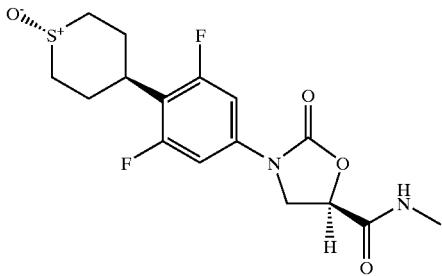

Following the general procedure of EXAMPLE 42 and making non-critical variations but substituting butyl (5R)-3-[3,5-difluoro-4-(trans-tetrahydro-1-oxido-2H-thiopyran-4-yl)phenyl]-2-oxo-5-oxazolidinecarboxylate (EXAMPLE 47, Step 1) for butyl (5R)-3-[3,5-difluoro-4-(4-morpholinyl)phenyl]-2-oxo-5-oxazolidinecarboxylate and purifying the product by silica gel chromatography (1.5–3% MeOH/CH$_2$Cl$_2$ eluent), the title compound is obtained, MS (ESI+) for $C_{16}H_{18}N_2O_4F_2S$ m/z 373 (M+H)$^+$; $^1$H NMR (DMSO-d$_6$, 400 MHz) δ 8.40 (m, 1H), 7.32 (m, 2H), 5.07 (dd, 1H), 4.24 (t, 1H), 4.00 (dd, 1H), 3.36 (m, 2H), 3.19 (m, 1H), 2.82 (m, 2H), 2.65 (d, 3H), 2.05 (m, 4H).

Example 49

(5R)-3-[(2R)-2,3-Dihydro-1-formyl-2-methyl-1H-indol-5-yl]-2-oxo-5-oxazolidinecarboxamide

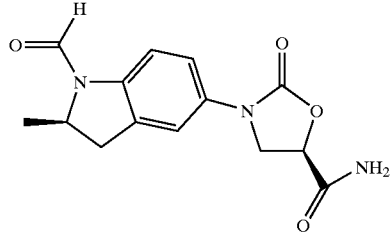

Step 1: Preparation of (2R)-2,3-dihydro-2-methyl-1H-indol-5-amine

A mixture of benzyl (2R)-5-{[(benzyloxy)carbonyl]amino}-2-methyl-2,3-dihydro-1H-indole-1-carboxylate (PCT/US00/08224; WO00/73301, 3.36 g, 8.07 mmol) and 10% palladium-on-carbon (108 mg) in THF/MeOH (1:1, 60 mL) is shaken on a Parr apparatus under a 36 psi hydrogen atmosphere overnight. The catalyst is removed by filtration through a pad of Celite, and the filtrate is concentrated under reduced pressure. Purification by chromatography on a Biotage Flash 40M 90 g silica gel cartridge (1–2% MeOH/CH$_2$Cl$_2$) affords the title compound, MS (ESI+) for $C_9H_{12}N_2$ m/z 149 (M+H)$^+$.

Step 2: Preparation of (2R)-5-(2,5-dimethyl-1H-pyrrol-1-yl)-2,3-dihydro-2-methyl-1H-indole To a stirred solution of (2R)-2,3-dihydro-2-methyl-1H-indol-5-amine (Step 1, 0.896 g, 6.05 mmol) in THF (180 mL) is added acetonylacetone (0.732 mL, 6.05 mmol) and p-toluenesulfonic acid (0.008 g). The reaction mixture is stirred at 68° C. for 6 h and then concentrated under reduced pressure, and the residue is purified by chromatography on a Biotage Flash 40M 90 g silica gel cartridge (10% EtOAc/Hexanes eluent) to give the title compound, MS (ESI+) for $C_{15}H_{18}N_2$ m/z 227 (M+H)$^+$.

Step 3: Preparation of phenylmethyl (2R)-5-(2,5-dimethyl-1H-pyrrol-1-yl)-2,3-dihydro-2-methyl-1H-indole-1-carboxylate To a stirred solution of (2R)-5-(2,5-dimethyl-1H-pyrrol-1yl)-2,3-dihydro-2-methyl-1H-indole (Step 2, 0.100 g, 0.442 mmol) in THF/H$_2$O (8:1, 4.5 mL) is added sodium bicarbonate (0.072 g, 0.884 mmol) followed by benzyl chloroformate (80 μL, 0.53 mmol) at 0° C. The reaction mixture is stirred at 0° C. for 30 mins and at ambient temperature for 2 h and is then concentrated under reduced pressure. The residue is taken up in CH$_2$Cl$_2$ (40 mL), washed with H$_2$O (2×10 mL) and saline (2×10 mL), dried over anhydrous sodium sulfate and concentrated under reduced pressure. The residue is purified by chromatography on a Biotage Flash 40S 40 g silica gel cartridge (1% EtOAc/Hexanes) to give the title compound, MS (ESI+) for $C_{23}H_{24}N_2O_2$ m/z 361 (M+H)$^+$.

Step 4: Preparation of phenylmethyl (2R)-5-amino-2,3-dihydro-2-methyl-1H-indole-1-carboxylate To a stirred solution of phenylmethyl (2R)-5-(2,5-dimethyl-1H-pyrrol-1-yl)-2,3-dihydro-2-methyl-1H-indole-1-carboxylate (Step 3, 2.11 g, 5.84 mmol) in water/ethanol (1:9, 60 mL) is added triethylamine (6.5 mL, 46.7 mmol) and hydroxylamine hydrochloride (6.49 g, 93.4 mmol). The reaction mixture is stirred at 90° C. for 20 h and is then concentrated under reduced pressure. The residue is taken up in CH$_2$Cl$_2$ (60 mL) and washed with H$_2$O (2×20 mL) and saline (2×20 mL), and the combined aqueous layer is extracted with CH$_2$Cl$_2$ (2×20 mL). The combined organic layer is dried over anhydrous sodium sulfate and concentrated under reduced pressure, and the residue is purified by chromatography on a Biotage Flash 40M 90 g silica gel cartridge (30–50% EtOAc/Hexanes eluent) to give the title compound, MS (ESI+) for C$_{17}$H$_{18}$N$_2$O$_2$ m/z 283 (M+H)$^+$.

Step 5: Preparation of phenylmethyl (2R)-2,3-dihydro-5-[(5R)-5-(methoxycarbonyl)-2-oxo-3-oxazolidinyl]-2-methyl-1H-indole-1-carboxylate Following the general procedure of EXAMPLE 38, Step 3, and making non-critical variations but substituting phenylmethyl (2R)-5-amino-2,3-dihydro-2-methyl-1H-indole-1-carboxylate (Step 4) for 6-amino-3-methyl-2(3H)-benzoxazolone and methyl 2(R)-glycidate for butyl 2(R)-glycidate, the title compound is obtained, MS (ESI+) for C$_{22}$H$_{22}$N$_2$O$_6$ m/z 433 (M+Na)$^+$.

Step 6: Preparation of methyl (5R)-3-[(2R)-2,3-dihydro-1-formyl-2-methyl-1H-indol-5-yl]-2-oxo-5-oxazolidinecarboxylate A mixture of phenylmethyl (2R)-2,3-dihydro-5-[(5R)-5-(methoxycarbonyl)-2-oxo-3-oxazolidinyl]-2-methyl-1H-indole-1-carboxylate (Step 5, 0.211 g, 0.51 mmol) and 10% palladium-on-carbon (0.006 g) in methanol/THF (1:1, 10 mL) is shaken on a Parr apparatus under a 36 psi hydrogen atmosphere for 4 h. The catalyst is removed by filtration through a pad of Celite, and the filtrate is concentrated under reduced pressure to give the methyl (5R)-3-[2(R)-2,3-dihydro-2-methyl-1H-indol-5-yl]-2-oxo-5-oxazolidinecarboxylate intermediate which is then dissolved in THF (6 mL) and treated with triethylamine (142 μL, 1.02 mmol) and 1H-benzotriazole-1-carboxaldehyde (0.092 g, 0.56 mmol). The reaction mixture is stirred at room temperature under N$_2$ for approximately 18 h, during which additional 1H-benzotriazole-1-carboxaldehyde (0.046 g, 0.28 mmol) is added concentrated under reduced pressure. The residue is taken up in CH$_2$Cl$_2$ (40 mL) and washed with H$_2$O (2×20 mL) and saline (2×20 mL). The combined aqueous layer is extracted with CH$_2$Cl$_2$ (2×20 mL), and the combined organic layer is dried over anhydrous sodium sulfate and concentrated under reduced pressure. The residue is purified by chromatography on a Biotage Flash 40M 90 g silica gel cartridge (50–100% EtOAc/Hexanes eluent) to give the title compound, MS (ESI+) for C$_{15}$H$_{16}$N$_2$O$_5$ m/z 305 (M+H)$^+$.

Step 7: Preparation of (5R)-3-[(2R)-2,3-dihydro-1-formyl-2-methyl-1H-indol-5-yl]-2-oxo-5-oxazolidinecarboxamide Following the general procedure of EXAMPLE 18, Step 3, and making non-critical variations but substituting methyl (5R)-3-[(2R)-2,3-dihydro-1-formyl-2-methyl-1H-indol-5-yl]-2-oxo-5-oxazolidinecarboxylate (Step 6) for butyl (5R)-3-[4-(thiomorpholin-4-yl)phenyl]-2-oxo-5-oxazolidinecarboxylate S,S-dioxide, the title compound is obtained, mp 228–230° C.; MS (ESI+) for C$_{14}$H$_{15}$N$_3$O$_4$ m/z 290 (M+H)$^+$.

Example 50

(5R)-3-[(2R)-2,3-Dihydro-1-(hydroxyacetyl)-2-methyl-1H-indol-5-yl]-2-oxo-5-oxazolidinecarboxamide

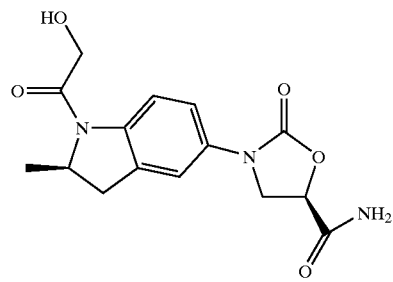

Step 1: Preparation of methyl (5R)-3-[(2R)-2,3-dihydro-1-[(phenylmethoxy)acetyl]-2-methyl-1H-indol-5-yl]-2-oxo-5-oxazolidinecarboxylate Following the general procedure of EXAMPLE 49, Step 6, and making non-critical variations but substituting benzyloxyacetyl chloride for 1H-benzotriazole-1-carboxaldehyde and purifying the product by silica gel chromatography (1–2% MeOH/CH$_2$Cl$_2$ eluent), the title compound is obtained, MS (ESI+) for C$_{23}$H$_{24}$N$_2$O$_6$ m/z 425 (M+H)$^+$.

Step 2: Preparation of methyl (5R)-3-[(2R)-2,3-dihydro-1-(hydroxyacetyl)-2-methyl-1H-indol-5-yl]-2-oxo-5-oxazolidinecarboxylate A mixture of methyl (5R)-3-[(2R)-2,3-dihydro-1-[(phenylmethoxy)acetyl]-2-methyl-1H-indol-5-yl]-2-oxo-5-oxazolidinecarboxylate (Step 1, 0.301 g, 0.71 mmol) and Pearlman's catalyst (0.032 g) in methanol (30 mL) is shaken on a Parr apparatus under a 36 psi hydrogen atmosphere for approximately 24 h, during which additional Pearlman's catalyst (0.044 g) is added. The catalyst is removed by filtration through a pad of Celite, and the filtrate is concentrated under reduced pressure. The residue is purified by chromatography on a Biotage Flash 40S silica gel cartridge (2% MeOH/CH$_2$Cl$_2$ eluent) to give the title compound, MS (ESI+) for C$_{16}$H$_{18}$N$_2$O$_6$ m/z 335 (M+H)$^+$.

Step 3: Preparation of (5R)-3-[(2R)-2,3-dihydro-1-(hydroxyacetyl)-2-methyl-1H-indol-5-yl]-2-oxo-5-oxazolidinecarboxamide Following the general procedure of EXAMPLE 18, Step 3, and making non-critical variations but substituting methyl (5R)-3-[(2R)-2,3-dihydro-1-(hydroxyacetyl)-2-methyl-1H-indol-5-yl]-2-oxo-5-oxazolidinecarboxylate (Step 2) for butyl (5R)-3-[4-(thiomorpholin-4-yl)phenyl]-2-oxo-5-oxazolidinecarboxylate S,S-dioxide, the title compound is obtained, mp 198–200° C.; MS (ESI+) for C$_{15}$H$_{17}$N$_3$O$_5$ m/z 320 (M+H)$^+$.

Example 51

(5R)-(−)-N-Methyl-3-(2,3-dihydro-3-methyl-2-oxo-6-benzoxazolyl)-2-oxo-5-oxazolidinecarboxamide

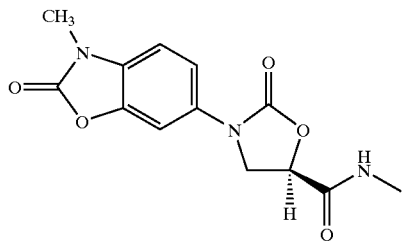

Following the general procedure of EXAMPLE 32, and making non-critical variations but substituting butyl (5R)-3-(2,3-dihydro-3-methyl-2-oxo-6-benzoxazolyl)-2-oxo-5-oxazolidinecarboxylate (EXAMPLE 38, Step 3) for butyl (5R)-3-(2,3-dihydro-3-methyl-2-oxo-6-benzothiazolyl)-2-oxo-5-oxazolidinecarboxylate, the title compound is obtained, mp 304–6° C.; MS (ESI−) for $C_{13}H_{13}N_3O_5$ m/z 290 (M−H)$^-$; $[\alpha]^{25}_D$ −34 (c 1.03, DMSO).

Example 52

(5R)-(−)-N-Methyl-3-(2,3-dihydro-3-ethyl-2-oxo-6-benzoxazolyl)-2-oxo-5-oxazolidinecarboxamide

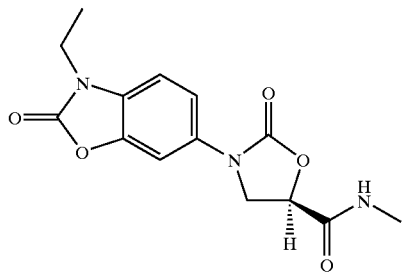

Following the general procedure of EXAMPLE 32, and making non-critical variations but substituting butyl (5R)-3-(2,3-dihydro-3-ethyl-2-oxo-6-benzoxazolyl)-2-oxo-5-oxazolidinecarboxylate (EXAMPLE 39, Step 3) for butyl (5R)-3-(2,3-dihydro-3-methyl-2-oxo-6-benzothiazolyl)-2-oxo-5-oxazolidinecarboxylate, the title compound is obtained, mp 263–5° C.; MS (ESI−) for $C_{14}H_{15}N_3O_5$ m/z 304 (M−H)$^-$; $[\alpha]^{25}_D$ −39 (c 0.94, DMSO).

Example 53

(5R)-(−)-N-Methyl-3-(2,3-dihydro-3-isopropyl-2-oxo-6-benzoxazolyl)-2-oxo-5-oxazolidinecarboxamide

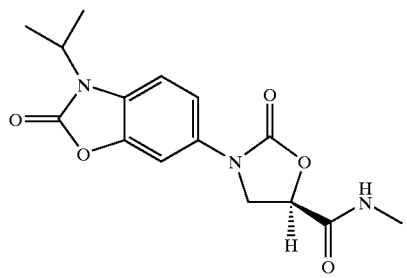

Following the general procedure of EXAMPLE 32, and making non-critical variations but substituting butyl (5R)-3-(2,3-dihydro-3-isopropyl-2-oxo-6-benzoxazolyl)-2-oxo-5-oxazolidinecarboxylate (EXAMPLE 40, Step 4) for butyl (5R)-3-(2,3-dihydro-3-methyl-2-oxo-6-benzothiazolyl)-2-oxo-5-oxazolidinecarboxylate, the title compound is obtained, mp 216–8° C.; MS (ESI−) for $C_{15}H_{17}N_3O_5$ m/z 318 (M−H)$^-$; $[\alpha]^{25}_D$ −39 (c 0.95, DMSO).

Example 54

(5R)-3-[4-(5,7-Dihydro-6H-pyrrolo[3,4-b]pyridin-6-yl)-3-fluorophenyl]-2-oxo-5-oxazolidinecarboxamide

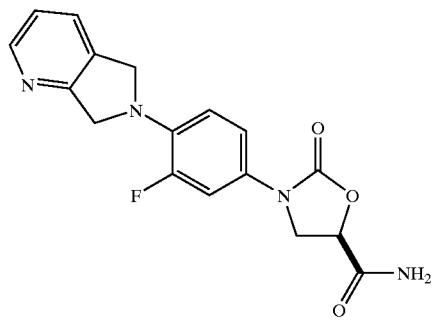

Step 1: Preparation of methyl (5R)-3-[4-(5,7-dihydro-6H-pyrrolo[3,4-b]pyridin-6-yl)-3-fluorophenyl]-2-oxo-5-oxazolidinecarboxylate Following the general procedure of EXAMPLE 31, Step 3, and making non-critical variations but substituting 5,7-dihydro-6-(2-fluoro-4-aminophenyl)-6H-pyrrolo[3,4-b]pyridine (WO 01/42242; PCT/US00/21093) for 6-amino-3-isopropyl-2(3H)-benzothiazolone and purifying the product by silica gel chromatography (20–30% EtOAc/hexanes eluent), the title compound is obtained, mp 239–240° C. (dec.); MS (ESI+) for $C_{18}H_{16}N_3O_4F$ m/z 358 (M+H)$^+$.

Step 2: Preparation of (5R)-3-[4-(5,7-dihydro-6H-pyrrolo[3,4-b]pyridin-6-yl)-3-fluorophenyl]-2-oxo-5-oxazolidinecarboxamide The methyl (5R)-3-[4-(5,7-dihydro-6H-pyrrolo[3,4-b]pyridin-6-yl)-3-fluorophenyl]-2-oxo-5-oxazolidinecarboxylate (Step 1) is suspended in saturated ammonia in methanol (25 mL), stirred at ambient temperature for 4 h and filtered to give the title compound, mp 257° C. (dec.); MS (ESI+) for $C_{17}H_{15}N_4O_3F$ m/z 343 (M+H)$^+$.

Example 55

(5R)-N-Methyl-3-[4-(5,7-dihydro-6H-pyrrolo[3,4-b]pyridin-6-yl)-3-fluorophenyl]-2-oxo-5-oxazolidinecarboxamide

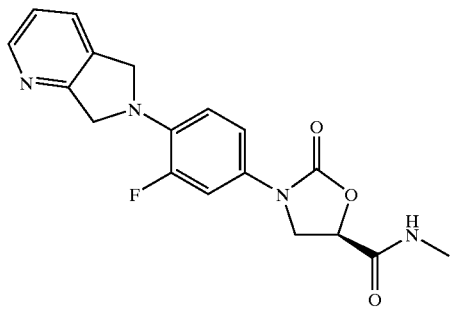

Following the general procedure of EXAMPLE 32, and making non-critical variations but substituting methyl (5R)-3-[4-(5,7-dihydro-6H-pyrrolo[3,4-b]pyridin-6-yl)-3-fluorophenyl]-2-oxo-5-oxazolidinecarboxylate (EXAMPLE 54, Step 1) for butyl (5R)-3-(2,3-dihydro-3-methyl-2-oxo-6-benzothiazolyl)-2-oxo-5-oxazolidinecarboxylate, the title compound is obtained, mp 275° C. (dec.); MS (ESI+) for $C_{18}H_{17}N_4O_3F$ m/z 357 (M+H)$^+$.

Example 56

(5R)-3-[4-(cis-1-Imino-1-oxido-1,1,3,4,5,6-hexahydro-2H-thiopyran-4-yl)-3-fluorophenyl]-2-oxo-5-oxazolidinecarboxamide

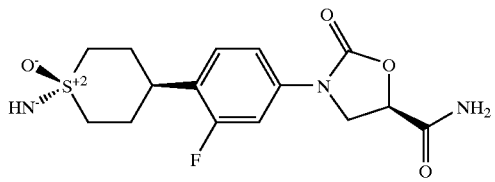

Step 1: Preparation of 3-fluoro-4-(cis-tetrahydro-1-oxido-2H-thiopyran-4-yl)aniline A suspension of 2.07 g of 2-methylpropyl [3-fluoro-4-(cis-tetrahydro-1-oxido-2H-thiopyran-4-yl)phenyl]carbamate (U.S. Pat. No. 6,239,283) in 25 ml ethylene glycol is treated with 5 ml 45% aqueous KOH, placed under $N_2$ and heated with stirring to 90° C. for 10 h. The resulting dark brown colored solution is cooled to ambient temperature, diluted with water and extracted with 5% MeOH/CH$_2$Cl$_2$. The organic extracts are combined, dried (NaSO$_4$), filtered and concentrated to give the crude product which is chromatographed over silica gel eluting first with 5% MeOH/EtOAc (to remove a non-polar impurity) followed by elution with 3% MeOH/CHCl$_3$ (+0.1% NH$_4$OH) to give the title compound, TLC (UV) R$_f$=0.40 in 5% MeOH/CHCl$_3$ (+0.5% NH$_4$OH); MS (+ESI) for $C_{11}H_{14}FNOS$ m/z 228 (M+H)$^+$.

Step 2: Preparation of methyl (5R)-3-[3-fluoro-4-(cis-tetrahydro-1-oxido-2H-thiopyran-4-yl)phenyl]-2-oxo-5-oxazolidinecarbolaxylate A suspension of 389 mg (1.71 mmole) of 3-fluoro-4-(cis-tetrahydro-1-oxido-2H-thiopyran-4-yl)aniline (Step 1) in 2 ml CH$_3$CN is treated with 372 mg (1.74 mmole) LiOTf and 150 μL (1.72 mmole) of (R)-methyl glycidate. This mixture is placed under $N_2$ and heated to 80° C. with vigorous stirring. After 17 h the reaction is cooled to ambient temperature, diluted with MeOH and then concentrated under reduced pressure to give crude product which is chromatographed over silica gel eluting with 4% MeOH/CHCl$_3$ (+0.1% NH$_4$OH) to give the amino alcohol intermediate [TLC (UV) R$_f$=0.25 in 5% MeOH/CHCl$_3$ (+0.5% NH$_4$OH); MS (+ESI) for $C_{15}H_{20}FNO_4S$ m/z 330 (M+H)$^+$]. A solution of 0.91 g (2.8 mmole, from a different lot) of the amino alcohol intermediate in 10 ml CH$_3$CN under $N_2$ is treated with 0.63 g (3.9 mmole) of 1,1'-carbonyldiimidazole and stirred at ambient temperature for 24 h. The milky suspension is diluted with CH$_2$Cl$_2$ and washed with water several times. The washes are extracted with CH$_2$Cl$_2$ and the combined organic extracts are dried (Na$_2$SO$_4$), filtered and concentrated to give the title compound: TLC (UV) R$_f$=0.21 in 5% MeOH/CHCl$_3$ (+0.5% NH$_4$OH); MS (+ESI) for $C_{16}H_{18}FNO_5S$ m/z 356 (M+H)$^+$.

Step 3: Preparation of (5R)-3-[4-(cis-1-Imino-1-oxido-1,1,3,4,5,6-hexahydro-2H-thiopyran-4-yl)-3-fluorophenyl]-2-oxo-5-oxazolidinecarboxamide Preparation of the MSH reagent: A solution of ethyl O-mesitylsulfonylacetohydroxamate (2.53 g, 8.87 mmole) in 7 ml dioxane is cooled to 0° C. and treated dropwise with 1.0 ml (11.6 mmole) of 70% HClO$_4$ over ca. 5 min. The solution is stirred at ice bath temperature for 7.5 h and then poured into rapidly stirring ice-cold water (35 ml). Stirring is continued for 30 min and then the white solid is collected by suction filtration through a polypropylene filter tube, washed several times with ice-cold water and dissolved in ice-cold CH$_2$Cl$_2$. This solution is washed twice with cold water and quickly dried by filtration through a plug of anhydrous K$_2$CO$_3$ to give a stock solution of MSH in CH$_2$Cl$_2$.

All of the MSH stock solution is added directly to 857 mg (2.41 mmole) of methyl (5R)-3-[3-fluoro-4-(cis-tetrahydro-1-oxido-2H-thiopyran-4-yl)phenyl]-2-oxo-5-oxazolidinecarboxylate (Step 2) suspended in a minimal amount of CH$_2$Cl$_2$, and the resulting mixture is rapidly stirred at ambient temperature. After 33 h a thick milky suspension forms and the reaction looks complete by TLC [(UV) R$_f$=0.30 in 5% MeOH/CHCl$_3$ (+0.5% NH$_4$OH) for sulfoximine intermediate].

The milky suspension is dissolved in MeOH, treated with 10 ml 2.0 M NH$_3$/MeOH and concentrated under reduced pressure until most of the CH$_2$Cl$_2$ has been removed. Another 10 ml 2.0 M NH$_3$/MeOH is added and the solution is stirred at ambient temperature for 2 h. Additional NH$_3$/MeOH reagent is added as necessary until all of the ester has been consumed. The solution is concentrated and the crude product is chromatographed over silica gel, eluting with 7.5% MeOH/CHCl$_3$, and recrystallized from MeOH/CHCl$_3$ to give the title compound, mp 226–227° C.; TLC (UV) R$_f$=0.09 in 5% MeOH/CHCl$_3$ (+0.5% NH$_4$OH; MS (+ESI) for $C_{15}H_{18}FN_3O_4S$ m/z 356 (M+H)$^+$; $^1$H NMR (d$_6$-DMSO) δ 7.87 (s, 1H), 7.63 (s, 1H), 7.50 (m, 1H), 7.35 (m, 2H), 5.03 (dd, J$_1$=9.5 Hz, J$_2$=5.9 Hz, 1H), 4.27 (t, J=9.3 Hz, 1H), 4.01 (dd, J$_1$=9.3 Hz, J$_2$=5.9 Hz, 1H), 3.77 (s, 1H), 3.25–3.08 (m, 3H), 3.06–2.98 (m, 2H), 2.19–2.06 (m, 2H), 2.01–1.92 (m, 2H).

Example 57

(5R)-(−)-3-[3,5-Difluoro-4-(1-methoxycarbonyl-3-methylazetidin-3-yl)phenyl]-2-oxo-5-oxazolidinecarboxamide

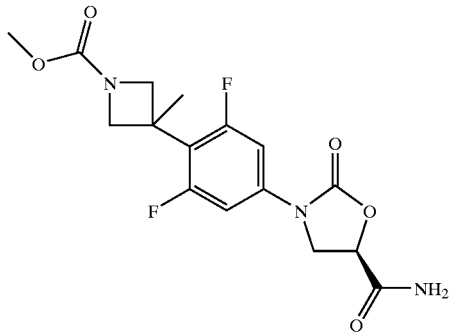

Step 1: Preparation of ethyl 2-cyano-2-(4-nitro-2,6-difluorophenyl)propionate

A stirred suspension of anhydrous $K_2CO_3$ (79.5 g, 575 mmol) in anhydrous DMF (365 mL) is heated to 150° C. and treated with ethyl 2-cyanopropionate (71.8 g, 564 mmol) via addition funnel over 20 min. The reaction is allowed to cool gradually to ambient temperature over 90 min, and then cooled further (to ca. 12° C.) with a mild ice bath. The yellow reaction mixture is at this point treated with 3,4,5-trifluoronitrobenzene (94.8 g, 535 mmol) via addition funnel over 20 min. The deep purple reaction mixture is stirred overnight at ambient temperature. The deep green reaction mixture is then poured into ice/water (950 mL) and made acidic (from pH 11 to pH 5) with 20% v/v $H_2SO_4/H_2O$ while stirring vigorously and ensuring ample cooling with ice bath. The mixture is then chilled in a refrigerator for 2 h. The amber-brown liquid is extracted with $Et_2O$ (1.2 L), taking care to dissolve the large clumps of green-black solid (which accounts for a significant amount of the product). The ethereal layer is washed with $H_2O$ (250 mL), saturated aqueous $NaHCO_3$ (2×150 mL), and $H_2O$ (2×150 mL), dried over $MgSO_4$, and concentrated under reduced pressure. Trituration (cold hexanes) affords the title compound as a pale tan solid in 77% yield; $^1H$ NMR (400 MHz, $CDCl_3$) δ 7.86 (m, 2H), 4.35 (q, 2H), 2.06 (t, 3H), 1.31 (t, 3H).

Step 2: Preparation of 3-methyl-3-(4-amino-2,6-difluorophenyl)azetidinone

A solution of ethyl 2-cyano-2-(4-nitro-2,6-difluorophenyl)propionate (Step 1, 117.3 g, 413 mmol) in anhydrous THF (1.1 L) is treated with 10% Pd/C (11.73 g) and placed under a hydrogen atmosphere (balloon). The reaction mixture is stirred at ambient temperature for 67 h under hydrogen, then filtered to remove Pd/C and concentrated under reduced pressure to afford the crude nitrile-aniline intermediate (155 g) as a dark brown oil. This crude intermediate is dissolved in absolute EtOH (2.0 L), treated with Raney nickel (240 g of a 50% slurry in $H_2O$), and subjected to hydrogenation in a Parr apparatus for 24 h (25–30 psi $H_2$, ambient temperature). The reaction mixture is then filtered through Celite (repeated EtOH washings) and concentrated under reduced pressure. Flash column chromatography (eluting with 2–3% $MeOH/CH_2Cl_2$ and then with 4–5% $MeOH(NH_3)/CH_2Cl_2$) provides the uncyclized amino aniline intermediate (74.2 g, 287 mmol) as a pale amber oil in 70% yield (two steps). A solution of this amino aniline (36.1 g, 140 mmol) in THF (800 mL) is added dropwise to a 0° C. solution of methyl magnesium bromide (220 mL, 3.18 M in $Et_2O$) in THF (1.32 L). The reaction mixture is then stirred for 22 h with ice bath expiring, and then the reaction contents are poured into ice-cold saturated aqueous $NH_4Cl$ (1.8 L). The organic and aqueous layers are separated, and the aqueous layer is extracted with THF (3×300 mL). All organic layers are combined and concentrated under reduced pressure. The resulting orange-amber syrup is dissolved in EtOAc (800 mL), washed with $H_2O$ (200 mL) and saline (200 mL), dried over $MgSO_4$, and concentrated under reduced pressure. Trituration (cold $Et_2O$) affords the title compound as a pale orange solid in 74% yield; $^1H$ NMR (400 MHz, DMSO-$d_6$) δ 7.83 (s, 1 H), 6.16 (d, 2 H), 5.65 (s, 2 H), 3.31 (m, 1 H), 3.27 (d, 1 H), 1.51 (s, 3 H); hMS (ESI) calcd for $C_{10}H_{10}F_2N_2O+H_1$ 213.0839, found 213.0849.

Step 3: Preparation of methyl 3-(4-amino-2,6-difluorophenyl)-3-methylazetidine-1-carboxylate A solution of $LiAlH_4$ (120.9 mL, 1.0 M in THF) is diluted with THF (117 mL) and cooled to 0° C. To this is added a solution of 3-methyl-3-(4-amino-2,6-difluorophenyl)azetidinone (Step 2, 8.55 g, 40.3 mmol) in THF (177 mL), with gas evolution. The ice bath is removed and the pale yellow solution is heated to reflux (75° C. oil bath) for 22 h, during which time the reaction becomes a white suspension. After cooling to ambient temperature, the mixture is treated successively with $H_2O$ (4.59 mL), 5 N aqueous NaOH (4.13 mL), and $H_2O$ (16.08 mL). The resulting suspension is diluted with $CHCl_3$ and filtered through a pad of Celite, rinsing the Celite with additional $CHCl_3$. Concentration under reduced pressure followed by purification via silica gel chromatography (eluting with 5% $MeOH(NH_3)/CH_2Cl_2$) affords the azetidinyl aniline intermediate (5.80 g, 29.3 mmol) as a golden syrup in 73% yield. A solution of this intermediate (4.93 g, 24.9 mmol) in $CH_2Cl_2$ (75 mL) is treated with $Et_3N$ (6.93 mL, 49.7 mmol), cooled to 0° C., and treated with methyl chloroformate (2.11 mL, 27.3 mmol) dropwise via syringe. The reaction is stirred for 2 h with ice bath expiring and then diluted with $CH_2Cl_2$, washed with $H_2O$ and saline, dried over $MgSO_4$, and concentrated under reduced pressure. Purification of the crude product via silica gel chromatography (eluting with 30% EtOAc/hexane) affords the title compound as a deliquescent yellow-white solid in 79% yield; $^1H$ NMR (400 MHz, DMSO-$d_6$) δ 6.17 (d, 2 H), 5.64 (s, 2 H), 4.15 (m, 2 H), 3.81 (m, 2 H), 3.56 (s, 3 H), 1.50 (s, 3H); HRMS (ESI) calcd for $C_{12}H_{14}F_2N_2O_2+H_1$ 257.1101, found 257.1095.

Step 4: Preparation of methyl (5R)-3-[3,5-difluoro-4-(1-methoxycarbonyl-3-methylazetidin-3-yl]-2-oxo-5-oxazolidinecarboxylate A solution of methyl 3-(4-amino-2,6-difluorophenyl)-3-methylazetidine-1-carboxylate (Step 3, 4.93 g, 19.2 mmol) in $CH_3CN$ (20 mL) is treated with methyl (2R)-glycidate (1.64 mL, 19.2 mmol) and heated to 50° C. To this stirred solution is added LiOTf (3.00 g, 19.2 mmol) portionwise, and the reaction mixture is then heated at 100° C. for 4 h. After this time the reaction is allowed to cool to ambient temperature with stirring overnight. The reaction is then diluted with EtOAc and washed with $H_2O$. The $H_2O$ layer is back-extracted with EtOAc, and organic layers are combined, dried over $MgSO_4$, and concentrated under reduced pressure. Purification via flash column chromatography (eluting with 30–40% EtOAc/hexane) affords the hydroxy ester intermediate (4.01 g, 11.2 mmol) as a pale yellow solid in 58% yield. A solution of this hydroxy ester intermediate (3.74 g, 10.4 mmol) in $CH_3CN$ (33 mL) is treated with CDI (2.03 g, 12.5 mmol) and a single crystal of DMAP. After stirring for 7 days at ambient temperature, the reaction contents are poured into H₂O (150 mL). The resulting phase is then extracted with EtOAc (3×100 mL), and the combined organic layers are dried over MgSO₄ and concentrated under reduced pressure. Purification of the crude product via silica gel chromatography (eluting with 35–45% EtOAc/hexane) affords the title compound as a white solid in 83% yield; ¹H NMR (400 MHz, DMSO-d₆) δ 7.34 (d, 2 H), 5.37 (dd, 1H), 4.34 (t, 1 H), 4.25 (m, 2 H), 4.18 (dd, 1 H), 3.87 (d, 2 H), 3.77 (s, 3 H), 3 H), 3.57 (s, 3 H), 1.57 (s, 3H); hMS (ESI) calcd for $C_{17}H_{18}F_2N_2O_6+H_1$ 385.1211, found 385.1199.

Step 5: Preparation of (5R)-(−)-3-[3,5-difluoro-4-(1-methoxycarbonyl-3-methylazetidin-3-yl)phenyl]-2-oxo-5-oxazolidinecarboxamide A suspension of methyl (5R)-3-[3,5-difluoro-4-(1-methoxycarbonyl-3-methylazetidin-3-yl]-2-oxo-5-oxazolidinecarboxylate (Step 4, 500 mg, 1.30 mmol) in MeOH (10 mL) is heated at 50° C. to achieve full dissolution, then cooled to 0° C. and treated with NH₃-MeOH (5 mL). The ice bath is removed and the reaction mixture stirred for 10 min and then concentrated under reduced pressure. Trituration (Et₂O) affords the title compound as a white solid in 97% yield; ¹H NMR (400 MHz, DMSO-d₆) δ 7.88 (s, 1 H), 7.64 (s, 1 H), 7.35 (d, 2 H), 5.05 (dd, 1 H), 4.26 (m, 2 H), 4.25 (t, 1 H), 4.01 (dd, 1 H), 3.87 (d, 2 H), 3.56 (s, 3 H), 1.57 (s, 3H); hMS (ESI) calcd for $C_{16}H_{17}F_2N_3O_5+H_1$ 370.1214, found 370.1206; $[\alpha]^{25}_D=-20$ (c 0.88, DMSO).

Example 58

(5R)-(−)-N-Methyl-3-[3,5-difluoro-4-(1-methoxycarbonyl-3-methylazetidin-3-yl)phenyl]-2-oxo-5-oxazolidinecarboxamide

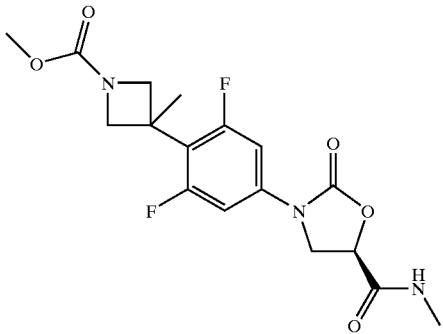

A suspension of methyl (5R)-3-[3,5-difluoro-4-(1-methoxycarbonyl-3-methylazetidin-3-yl]-2-oxo-5-oxazolidinecarboxylate (EXAMPLE 57, Step 4, 500 mg, 1.30 mmol) in MeOH (10 mL) is heated at 50° C. to achieve full dissolution, then cooled to 0° C. and treated with methylamine (15 mL, 2.0 M in MeOH). The reaction mixture is stirred for 20 min at 0° C. and then concentrated under reduced pressure. Trituration (Et₂O) affords the title compound as a white solid in 90% yield; ¹H NMR (400 MHz, DMSO-d₆) δ 8.41 (d, 1 H), 7.35 (d, 2 H), 5.09 (dd, 1 H), 4.26 (m, 2 H), 4.25 (t, 1 H), 4.02 (dd, 1 H), 3.86 (d, 2 H), 3.56 (s, 3 H), 2.66 (d, 3 H), 1.56 (s, 3H); hMS (ESI) calcd for $C_{17}H_{19}F_2N_3O_5+H_1$ 384.1371, found 384.1360; $[\alpha]^{25}_D=-35$ (c 0.90, DMSO).

Example 59

(5R)-3-(3,4-Dihydro-4-methyl-3-oxo-2H-1,4-benzoxazin-7-yl)-2-oxo-5-oxazolidinecarboxamide

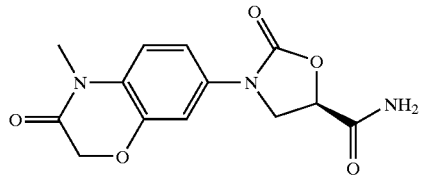

Step 1: Preparation of 4-methyl-7-amino-2H-1,4-benzoxazin-3-one

To a stirred suspension of 4-methyl-7-nitro-2H-1,4-benzoxazin-3-one (DE 19802239, 2.43 g, 11.67 mmol) in EtOH (20 mL) and water (10 mL) is added ammonium chloride (6.25 g, 116.70 mmol). To this mixture is added iron (1.95 g, 35.00 mmol) in 3 equal portions. The resulting mixture is heated to 80° C. for 2 h at which time the reaction is cooled to room temperature followed by addition of CH₂Cl₂ (100 mL). The resulting mixture is filtered through celite and the filtrate is further diluted with water (100 mL). The organic layer is separated followed by further extraction of the aqueous phase with CH₂Cl₂ (3×50 mL). The organic phases are combined, dried over Na₂SO₄ and concentrated under reduced pressure, and the product is purified by silica gel column chromatography (EtOAc) to give the title compound in quantitative yield, MS m/z 179.1 (M+H)⁺.

Step 2: Preparation of (5R)-3-(3,4-dihydro-4-methyl-3-oxo-2H-1,4-benzoxazin-7-yl)-2-oxo-5-oxazolidinecarboxylic acid methyl ester To a stirred solution 4-methyl-7-amino-2H-1,4-benzoxazin-3-one (Step 1, 7.24 g, 40.63 mmol) in CH₃CN (75 mL) is added LiOTf (6.97 g, 44.69 mmol) followed by methyl (R)-glycidate (4.55 g, 44.69 mmol). The resulting mixture is heated to 50° C. over night at which time HPLC indicates complete consumption of the starting material. The reaction is quenched by addition of water (300 mL), EtOAc (500 mL) and saline (50 mL). The organic phase is separated followed by further extraction of the aqueous phase with EtOAc (3×10 mL). The combined organic phase is dried over Na₂SO₄, filtered and concentrated under reduced pressure to yield crude amino alcohol intermediate which is passed through a short silica gel column (EtOAc) to remove the polar impurities (material balance: 12.24 g). The product obtained above is dissolved in anhydrous CH₃CN (100 mL) followed by addition of CDI (19.74, 121.89 mmol, 3 eq. wrt aniline above) at ambient temperature. The resulting reaction mixture is stirred overnight at which time it is diluted with 0.1 N HCl (50 mL). The resulting white precipitate is filtered off, washed with additional 0.1 N HCl (25 mL) and water (100 mL) and dried under high vacuum to give the title compound (7.68 g, 61% for two steps), MS m/z 307.5 (M+H)⁺.

Step 3: Preparation of (5R)-3-(3,4-dihydro-4-methyl-3-oxo-2H-1,4-benzoxazin-7-yl)-2-oxo-5-oxazolidinecarboxamide To a stirred solution of (5R)-3-(3,4-dihydro-4-methyl-3-oxo-2H-1,4-benzoxazin-7-yl)-2-oxo-oxazolidine-5-carboxylic acid methyl ester (Step 2, 2.41 g, 7.87 mmol) in MeOH (25 mL) is added 2M NH₃ in MeOH (25 mL, 50 mmol). The resulting clear solution becomes turbid after ~10 min. This mixture is stirred for 16 h at which time the reaction is diluted with ether (20 mL) and the resulting white solid filtered off. This white solid is washed with several portion of ether (50 mL) and dried under high vacuum to give the title compound (1.87 g, 81%), $^1$H NMR (300 MHz, DMSO) δ 7.85 (br s, 1H), 7.60 (br s, 1H), 7.31–7.14 (m, 3H), 5.00 (dd, 1H), 4.65 (s, 2H), 4.21 (t, 1H), 3.97 (dd, 1H), 3.32 (s, 3H); MS for $C_{14}H_{13}N_3O_5$ m/z 292.5 (M+H)$^+$.

Example 60

(5R)-N-Methyl-3-(3,4-dihydro-4-methyl-3-oxo-2H-1,4-benzoxazin-7-yl)-2-oxo-5-oxazolidinecarboxamide

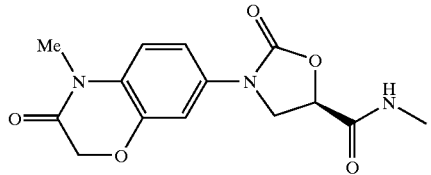

To a stirred suspension of (5R)-3-(3,4-dihydro-4-methyl-3-oxo-2H-1,4-benzoxazin-7-yl)-2-oxo-oxazolidine-5-carboxylic acid methyl ester (EXAMPLE 59, Step 3, 200 mg, 0.65 mmol) in MeOH (5 mL) is added MeNH$_2$ (5 mL, 10 mmol, 2 M solution in MeOH). The resulting solution is stirred for 3 h at room temperature at which time the resulting white precipitate is filtered, washed with additional MeOH (5 mL), and dried under high vacuum to give the title compound (153 mg, 77%); $^1$H NMR (300 MHz, DMSO) δ 8.56 (br t, 1H), 7.50 (d, 1H), 7.41–7.33 (m, 2H), 5.23 (dd, 1H), 4.85 (s, 2H), 4.45 (dd, 1H), 4.15 (dd, 1H), 3.45 (s, 3H), 2.84 (d, 2H); MS for $C_{14}H_{15}N_3O_5$ m/z 306.5 (M+H)$^+$.

Example 61

(5R)-N-(2-Fluoroethyl)-3-(3,4-dihydro-4-methyl-3-oxo-2H-1,4-benzoxazin-7-yl)-2-oxo-5-oxazolidinecarboxamide

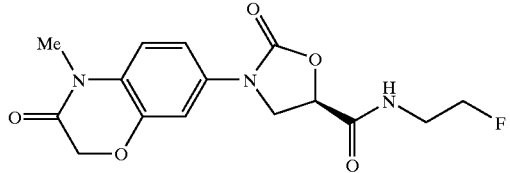

To a stirred suspension of (5R)-3-(3,4-dihydro-4-methyl-3-oxo-2H-1,4-benzoxazin-7-yl)-2-oxo-oxazolidine-5-carboxylic acid methyl ester (EXAMPLE 59, Step 3, 200 mg, 0.65 mmol) in MeOH (7.5 mL) is added FCH$_2$CH$_2$NH$_2$.HCl (325 mg, 3.25 mmol). To this resulting suspension is added triethylamine (453 μL, 3.25 mmol), and the solution is heated to 55° C. for 5 h followed by stirring for 16 h at room temperature. The reaction mixture is then concentrated to dryness under reduced pressure and the residue is purified by silica gel column chromatography (eluent: EtOAc) to give the title compound (153 mg, 63%); $^1$H NMR (300 MHz, DMSO) δ 8.68 (br t, 1H), 7.30 (d, 1H), 7.22–7.14 (m, 2H), 5.08 (dd, 1H), 4.65 (s, 2H), 4.54 (dd, 1H), 4.38 (t, 1H), 4.26 (t, 1H), 3.45 (s, 3H), 3.96 (dd, 1H), 3.50–3.35 (m, 5H); MS for $C_{15}H_{16}FN_3O_5$ m/z 338.5 (M+H)$^+$.

Example 62

(5R)-3-(3,4-Dihydro-4-methyl-3-oxo-2H-1,4-benzothiazin-7-yl)-2-oxo-5-oxazolidinecarboxamide

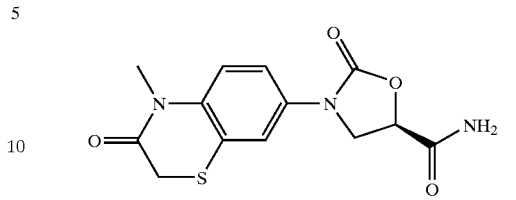

Step 1: Preparation of 2-amino-5-nitrobenzenethiol

To a stirred solution of 6-nitrobenzothiazole (30 g, 0.1665 mol) in ethanol (500 mL) is added 100% hydrazine hydrate (60.2 mL, 1.931 mol). The mixture is refluxed for 2 h at which time the solution turns red. The reaction is quenched by the addition of ice cold conc. HCl until the red color disappears. The resulting solid is filtered, washed with water (25 mL) and dried under high vacuum to give the title compound as a yellow solid (28.96 g, 84%), MS m/z 171.5 (M+H)$^+$.

Step 2: Preparation of 3,4-dihydro-7-nitro-2H-1,4-benzothiazin-3-one

To a stirred suspension of 2-amino-5-nitrobenzenethiol (Step 1, 29 g, 139.8 mmol) and potassium carbonate (115.93 g, 838.8 mmol) in dry DMF (150 mL) is added methyl bromoacetate (15.88 mL, 167.8 mmol). The reaction mixture is heated at 50° C. for 16 h at which time the reaction is quenched with ice and water (50 mL). The precipitate is filtered and dried under high vacuum to give the title compound as a yellow solid (21.69 g, 74%), MS m/z 211.5 (M+H)$^+$.

Step 3: Preparation of 3,4-dihydro-4-methyl-7-nitro-2H-1,4-benzothiazin-3-one

To a stirred suspension of 3,4-dihydro-7-nitro-2H-1,4-benzothiazin-3-one (Step 2, 4.7 g, 22.3 mmol) and potassium carbonate (3.70 g, 26.8 mmol) in dry DMF (40 mL) in an ice bath is added iodomethane (4.16 mL, 66.8 mmol). The reaction mixture is taken out of the ice bath and heated at 50° C. for 1–2h. The resulting mixture is allowed to cool down. Water (35 mL) and ice are added and the precipitate is filtered off and washed with water (10 mL). The resulting solid is dried under high vacuum to give the title compound as a yellow solid (4.5 g, 90%), MS m/z 225.5 (M+H)$^+$.

Step 4: Preparation of 3,4-dihydro-4-methyl-7-amino-2H-1,4-benzothiazin-3-one

To a stirred solution of 3,4-dihydro-4-methyl-7-nitro-2H-1,4-benzothiazin-3-one (4.50 g, 20.07 mmol) in EtOH (100 mL) and water (50 mL) is added ammonium chloride (10.76 g, 200.7 mmol). To this mixture is added iron (3.37 g, 60.21 mmol) in 3 equal portions. The resulting mixture is heated to 80° C. for 2 h at which time the reaction is cooled to room temperature. This mixture is filtered and the filtrate is concentrated under reduced pressure and extracted with EtOAc (3×50 mL). The organic phase is washed with water and saline, dried over MgSO$_4$, and concentrated under reduced pressure to give the title compound (for reference see DE 19802239) as a dark brown oil (3.60 g, 93%), MS m/z 195.5 (M+H)$^+$.

Step 5: Preparation of (5R)-3-(3,4-dihydro-4-methyl-3-oxo-2H-1,4-benzothiazin-7-yl)-2-oxo-5-oxazolidinecarboxylic acid methyl ester To a stirred solution of 3,4-dihydro-4-methyl-7-amino-2H-1,4-benzothiazin-3-one (Step 4, 3.60 g, 18.54 mmol) in dry CH$_3$CN (15 mL) is added LiOTf (3.47 g, 22.24 mmol)

and (R)-methyl glycidate (1.9 mL, 22.24 mmol). The resulting mixture is stirred at 100° C. for 4 h at which time the reaction is cooled to room temperature and worked up in CH$_2$Cl$_2$ (3×60 mL) and water (60 mL). The combined organic phase is washed with saline, dried over MgSO$_4$, and concentrated under reduced pressure to give a dark oil that is purified by column chromatography (25% acetone/CH$_2$Cl$_2$) to give the amino alcohol intermediate as a dark yellow oil (3.39 g, 62%, MS m/z 297.5 (M+H)$^+$). To a stirred solution of this intermediate (3.39 g, 11.44 mmol) in dry CH$_3$CN (15 mL) is added CDI (5.56 g, 34.32 mmol). The resulting mixture is heated at 50° C. for 30 min at which time the reaction is cooled to room temperature and concentrated under reduced pressure. The crude product is purified by column chromatography (100% EtOAc) to give the title compound as white-yellow solid (3.14 g, 85%), MS m/z 323.5 (M+H)$^+$.

Step 6: Preparation of (5R)-3-(3,4-dihydro-4-methyl-3-oxo-2H-1,4-benzothiazin-7-yl)-2-oxo5-oxazolidinecarboxamide To a stirred suspension of the (5R)-3-(3,4-dihydro-4-methyl-3-oxo-2H-1,4-benzothiazin-7-yl)-2-oxo-5-oxazolidinecarboxylic acid methyl ester (Step 5, 200 mg, 0.6205 mmol) in MeOH (3 mL) is added a 2.0 M solution of ammonia in MeOH (2.0 mL). This mixture is stirred for 3 h at which time the reaction is concentrated under reduced pressure, washed with ethyl ether (6 mL) and filtered to give the title compound as a white solid (108 mg, 57%), $^1$H NMR (300 MHz, DMSO) δ 7.86 (s, 1H), 7.63 (d, 2H), 7.47 (dd, 1H), 7.27 (d, 1H), 5.01 (dd, 1H), 4.26 (t, 1H), 4.00 (dd, 1H), 3.52 (s, 2H), 3.32 (s, 3H); MS for C$_{13}$H$_{13}$N$_3$O$_4$SMS m/z 308.5 (M+H)$^+$.

Example 63

(5R)-N-Methyl-3-(3,4-dihydro-4-methyl-3-oxo-2H-1,4-benzothiazin-7-yl)-2-oxo-5-oxazolidinecarboxamide

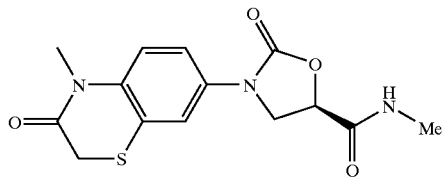

To a stirred suspension of the (5R)-3-(3,4-dihydro-4-methyl-3-oxo-2H-1,4-benzothiazin-7-yl)-2-oxo-5-oxazolidinecarboxylic acid methyl ester (EXAMPLE 62, Step 5, 200 mg, 0.6205 mmol) in MeOH (3 mL) is added a 2.0 M solution of methylamine in MeOH (2.0 mL). This mixture is stirred for 30 min at which time the reaction is concentrated under reduced pressure, washed with ethyl ether (6 mL) and filtered to give the title compound as a white solid (190 mg, 95%), $^1$H NMR (300 MHz, DMSO) δ 8.38 (d, 1H), 7.63 (d, 1H), 7.46 (dd, 1H), 7.27 (d, 1H), 5.05 (dd, 1H), 4.27 (t, 1H), 4.01 (dd, 1H), 3.52 (s, 2H), 3.32 (s, 3H), 2.65 (d, 3H); MS for C$_{14}$H$_{15}$N$_3$O$_4$SMS m/z 322.5 (M+H)$^+$.

Example 64

(5R)-3-[3-Fluoro-4-(5-oxo-5,6-dihydro-4H-[1,3,4]thiadiazin-2-yl)phenyl]-2-oxo-5-oxazolidinecarboxamide

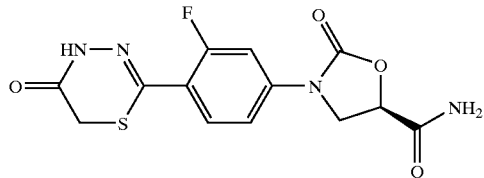

Step 1: Preparation of N'-(2-fluoro-4-nitrobenzoyl)hydrazinecarboxylic acid tert-butyl ester N,N-Diisopropylethylamine (14.1 ml, 0.081 mol) is added to 2-fluoro-4-nitrobenzoic acid (5 g, 0.027 mol) and O-(7-azabenzotriazol-1-yl)-N,N, N', N'-tetramethyluronium hexafluorophosphate (10.8 g, 0.0284 mol) in DMF (100 ml) and the mixture stirred at room temperature for 20 minutes. tert-Butyl carbazate (3.57 g, 0.0270 mol) is added in one portion and the reaction stirred overnight at room temperature. The mixture is concentrated and diluted with water (100 ml). The resulting precipitate is filtered, washed well with water, and dried under vacuum to give the title compound as a white solid (4.63 g, 57%), [M+H]$^+$=300.

Step 2: Preparation of N'-(2-fluoro-4-nitro-thiobenzoyl)hydrazinecarboxylic acid tert-butyl ester N'-(2-Fluoro-4-nitro-benzoyl)hydrazinecarboxylic acid tert-butyl ester (Step 1, 2.32 g, 7.75 mmol) and Lawesson's reagent (2.35 g, 5.81 mmol) in dioxane (50 ml) are heated at 85° C. overnight. The mixture is evaporated under vacuum and the residue purified by flash column chromatography (70% dichloromethane/hexane) to give the title compound as a bright orange solid (2.02 g, 82%), [M+H]$^+$=316.

Step 3: Preparation of [(tert-Butoxycarbonylhydrazono)-(2-fluoro-4-nitro-phenyl)methylsulfanyl]acetic acid methyl ester Triethylamine (1.33 ml, 9.57 mmol) is added dropwise at room temperature to N'-(2-fluoro-4-nitro-thiobenzoyl)hydrazinecarboxylic acid tert-butyl ester (Step 2, 2.02 g, 6.38 mmol) and methyl bromoacetate (0.633 ml, 6.69 mmol) in DMF (20 ml). The mixture is stirred at room temperature for 30 minutes and then concentrated under vacuum. The residue is purified by flash column chromatography (50% ethyl acetate/hexane) to give the title compound as an oil (2.20 g, 86%), [M+H]$^+$=388.

Step 4: Preparation of 2-(2-fluoro-4-nitrophenyl)-4H-[1,3,4]thiadiazin-5-one

[(tert-Butoxycarbonylhydrazono)-(2-fluoro-4-nitrophenyl)methylsulfanyl]acetic acid methyl ester (Step 3, 2.00 g, 5.16 mmol) is dissolved in 20% trifluoroacetic acid in dichloromethane and stirred at room temperature for 45 minutes. The reaction mixture is evaporated under vacuum to give the title compound as a yellow solid (1.30 g, 99%), [M+H]$^+$=256.

Step 5: Preparation of 2-(4-amino-2-fluorophenyl)-4H-[1,3,4]thiadiazin-5-one 2-(2-Fluoro-4-nitrophenyl)-4H-[1,3,4]thiadiazin-5-one (Step 4, 0.964 g, 0.00378 mol) is heated in ethanol (20 ml) until dissolved. Water (10 ml) and ammonium chloride (2.02 g, 0.0378 mol) are added and the mixture heated to 90° C. Iron powder (0.84 g, 0.0151 mol) is added portionwise and the mixture stirred and heated for 30 minutes. The reaction is cooled and dichloromethane (100 ml) added. The mixture is filtered and the organic layer separated, washed with saline, dried (MgSO$_4$) and evaporated to give the title compound as a yellow solid (0.78 g, 92%), [M+H]$^+$=226.

Step 6: Preparation of (5R)-3-[3-fluoro-4-(5-oxo-5,6-dihydro-4H-[1,3,4]thiadiazin-2-yl)phenyl]-2-oxo-5-oxazolidinecarboxylic acid butyl ester 2-(4-Amino-2-fluorophenyl)-4H-[1,3,4]thiadiazin-5-one (Step 5, 0.71 g, 3.15 mmol), butyl (2R)-epoxypropanoate (0.91 g, 6.30 mmol) and lithium trifluoromethanesulfonate (0.74 g, 4.73 mmol) in acetonitrile (10 ml) are heated at 90° C. overnight. The reaction is concentrated and the residue diluted with ethyl acetate, washed with water and saline, dried (MgSO$_4$) and evaporated. The residue is purified by flash column chromatography (50% ethyl acetate/hexane) to give the amino alcohol intermediate as an oil (0.99 g, 85%, MS (m/z): [M+H]$^+$=370). Phosgene (20% solution in toluene, 0.89 ml, 1.68 mmol) is added dropwise at 0° C. to a portion of this intermediate (0.516 g, 1.40 mmol) and triethylamine (0.29 ml, 2.10 mmol) in dichloromethane (10 ml). The mixture is allowed to warm to room temperature and stirred for an additional hour. The reaction is washed with 2N aqueous hydrochloric acid and saline, dried (MgSO$_4$) and evaporated. The residue is purified by flash column chromatography (50% ethyl acetate/hexane) to give the title compound as a white solid (0.33 g, 60%); MS (m/z): [M+H]$^+$=396.

Step 7: Preparation of (5R)-3-[3-fluoro-4-(5-oxo-5,6-dihydro-4H-[1,3,4]thiadiazin-2-yl)phenyl]-2-oxo-5-oxazolidinecarboxamide 3-[3-Fluoro-4-(5-oxo-5,6-dihydro-4H-[1,3,4]thiadiazin-2-yl)phenyl]-2-oxo-5-oxazolidinecarboxylic acid butyl ester (Step 6, 0.300 g, 0.758 mmol) is dissolved in 2M ammonia in methanol solution (8 ml) and stirred overnight at room temperature. The reaction is concentrated under vacuum and purified by PTLC (10% methanol/CH$_2$Cl$_2$) to give the title compound as a white solid (0.22 g, 87%), mp 249–251° C.; $^1$H NMR (300 Mhz, CDCl$_3$) δ 3.59 (s, 2H), 4.04 (dd, 1H), 4.30 (t, 1H), 5.05 (dd, 1H), 7.49–7.72 (m, 4H), 7.88 (br s, 1H), 11.63 (s, 1H); MS (m/z) for C$_{13}$H$_{11}$FN$_4$O$_4$S: [M+H]$^+$=339.

Example 65

(5R)-3-[4-(1,1-Dioxido-2,3-dihydro-4H-1,4-thiazin-4-yl)-3,5-difluorophenyl]-2-oxo-5-oxazolidinecarboxamide

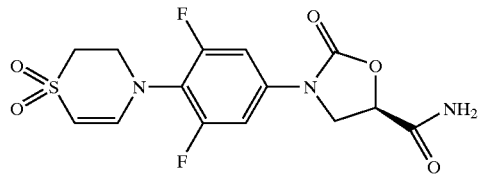

Step 1: Preparation of methyl (2R)-3-{[4-(1,1-dioxidothiomorpholin-4-yl)-3,5-difluorophenyl]amino}-2-hydroxypropanoate A solution of 4-(1,1-dioxidothiomorpholin-4-yl)-3,5-difluoroaniline (EXAMPLE 15, Step 3, 1.30 g, 5.0 mmol) in acetonitrile (7.5 mL) is treated with lithium triflate (0.60 g, 5.0 mmol) and methyl (2R)-2,3-epoxypropanoate (0.51 g, 0.46 mL, 5.0 mmol) and heated to 70° C. for 2 h. At this time an additional amount (1.5 mmol each) of the two reagents is added and the mixture stirred for another 7 h at 70° C. The reaction mixture is then cooled to room temperature, concentrated, and purified by column chromatography (50→60% ethyl acetate-hexane) to provide the title compound (1.03 g, 57%), MS (m/z): [M+H]$^+$=365; $^1$H NMR (300 MHz, CDCl$_3$): δ 3.04 (d, 1H), 3.15 (m, 4H), 3.31–3.46 (m, 2H), 3.47–3.56 (m, 4H), 3.83 (s, 3H), 4.20 (t, 1H), 4.40 (m, 1H), 6.17 (d, 2H).

Step 2: Preparation of methyl (5R)-3-[4-(1,1-dioxidothiomorpholin-4-yl)-3,5-difluorophenyl]-2-oxo-5-oxazolidinecarboxylate A solution of methyl (2R)-3-{[4-(1,1-dioxidothiomorpholin-4-yl)-3,5-difluorophenyl]amino}-2-hydroxypropanoate (Step 1, 1.02 g, 2.90 mmol) in CH$_2$Cl$_2$ (25 mL) and triethylamine (1.0 g, 1.5 mL, 10.5 mmol) is cooled to 0° C. and treated with phosgene (1.94 mL of a 20% solution in toluene, 3.6 mmol). After stirring at room temperature for one hour, the reaction mixture is diluted with CH$_2$Cl$_2$ and washed with dilute NaHCO$_3$, saline, and dried (MgSO$_4$), filtered and concentrated. Chromatography on silica gel (10% acetonitrile-dichloromethane) provides the title compound (0.91 g, 83%), MS (m/z): [M+H]$^+$=391; $^1$H NMR (300 MHz, CDCl$_3$): δ 3.16–3.20 (m, 4H), 3.64 (m, 4H), 3.88 (s, 3H), 4.06–4.11 (m, 1H), 4.23 (t, 1H), 5.06–5.11 (m, 1H), 7.16 (d, 2H).

Step 3: Preparation of methyl (5R)-3-[4-(1,1-dioxido-2,3-dihydro-4H-1,4-thiazin-4-yl)-3,5-difluorophenyl]-2-oxo-5-oxazolidinecarboxylate A solution of methyl (5R)-3-[4-(1,1-dioxidothiomorpholin-4-yl)-3,5-difluorophenyl]-2-oxo-5-oxazolidinecarboxylate (Step 2, 0.73 g, 1.87 mmol) and 2,3-dichloro-5,6-dicyano-1,4-benzoquinone (DDQ) (1.27 g, 5.6 mmol) in dioxane (9 mL) is heated to 100° C. for two days. The solution is cooled and treated with 20 mL of 10% aqueous Na$_2$SO$_3$ and stirred for 30 minutes. The solution is then diluted with water and extracted three times with ethyl acetate. The combined organic phases are washed with satd NaHCO$_3$ and saline and dried (MgSO$_4$), filtered and concentrated. The crude residue is purified by column chromatography (0→5% ethyl ether-dichloromethane) to provide the title compound (0.28 g, 38%); $^1$H NMR (300 MHz, CDCl$_3$): δ 3.31–3.35 (m, 2H), 3.89 (s, 3H), 4.00–4.15 (m, 3H), 4.25 (t, 1H), 5.11 (m, 1H), 5.45 (d, 1H), 6.54 (d, 1H), 7.29 (d, 2H).

Step 4: Preparation of (5R)-3-[4-(1,1-dioxido-2,3-dihydro-4H-1,4-thiazin-4-yl)-3,5-difluorophenyl]-2-oxo-5-oxazolidinecarboxamide A solution of methyl (5R)-3-[4-(1,1-dioxido-2,3-dihydro-4H-1,4-thiazin-4-yl)-3,5-difluorophenyl]-2-oxo-1,3-oxazolidine-5-carboxylate (Step 3, 0.090 g, 0.23 mmol) in methanol (2 mL) is treated with a solution of ammonia in methanol (2 mL of a 2.0M solution). The mixture is stirred for 1.5 h and concentrated. The residual solids are washed with methanol to provide 75 mg (86%) of the title compound as a white solid, MS (m/z) for C$_{14}$H$_{13}$F$_2$N$_3$O$_5$S: [M+H]$^+$=374; $^1$H NMR (300 MHz, d6-DMSO): δ 3.33–3.39 (m, 2H), 3.99–4.06 (m, 3H), 4.26 (t, 1H), 5.04–5.09 (m, 1H), 5.48 (d, 1H), 6.93 (d, 1H), 7.50 (d, 2H), 7.65 (s, 1H), 7.90 (s, 1H).

Example 66

(5R)-3-[4-(2,5-Dihydro-1H-pyrrol-1-yl)-3,5-difluorophenyl]-2-oxo-5-oxazolidinecarboxamide

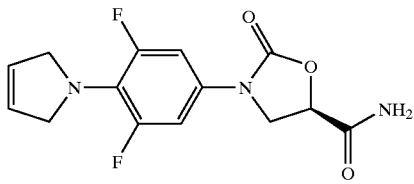

Step 1: Preparation of 1-(2,6-difluoro-4-nitrophenyl)-2,5-dihydro-1H-pyrrole

Trifluoronitrobenzene (5 g, 28.2 mmol) and 3-pyrroline (1.95 g, 28.2 mmol) are taken up in CH$_3$CN (70.0 mL) and diisopropylethylamine (5.4 mL, 31.02 mmol) and heated to 60° C. for 4 h. The reaction mixture is cooled to room temperature, dissolved in ethyl acetate and washed with 0.1 N HCl, sat. NaHCO$_3$, water, and saline, and dried (MgSO$_4$), filtered and concentrated to provide the title compound (6.2 g, 96%), $^1$H NMR (300 MHz, CDCl$_3$): δ 4.64 (s, 4H), 5.85 (s, 2H), 7.71 (d, 2H).

Step 2: Preparation of 4-(2,5-dihydro-1H-pyrrol-1-yl)-3,5-difluoroaniline

Ammonium chloride (1.18 g, 22.1 mmol) is added to a mixture of 1-(2,6-difluoro-4-nitrophenyl)-2,5-dihydro-1H-pyrrole (Step 1, 0.5 g, 2.21 mmol) dissolved in EtOH/water (2:1, 18.0 mL) and heated to reflux. Iron powder (0.37 g, 6.63 mmol) is added in portions over one hour. After refluxing for another 45 min, the reaction mixture is cooled, filtered, and extracted three times with dichloromethane. The organic layers are washed with saline, dried (MgSO$_4$) and concentrated to provide the title compound (0.43 g, >95%), MS (m/z): [M+H]$^+$=197; $^1$H NMR (300 MHz, CDCl$_3$): δ 3.63 (bs, 2H), 4.10 (s, 4H), 5.84 (s, 2H), 6.17 (d, 2H).

Step 3: Preparation of methyl (2R)-3-{[4-(2,5-dihydro-1H-pyrrol-1-yl)-3,5-difluorophenyl]amino-2-hydroxypropanoate Methyl (2R)-2,3-epoxypropanoate (0.34 g, 3.3 mmol) and lithium triflate (0.52 g, 3.3 mmol) are added to a solution of 4-(2,5-dihydro-1H-pyrrol-1-yl)-3,5-difluoroaniline (Step 2, 0.43 g, 2.2 mmol) in acetonitrile (7.5 mL), and the mixture is heated to 60° C. for 16 h. The reaction mixture is then concentrated and the residue purified by pTLC (50% EtOAc/hexanes) to provide the title compound (0.30 g, 46%), MS (m/z): [M+H]$^+$=299.5; $^1$H NMR (300 MHz, CDCl$_3$): δ 3.34–3.41 (m, 2H), 3.77 (s, 3H), 4.08 (s, 4H), 4.35–4.37 (m, 1H), 5.82 (s, 2H), 6.16 (d, 2H).

Step 4: Preparation of methyl (5R)-3-[4-(2,5-dihydro-1H-pyrrol-1-yl)-3,5-difluorophenyl]-2-oxo-5-oxazolidinecarboxylate A solution of methyl (2R)-3-{[4-(2,5-dihydro-1H-pyrrol-1-yl)-3,5-difluorophenyl]amino}-2-hydroxypropanoate (Step 3, 0.3 g, 1.0 mmol) in acetonitrile (10.0 mL) is treated with 1,1'-carbonyldiimidazole (0.33 g, 2.0 mmol) and stirred at room temperature for 16 h. The reaction mixture is concentrated and the residue taken up in ethyl acetate. This organic solution is washed with dilute citric acid, water, and saline and dried (MgSO$_4$). Purification by pTLC (50% EtOAc/hexanes) provides the title compound (0.15 g, 46%), MS (m/z): [M+H]$^+$=325.5; $^1$H NMR (300 MHz, CDCl$_3$): δ 3.88 (s, 3H), 4.03–4.08 (m, 1H), 4.20 (t, 1H), 4.37 (s, 4H), 5.03–5.08 (m, 1H), 5.87 (s, 2H), 7.06 (d, 2H).

Step 5: Preparation of (5R)-3-[4-(2,5-dihydro-1H-pyrrol-1-yl)-3,5-difluorophenyl]-2-oxo-5-oxazolidinecarboxamide A solution of methyl (5R)-3-[4-(2,5-dihydro-1H-pyrrol-1-yl)-3,5-difluorophenyl]-2-oxo-5-oxazolidine-5-carboxylate (Step 4, 0.09 g, 0.28 mmol) in 2.0M ammonia in MeOH (2.8 mL) is heated to 55° C. for 4 h. The reaction mixture is cooled, concentrated and the residue purified by pTLC (5% MeOH/CH$_2$Cl$_2$) to give the title compound (50 mg, 58%); MS for C$_{14}$H$_{13}$F$_2$N$_3$O$_3$MS m/z 310.5 (M+H)$^+$; $^1$H NMR (300 MHz, d$_6$-DMSO): δ 3.93–3.98 (m, 1H), 4.17–4.25 (m, 5H), 4.97–5.02 (m, 1H), 5.93 (s, 2H), 7.27 (d, 2H), 7.61 (s, 1H), 7.85 (s, 1H).

Example 67

(5R)-3-(1-Methyl-2-oxo-1,2,3,4-tetrahydroquinolin-6-yl)-2-oxo-5-oxazolidinecarboxamide

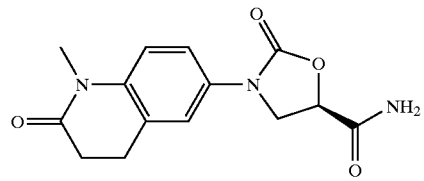

Step 1: Preparation of 6-nitro-3,4-dihydro-1H-quinolin-2-one 3,4-Dihydro-2(1H)-quinolinone (1.0 g, 6.70 mmol) is dissolved in 20 mL of concentrated sulfuric acid at −10° C., and then 5 mL of water is added slowly to the solution. After 5 minutes, 61% nitric acid (0.5 mL, 6.70 mmol) is added drdpwise to the solution. The reaction mixture turns from yellow to dark red, and eventually solidifies. After 1 hour, water (50 mL) is added slowly at −10° C. and precipitate appears. The solution is poured into a separatory funnel, extracted with ethyl acetate (20 mL×2) and washed with saline (20 mL). The organic layers are collected and dried over MgSO$_4$. Solvent is removed and the title compound is obtained as a pale yellow solid (1.0 g, 76%); $^1$H NMR (300 MHz, DMSO) δ 10.66 (s, 1H), 8.08–8.01 (m, 2H), 6.96 (d, 1H), 2.98 (t, 2H), 2.49 (dd, 2H).

Step 2: Preparation of 1-methyl-6-nitro-3,4-dihydro-1H-quinolin-2-one

To a stirred suspension of 6-nitro-3,4-dihydro-1H-quinolin-2-one (Step 1, 990 mg, 5.15 mmol) in DMF (3.0 mL) is added K$_2$CO$_3$ (855 mg, 1.2 equiv.) followed by MeI (0.64 mL, 2.0 equiv.). The resulting solution is stirred overnight at room temperature. Water (20 mL) is then added and the reaction mixture is extracted with ethyl acetate (20 mL×2) and washed with saline (20 mL). The organic layers are collected and dried over MgSO$_4$. Solvent is removed to yield the title compound as a yellow solid (956 mg, 90%). $^1$H NMR (300 MHz, DMSO) δ 8.16–7.26 (m, 3H), 3.30 (s, 3H), 3.00 (t, 2H), 2.61 (m, 2H).

Step 3: Preparation of 6-amino-1-methyl-3,4-dihydro-1H-quinolin-2-one

To a stirred suspension of 1-methyl-6-nitro-3,4-dihydro-1H-quinolin-2-one (Step 2, 1.04 g, 5.05 mmol) in EtOH (10 mL) and water (5 mL) is added ammonium chloride (2.70 g, 10.0 equiv.). To this mixture is added iron powder (0.85 g, 3.0 equiv.) in 3 portions. The resulting mixture is heated at reflux for 2 h and then is cooled to room temperature. The resulting mixture is filtered through celite and the filtrate is further diluted with water (100 mL). The filtrate is extracted with ethyl acetate (2×50 mL) and washed with saline (100 mL). The organic layers are combined, dried over MgSO$_4$ and concentrated under reduced pressure to yield the title compound as a yellow solid (0.86 g, 97%), MS (m/z): 177.5 [M+H]$^+$.

Step 4: Preparation of 3-(1-methyl-2-oxo-1,2,3,4-tetrahydroquinolin-6-yl)-2-oxo-5-oxazolidinecarboxylic acid methyl ester To a stirred solution 6-amino-1-methyl-3,4-dihydro-1H-quinolin-2-one (Step 3, 0.86 g, 4.91 mmol) in acetonitrile (5 mL) is added lithium triflate (0.77 g, 4.91 mmol) followed by methyl-(R)-glycidate (0.42 mL, 4.91 mmol). The resulting mixture is heated at 100° C. for 3 h at which time HPLC indicates complete consumption of the starting material. The reaction is quenched by the addition of water (50 mL), and the reaction mixture is extracted with dichloromethane (50 mL×2). The combined organic layer is washed with saline (100 mL), dried over MgSO$_4$ and concentrated under reduced pressure, and the resulting crude oil is purified by silica gel chromatography (20% acetone/CH$_2$Cl$_2$) to give the amino alcohol intermediate as a yellow solid (0.72 g). This intermediate is dissolved in anhydrous acetonitrile (3 mL) followed by addition of CDI (0.95 g, 2.25 equiv.) at room temperature. The resulting reaction mixture is stirred for 1 hour at room temperature. Solvent is removed and the residue is purified by silica gel chromatography (100% EtOAc) to give the title compound as a white solid (0.60 g, 76%), MS (m/z): 305.5 [M+H]$^+$.

Step 5: Preparation of (5R)-3-(1-methyl-2-oxo-1,2,3,4-tetrahydroquinolin-6-yl)-2-oxo-5-oxazolidinecarboxamide To a stirred solution of 3-(1-methyl-2-oxo-1,2,3,4-tetrahydroquinolin-6-yl)-2-oxo-oxazolidine-5-carboxylic acid methyl ester (Step 4, 150 mg, 0.49 mmol) in MeOH (1 mL) is added 2.0 M NH$_3$ in MeOH (1 mL, 2.0 mmol). The reaction mixture is then heated at 50–60° C. until all of the solid disappears. Solvent is removed and the residue is dissolved in 20% MeOH/CH$_2$Cl$_2$ and purified by silica gel chromatography (10% MeOH/CH$_2$Cl$_2$) to give the title compound as a white solid (120 mg, 84%), $^1$H NMR (300 MHz, DMSO) δ 7.85 (br s, 1H), 7.60 (br s, 1H), 7.45–7.08 (m, 3H), 5.01 (dd, 1H), 4.25 (t, 1H), 3.99 (dd, 1H), 3.23 (s, 3H), 2.86 (t, 2H), 2.50 (m, 2H); MS for C$_{14}$H$_{15}$N$_3$O$_4$ m/z 290.5 (M+H)$^+$.

Example 68

(5R)-N-Methyl-3-(1-methyl-2-oxo-1,2,3,4-tetrahydroquinolin-6-yl)-2-oxo-5-oxazolidinecarboxamide

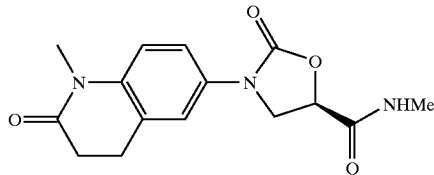

To a stirred solution of 3-(1-methyl-2-oxo-1,2,3,4-tetrahydroquinolin-6-yl)-2-oxo-5-oxazolidinecarboxylic acid methyl ester (EXAMPLE 67, Step 4, 150 mg, 0.49 mmol) in MeOH (2 mL) is added MeNH$_2$ (2 mL, 4.0 mmol, 2.0 M solution in MeOH). The reaction mixture is then stirred for 30 minutes at room temperature. Solvent is removed and the residue is washed with ether to give the title compound as a white solid (120 mg, 80%), $^1$H NMR (300 MHz, DMSO) δ 8.37 (d, 1H), 7.44–7.07 (m, 3H), 5.04 (dd, 1H), 4.25 (t, 1H), 3.99 (dd, 1H), 3.23 (s, 3H), 2.86 (t, 2H), 2.65 (d, 3H), 2.50 (m, 2H); MS for C$_{15}$H$_{17}$N$_3$O$_4$ m/z 304.5 (M+H)$^+$.

Example 69

(5R)-3-[4-(4-oxo-3,4-Dihydro-1(2H)-pyridinyl)-3-fluorophenyl]-2-oxo-5-oxazolidinecarboxamide

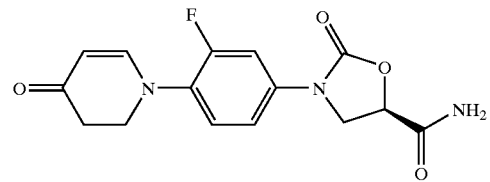

Step 1: Preparation of 1-(2-fluoro-4-nitrophenyl)piperidin-4-one

To a stirring solution of 4-piperidone monohydrate hydrochloride (258.7 g, 1.68 mol) and diisopropylethylamine (590 ml, 3.39 mol) in acetonitrile (2.5 liter) is added 3,4-difluoronitrobenzene (186.3 ml, 1.68 mol). The mixture is heated to 80° C. and stirred overnight. The solvent is cooled to ambient temperature and removed under reduced pressure. The residue is partitioned between ethyl acetate and 10% aqueous HCl (1.20 liter each). The layers are shaken, and the organic layer is separated and washed with 10% HCl and saline (800 ml each). The organic layer is dried over MgSO$_4$ and filtered. As the solvent is removed under reduced pressure a solid begins to precipitate out (~1/4 volume). The resulting slurry is cooled to 0–5° C. and filtered to afford 333.7 g of the title compound, $^1$H NMR (400 MHz, CDCl$_3$) δ 2.65 (m, 4 H), 3.65 (m, 4 H), 6.98 (m, 1 H), 7.26 (s, 1 H), 8.00 (m, 1H).

Step 2: Preparation of 1-(2-fluoro-4-nitrophenyl)-4-[(trimethylsilyl)oxy]-1,2,3,6-tetrahydropyridine To a stirred solution of 1-(2-fluoro-4-nitrophenyl)piperidin-4-one (Step 1, 250 g, 1.05 mol) and triethylamine (223 g, 2.20 mol) in toluene (4.2 liter) at 0° C. is slowly added trimethylsilyl trifluoromethanesulfonate (TMS-OTf, 280 g, 1.26 mol) via addition funnel. The stirring is continued for 30 min and the mixture allowed to warm to ambient temperature. Water (5 liter) is added and the aqueous layer extracted with EtOAc (3×500 ml). The organics are combined, dried over MgSO$_4$ and the solvent removed under reduced pressure. Hexane (4×500 ml) is added and the solvent removed under reduced pressure. At the fourth co-distillation, a slurry forms (~300 ml). The mixture is cooled to 0° C. and the solids filtered. The filtrate is concentrated to a slurry, cooled and filtered (2$^{nd}$ crop). Solids are combined to give 273.7 g (84%) of the title compound as a yellow solid, $^1$H NMR (CDCl$_3$) δ 0.21 (s, 9 H), 2.20 (brs, 2 H), 3.52 (brs, 2 H), 3.62 (brs, 2 H), 4.89 (brs, 1 H), 6.65 (t, 1 H), 7.67 (d, 1 H), 7.73 (d, 1H).

Step 3: Preparation of 1-(2-fluoro-4-nitrophenyl)-2,3-dihydro-1H-pyridin-4-one

To a stirring solution of 1-(2-fluoro-4-nitrophenyl)-4-[(trimethylsilyl)oxy]-1,2,3,6-tetrahydropyridine (Step 2, 100.0 g, 322 mmol) and allyl methyl carbonate (43.6 g, 386 mmol) in DMSO (625 ml) at ambient temperature is added Pd(OAc)$_2$ (7.20 g, 32 mmol). The resulting solution is stirred under N$_2$ at ambient temperature overnight. H$_2$O (1 liter) is added and solvent allowed to cool to ambient temperature. The aqueous layer is extracted with EtOAc (2×800 ml), and the combined organic layers are washed with saline (800 ml) and dried over MgSO$_4$. The solvent is removed and the residue recrystallized from EtOAc/MTBE to afford 53.6 g (70%) of the title compound as a yellow solid, $^1$H NMR (CDCl$_3$) δ 2.71 (m, 2 H), 4.06 (m, 2 H), 5.41 (d, 1 H), 7.25 (m, 1 H), 7.35 (d, 1 H), 8.08 (m, 2H).

Step 4: Preparation of 1-(4-amino-2-fluorophenyl)-2,3-dihydro-1H-pyridin-4-one

In a 500 ml Parr bottle, 1-(2-fluoro-4-nitrophenyl)-2,3-dihydro-1H-pyridin-4-one (Step 3, 35 g, 148.3 mmol), Pd/CaCO$_3$ (3.5 g, 10 wt %) and acetic acid (17 ml, 297 mmol) are combined in THF (350 ml). The mixture is hydrogenated at 40° C. under 15 psi hydrogen for 6 h at which time the reaction is complete by HPLC. The reaction mixture is filtered through a GF/F filter and the catalyst cake washed with THF (350 ml). The filtrate is partitioned between 500 ml of NaHCO$_3$ and 500 ml of ethyl acetate. The organic layer is washed again with 500 ml of NaHCO$_3$. The organic layer is separated and dried over MgSO$_4$. The mixture is filtered, and the filtrate is concentrated under reduced pressure to afford 29.0 g (95% recovery) of the title compound, MS (ESI−) for C$_{11}$H$_{11}$FN$_2$O m/z 205.0 (M−H)$^-$; $^1$H NMR (MeOD) δ 7.37 (d, 1 H), 7.02 (t, 1 H), 6.47 (m, 3 H), 5.07 (d, 1 H), 3.84 (t, 2 H), 2.58 (t, 1H).

Step 5: Preparation of 3-[3-fluoro-4-(4-oxo-3,4-dihydro-2H-pyridin-1-yl)phenylamino]-2(R)-hydroxypropionic acid ethyl ester A solution of 1-(4-amino-2-fluorophenyl)-2,3-dihydro-1H-pyridin-4-one (Step 4, 0.412 g, 2.0 mmol) and oxirane-2(R)-carboxylic acid ethyl ester (0.394 g, 3.4 mmol) with lithium triflate (0.360 g, 3.0 mmol) in dry acetonitrile (5.0 mL) is heated at 50–60° C. for 24 h. Volatiles are removed under vacuum, and the crude material purified by silica gel flash chromatography (eluent: 5% acetone in CH$_2$Cl$_2$) to afford the title compound (290 mg, 45%) as a viscous yellow oil, MS (m/z): 323 [M +H]$^+$.

Step 6: Preparation of 5(R)-3-[4-(4-oxo-3,4-dihydro-1(2H)-pyridinyl)-3-fluorophenyl]-2-oxo-5-oxazolidinecarboxamide CDI (162.0 mg, 1.0 mmol) is added with stirring to a solution of 3-[3-fluoro-4-(4-oxo-3,4-dihydro-2H-pyridin-1-yl)phenylamino]-2(R)-hydroxypropionic acid ethyl ester (Step 5, 146.0 mg, 0.45 mmol) in acetonitrile (4.0 mL), and the mixture is stirred at room temperature overnight. Solvent is removed under vacuum, and the residue partitioned between EtOAc (30 mL) and aq. 3% citric acid (30 mL). The aqueous layer is extracted with EtOAc (2×30 mL), and the combined organic layers are washed with water and saline and dried (MgSO$_4$). EtOAc is removed under vacuum to afford the crude 3-[3-fluoro-4-(4-oxo-3,4-dihydro-2H-pyridin-1-yl)phenyl]-2-oxo-5-oxazolidinecarboxylic acid ethyl ester which is used in the next step w/o further purification (MS (m/z): 349 [M+H]$^+$). The ester intermediate is taken up in 2M methanolic ammonia (8.0 mL, 16.0 mmol), and the resulting solution heated in a closed vial at 60° C. for 1 h. Volatiles are removed under vacuum, and the crude material purified by silica gel chromatography (eluent: 2% MeOH in CH$_2$Cl$_2$) to afford the title compound (55.0 mg, 38% for two steps) as white crystals, MS for C$_{15}$H$_{14}$FN$_3$O$_4$ m/z 320 (M+H)$^+$; $^1$H NMR (CD$_3$CN): δ 2.51 (m, 2 H), 3.89 (m, 2 H), 4.05 (m, 1 H), 4.24 (dd, 1 H), 4.97 (m, 1 H), 5.03 (d, 1 H), 6.18 (br. s, 1 H), 6.72 (br. s, 1 H), 7.20–7.40 (m, 3 H), 7.57 (d, 1 H).

Example 70

(5R)-N-Methyl-3-[4-(4-oxo-3,4-dihydro-1(2H)-pyridinyl)-3-fluorophenyl]-2-oxo-5-oxazolidinecarboxamide

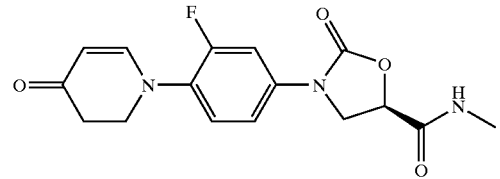

To a stirred solution of 3-[4-(4-oxo-3,4-dihydro-2H-pyridin-1-yl)-3-fluorophenyl]-2-oxo-5-oxazolidinecarboxylic acid ethyl ester (EXAMPLE 69, within Step 6, 120 mg, 0.34 mmol) in MeOH (1 mL) is added MeNH$_2$ (2 mL, 4.0 mmol, 2.0 M solution in MeOH). The reaction mixture is stirred for 1 h at room temperature. Solvent is removed and the residue purified by column chromatography (10% MeOH/CH$_2$Cl$_2$) to give the title compound as a pale yellow solid (60 mg, 52%), $^1$H NMR (300 MHz, DMSO) δ 8.39 (m, 1H), 7.65–7.38 (m, 4H), 5.06 (dd, 1H), 4.98 (d, 1H), 4.27 (t, 1H), 4.02 (dd, 1H), 3.87 (t, 2H), 2.65 (d, 3H); MS for C$_{16}$H$_{16}$FN$_3$O$_4$ m/z 334.5 (M+H)$^+$.

Example 71

(5R)-N-Ethyl-3-[4-(4-oxo-3,4-dihydro-1(2H)-pyridinyl)-3-fluorophenyl]-2-oxo-5-oxazolidinecarboxamide

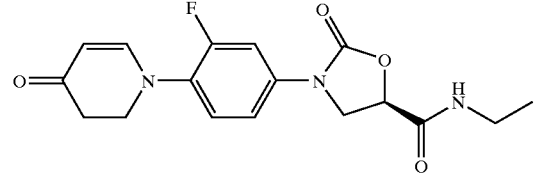

To a stirred solution of 3-[4-(4-oxo-3,4-dihydro-2H-pyridin-1-yl)-3-fluorophenyl]-2-oxo-5-oxazolidinecarboxylic acid ethyl ester (EXAMPLE 69, within Step 6, 108 mg, 0.31 mmol) in MeOH (1 mL) is added EtNH$_2$ (2 mL, 4.0 mmol, 2.0 M solution in THF). The reaction mixture is stirred for 1 h at room temperature. Solvent is removed and the residue purified by column chromatography (10% MeOH/CH$_2$Cl$_2$) to give the title compound as a pale yellow solid (100 mg, 93%), $^1$H NMR (300 MHz, DMSO) δ 8.46 (t, 1H), 7.65–7.38 (m, 4H), 5.05 (dd, 1H), 4.99 (d, 1H), 4.27 (t, 1H), 4.01 (dd, 1H), 3.87 (t, 2H), 3.20–3.10 (m, 2H), 1.04 (t, 3H); MS for C$_{17}$H$_{18}$FN$_3$O$_4$ m/z 348.5 (M+H)$^+$.

Example 72

(5R)-3-[4-(4-oxo-3,4-Dihydro-1(2H)-pyridinyl)phenyl]-2-oxo-5-oxazolidinecarboxamide

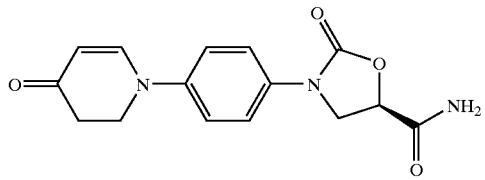

Step 1: Preparation of 1-(4-nitrophenyl)piperidin-4-one

The title compound is prepared following the method described in EXAMPLE 69, Step 1, using 4-fluoronitrobenzene (9.5 g, 67.3 mmol) in place of 3,4-difluoronitrobenzene. The reaction is performed at 50° C. overnight. Yield: 9.90 g (72%). MS (m/z): 221 [M+1]+; $^1$H NMR (300 MHz, CDCl$_3$); δ 8.15 (d, 2H), 6.83 (d, 2H), 3.80 (t, 4H), 2.61 (t, 4H).

Step 2: Preparation of 1-(4-Nitrophenyl)-4-(triisopropylsilanyloxy)-1,2,3,6-tetrahydropyridine The title compound is prepared from 1-(4-nitrophenyl)piperidin-4-one (Step 1, 9.90 g, 45 mmol) following the method described for EXAMPLE 69, Step 2, and purified by silica gel flash column chromatography (gradient 0 to 15% EtOAc in hexanes). Yield 9.70 g (57%). MS (m/z): 377 [M+1]+; $^1$H NMR (300 MHz, DMSO): δ 8.04 (d, 2H), 4.92 (d, 2H), 4.92 (t, 1H), 3.88 (br. d, 2H), 3.66 (t, 2H), 2.50–2.20 (m, 2H), 1.97–1.12 (m, 3H), 1.02 (d, 18H).

Step 3: 1-(4-nitrophenyl)-2,3-dihydro-1H-pyridin-4-one

The title compound is prepared from 1-(4-nitrophenyl)-4-(triisopropylsilanyloxy)-1,2,3,6-tetrahydropyridine (Step 2, 2.50 g, 6.65 mmol) following the method described for EXAMPLE 69, Step 3. The reaction is performed for 4 h, and the product purified by silica gel flash column chromatography (gradient 5% to 60% EtOAc inhexanes). Yield 2.10 g (57%). MS (m/z): 219 [M+1]+; $^1$H NMR (300 MHz, CDCl$_3$,): δ 8.39 (d, 2H), 7.49 (d, 1H), 7.14 (d, 2H), 5.39 (d, 1H), 4.06 (t, 4H), 2.72 (t, 4H).

Step 4: Preparation of 1-(4-aminophenyl)-2,3-dihydro-1H-pyridin-4-one

The title compound is prepared from 1-(4-nitrophenyl)-2,3-dihydro-1H-pyridin-4-one (Step 3, 2.75 g, 12.6 mmol) following the method described for EXAMPLE 69, Step 4. Yield 2.0 g (84%). MS (m/z): 211 (M+Na)+.

Step 5: Preparation of (5R)-3-[4-(4-oxo-3,4-dihydro-2H-pyridin-1-yl)phenyl]-2-oxo-5-oxazolidinecarboxylic acid ethyl ester To a stirred solution of 1-(4-aminophenyl)-2,3-dihydro-1H-pyridin-4-one (Step 4, 550 mg, 2.90 mmol) in acetonitrile (5 mL) is added ethyl-(2R)-2,3-epoxypropanate (563 mg, 4.90 mmol) and LiOTf (522 mg, 4.40 mmol). The resulting solution is stirred at 50–60° C. for 22 h at which time the reaction mixture is concentrated under reduced pressure and the residue is purified by silica gel chromatography (5% acetone in CH$_2$Cl$_2$) to afford the amino alcohol intermediate as an orange-colored oil (275 mg, 31%, MS (m/z): 305.5 [M+H]+). The oil (258 mg, 0.85 mmol) is dissolved in acetonitrile (5 mL) followed by addition of CDI (309.5 mg, 1.91 mmol). The resulting reaction mixture is stirred at room temperature for 36 h at which time the reaction is concentrated under reduced pressure to dryness. The residue is dissolved in EtOAc (50 mL) and washed with 50% aqueous citric acid solution (50 mL). The aqueous phase is washed with EtOAc (5 mL×2), and the combined organic phase is dried over MgSO$_4$, filtered and concentrated under reduced pressure. The crude product is purified by silica gel chromatography (2% MeOH in CH$_2$Cl$_2$) to give the title compound as a yellow solid (260 mg, 92%), MS (m/z): 331.5 [M+H]+.

Step 6: Preparation of 5(R)-3-[4-(4-oxo-3,4-dihydro-1(2H)-pyridinyl)phenyl]-2-oxo-5-oxazolidinecarboxamide (5R)-2-Oxo-3-[4-(4-oxo-3,4-dihydro-2H-pyridin-1-yl)phenyl]oxazolidine-5-carboxylic acid ethyl ester (Step 5, 213 mg, 0.64 mmol) is dissolved in 2.0 M NH$_3$ in MeOH (8 mL) in a sealed glass vial. This mixture is heated at 60° C. for 1.25 h at which time the reaction is concentrated under reduced pressure and purified by silica gel column chromatography (using 2% MeOH in EtOAc and 2% MeOH in CH$_2$Cl$_2$) to obtain the title compound as a light yellow solid (85 mg, 44%), $^1$H NMR (300 MHz, DMSO) δ 7.85 (br s, 1H), 7.73 (d, 1H), 7.60–7.55 (m, 3H), 7.30–7.26 (m, 2H), 5.03–4.97 (m, 2H), 4.27 (t, 1H), 4.01–3.93 (m, 3H); MS for C$_{15}$H$_{15}$N$_3$O$_4$ m/z 302.5 (M+H)+.

Example 73

(5R)-N-Methyl-3-[4-(4-oxo-3,4-dihydro-1(2H)-pyridinyl)phenyl]-2-oxo-5-oxazolidinecarboxamide

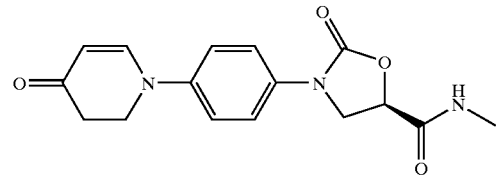

The title compound is prepared from (5R)-2-oxo-3-[4-(4-oxo-3,4-dihydro-2H-pyridin-1-yl)phenyl]oxazolidine-5-carboxylic acid ethyl ester (EXAMPLE 72, Step 5, 250 mg, 0.76 mmol) following the method described for EXAMPLE 70. Yield 130 mg (54%). MS for C$_{16}$H$_{17}$N$_3$O$_4$ m/z 316.3 (M+H)+.

Example 74

(5R)-N-Ethyl-3-[4-(4-oxo-3,4-dihydro-1(2H)-pyridinyl)phenyl]-2-oxo-5-oxazolidinecarboxamide

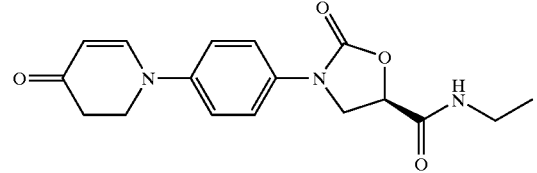

The title compound is prepared from (5R)-2-oxo-3-[4-(4-oxo-3,4-dihydro-2H-pyridin-1-yl)phenyl]oxazolidine-5-carboxylic acid ethyl ester (Example 72, Step 5, 50 mg, 0.15 mmol) following the method described for EXAMPLE 71. Yield 27 mg (55%). MS for C$_{17}$H$_{19}$N$_3$O$_4$ m/z 330.5 (M+H)+.

Example 75

(5R)-N-(2-Fluoroethyl)-3-[4-(4-oxo-3,4-dihydro-1 (2H)-pyridinyl)phenyl]-2-oxo-5-oxazolidinecarboxamide

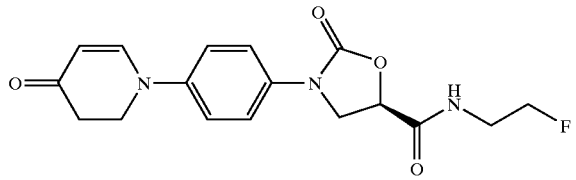

To a stirred solution of (5R)-3-[4-(4-oxo-3,4-dihydro-2H-pyridin-1-yl)phenyl]-2-oxo-5-oxazolidinecarboxylic acid ethyl ester (EXAMPLE 72, Step 5, 226 mg, 0.68 mmol) in MeOH (2 mL) is added triethylamine (0.48 mL, 5.0 equiv.). Then 2-fluoroethylamine hydrochloride (136 mg, 2.0 equiv.) is added to the solution. The reaction mixture is heated at 50–60° C. for 5 h, followed by stirring overnight at room temperature. Solvent is removed and the residue is dissolved in 20% MeOH/$CH_2Cl_2$ and purified by column chromatography (10% MeOH/$CH_2Cl_2$). The title compound is obtained as a yellow solid (100 mg, 42%), $^1$H NMR (300 MHz, DMSO) δ 8.69 (t, 1H), 7.75–7.27 (m, 5H), 5.09 (dd, 1H), 4.98 (d, 1H), 4.55 (t, 1H), 4.39 (t, 1H), 4.29 (t, 1H), 4.02–3.93 (m, 3H), 3.51–3.37 (m, 2H), 2.50–2.45 (m, 2H); MS for $C_{17}H_{18}FN_3O_4$ m/z 348.5 (M+H)$^+$.

Example 76

(5R)-3-[4-(4-oxo-3,4-Dihydro-1(2H)-pyridinyl)-3,5-difluorophenyl]-2-oxo-5-oxazolidinecarboxamide

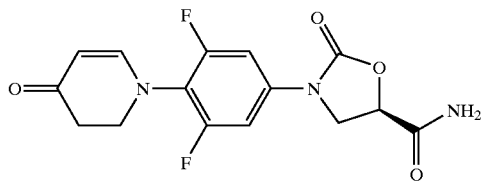

Step 1: Preparation of 1-(2,6-difluoro-4-nitrophenyl)piperidin-4-one

The title compound is prepared following the method described for EXAMPLE 69, Step 1, using 3,4,5-trifluoronitrobenzene (3.00 g, 16.94 mmol). Yield 1,71 g, (40%). MS (m/z): 257 [M+1]$^+$; $^1$H NMR (300 MHz, CDCl$_3$): δ 7.80 (d, 1H), 3.63 (dd, 4H), 2.59 (dd, 4H).

Step 2: Preparation of 1-(2,6-difluoro-4-nitrophenyl)-4-(triisopropylsilanyloxy)-1,2,3,6-tetrahydro-pyridine The title compound is prepared from 1-(2,6-difluoro-4-nitrophenyl)piperidin-4-one (Step 1, 1.73 g, 6.75 mmol) following the method described for EXAMPLE 69, Step 2, and purified by silica gel flash chromatography (0 to 25% EtOAc in hexanes). Yield 2.78 g (quant). $^1$H NMR (300 MHz, CDCl$_3$): δ 7.73 (d, 2H), 4.89–4.86 (m, 1H), 3.90–3.87 (m, 2H), 3.50–3.45 (m, 2H), 2.34–2.30 (m, 2H), 1.07–0.99 (m, 21H).

Step 3: Preparation of 1-(2,6-difluoro-4-nitro-phenyl)-2,3-dihydro-1H-pyridin-4-one The title compound is prepared from 1-(2,6-difluoro-4-nitrophenyl)-4-(triisopropylsilanyloxy)-1,2,3,6-tetrahydropyridine (Step 2, 3.10 g, 7.51 mmol) following the method described in EXAMPLE 69, Step 3, in 30 min and purified by silica gel flash chromatography (eluent: 50% EtOAc in hexanes). Yield 1.34 g (70%). MS (m/z): 255 [M+1]$^+$; $^1$H NMR (300 MHz, CDCl$_3$): δ 8.23 (d, 2H), 7.53–7.49 (m, 1H), 5.23 (d, 1H), 3.95 (t, 2H), 2.53–2.47 (m, 2H).

Step 4: Preparation of 1-(4-amino-2,6-fluorophenyl)-2,3-dihydro-1H-pyridin-4-one The title compound is prepared from 1-(2,6-difluoro-4-nitrophenyl)-2,3-dihydro-1H-pyridin-4-one (Step 3, 1.34 g, 5.27 mmol) following the method described for EXAMPLE 69, Step 4. Yield 1.08 g (91%).

Step 5: Preparation of (5R)-3-[3,5-difluoro-4-(4-oxo-3,4-dihydro-2H-pyridin-1-yl)phenyl]-2-oxo-5-oxazolidinecarboxylic To a stirred solution of 1-(4-amino-2,6-fluorophenyl)-2,3-dihydro-1H-pyridin-4-one (Step 4, 553 mg, 2.46 mmol) in acetonitrile (20 mL) is added by butyl-(R)-glycidate (532 mg, 3.69 mmol) followed by LiOTf (770 mg, 4.93 mmol). The resulting solution is stirred at 50° C. for 16 h at which time the reaction is quenched by addition of water (20 mL) and extracted with EtOAc (20 mL×3). The combined organic phase is dried over Na$_2$SO$_4$, filtered and concentrated under reduced pressure to yield crude product that is passed through a short silica gel column (EtOAc) to give the amino alcohol intermediate (620 mg; MS (m/z): 369.4 [M+H]$^+$) which is used without further purification. To a stirred solution of this intermediate in acetonitrile (20 mL) is added CDI (750 mg, 4.62 mmol). The resulting solution is stirred at room temperature for 16 h at which time the reaction is quenched by the addition of water (20 mL) and diluted with EtOAc (25 mL). The organic phase is separated followed by extraction of the aqueous phase with EtOAc (20 mL×2). The combined organic phase is washed with water (20 mL) and saline (20 mL), dried over Na$_2$SO$_4$ and concentrated under reduced pressure and the residue is purified by silica gel chromatography (50% EtOAc in hexane to EtOAc) to give the title compound (219 mg, 24% over 2 steps), MS (m/z): 395.6 [M+H]$^+$.

Step 6: Preparation of (5R)-3-[4-(4-oxo-3,4-dihydro-1(2H)-pyridinyl)-3,5-difluorophenyl]-2-oxo-5-oxazolidinecarboxamide (5R)-3-[3,5-Difluoro-4-(4-oxo-3,4-dihydro-2H-pyridin-1-yl)phenyl]-2-oxo-5-oxazolidinecarboxylic acid butyl ester (Step 5, 200 mg, 0.50 mmol) is dissolved in a 2M solution of NH$_3$ in MeOH (4 mL, 8 mmol). The resulting solution is stirred at room temperature for 3 h at which time the reaction mixture is concentrated under reduced pressure. The residue is washed with ether to give the title compound as an off white solid (139 mg, 82%), $^1$H NMR (300 MHz, DMSO) δ 7.89 (br s, 1H), 7.64 (br s, 1H), 7.54–7.38 (m, 3H), 5.07–4.98 (m, 2H), 4.26 (t, 1H), 4.01 (dd, 1H), 3.78 (t, 2H); MS for $C_{15}H_{13}F_2N_3O_4$ m/z 338.4 (M+H)$^+$.

Example 77

(5R)-N-Methyl-3-[4-(4-oxo-3,4-dihydro-1(2H)-pyridinyl)-3,5-difluorophenyl]-2-oxo-5-oxazolidinecarboxamide

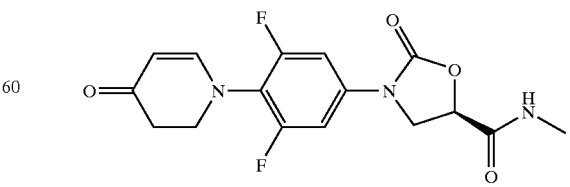

To a stirred solution of (5R)-3-[3,5-Difluoro-4-(4-oxo-3, 4-dihydro-2H-pyridin-1-yl)phenyl]-2-oxo-5- oxazolidinecarboxylic acid butyl ester (EXAMPLE 76, Step 5, 132 mg) in MeOH (1 mL) is added MeNH₂ (2 mL, 4.0 mmol, 2.0 M solution in MeOH). The reaction mixture is then heated at 40–50° C. until all of the solid disappears. Solvent is removed and the residue is dissolved in 20% MeOH/CH₂Cl₂ and purified by silica gel chromatography (10% MeOH/CH₂Cl₂) to give the title compound as a yellow solid (100 mg, 76%), ¹H NMR (300 MHz, DMSO) δ 8.40 (m, 1H), 7.52–7.38 (m, 3H), 5.08 (dd, 1H), 5.00 (d, 1H), 4.26 (t, 1H), 4.01 (dd, 1H), 3.78 (t, 2H), 2.65 (d, 3H); MS for $C_{16}H_{15}F_2N_3O_4$ m/z 352.5 (M+H)⁺.

Example 78

(5R)-N-Ethyl-3-[4-(4-oxo-3,4-dihydro-1(2H)-pyridinyl)-3,5-difluorophenyl]-2-oxo-5-oxazolidinecarboxamide

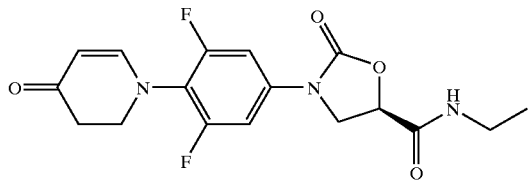

The title compound is prepared from (5R)-3-[3,5-difluoro-4-(4-oxo-3,4-dihydro-2H-pyridin-1-yl)phenyl]-2-oxo-5-oxazolidinecarboxylic acid butyl ester (EXAMPLE 76, Step 5, 60 mg) following the method described for EXAMPLE 71.

¹H NMR (300 MHz, DMSO) δ 8.48 (t, 1H), 7.52–7.38 (m, 3H), 5.06 (dd, 1H), 4.99 (d, 1H), 4.26 (t, 1H), 4.01 (dd, 1H), 3.79 (t, 2H), 3.20–3.10 (m, 2H), 1.04 (t, 3H); MS for $C_{17}H_{17}F_2N_3O_4$ m/z 366.5 (M+H)⁺.

Example 79

(5R)-3-[4-[3,4-Dihydro-4-(hydroxyimino)-1(2H)-pyridinyl]-3-fluorophenyl]-2-oxo-5-oxazolidinecarboxamide

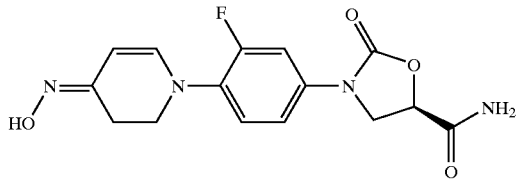

To a stirred solution of 5(R)-3-[4-(4-oxo-3,4-dihydro-1(2H)-pyridinyl)-3-fluorophenyl]-2-oxo-5-oxazolidinecarboxamide (EXAMPLE 69, 110 mg, 0.34 mmol) in pyridine (2 mL) is added hydroxylamine hydrochloride (95 mg, 1.38 mmol). To this mixture is added MeOH (1 mL) and CH₂Cl₂ (1 mL) and the solution becomes clear. This solution is stirred for 16 h at which time it is concentrated under reduced pressure. The residue is purified by silica gel chromatography (2 to 5% MeOH in EtOAc) to give the title compound as a white solid (18 mg, 16%) as a mixture of E and Z isomers, ¹H NMR (300 MHz, DMSO) δ 10.32 (s, 1H, minor isomer), 10.06 (s, 1H, major isomer), 7.61–7.53 (m, 2H), 7.35–7.7.20 (m, 2H), 6.76–6.64 (m, 1H), 5.59 (d, 1H, major isomer), 5.19 (d, 1H, minor isomer), 5.04–4.99 (m, 1H), 4.25 (t, 1H), 4.02–3.96 (m, 1H), 3.65–3.50 (m, 2H), 2.71–2.66 (m, 2H); MS (ESI+) for $C_{15}H_{15}FN_4O_4$ m/z 335 (M+H)⁺.

Example 80

(5R)-3-(2,2-Difluoro-4-methyl-3,4-dihydro-3-oxo-2H-1,4-benzoxazin-7-yl)-2-oxo-5-oxazolidinecarboxamide

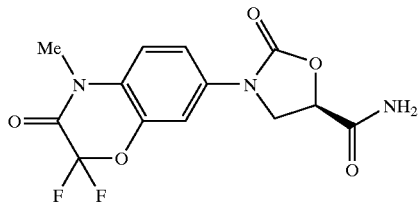

Step 1: Preparation of 2,2-difluoro-4-methyl-7-nitro-4H-1,4-benzoxazin-3-one

To a stirred suspension of 2,2-difluoro-7-nitro-4H-1,4-benzoxazin-3-one (WO 99/40094, 2.16 g, 9.38 mmol) in DMF (10 mL) is added K₂CO₃ (1.94 g, 14.07 mmol) followed by addition of MeI (0.87 mL, 14.07 mmol). The resulting solution is stirred over night at room temperature. To this reaction mixture is added water (50 mL), and the resulting solution is extracted with EtOAc (50 mL×3). The combined organic phases are washed with water (50 mL) and saline (50 mL), dried over Na₂SO₄ and concentrated under reduced pressure to give the title compound that is purified by passing through a short silica gel column with EtOAc (1.3 g, 57%), ¹H NMR (300 MHz, DMSO) δ 8.25–8.17 (m, 2H), 7.62 (d, 1H), 3.47 (s, 3H).

Step 2: Prepartion of 2,2-difluoro-4-methyl-7-amino-4H-1,4-benzoxazin-3-one

To a stirred suspension of 2,2-difluoro-4-methyl-7-nitro-4H-1,4-benzoxazin-3-one (Step 1, 1.3 g, 5.32 mmol) in EtOH (20 mL) and water (10 mL) is added ammonium chloride (2.85 g, 53.32 mmol). To this mixture is added iron (892 mg, 15.09 mmol) in 3 equal portions. The resulting mixture is heated to 80° C. for 2 h at which time the reaction is cooled to room temperature followed by addition of CH₂Cl₂ (50 mL). The resulting mixture is filtered through celite and the filtrate is further diluted with water (50 mL). The organic layer is separated followed by further extraction of the aqueous phase with CH₂Cl₂ (50 mL×3). The combined organic phase is dried over Na₂SO₄ and concentrated under reduced pressure, and the residue is purified by passing it through a short silica gel column with EtOAc to give the title compound (1.05 g, Quant.), MS (m/z): 215.5 [M+H]⁺.

Step 3: Preparation of (5R)-3-(2,2-difluoro-4-methyl-3,4-dihydro-3-oxo-2H-1,4-benzoxazin-7-yl)-2-oxo-5-oxazolidinecarboxylic acid methyl ester To a stirred solution 2,2-difluoro-7-amino-4-methyl-4H-1,4-benzoxazin-3-one (Step 2, 1.05 g, 4.90 mmol) in acetonitrile (25 mL) is added LiOTf (841 mg, 5.39 mmol) followed by methyl-(R)-glycidate (549 mg, 5.39 mmol). The resulting mixture is heated to 50° C. over night at which time HPLC indicates complete consumption of the starting material. The reaction is quenched by addition of water (50 mL), EtOAc (100 mL) and saline (50 mL). The organic phase is separated followed by further extraction of the aqueous phase with EtOAc (20 mL×3). The combined organic phase is dried over Na₂SO₄, filtered and concentrated under reduced pressure, and the residue is passed through a short silica gel column (EtOAc) to remove the polar impurities from the amino alcohol intermediate (MS (m/z): 317.5

[M+H]⁺). This intermediate is dissolved in anhydrous acetonitrile (20 mL) followed by addition of CDI (1.58 g, 9.80 mmol, 2 eq. wrt aniline above) at room temperature. The resulting reaction mixture is stirred overnight at which time it is diluted with 0.1 N HCl (10 mL). The resulting pale yellow precipitate is filtered off, washed with additional 0.1 N HCl (25 mL) and water (100 mL) and dried under high vacuum to give the title compound (1.30 g, 77% for two steps), MS (m/z): 342.7 [M+H]⁺.

Step 4: Preparation of (5R)-3-(2,2-difluoro-4-methyl-3,4-dihydro-3-oxo-2H-1,4-benzoxazin-7-yl)-2-oxo-5-oxazolidinecarboxamide To a stirred solution of (5R)-3-(2,2-difluoro-4-methyl-3-oxo-3,4-dihydro-2H-1,4-benzoxazin-7-yl)-2-oxo-5-oxazolidinecarboxylic acid methyl ester (Step 3, 50 mg, 0.14 mmol) in MeOH (1 mL) is added 2M NH₃ in MeOH (2 mL, 4 mmol). The resulting mixture is stirred for 16 h at which time the reaction is concentrated under reduced pressure and purified by silica gel chromatography (EtOAc) to give the title compound as a light yellow solid (21 mg, 44%), ¹H NMR (300 MHz, DMSO) δ 7.86 (br s, 1H), 7.61 (d, 2H), 7.52–7.41 (m, 2H), 5.02 (dd, 1H), 4.28 (t, 1H), 4.02 (dd, 1H), 3.42 (s, 3H); MS for C₁₃H₁₁F₂N₃O₅ m/z 328.5 (M+H)⁺.

Example 81

(5R)-N-Methyl-3-(2,2-difluoro-4-methyl-3,4-dihydro-3-oxo-2H-1,4-benzoxazin-7-yl)-2-oxo-5-oxazolidinecarboxamide

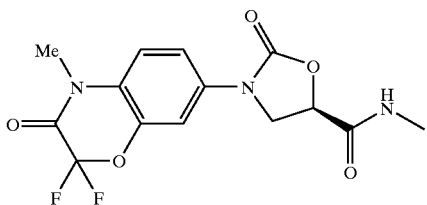

To a stirred solution of (5R)-3-(2,2-Difluoro-4-methyl-3-oxo-3,4-dihydro-2H-1,4-benzoxazin-7-yl)-2-oxo-5-oxazolidinecarboxylic acid methyl ester (EXAMPLE 80, Step 3,50 mg, 0.14 mmol) in MeOH (1 mL) is added 2M MeNH₂ in MeOH (2 mL, 4 mmol). The resulting mixture is stirred for 16 h at which time a precipitate forms. The mixture is heated until it becomes clear, and the product is allowed to crystallize at room temperature in the form of white needles. The crystals are separated, washed with ether and dried under high vacuum at 50° C. to give the title compound (25 mg, 50%), ¹H NMR (300 MHz, DMSO) δ 8.38 (br d, 1H), 7.60 (d, 1H), 7.51–7.41 (m, 2H), 5.06 (dd, 1H), 4.29 (t, 1H), 4.03 (dd, 1H), 3.41 (s, 3H), 2.65 (d, 2H); MS for C₁₄H₁₃F₂N₃O₅ m/z 342.5 (M+H)⁺.

Example 82

(5R)-3-(8-Fluoro-1-methyl-2-oxo-1,2,3,4-tetrahydroquinolin-6-yl)-2-oxo-5-oxazolidinecarboxamide

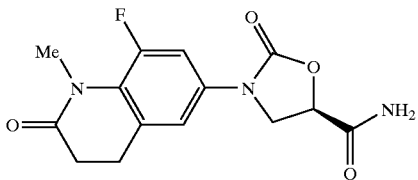

Step 1: Preparation of 8-fluoro-6-nitro-3,4-dihydro-1H-quinolin-2-one

8-Fluoro-3,4-dihydro-1H-quinolin-2-one [prepared according to the procedure found in EP0524846] (2.62 g, 0.0159 mol) is dissolved in concentrated sulfuric acid (20 ml) and cooled to −5° C. Nitric acid (70%, 1.02 ml, 0.0159 mol) is added dropwise and the reaction stirred at −5° C. for 20 minutes. The mixture is poured onto ice and the resulting precipitate collected by filtration, washed well with water, and dried under vacuum. Purification by flash column chromatography (30% ethyl acetate/hexane) gives the title compound as a light yellow solid (2.50 g, 75%); [M+H]⁺=211.

Step 2: Preparation of 8-fluoro-1-methyl-6-nitro-3,4-dihydro-1H-quinolin-2-one

8-Fluoro-6-nitro-3,4-dihydro-1H-quinolin-2-one (Step 1, 3.13 g, 0.0149 mol) and iodomethane (1.39 ml, 0.0223 mol) in DMF (25 ml) are stirred at room temperature overnight. The reaction is diluted with water and the resulting precipitate collected by filtration, washed well with water, and dried under vacuum to give the title compound as an orange solid (2.97 g, 89%); ¹H NMR (300 MHz, CDCl₃) δ 2.56–2.61 (m, 2H), 2.99–3.04 (m, 2H), 3.32 (s, 3H), overlapping 8.06 (s, 1H) and 8.08 (dd, 1H); [M+H]⁺=225.

Step 3: Preparation of 6-amino-8-fluoro-1-methyl-3,4-dihydro-1H-quinolin-2-one

8-Fluoro-1-methyl-6-nitro-3,4-dihydro-1H-quinolin-2-one (Step 2, 2.28 g, 0.0102 mol) is heated in ethanol (75 ml) until dissolved. Water (25 ml) and ammonium chloride (5.46 g, 0.102 mol) are added and the mixture heated to 90° C. Iron powder (2.27 g, 0.0407 mol) is added portionwise and the mixture stirred and heated for 30 minutes. The reaction is cooled and dichloromethane (200 ml) added. The mixture is filtered and the organic layer separated, washed with saline, dried (MgSO₄) and evaporated to give the title compound as a yellow solid (1.98 g, 99%); [M+H]⁺=195.

Step 4: Preparation of 3-(8-fluoro-1-methyl-2-oxo-1,2,3,4-tetrahydroquinolin-6-ylamino)-2-hydroxypropionic acid methyl ester 6-Amino-8-fluoro-1-methyl-3,4-dihydro-1H-quinolin-2-one (Step 3, 2.25 g, 0.0116 mol), methyl (2R)-glycidate (1.18 g, 0.0116 mol) and lithium trifluoromethanesulfonate (1.81 g, 0.0116 mol) in acetonitrile (10 ml) are heated at 90° C. overnight. The reaction is concentrated and the residue diluted with ethyl acetate, washed with water and saline, dried (MgSO₄) and evaporated. The residue is purified by flash column chromatography (50% ethyl acetate/hexane) to give the title compound as a yellow solid (2.13 g, 62%); MS (m/z): [M+H]⁺=297.

Step 5: Preparation of (5R)-3-(8-fluoro-1-methyl-2-oxo-1,2,3,4-tetrahydroquinolin-6-yl)-2-oxo-5-oxazolidinecarboxylic acid methyl ester Phosgene (20% solution in toluene, 4.07 ml, 7.69 mmol) is added dropwise at 0° C. to 3-(8-fluoro-1-methyl-2-oxo- 1,2,3,4-tetrahydroquinolin-6-ylamino)-2-hydroxypropionic acid methyl ester (Step 4, 1.81 g, 6.41 mmol) and triethylamine (2.23 ml, 16.0 mmol) in dichloromethane (25 ml). The mixture is allowed to warm. to room temperature and stirred for an additional hour. The reaction is washed with 2N aqueous hydrochloric acid and saline, dried (MgSO$_4$) and evaporated. The residue is purified by flash column chromatography (50% ethyl acetate/hexane) to give the title compound as a white solid (1.71 g, 83%); MS (m/z): [M+H]$^+$=323.

Step 6: Preparation of (5R)-3-(8-fluoro-1-methyl-2-oxo-1,2,3,4-tetrahydroquinolin-6-yl)-2-oxo-5-oxazolidinecarboxamide 3-(8-Fluoro-1-methyl-2-oxo-1,2,3,4-tetrahydroquinolin-6-yl)-2-oxo-5-oxazolidinecarboxylic acid methyl ester (Step 5, 0.300 g, 9.31 mmol) is dissolved in 2M ammonia in methanol solution (8 ml) and stirred overnight at room temperature. The resulting precipitate is filtered, washed with methanol, and dried under vacuum to give the title compound as a white solid (0.185 g, 65%), mp 260–2° C.; $^1$H NMR (300 MHz, CDCl$_3$) δ 2.48–2.52 (m, 2H), 2.85–2.89 (m, 2H), 3.28 (d, 3H), 4.00 (dd, 1H), 4.24 (t, 1H), 5.03 (dd, 1H), 7.27 (s, 1H), 7.46 (dd, 1H), 7.62 (br s, 1H), 7.87 (br s, 1H); MS for C$_{14}$H$_{14}$FN$_3$O$_4$ m/z 308 (M+H)$^+$.

Example 83

(5R)-N-Methyl-3-(8-fluoro-1-methyl-2-oxo-1,2,3,4-tetrahydroquinolin-6-yl)-2-oxo-5-oxazolidinecarboxamide

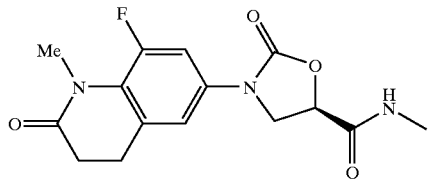

3-(8-Fluoro-1-methyl-2-oxo-1,2,3,4-tetrahydroquinolin-6-yl)-2-oxo-5-oxazolidinecarboxylic acid methyl ester (EXAMPLE 82, Step 5, 0.300 g, 9.31 mmol) is dissolved in 2M methylamine in methanol solution (8 ml) and stirred overnight at room temperature. The resulting precipitate is filtered, washed with methanol, and dried under vacuum to give the title compound as a white solid (0.145 g, 48%), mp 264–5° C.; $^1$H NMR (300 MHz, CDCl$_3$) δ 2.47–2.52 (m, 2H), 2.64 (d, 3H), 2.84–2.89 (m, 2H), 3.27 (d, 3H), 4.00 (dd, 1H), 4.24 (t, 1H), 5.06 (dd, 1H), 7.26 (s, 1H), 7.46 (dd, 1H), 8.39 (d, 1H); MS for C$_{15}$H$_{16}$FN$_3$O$_4$ m/z 322 (M+H)$^+$.

Example 84

3-(4-Methyl-3-thioxo-3,4-dihydro-2H-1,4-benzothiazin-7-yl)-2-oxo-5-oxazolidinecarboxamide

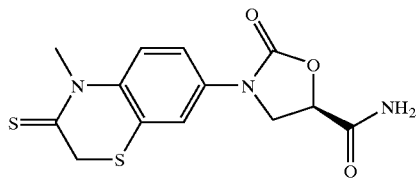

Step 1: Preparation of (5R)-3-(3,4-dihydro-4-methyl-3-thioxo-2H-1,4-benzothiazin-7-yl)-2-oxo-5-oxazolidinecarboxylic acid methyl ester To a stirred suspension of the (5R)-3-(3,4-dihydro-4-methyl-3-oxo-2H-1,4-benzothiazin-7-yl)-2-oxo-5-oxazolidinecarboxylic acid methyl ester (EXAMPLE 62, Step 5, 1.26 g, 3.907 mmol) in dry dioxane (25 mL) is added Lawesson's reagent (2.37 g, 5.861 mmol). This reaction mixture is heated at 70–80° C. for 1.5–2 h at which time the reaction is cooled to room temperature and concentrated under reduced pressure. The residue is washed with EtOAc (15 mL×3), sonicated and filtered to give the title compound as a yellow solid (1.18 g, 89%), MS (m/z): 339.5 [M+H]$^+$.

Step 2: Preparation of 3-(4-methyl-3-thioxo-3,4-dihydro-2H-1,4-benzothiazin-7-yl)-2-oxo-5-oxazolidinecarboxamide To a stirred suspension of (5R)-3-(3,4-dihydro-4-methyl-3-thioxo-2H-1,4-benzothiazin-7-yl)-2-oxo-5-oxazolidinecarboxylic acid methyl ester (Step 1, 100 mg, 0.2955 mmol) in MeOH (3 mL) is added 2.0 M ammonia in MeOH (1.0 mL). This mixture is heated at 40° C. for 24 h at which time the reaction is concentrated under reduced pressure. The residue is washed with MeOH (4 mL) and purified by column chromatography (2% MeOH/CH$_2$Cl$_2$) to give the title compound as a white solid (25 mg, 26%), $^1$H NMR (300 MHz, DMSO) δ 7.87 (br s, 1H), 7.64 (d, 2H), 7.51 (s, 2H), 5.03 (dd, 1H), 4.28 (t, 1H), 4.02 (dd, 1H), 3.85 (s, 2H), 3.32 (s, 3H); MS for C$_{13}$H$_{13}$N$_3$O$_3$S$_2$ m/z 324.5 (M+H)$^+$.

Example 85

(5R)-N-Methyl-3-[3-fluoro-4-(trans-tetrahydro-1-oxido-2H-thiopyran-4-yl)phenyl]-2-oxo-5-oxazolidinecarboxamide

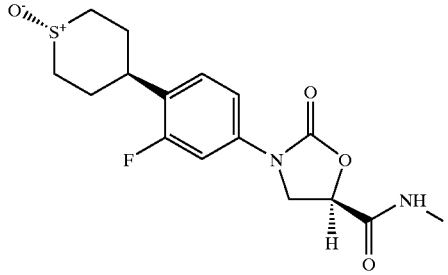

Following the general procedure of EXAMPLE 42, and making non-critical variations but substituting butyl (5R)-3-[3-fluoro-4-(trans-tetrahydro-2H-thiopyran-4-yl)phenyl]-2-oxo-5-oxazolidinecarboxylate (EXAMPLE 24, Step 1) for butyl (5R)-3-[3,5-difluoro-4-(4-morpholinyl)phenyl]-2-oxo-5-oxazolidinecarboxylate and purifying the residue by chromatography on a Biotage Flash 40S 40 g silica gel cartridge, eluting with a gradient of MeOH/CH$_2$Cl$_2$ (2/98–4/96), the title compound [R$_f$=0.48 by TLC (MeOH/CHCl$_3$, 10/90)] is obtained, $^1$H NMR (400 MHz, DMSO-d$_6$) δ 8.40 (m, 1H), 7.47 (dd, 1H), 7.33 (m, 2H), 5.06 (dd, 1H), 4.27 (t, 1H), 4.00 (dd, 1H), 3.38 (m, 2H), 3.06 (m, 1H), 2.81 (m, 2H), 1.99 (m, 2H), 1.88 (m, 2H); MS (ESI+) for C$_{16}$H$_{19}$N$_2$O$_4$FS m/z 355 (M+H)$^+$.

Example 86

(5R)-3-(4-Fluoro-3-methyl-2-oxo-2,3-dihydro-6-benzoxazolyl)-2-oxo-5-oxazolidinecarboxamide

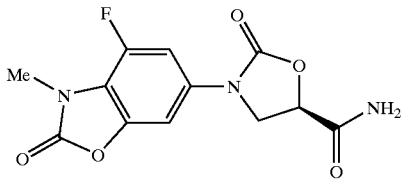

Step 1: Preparation of 2-(benzyloxy)-6-fluorobenzamide

Benzyl alcohol (24 ml, 0.229 mol) is added portionwise to a suspension of sodium hydride (9.16 g, 0.229 mol) in DMF (300 ml) and stirred at room temperature for 1 h. 2,6-Difluorobenzamide (30 g, 0.190 mol) is added in one portion and stirring is continued overnight at room temperature. The reaction mixture is poured into 1N HCl (1.5 l) and extracted with dichloromethane. The extract is washed with water and saline, dried (MgSO$_4$), and evaporated to give product as a white solid suitable for use in the next step (39.6 g, 85%); MS for $C_{14}H_{12}FNO_2$ m/z 246 (M+H)$^+$.

Step 2: Preparation of 2-(benzyloxy)-6-fluoroaniline

Sodium hypochlorite (10% aqueous solution, 69.1 ml, 0.112 mol) is added at 0° C. in portions to a mixture of 2-(benzyloxy)-6-fluorobenzamide (Step 1, 22.89 g, 0.0933 mol) and sodium hydroxide (9.33 g, 0.233 mol) dissolved in water (200 ml) and dioxane (200 ml). The mixture is heated at 70° C. for 1 h, cooled to room temperature, and then extracted with ether. The ether extract is washed with water and saline, dried (MgSO$_4$), and evaporated to give a light brown oil. Purification by flash column chromatography (10% ethyl acetate/hexane) gives pure product as a colorless oil (18.2 g, 90%).

Step 3: Preparation of 2-amino-3-fluorophenol 2-(Benzyloxy)-6-fluoroaniline (Step 2, 5.00 g, 0.0230 mol) and 10% palladium on carbon (0.5 g) in methanol (100 ml) are stirred under a hydrogen atmosphere (balloon) for 2 h. The catalyst is removed by filtration through a pad of celite and the filtrate concentrated to give pure product as a tan solid (2.9 g, 99%); mp 125–6° C.

Step 4: Preparation of 4-fluoro-1,3-benzoxazol-2(3H)-one 1,1'-Carbonyldiimidazole (11.4 g, 0.0703 mol) is added portionwise to a solution of 2-amino-3-fluorophenol (Step 3, 8.94 g, 0.0703 mol) in THF (200 ml) and warmed at 60° C. for 2 h. The reaction mixture is diluted with ethyl acetate (200 ml), washed with 2N HCl and saline, dried (MgSO$_4$), and evaporated to give product as a white solid suitable for use in the next step (10.6 g, 99%); mp 131–3° C.

Step 5: Preparation of 4-fluoro-6-nitro-1,3-benzoxazol-2(3H)-one

Nitric acid (70%, 2.50 ml, 0.0389 mol) is added dropwise at –10° C. to a solution of 4-fluoro-1,3-benzoxazol-2(3H)-one (Step 4, 5.95 g, 0.0389 mol) in concentrated sulfuric acid (60 ml). The reaction is stirred at –10° C. for 30 minutes and then poured into ice water. The resulting precipitate is collected by filtration and dried under reduced pressure to give desired product contaminated with approximately 10–15% of the undesired 5-nitro isomer (7.2 g, 93%); mp 177–9° C.

Step 6: Preparation of 4-fluoro-3-methyl-6-nitro-1,3-benzoxazol-2(3H)-one

Iodomethane (0.393 ml, 6.31 mmol) is added in portions to crude 4-fluoro-6-nitro-1,3-benzoxazol-2(3H)-one (Step 5, 1.00 g, 5.05 mmol) and 1,8-diazabicyclo[5.4.0]undec-7-ene (0.94 ml, 6.31 mmol) in DMF (10 ml). The reaction is stirred at 65° C. overnight, diluted with ethyl acetate, washed with 2N HCl and saline, dried (MgSO$_4$), and evaporated to give crude product containing trace amounts of undesired 5-nitro isomer. Purification by flash column chromatography (20% ethyl acetate/hexane) gives pure product as a white solid (0.89 g, 83%); mp 118–9° C.

Step 7: Preparation of 6-amino-4-fluoro-3-methyl-1,3-benzoxazol-2(3H)-one

Iron powder (0.77 g, 0.0138 mol) is added in small portions to a mixture of 4-fluoro-3-methyl-6-nitro-1,3-benzoxazol-2(3H)-one (Step 6, 0.73 g, 3.44 mmol) and ammonium chloride (1.84 g, 3.44 mmol) in ethanol (30 ml) and water (15 ml) at 95° C. The reaction mixture is stirred vigorously and heated for 1 h, cooled to room temperature, and diluted with dichloromethane (150 ml). The mixture is filtered, washed with water and saline, dried (MgSO$_4$) and evaporated to give product as a tan solid suitable for use in the next step (0.64 g, 99%).

Step 8: Preparation of methyl (2R)-3-[(4-fluoro-3-methyl-2-oxo-2,3-dihydro-6-benzoxazolyl)amino]-2-hydroxypropanoate A mixture of 6-amino-4-fluoro-3-methyl-1,3-benzoxazol-2(3H)-one (Step 7, 0.630 g, 3.46 mmol), methyl (2R)-glycidate (0.353 g, 3.46 mmol) and lithium trifluoromethanesulfonate (0.540 g, 3.46 mmol) in acetonitrile (10 ml) is stirred and heated at 90° C. overnight. The reaction mixture is diluted with ethyl acetate, washed with water and saline, dried (MgSO$_4$), and evaporated under reduced pressure. Final purification by flash column chromatography (50% ethyl acetate/hexane) gives pure product as a white solid (0.98 g, 60%); MS for $C_{12}H_{13}FN_2O_5$ m/z 285 (M+H)$^+$.

Step 9: Preparation of methyl (5R)-3-(4-fluoro-3-methyl-2-oxo-2,3-dihydro-6-benzoxazolyl)-2-oxo-5-oxazolidinecarboxylate A mixture of methyl (2R)-3-[(4-fluoro-3-methyl-2-oxo-2,3-dihydro-6-benzoxazolyl)amino]-2-hydroxypropanoate (Step 8, 0.84 g, 2.96 mmol) and 1,1'-carbonyldiimidazole (0.48 g, 2.96 mmol) in acetonitrile is stirred and heated at 60° C. overnight. The reaction is diluted with ethyl acetate, washed with 2N HCl and saline, and evaporated under reduced pressure. The resulting solid is triturated with methanol to give pure product as a white solid (0.88 g, 96%); MS for $C_{13}H_{11}FN_2O_6$ m/z 311 (M+H)$^+$.

Step 10: Preparation of (5R)-3-(4-fluoro-3-methyl-2-oxo-2,3-dihydro-6-benzoxazolyl)-2-oxo-5-oxazolidinecarboxamide A solution of ammonia in methanol (2M, 5 ml) is added to solid methyl (5R)-3-(4-fluoro-3-methyl-2-oxo-2,3-dihydro-6-benzoxazolyl)-2-oxo-1,3-oxazolidine-5-carboxylate (Step 9, 0.250 g, 0.806 mmol) and the suspension stirred overnight at room temperature. The reaction mixture is concentrated under reduced pressure and the residue purified by PTLC (10% methanol/dichloromethane) to give product as a white solid (0.13 g, 55%); MS for $C_{12}H_{10}FN_3O_5$ m/z 296 (M+H)$^+$; $^1$H NMR (DMSO-d$_6$, 300 Mhz) δ 7.87 (br s, 1H), 7.63 (br s, 1H), 7.50 (d, 1H), 7.42 (dd, 1H), 5.03 (dd, 1H), 4.26 (t, 1H), 4.01 (dd, 1H), 3.42 (s, 3H).

Example 87

(5R)-3-(3-Ethyl-4-fluoro-2-oxo-2,3-dihydro-6-benzoxazolyl)-2-oxo-5-oxazolidinecarboxamide

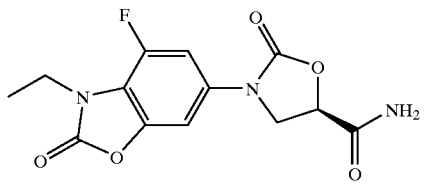

Step 1: Preparation of 3-Ethyl-4-fluoro-6-nitro-1,3-benzoxazol-2(3H)-one

Prepared from iodoethane (0.61 ml, 7.57 mmol), 4-fluoro-6-nitro-1,3-benzoxazol-2(3H)-one (EXAMPLE 86, Step 5, 1.2 g, 6.06 mmol) and 1,8-diazabicyclo[5.4.0]undec-7-ene (1.13 ml, 7.57 mmol) in DMF (10 ml) according to the method of EXAMPLE 86, Step 6 (1.10 g, 80%); mp 121–2° C.

Step 2: Preparation of 6-amino-3-ethyl-4-fluoro-1,3-benzoxazol-2(3H)-one

Prepared from 3-ethyl-4-fluoro-6-nitro-1,3-benzoxazol-2(3H)-one (Step 1, 1.05 g, 4.90 mmol), ammonium chloride (2.62 g, 49 mmol) and iron powder (1.09 g, 19.6 mmol) in ethanol (30 ml) and water (15 ml) according to the method of EXAMPLE 86, Step 7 (0.95 g, 99%).

Step 3: Preparation of methyl (2R)-3-[(3-ethyl-4-fluoro-2-oxo-2,3-dihydro-6-benzoxazolyl)amino]-2-hydroxypropanoate Prepared from 6-amino-3-ethyl-4-fluoro-1,3-benzoxazol-2(3H)-one (Step 2, 0.90 g, 4.59 mmol), methyl (2R)-glycidate (0.469 g, 4.59 mmol) and lithium trifluoromethanesulfonate (0.716 g, 4.59 mmol) in acetonitrile (10 ml) according to the method of EXAMPLE 86, Step 8 (1.11 g, 81%); MS for $C_{13}H_{15}FN_2O_5$ m/z 299 (M+H)$^+$.

Step 4: Preparation of methyl (5R)-3-(3-ethyl-4-fluoro-2-oxo-2,3-dihydro-6-benzoxazolyl)-2-oxo-5-oxazolidinecarboxylate Prepared from methyl (2R)-3-[(3-ethyl-4-fluoro-2-oxo-2,3-dihydro-6-benzoxazolyl)amino]-2-hydroxypropanoate (Step 3, 1.01 g, 3.39 mmol) and 1,1'-carbonyldiimidazole (0.549 g, 3.39 mmol) according to the method of EXAMPLE 86, Step 9 (1.10 g, 99%); MS for $C_{14}H_{13}FN_2O_6$ m/z 325 (M+H)$^+$.

Step 5: Preparation of (5R)-3-(3-ethyl-4-fluoro-2-oxo-2,3-dihydro-6-benzoxazolyl)-2-oxo-5-oxazolidinecarboxamide Prepared from methyl (5R)-3-(3-ethyl-4-fluoro-2-oxo-2,3-dihydro-6-benzoxazolyl)-2-oxo-5-oxazolidinecarboxylate (Step 4, 0.250 g, 0.771 mmol) and ammonia in methanol (5 ml) according to the method of EXAMPLE 86, Step 10 (0.15 g, 63%); MS for $C_{13}H_{12}FN_3O_5$ m/z 310 (M+H)$^+$; $^1$H NMR (DMSO-d$_6$, 300 Mhz) δ 7.87 (br s, 1H), 7.63 (br s, 1H), 7.52 (d, 1H), 7.44 (dd, 1H), 5.03 (dd, 1H), 4.26 (t, 1H), 4.02 (dd, 1H), 3.86 (q, 2H), 1.28 (t, 3H).

Example 88

(5R)-3-(4-Fluoro-3-isopropyl-2-oxo-2,3-dihydro-6-benzoxazolyl)-2-oxo-5-oxazolidinecarboxamide

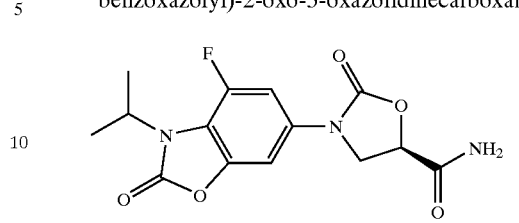

Step 1: Preparation of 4-fluoro-3-isopropyl-6-nitro-1,3-benzoxazol-2(3H)-one

Prepared from 2-iodopropane (0.76 ml, 7.57 mmol), 4-fluoro-6-nitro-1,3-benzoxazol-2(3H)-one (EXAMPLE 86, Step 5, 1.2 g, 6.06 mmol) and 1,8-diazabicyclo[5.4.0]undec-7-ene (1.13 ml, 7.57 mmol) in DMF (10 ml) according to the method of EXAMPLE 86, Step 6 (0.87 g, 60%); mp 122–3° C.

Step 2: Preparation of 6-amino-4-fluoro-3-isopropyl-1,3-benzoxazol-2(3H)-one

Prepared from 4-fluoro-3-isopropyl-6-nitro-1,3-benzoxazol-2(3H)-one (Step 1, 0.87 g, 3.64 mmol), ammonium chloride (1.95 g, 36.4 mmol) and iron powder (0.81 g, 14.6 mmol) in ethanol (30 ml) and water (15 ml) according to the method of EXAMPLE 86, Step 7 (0.77 g, 99%).

Step 3: Preparation of methyl (2R)-3-[(4-fluoro-3-isopropyl-2-oxo-2,3-dihydro-6-benzoxazolyl)amino]-2-hydroxypropanoate Prepared from 6-amino-4-fluoro-3-isopropyl-1,3-benzoxazol-2(3H)-one (Step 2, 0.77 g, 3.66 mmol), methyl (2R)-glycidate (0.374 g, 3.66 mmol) and lithium trifluoromethanesulfonate (0.57 g, 3.66 mmol) in acetonitrile (10 ml) according to the method of EXAMPLE 86, Step 8 (0.89 g, 78%); MS for $C_{14}H_{17}FN_2O_5$ m/z 313 (M+H)$^+$.

Step 4: Preparation of methyl (5R)-3-(4-fluoro-3-isopropyl-2-oxo-2,3-dihydro-6-benzoxazolyl)-2-oxo-5-oxazolidinecarboxylate Prepared from methyl (2R)-3-[(4-fluoro-3-isopropyl-2-oxo-2,3-dihydro-6-benzoxazolyl)amino]-2-hydroxypropanoate (Step 3, 0.908 g, 2.91 mmol) and 1,1'-carbonyldiimidazole (0.471 g, 2.91 mmol) according to the method of EXAMPLE 86, Step 9 (0.90 g, 92%); MS for $C_{15}H_{15}FN_2O_6$ m/z 339 (M+H)$^+$.

Step 5: Preparation of (5R)-3-(4-fluoro-3-isopropyl-2-oxo-2,3-dihydro-6-benzoxazolyl)-2-oxo-5-oxazolidinecarboxamide Prepared from methyl (5R)-3-(4-fluoro-3-isopropyl-2-oxo-2,3-dihydro-6-benzoxazolyl)-2-oxo-5-oxazolidinecarboxylate (Step 4, 0.250 g, 7.39 mmol) and ammonia in methanol (5 ml) according to the method of EXAMPLE 86, Step 10 (0.14 g, 59%); MS for $C_{14}H_{14}FN_3O_5$ m/z 324 (M+H)$^+$; $^1$H NMR (DMSO-d$_6$, 300 Mhz) δ 7.88 (br s, 1H), 7.63 (br s, 1H), 7.53 (d, 1H), 7.44 (dd, 1H), 5.04 (dd, 1H), 4.55 (m, 1H), 4.26 (t, 1H), 4.02 (dd, 1H), 1.41 (dd, 6H).

Example 89

(5R)-3-(4-Fluoro-3-methyl-2-oxo-2,3-dihydro-6-benzoxazolyl)-N-methyl-2-oxo-5-oxazolidinecarboxamide

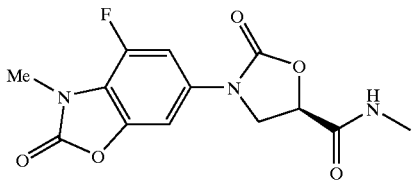

A solution of methylamine in methanol (2M, 5 ml) is added to solid methyl (5R)-3-(4-fluoro-3-methyl-2-oxo-2,3-dihydro-6-benzoxazolyl)-2-oxo-5-oxazolidinecarboxylate (EXAMPLE 86, Step 9, 0.250 g, 0.806 mmol) and the suspension stirred overnight at room temperature. The reaction mixture is concentrated under reduced pressure and the residue purified by PTLC (10% methanol/dichloromethane) to give product as a white solid (0.049 g, 19%); MS for $C_{13}H_{12}FN_3O_5$ m/z 310 (M+H)$^+$; $^1$H NMR (DMSO-d$_6$, 300 Mhz) δ 8.40 (m, 1H), 7.49 (d, 1H), 7.42 (dd, 1H), 5.07 (dd, 1H), 4.26 (t, 1H), 4.02 (dd, 1H), 3.42 (s, 3H), 2.65 (d, 3H).

Example 90

(5R)-3-(3-Ethyl-4-fluoro-2-oxo-2,3-dihydro-6-benzoxazolyl)-N-methyl-2-oxo-5-oxazolidinecarboxamide

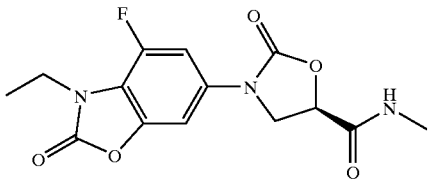

A solution of methylamine in methanol (2M, 5 ml) is added to solid methyl (5R)-3-(3-ethyl-4-fluoro-2-oxo-2,3-dihydro-6-benzoxazolyl)-2-oxo-5-oxazolidinecarboxylate (EXAMPLE 87, Step 4, 0.250 g, 0.771 mmol) and the suspension stirred overnight at room temperature. The reaction mixture is concentrated under reduced pressure and the residue purified by PTLC (10% methanol/dichloromethane) to give product as a white solid (0.10 g, 40%); MS for $C_{14}H_{14}FN_3O_5$ m/z 324 (M+H)$^+$; $^1$H NMR (DMSO-d$_6$, 300 Mhz) δ 8.40 (m, 1H), 7.51 (d, 1H), 7.44 (dd, 1H), 5.07 (dd, 1H), 4.27 (t, 1H), 4.02 (dd, 1H), 3.85 (q, 2H), 2.65 (d, 31H), 1.28 (t, 31H).

Example 91

(5R)-3-(4-Fluoro-3-isopropyl-2-oxo-2,3-dihydro-6-benzoxazolyl)-N-methyl-2-oxo-5-oxazolidinecarboxamide

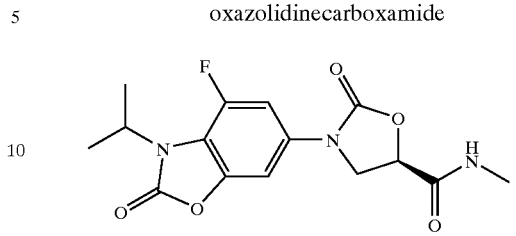

A solution of methylamine in methanol (2M, 5 ml) is added to solid methyl (5R)-3-(4-fluoro-3-isopropyl-2-oxo-2,3-dihydro-6-benzoxazolyl)-2-oxo-5-oxazolidinecarboxylate (EXAMPLE 88, Step 4, 0.250 g, 0.739 mmol) and the suspension stirred overnight at room temperature. The reaction mixture is concentrated under reduced pressure and the residue purified by PTLC (10% methanol/dichloromethane) to give product as a white solid (0.05 g, 20%); MS for $C_{15}H_{16}FN_3O_5$ m/z 338 (M+H)$^+$; $^1$H NMR (DMSO-d$_6$, 300 Mhz) δ 8.40 (m, 1H), 7.52 (d, 1H), 7.43 (dd, 1H), 5.08 (dd, 1H), 4.54 (m, 1H), 4.27 (t, 1H), 4.03 (dd, 1H), 2.65 (d, 3H), 1.41 (dd, 6H).

Example 92

Additional Compounds

Other compounds of this invention may be synthesized via the methodology described herein. Additional compounds of the invention include, but are not limited to, the following:

1. (5R)-3-(2-Formyl-2,3,4,5-tetrahydro-1H-2-benzazepin-7-yl)-2-oxo-5-oxazolidinecarboxamide
2. (5R)-N-Methyl-3-(2-formyl-2,3,4,5-tetrahydro-1H-2-benzazepin-7-yl)-2-oxo-5-oxazolidinecarboxamide
3. (5R)-3-[2-(Hydroxyacetyl)-2,3,4,5-tetrahydro-1H-2-benzazepin-7-yl]-2-oxo-5-oxazolidinecarboxamide
4. (5R)-N-Methyl-3-[2-(hydroxyacetyl)-2,3,4,5-tetrahydro-1H-2-benzazepin-7-yl]-2-oxo-5-oxazolidinecarboxamide
5. (5R)-3-(3-Formyl-2,3,4,5-tetrahydro-1H-3-benzazepin-7-yl)-2-oxo-5-oxazolidinecarboxamide
6. (5R)-N-Methyl-3-(3-formyl-2,3,4,5-tetrahydro-1H-3-benzazepin-7-yl)-2-oxo-5-oxazolidinecarboxamide
7. (5R)-3-[3-(Hydroxyacetyl)-2,3,4,5-tetrahydro-1H-3-benzazepin-7-yl]-2-oxo-5-oxazolidinecarboxamide
8. (5R)-N-Methyl-3-[3-(hydroxyacetyl)-2,3,4,5-tetrahydro-1H-3-benzazepin-7-yl]-2-oxo-5-oxazolidinecarboxamide
9. (5R)-3-[3,5-Difluoro-4-(1-formyl-3-methylazetidin-3-yl)phenyl]-2-oxo-5-oxazolidinecarboxamide
10. (5R)-N-Methyl-3-[3,5-difluoro-4-(1-formyl-3-methylazetidin-3-yl)phenyl]-2-oxo-5-oxazolidinecarboxamide
11. (5R)-3-[3-Fluoro-4-(1-formyl-3-methylazetidin-3-yl)phenyl]-2-oxo-5-oxazolidinecarboxamide
12. (5R)-N-Methyl-3-[3-fluoro-4-(1-formyl-3-methylazetidin-3-yl)phenyl]-2-oxo-5-oxazolidinecarboxamide
13. (5R)-3-[4-(cis-1-(methylimino)-1-oxido-1,1,3,4,5,6-hexahydro-2H-thiopyran-4-yl)-3-fluorophenyl]-2-oxo-5-oxazolidinecarboxamide
14. (5R)-N-Methyl-3-[4-(cis-1-imino-1-oxido-1,1,3,4,5,6-hexahydro-2H-thiopyran-4-yl)-3-fluorophenyl]-2-oxo-5-oxazolidinecarboxamide 15. (5R)-N-Methyl-3-[4-(cis-1-(methylimino)-1-oxido-1,1,3,4,5,6-hexahydro-2H-thiopyran-4-yl)-3-fluorophenyl]-2-oxo-5-oxazolidinecarboxamide
16. (5R)-3-[4-(trans-1-(imino)-1-oxido-1,1,3,4,5,6-hexahydro-2H-thiopyran-4-yl)-3-fluorophenyl]-2-oxo-5-oxazolidinecarboxamide
17. (5R)-N-Methyl-3-[4-(trans-1-(imino)-1-oxido-1,1,3,4,5,6-hexahydro-2H-thiopyran-4-yl)-3-fluorophenyl]-2-oxo-5-oxoazolidinecarboxamide
18. (5R)-3-[4-(trans-1-(methylimino)-1-oxido-1,1,3,4,5,6-hexahydro-2H-thiopyran-4-yl)-3-fluorophenyl]-2-oxo-5-oxazolidinecarboxamide
19. (5R)-N-Methyl-3-[4-(trans-1-(methylimino)-1-oxido-1,1,3,4,5,6-hexahydro-2H-thiopyran-4-yl)-3-fluorophenyl]-2-oxo-5-oxazolidinecarboxamide
20. (5R)-3-[4-(1-(2(S)-Hydroxy-3-phosphorylpropanoyl)-1,2,5,6-tetrahydropyrid-4-yl)-3,5-difluorophenyl]-2-oxo-5-oxazolidinecarboxamide
21. (5R)-N-Methyl-3-[4-(1-(2(S)-hydroxy-3-phosphorylpropanoyl)-1,2,5,6-tetrahydropyrid-4-yl)-3,5-difluorophenyl]-2-oxo-5-oxazolidinecarboxamide
22. (5R)-3-[4-(1-(2(S),3-Dihydroxypropanoyl)-1,2,5,6-tetrahydropyrid-4-yl)-3,5-difluorophenyl]-2-oxo-5-oxazolidinecarboxamide
23. (5R)-N-Methyl-3-[4-(1-(2(S),3-dihydroxypropanoyl)-1,2,5,6-tetrahydropyrid-4-yl)-3,5-difluorophenyl]-2-oxo-5-oxazolidinecarboxamide
24. (5R)-3-[4-(1-(2(S)-Hydroxy-3-phosphorylpropanoyl)-1,2,5,6-tetrahydropyrid-4-yl)-3-fluorophenyl]-2-oxo-5-oxazolidinecarboxamide
25. (5R)-N-Methyl-3-[4-(1-(2(S)-hydroxy-3-phosphorylpropanoyl)-1,2,5,6-tetrahydropyrid-4-yl)-3-fluorophenyl]-2-oxo-5-oxazolidinecarboxamide
26. (5R)-3-[4-(1-(2(S),3-Dihydroxypropanoyl)-1,2,5,6-tetrahydropyrid-4-yl)-3-fluorophenyl]-2-oxo-5-oxazolidinecarboxamide; and
27. (5R)-N-Methyl-3-[4-(1-(2(S),3-dihydroxypropanoyl)-1,2,5,6-tetrahydropyrid-4-yl)-3-fluorophenyl]-2-oxo-5-oxazolidinecarboxamide
28. (5R)-3-(3,4-Dihydro-5-fluoro-4-methyl-3-oxo-2H-1,4-benzothiazin-7-yl)-2-oxo-5-oxazolidinecarboxamide
29. (5R)-N-Methyl-3-(3,4-dihydro-5-fluoro-4-methyl-3-oxo-2H-1,4-benzothiazin-7-yl)-2-oxo-5-oxazolidinecarboxamide
30. (5R)-3-(3,4-Dihydro-5-fluoro-4-methyl-3-oxo-2H-1,4-benzoxazin-7-yl)-2-oxo-5-oxazolidinecarboxamide
31. (5R)-N-Methyl-3-(3,4-dihydro-5-fluoro-4-methyl-3-oxo-2H-1,4-benzoxazin-7-yl)-2-oxo-5-oxazolidinecarboxamide
32. (5R)-3-(2,3-Dihydro-3-methyl-4-fluoro-2-oxo-6-benzothiazolyl)-2-oxo-5-oxazolidinecarboxamide
33. (5R)-N-Methyl-3-(2,3-dihydro-3-methyl-4-fluoro-2-oxo-6-benzothiazolyl)-2-oxo-5-oxazolidinecarboxamide
34. (5R)-3-(2,3-Dihydro-3-ethyl-4-fluoro-2-oxo-6-benzothiazolyl)-2-oxo-5-oxazolidinecarboxamide
35. (5R)-N-Methyl-3-(2,3-dihydro-3-ethyl-4-fluoro-2-oxo-6-benzothiazolyl)-2-oxo-5-oxazolidinecarboxamide
36. (5R)-3-(2,3-Dihydro-3-isopropyl-4-fluoro-2-oxo-6-benzothiazolyl)-2-oxo-5-oxazolidinecarboxamide
37. (5R)-N-Methyl-3-(2,3-dihydro-3-isopropyl-4-fluoro-2-oxo-6-benzothiazolyl)-2-oxo-5-oxazolidinecarboxamide
38. (5R)-3-[4-(3,6-Dihydro-2H-thiopyran-4-yl)-3,5-difluorophenyl]-2-oxo-5-oxazolidinecarboxamide S,S-dioxide
39. (5R)-3-[4-(3,6-Dihydro-2H-thiopyran-4-yl)-3,5-difluorophenyl]-N-methyl-2-oxo-5-oxazolidinecarboxamide S,S-dioxide
40. (5R)-3-[3-Fluoro-4-(1-imino-1-oxido-4-thiomorpholinyl)phenyl]-2-oxo-5-oxazolidinecarboxamide
41. (5R)-N-Methyl-3-[3-Fluoro-4-(1-imino-1-oxido-4-thiomorpholinyl)phenyl]-2-oxo-5-oxazolidinecarboxamide
42. (5R)-3-[3-Fluoro-4-(1-methylimino-1-oxido-4-thiomorpholinyl)phenyl]-2-oxo-5-oxazolidinecarboxamide
43. (5R)-N-Methyl-3-[3-Fluoro-4-(1-methylimino-1-oxido-4-thiomorpholinyl)phenyl]-2-oxo-5-oxazolidinecarboxamide
44. (5R)-3-[3,5-Difluoro-4-(1-imino-1-oxido-4-thiomorpholinyl)phenyl]-2-oxo-5-oxazolidinecarboxamide
45. (5R)-N-Methyl-3-[3,5-Difluoro-4-(1-imino-1-oxido-4-thiomorpholinyl)phenyl]-2-oxo-5-oxazolidinecarboxamide
46. (5R)-3-[3,5-Difluoro-4-(1-methylimino-1-oxido-4-thiomorpholinyl)phenyl]-2-oxo-5-oxazolidinecarboxamide
47. (5R)-N-Methyl-3-[3,5-Difluoro-4-(1-methylimino-1-oxido-4-thiomorpholinyl)phenyl]-2-oxo-5-oxazolidinecarboxamide MIC Test Method The in vitro MICs of test compounds are determined by a standard agar dilution method. A stock drug solution of each analog is prepared in the preferred solvent, usually DMSO:$H_2O$ (1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35° C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using Steers replicator, yielding approximately $10^4$ to $10^5$ cells per spot. The plates are incubated overnight 35° C.

Following incubation the Minimum Inhibitory Concentration (MIC $\mu$g/ml), the lowest concentration of drug that inhibits visible growth of the organism, is read and recorded. The data is shown in Table I.

TABLE 1

MIC of Compounds of Formula I for *Staphylococcus aureus* (SAUR 9213)

| Example No. | MIC ($\mu$g/ml) |
|---|---|
| 1 | 4 |
| 2 | 8 |
| 3 | 8 |
| 4 | 16 |
| 5 | 16 |
| 6 | 16 |
| 7 | 2 |
| 8 | 1 |
| 9 | 4 |
| 10 | 4 |
| 11 | 4 |
| 12 | 2 |

TABLE 1-continued

MIC of Compounds of Formula I for
Staphylococcus aureus (SAUR 9213)

| Example No. | MIC (μg/ml) |
|---|---|
| 13 | 2 |
| 14 | 4 |
| 15 | 2 |
| 17 | 4 |
| 18 | 16 |
| 20 | 4 |
| 21 | 8 |
| 22 | 4 |
| 23 | 4 |
| 24 | 2 |
| 25 | 8 |
| 26 | 16 |
| 27 | 8 |
| 29 | 1 |
| 30 | 1 |
| 31 | 1 |
| 32 | 1 |
| 33 | 4 |
| 34 | 8 |
| 35 | 2 |
| 36 | 2 |
| 37 | 2 |
| 38 | 1 |
| 39 | 1 |
| 40 | 4 |
| 41 | 2 |
| 42 | 4 |
| 43 | 4 |
| 44 | 4 |
| 45 | 4 |
| 46 | 8 |
| 47 | 4 |
| 48 | 2 |
| 49 | 8 |
| 50 | 2 |
| 51 | 2 |
| 52 | 2 |
| 53 | 2 |
| 54 | 0.5 |
| 55 | 1 |
| 56 | 4 |
| 57 | 8 |
| 58 | 8 |
| 59 | 2 |
| 60 | 2 |
| 61 | 8 |
| 62 | 4 |
| 63 | 4 |
| 64 | 0.5 |
| 65 | 2–4 |
| 66 | 4 |
| 67 | 2 |
| 68 | 4 |
| 69 | 2 |
| 70 | 2 |
| 71 | 4 |
| 72 | 2 |
| 73 | 2 |
| 74 | 8 |
| 75 | 8 |
| 76 | 4 |
| 77 | 2 |
| 78 | 8 |
| 79 | 1 |
| 80 | 2 |
| 81 | 4 |
| 82 | 1 |
| 83 | 2 |
| 84 | 2 |
| 85 | 2 |
| 86 | 4 |
| 87 | 2 |
| 88 | 4 |
| 89 | 16 |

TABLE 1-continued

MIC of Compounds of Formula I for
Staphylococcus aureus (SAUR 9213)

| Example No. | MIC (μg/ml) |
|---|---|
| 90 | 4 |
| 91 | 4 |

What is claimed is:

1. A compound of formula I

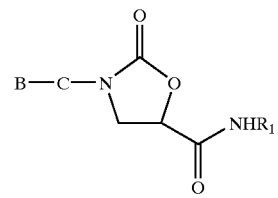

C is aryl, optionally substituted with 1–3 of $R_2$;
B is het or substituted het;
provided that B is not furanyl, thienyl, or when C is phenyl optionally substituted with $R_2$ then B is not

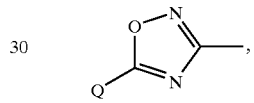

where Q is independently selected from H, $C_1$–$C_6$ alkyl, —O—$C_1$–$C_6$ alkyl, phenyl, benzyl, —OH, $CF_3$, $CCl_3$, —$NR_3R_3$, —$C_1$–$C_6$ alkylene-$NR_3R_3$, $C_1$–$C_6$ alkylene-($CH_2$phenyl)-$NR_3R_3$, $C_1$–$C_6$ alkylene-($CH_2$benzyl)-$NR_3R_3$, and

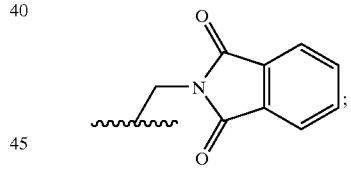

$R^1$ is selected from H, —OH, alkyl, cycloalkyl, alkoxy, alkenyl, amino, substituted alkyl, substituted alkoxy, and substituted alkenyl;
Each $R_2$ is independently selected from H, alkyl, amino, $NO_2$, —CN, halo, and substituted alkyl; and
Each $R_3$ is independently selected from H or $C_1$–$C_6$ alkyl.

2. A compound of formula II

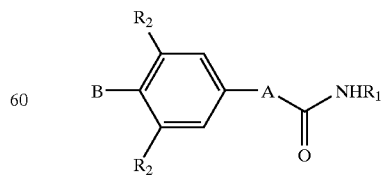

or a pharmaceutically acceptable salt thereof wherein:
B is het or substituted het, provided that B is not furanyl, thienyl, or B is not

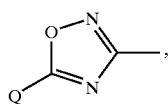

where Q is independently selected from H, $C_1$–$C_6$ alkyl, —O—$C_1$–$C_6$ alkyl, phenyl, benzyl, —OH, $CF_3$, $CCl_3$, —$NR_3R_3$, —$C_1$–$C_6$ alkylene-$NR_3R_3$, $C_1$–$C_6$ alkylene-($CH_2$phenyl)-$NR_3R_3$, $C_1$–$C_6$ alkylene-($CH_2$benzyl)-$NR_3R_3$, and

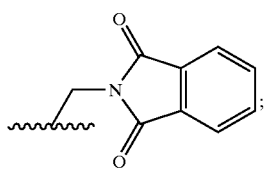

$R_1$ is selected from H, —OH, alkyl, cycloalkyl, alkoxy, alkenyl, amino, substituted alkyl, substituted alkoxy, and substituted alkenyl;

Each $R_2$ is independently selected from H, alkyl, amino, $NO_2$, —CN, halo, and substituted alkyl; and Each $R_3$ is independently selected from H or $C_1$–$C_6$ alkyl.

3. The compound of claim 2, wherein each $R_2$ is independently selected from H, F, Cl, Br, CN, $NH_2$, $NO_2$, $CF_3$, and $CH_3$.

4. The compound of claim 2, wherein $R_1$ is H, —$NH_2$, —OH, $C_{1-4}$ alkyl, $C_{3-5}$ cycloalkyl, $C_{1-4}$ alkoxy, or $C_{2-4}$ alkenyl, the alkyl, alkoxy and alkenyl each optionally being substituted with one or more halo, —OH, —CN.

5. The compound of claim 2, wherein $R_1$ is H, —OH, —$CH_2$—CH=$CH_2$, methyl, ethyl, propyl, —$CH_2$—$CH_2$F, —$CH_2$—$CH_2$OH, or methoxy.

6. The compound of claim 2, wherein B is morpholinyl, piperazinyl, pyridyl, thiomorpholinyl, 3,6-dihydro-2H-thiopyranyl, tetrahydro-2H-thiopyranyl, 3,6-dihydro-2H-pyranyl, tetrahydro-2H-pyranyl, azetidinyl, 5,6-dihydro-4H-[1,3,4]thiadiazinyl, 2,5-dihydro-1H-pyrrolyl, 3,4-dihydro-1(2H)-pyridiuyl, tetrahydropyridyl, 5,7-dihydro-6H-pyrrolo[3,4-b]pyridinyl, 2,3-dihydro-4H-1,4-thiazinyl, each of the morpholinyl, piperazinyl, pyridyl, thiomorpholinyl, 3,6-dihydro-2H-thiopyranyl, tetrahydro-2H-thiopyranyl, 3,6-dihydro-2H-pyranyl, tetrahydro-2H-pyranyl, azetidinyl, 5,6-dihydro-4H-[1,3,4]thiadiazinyl, 2,5-dihydro-1H-pyrrolyl, 34-dihydro-1(2H)-pyridinyl, tetrahydropyridyl, 5,7-dihydro-6H-pyrrolo[3,4-b]pyridinyl, 2,3-dihydro-4H-1,4-thiazinyl being optionally substituted with 1–4 groups selected from =O, alkyl, substituted alkyl, amino, substituted amino, —OH, =NOH, =$NC_{1-4}$ alkyl, and halo.

7. The compound of claim 2, wherein B is selected from

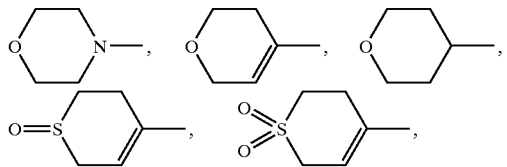

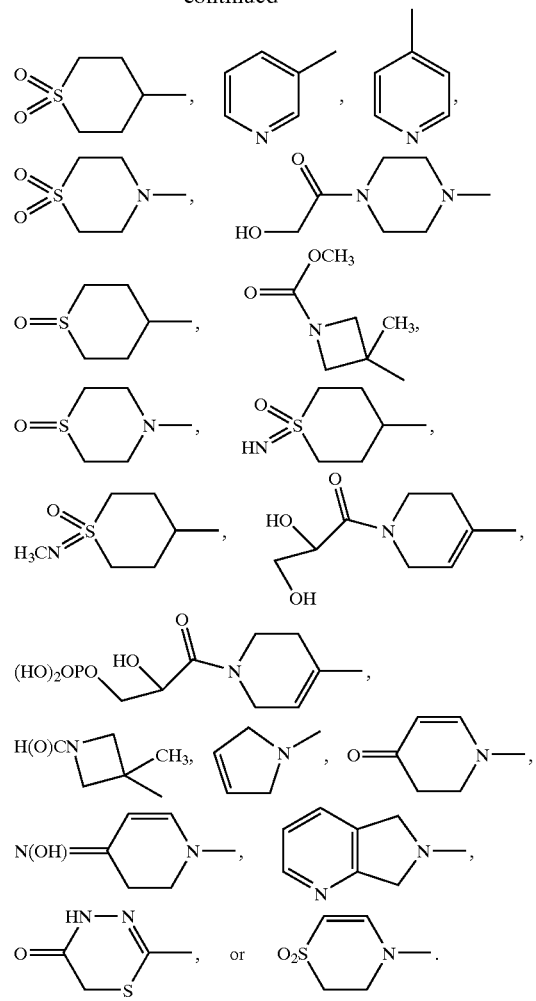

8. The compound of claim 7, wherein one $R_2$ is hydrogen and the other $R_2$ is F.

9. The compound of claim 7, wherein both $R_2$ substituents are F.

10. A compound of formula III

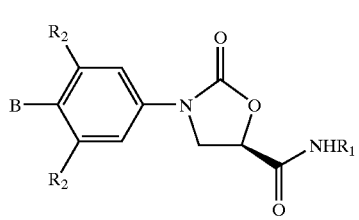

III or a pharmaceutically acceptable salt thereof wherein:

B is

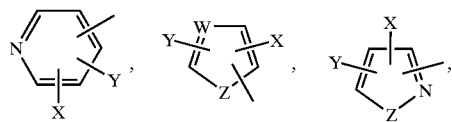

153

-continued

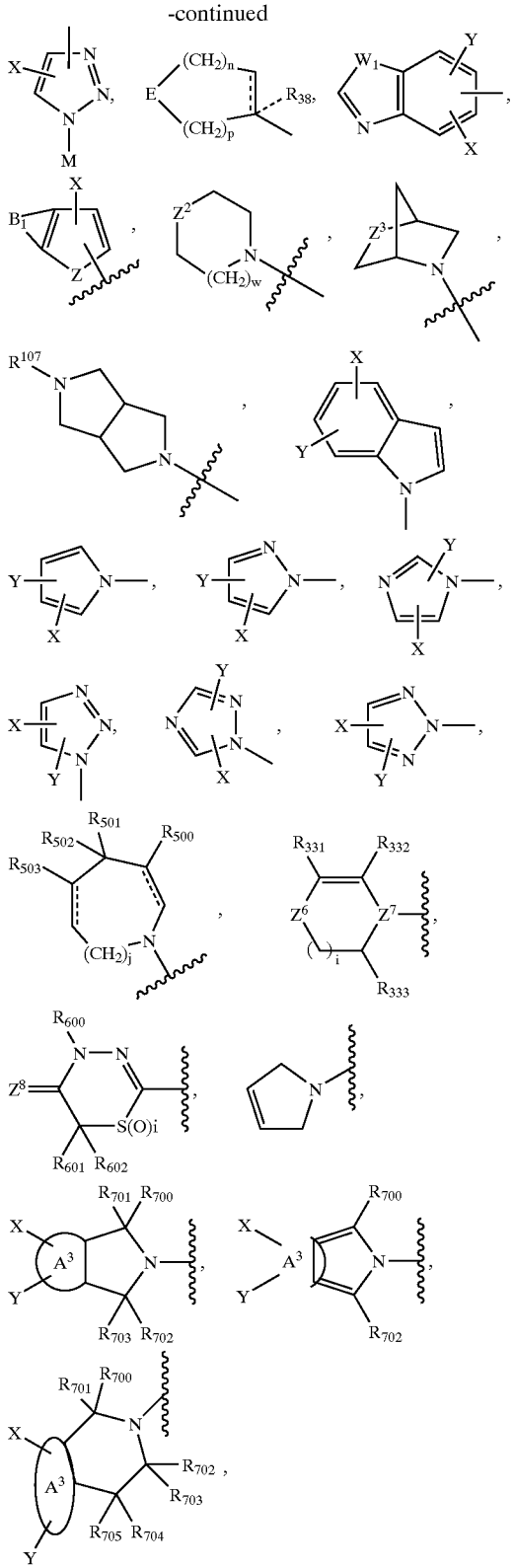

a diazinyl group optionally substituted with X and Y,
a triazinyl group optionally substituted with X and Y,
a quinolinyl group optionally substituted with X and Y,
a quinoxalinyl group optionally substituted with X and Y, or

154 a naphthyridinyl group optionally substituted with X and Y;

$A^1$ is
  a) H—, or
  b) $CH_3$;

$A^2$ is
  a) H—,
  b) HO—,
  c) $CH_3$—,
  d) $CH_3O$—,
  e) $R^{102}O$—$CH_2$—C(O)—NH—
  f) $R^{103}O$—C(O)—NH—,
  g) ($C_1$-$C_2$)alkyl-O—C(O)—,
  h) HO—$CH_2$—,
  i) $CH_3O$—NH—,
  j) ($C_1$-$C_3$)alkyl-$O_2C$—
  k) $CH_3$—C(O)—,
  l) $CH_3$—C(O)—$CH_2$—,
  m)

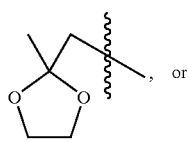, or n)

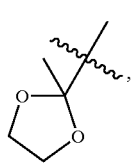, $A^1$ and $A^2$ taken together are:
  a)

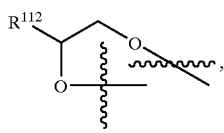, b)
    O=, or
  c)

;

$A^3$ represents any 5–10 membered aryl ring or aromatic het, the het having 1–4 heteroatoms selected from O, S, or N;

$B_1$ is
  a) —N=C(H)—C(H)=C(H)—, or
  b) —C(H)=N—C(H)=C(H)—;

E is
  a) $NR_{39}$,
  b) —S(=O)$_i$,
  c) O, or
  d) —S(=0)(=$NR_{315}$);

M is
  a) H,
  b) $C_{1-8}$ alkyl,
  c) $C_{3-8}$ cycloalkyl, d) $(CH_2)_m OR_{13}$, or
e) $-(CH_2)_n-NR_{21}R_{22}$;

W is
a) CH, or
b) N;

$W_1$ is
a) —NH—,
b) O, or
c) S;

X is
a) H,
b) —CN,
c) —$OR_{27}$,
d) halo,
e) —$NO_2$,
f) tetrazoyl,
g) —SH,
h) —$S(=O)_i R_4$,
i) —$SC(=O)R_7$,
j) —$C(=O)R_{25}$,
k) —$C(=O)NR_{27}R_{28}$,
l) —$C(=NR_{29})R_{25}$,
m) —$C(R_{25})(R_{28})$—$OR_{13}$,
n) —$C(R_{25})(R_{28})$—$OC(=O)R_{13}$,
o) —$C(R_{28})(OR_{13})$—$(CH_2)_n$—$NR_{27}R_{28}$,
p) —$NR_{27}R_{28}$,
q) —$N(R_{27})C(=O)R_7$,
r) —$N(R_{27})$—$S(=O)_i R_7$,
s) —$C(OR_{14})(OR_{15})R_{28}$,
t) —$C(R_{25})(R_{16})$—$NR_{27}R_{26}$, or
u) $C_{1-8}$ alkyl substituted with one or more halos, OH, =O other than at alpha position, —$S(=O)_i R_{17}$, —$NR_{27}R_{28}$, $C_{2-5}$ alkenyl, $C_{2-5}$ alkynyl, or $C_{3-8}$ cycloalkyl;

Y is
a) H,
b) F,
c) Cl,
d) Br,
e) $C_{1-3}$ alkyl, or
f) $NO_2$;

Z is
a) O,
b) S, or
c) NM;

$Z_1$ is
a) —$CH_2$—,
c) —C(O)—, or
d) —$CH_2CH_2CH_2$—;

$Z^2$ is
a) —S(O)i-,
b) —O—,
c) —$N(R^{107})$—, or
d) —$S(=O)(=NR^{315})$—;

$Z^3$ is
a) —S(O)i-, or
b) —O—, $Z_6$ is
a) $S(=O)_i$,
b) $S(=NR^{315})$, or
c) $S(=NR^{315})(=O)$;

$Z^7$ is
a) N,
b) $CR^{110}$,
c) $CR^{115}$, or
d) $CR^{116}$;

$Z^8$ is
a) O, or
b) S;

$R_1$ is
a) H,
b) —OH,
c) $C_{1-6}$ alkyl optionally substituted with one or more halos, —OH, —CN, aryl, het, alkoxy, substituted aryl or substituted het,
d) $C_{1-6}$ alkoxy optionally substituted wilt one or more halos, —OH, —CN, aryl, het, substituted aryl or substituted het,
e) $C_{2-6}$ alkenyl optionally substituted with aryl, het, substituted aryl or substituted het,
f) —$NH_2$, or
g) $C_{3-5}$ cycloalkyl;

$R_2$ is
a) H,
b) $C_{1-2}$ alkyl optionally substituted with one or more halos,
c) —$NH_2$,
d) —$NO_2$,
e) —CN, or
f) halo;

$R_4$ is
a) $C_{1-4}$ alkyl optionally substituted with one or more halos, OH, CN, $NR_{10}R_{11}$, or —$CO_2R_{13}$,
b) $C_{2-4}$ alkenyl,
c) —$NR_{16}R_{18}$,
d) —$NHC(=O)R_7$,
e) —$NR_{20}C(=O)R_7$,
f) —$NCR_{17})_2$,
g) —$NR_{16}R_{17}$, or
h) —$NR_{17}R_{20}$, $R_7$ is
a) $C_{1-4}$ alkyl optionally substituted with one or more halos;

$R_{10}$ and $R_{11}$ at each occurrence are the same or different and are
a) H,
b) $C_{1-4}$ alkyl, or
c) $C_{3-8}$ cycloalkyl;

$R_{13}$ is
a) H, or
b) $C_{1-4}$ alkyl;

$R_{14}$ and $R_{15}$ at each occurrence are the same or different and are
a) $C_{1-4}$ alkyl, or
b) $R_{14}$ and $R_{15}$ taken together are —$(CH_2)_l$—;

$R_{16}$ is
a) H,
b) $C_{1-4}$ alkyl, or
c) $C_{3-8}$ cycloalkyl;

$R_{17}$ is
a) $C_{1-4}$ alkyl, or
b) $C_{3-8}$ cycloalkyl;

$R_{18}$ is
a) H,
b) $C_{1-4}$ alkyl,
c) $C_{2-4}$ alkenyl,
d) $C_{3-4}$ cycloalkyl,
e) —$OR_{13}$ or
f) —$NR_{21}R_{22}$;

$R_{20}$ is a physiologically acceptable cation, such as sodium, potassium, lithium, calcium or magnesium;

$R_{21}$ and $R_{22}$ at each occurrence are the same or different and are
a) H,
b) $C_{1-4}$ alkyl, or
c) $R_{21}$ and $R_{22}$ taken together are —$(CH_2)_m$—;

$R_{25}$ is
a) H,
b) $C_{1-8}$ alkyl optionally substituted with one or more halos, $C_{3-8}$ cycloalkyl, $C_{1-4}$ alkyl substituted with one or more of —S(=O)$_t$R$_{17}$, —OR$_{13}$, or OC(=O)R$_{13}$, NR$_{27}$R$_{28}$, or
c) $C_{2-5}$ alkenyl optionally substituted with —C(O)H, or CO$_2$R$_{13}$;

$R_{26}$ is
a) $R_{28}$, or
b) —NR$_{27}$N$_{28}$;

$R_{27}$ and $R_{28}$ at each occurrence are the same or different and are
a) H,
b) $C_{1-8}$ alkyl,
c) $C_{3-8}$ cycloalkyl,
d) —(CH$_2$)$_m$OR$_{13}$,
e) —(CH$_2$)$_n$—NR$_{21}$R$_{22}$, or
f) $R_{27}$ and $R_{28}$ taken together are —(CH$_2$)$_2$O(CH$_2$)$_2$—, —(CH$_2$)$_h$CH(COR$_7$)—, or —(CH$_2$)$_2$N(CH$_2$)(R$_7$);

$R_{29}$ is
a) —NR$_{27}$R$_{28}$,
b) —OR$_{27}$, or
c) —NHC(=O)R$_{28}$;

$R_{38}$ is
a) H,
b) $C_{1-6}$ alkyl,
c) —(CH$_2$)$_q$-aryl, or
d) halo;

$R_{39}$ is
a) H,
b) $C_{1-4}$ alkyl optionally substituted with one or more OH, halo, or —CN,
c) —(CH$_2$)$_q$-aryl,
d) —CO$_2$R$_{40}$,
e) —COR$_{41}$,
f) C(=O)—(CH$_2$)$_q$—C(=O)R$_{40}$,
g) —S(=O)$_2$—C$_{1-6}$ alkyl,
h) S(O)$_2$—(CH$_2$)$_q$-aryl, or
i) —(C=O)$_j$-Het;

$R_{40}$ is
a) H,
b) $C_{1-4}$ alkyl optionally substituted with one or more OH, halo, or —CN,
c) —(CH$_2$)$_q$-aryl, or
d) —(CH$_2$)$_q$—OR$_{42}$;

$R_{41}$ is
a) $C_{1-6}$ alkyl optionally substituted with one or more OH, halo, —OP(O)(OH)$_2$, —OP(OH)$_2$, or —CN,
b) —(CH$_2$)$_q$-aryl, or
c) —(CH$_2$)$_q$—OR$_{42}$;

$R_{42}$ is
a) H,
b) $C_{1-6}$ alkyl,
c) —(CH$_2$)$_q$-aryl, or
d) —C(=O)—C$_{1-6}$ alkyl;

$R^{102}$ is
a) H—,
b) CH$_3$—,
c) phenyl-CH$_2$—, or
d) CH$_3$C(O)—;

$R^{103}$ is
a) (C$_1$–C$_3$)alkyl-, or
b) phenyl-;

$R^{104}$ is
a) H—, or
b) HO—;

$R^{107}$ is
a) $R^{102}$O—C(R$^{110}$)(R$^{111}$)—C(O)—,
b) $R^{103}$O—C(O)—,
c) $R^{108}$—C(O)—, d) 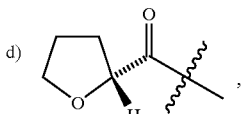, e) 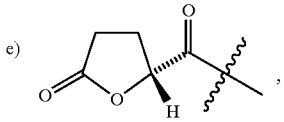, f) H$_3$C—C(O)—(CH$_2$)$_2$—C(O)—,
g) $R^{109}$—SO$_2$—, h) 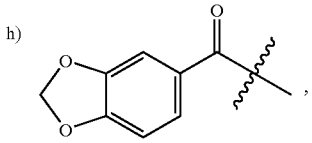, i) HO—CH$_2$—C(O)—,
j) $R^{116}$—(CH$_2$)$_2$—,
k) $R^{113}$—C(O)—O—CH$_2$—C(O)—,
l) (CH$_3$)$_2$N—CH$_2$—C(O)—NH—,
m) NC—CH$_2$—,
n) F$_2$—CH—CH$_2$—, or
o) $R^{150}$R$^{151}$NSO$_2$ $R^{108}$ is
a) H—,
b) (C$_1$–C$_4$)alkyl,
c) aryl-(CH$_2$)$_n$—,
d) ClH$_2$C—,
e) Cl$_2$HC—,
f) FH$_2$C—,
g) F$_2$HC—,
h) (C$_3$–C$_6$)cycloalkyl, or
i) CNCH$_2$—, $R^{109}$ is
a) $C_1$–C$_4$alkyl,
b) —CH$_2$Cl
c) —CH$_2$CH=CH$_2$,
d) aryl, or
e) —CH$_2$CN;

$R^{110}$ and $R^{111}$ are independently
a) H—,
b) CH$_3$—; or $R^{112}$ is
  a) H—,
  b) $CH_3O-CH_2O-CH_2-$, or
  c) $HOCH_2-$;
$R^{113}$ is
  a) $CH_3-$,
  b) $HOCH_2-$,
  c) $(CH_3)_2$N-phenyl, or
  d) $(CH_3)_2N-CH_2-$;
$R^{114}$ is
  a) HO—,
  b) $CH_3O-$,
  c) $H_2N-$,
  d) $CH_3O-C(O)-O-$,
  e) $CH_3-C(O)-O-CH_2-C(O)-O-$,
  f) phenyl-$CH_2-O-CH_2-C(O)-O-$,
  g) $HO-(CH_2)_2-O-$,
  h) $CH_3O-CH_2-O-(CH_2)_2-O-$, or
  i) $CH_3O-CH_2-O-$;
$R^{115}$ is
  a) H—, or
  b) Cl—;
$R^{116}$ is
  a) HO—
  b) $CH_3O-$, or
  c) F;
$R^{150}$ and $R^{151}$ are each independently
  a) H,
  b) $C_1$-$C_4$alkyl, or
  c) $R^{150}$ and $R^{151}$ taken together with the nitrogen atom, to which $R^{150}$ and $R^{151}$ are attached, form a monocyclic heterocyclic ring having from 3 to 6 carbon atoms;
$R_{315}$ is
  a) H,
  b) $C_{1-4}$ alkyl optionally substituted with halo, —OH, $C_{1-8}$ alkoxy, amino, $C_{1-8}$ alkylamino, or $C_{1-8}$dialkylamino,
  c) aryl-$S(O)_2-$,
  d) $C(=O)C_{1-4}$alkyl,
  e) $C(=O)OC_{1-4}$alkyl,
  f) $C(=O)NHR_{320}$,
  g) $C(=S)NHR_{320}$,
  h) —$OC(=O)C_{1-4}$alkyl,
  i) —$S(O)_tC_{1-4}$alkyl,
  j) $C_{1-4}$ alkyl-O—$C_{1-4}$ alkyl, or
  k) $C_{1-4}$ alkyl-S—$C_{1-4}$ alkyl;
$R_{320}$ is independently selected from
  a) H, or
  b) substituted alkyl;
$R_{331}$ is
  a) $R_{332}$,
  b) Cl,
  c) $NH_2$,
  d) OH,
  e) $NHC_1$-$C_4$alkyl, or
  f) $R_{315}$;
$R_{332}$ is
  a) H,
  b) $C_1$-$C_4$alkyl,
  c) $OC_1$-$C_4$alkyl,
  d) $SC_1$-$C_4$alkyl, or
  e) $NHC_1$-$C_4$alkyl;

$R_{333}$ is
  a) F, or
  b) $R_{332}$;
$R_{500}$ and $R_{503}$ are each and independently
  (a) H,
  (b) halo,
  (c) $C_1$-$C_8$ alkyl,
  (d) $C_3$-$C_6$ cycloalkyl,
  (e) —$(CH_2)_i$—$OR_{511}$, or
  (f) —$C(=O)-R_{541}$;
$R_{501}$ and $R_{502}$ are each and independently
  (a) hydrogen atom,
  (b) $C_1$-$C_8$ alkyl,
  (c) $C_1$-$C_8$ alkoxy,
  (d) $C_1$-$C_8$ alkylthio,
  (e) —$(CH_2)_i$—$OR_{551}$,
  (f) —O—$(CH_2)_j$—$OR_{551}$,
  (g) —$NR_{542}R_{552}$,
  (h) —$C(=O)-NR_{542}R_{552}$,
  (i) —$(CH_2)_i$—$C(=O)-R_{541}$,
or $R_{501}$ and $R_{502}$ together form
  (j) =O,
  (k) =$NR_{543}$,
  (l) =S,
  (m) =$CR_{544}R_{554}$, or
  (n) an unsaturated or saturated 5- or 6-membered hetero ring having 1–3 hetero atoms selected from the group consisting of a nitrogen atom, an oxygen atom and a sulfur atom;
$R_{511}$ and $R_{512}$ are each and independently
  (a) hydrogen atom,
  (b) $C_1$-$C_8$ alkyl;
$R_{541}$ is
  (a) hydrogen atom,
  (b) —$(CH_2)_m$—OH,
  (c) $C_1$-$C_8$ alkyl,
  (d) $C_1$-$C_8$ alkoxy, or
  (e) —O—$CH_2$—O—$C(=O)-R_{511}$,
$R_{542}$ and $R_{552}$ are each and independently
  (a) hydrogen atom,
  (b) —$(CH_2)_i$—OH,
  (c) $C_1$-$C_8$ alkyl,
  (d) —$C(=O)-R_{541}$,
  (e) —$C(=O)-NR_{511}R_{512}$,
  (f) —$(CH_2)_q$-phenyl, or
or $R_{542}$ and $R_{552}$ together form a pyrrolidino group, a piperidino group, a piperazino group, a morpholino group, or a thiomorpholino group, each of which may be substituted by $C_1$-$C_8$ alkyl or—$(CH_2)_i$—OH,
$R_{543}$ is
  a) H,
  (b) —$OR_{551}$,
  (c) $C_1$-$C_8$ alkyl,
  (d) $C_1$-$C_8$ alkoxy,
  (e) —$(CH_2)_q$-phenyl,
  (f) —$NR_{542}R_{552}$,
  (g) —NH—$C(=NH)-NH_2$, or
  (h) [1,2,4]triazol-4-yl;
$R_{544}$ and $R_{554}$ are each and independently
  (a) H,
  (b) $C_1$-$C_8$ alkyl,
  (c) —$C(=O)-R_{541}$, or
  (d) $(CH_2)_q$-phenyl;

R₅₅₁ is
(a) H,
(b) $C_1$–$C_8$ alkyl,
(c) $C_1$–$C_8$ alkyl substituted with 1–3 halo,
(d) —(CH₂)$_i$OR₅₁₁,
(e) —(CH₂)$_i$—C(=O)—R₅₄₁, or
(f) —C(=O)—(CH₂)$_i$—OR₅₄₄;

R₆₀₀ is
a) H,
b) $C_1$–$C_4$alkyl
c) het,
d) (CH₂)$_b$C(O)O$C_1$–$C_4$alkyl,
e) (CH₂)$_b$C(O)$C_1$–$C_4$alkyl, or
f) aryl;

R₆₀₁ and R₆₀₂ are each independently
a) H,
b) $C_1$–$C_4$alkyl,
c) het,
d) $C_3$–$C_6$cycloalkyl,
e) aryl,
f) O$C_1$–$C_4$alkyl,
g) C(O)O$C_1$–$C_4$alkyl; or
h) R₆₀₁ and R₆₀₂ taken together along with the carbon atom to which they attach form a $C_3$–$C_6$cycloalkyl;

Each R₇₀₀, R₇₀₁, R₇₀₂, R₇₀₃, R₇₀₄, and R₇₀₅ is independently selected from
a) H,
b) $C_{1-4}$ alkyl optionally substituted with 1–3 halo, =O, =S, —OH
c) C(O)NH₂,
d) —CN,
e) aryl,
f) substituted aryl,
g) het,
h) substituted hot,
i) C(O)OH,
j) C(O)O$C_{1-4}$ alkyl, or
k) R₇₀₀ and R₇₀₁ form =O or =S, or
l) R₇₀₂ and R₇₀₃ form =O or =S, or
m) R₇₀₄ and R₇₀₅ form =O or =S;

a is 1 or 2;
b is 0 or 1;
h is 1, 2, or 3;
i is 0, 1, or 2;
j is 0 or 1;
k is 3, 4, or 5;
l is 2 or 3;
m is 2, 3, 4 or 5;
n is 0, 1, 2, 3, 4, or 5;
p is 0, 1, 2, 3, 4, or 5; with the proviso that n and p together are 1, 2, 3, 4, or 5;
q is 1, 2, 3, or 4;
t is 0, 1, 2, 3, 4, 5, or 6; and
w is 0, 1, 2, or 3.

11. The compound of claim 10, wherein each R₂ is independently selected from H, F, Cl, Br, CN, NH₂, NO₂, CF₃, and CH₃.

12. The compound of claim 10, wherein R₁ is H, —NH₂, —OH, $C_{1-4}$alkyl, $C_{3-5}$ cycloalkyl, $C_{1-4}$ alkoxy, or $C_{2-4}$ alkenyl, the alkyl and alkoxy each optionally being substituted with one or more halo, —OH, —CN.

13. The compound of claim 10, wherein R₁ is H, —OH, —CH₂—CH=CH₂, methyl, ethyl, propyl, —CH₂—CH₂F, —CH₂—CH₂OH, or methoxy.

14. The compound of claim 10, wherein B is

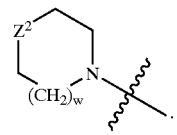

15. The compound of claim 10, wherein B is

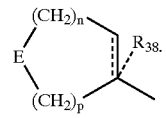

16. The compound of claim 10, wherein B is

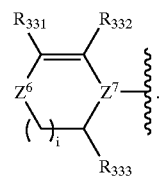

17. The compound of claim 10, wherein B is

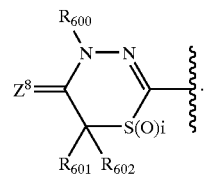

18. The compound of claim 10, wherein B is

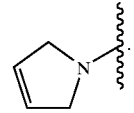

19. The compound of claim 10, wherein B is

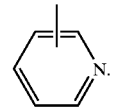

20. The compound of claim 10, wherein B is

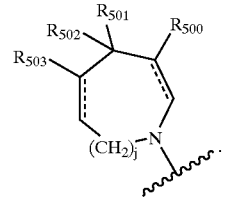

21. The compound of claim 10, wherein B is

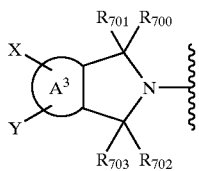

22. The compound of claim 10, wherein B is

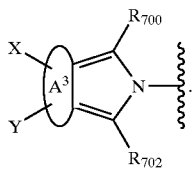

23. The compound of claim 10, wherein B is

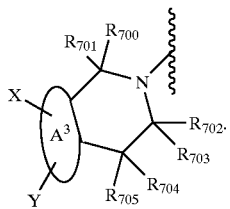

24. The compound claim 10, wherein one $R_2$ is hydrogen and the other $R_2$ is F.

25. The compound of claim 10, wherein both $R_2$ substituents are F.

26. A compound selected from
(5R)-(−)-3-[3-Fluoro-4-(4-morpholinyl)phenyl]-2-oxo-5-oxazolidinecarboxamide;
(5R)-(−)-3-[3-Fluoro-4-(4-morpholinyl)phenyl]-N-methyl-2-oxo-5-oxazolidinecarboxamide;
(5R)-(−)-3-[3-Fluoro-4-(4-morpholinyl)phenyl]-N-allyl-2-oxo-5-oxazolidinecarboxamide;
(5R)-(−)-3-[3-Fluoro-4-(4-morpholinyl)phenyl]-N-propyl-2-oxo-5-oxazolidinecarboxamide;
(5R)-(−)-3-[3-Fluoro-4-(4-morpholinyl)phenyl]-N-methoxy-2-oxo-5-oxazolidinecarboxamide;
(5R)-(−)-N-Methyl-3-[3,5-difluoro-4-(4-morpholinyl)phenyl]-2-oxo-5-oxazolidinecarboxamide;
(5R)-(−)-3-[3-Fluoro-4-(4-morpholinyl)phenyl]-N-hydroxy-2-oxo-5-oxazolidinecarboxamide; and
(5R)-(−)-3-[3,5-Difluoro-4-(4-morpholinyl)phenyl]-2-oxo-5-oxazolidinecarboxamide.

27. A compound selected from
(5R)-(−)-3-[4-(3-Pyridyl)-3-fluorophenyl]-2-oxo-5-oxazolidinecarboxamide; and (5R)-(−)-3-(4-(4-Pyridyl)-3-fluorophenyl]-2-oxo-5-oxazolidinecarboxamide.

28. A compound selected from
(5R)-(−)-3-[4-(3,6-Dihydro-2H-pyran-4-yl)-3-fluorophenyl]-2-oxo-5-oxazolidinecarboxamide: and
(5R)-(−)-3-[4-(Tetrahydro-2H-pyran-4-yl)-3-fluorophenyl]-2-oxo-5-oxazolidinecarboxamide.

29. A compound selected from
(5R)-3-[4-(3,6-Dihydro-2H-thiopyran-4-yl)-3-fluorophenyl]-2-oxo-5-oxazolidinecarboxamide S-oxide;
(5R)-(−)-3-[4-(3,6-Dihydro-2H-thiopyran-4-yl)-3-fluorophenyl]-2-oxo-5-oxazolidinecarboxamide S,S-dioxide;
(5R)-(−)-3-[4-(Tetrahydro-2H-thiopyran-4-yl)-3-fluorophenyl]-2-oxo-5-oxazolidinecarboxamide S,S-dioxide;
(5R)-3-[3-Fluoro-4-(cis-tetrahydro-1-oxido-2H-thiopyran-4-yl)phenyl]-2-oxo-5-oxazolidinecarboxamide;
(5R)-3-[3-Fluoro-4-(trans-tetrahydro-1-oxido-2H-thiopyran-4-yl)phenyl]-2-oxo-5-oxazolidinecarboxamide;
(5R)-(−)-3-[4-(tetrahydro-2H-thiopyran-4-yl)phenyl]-2-oxo-5-oxazolidinecarboxamide S,S-dioxide;
(5R)-3-[4-(cis-tetrahydro-1-oxido-2H-thiopyran-4-yl)phenyl]-2-oxo-5-oxazolidinecarboxamide;
(5R)-3-[4-(trans-tetrahydro-1-oxido-2H-thiopyran-4-yl)phenyl]-2-oxo-5-oxazolidinecarboxamide;
(5R)-(−)-N-Methyl-3-[4-(Tetrahydro-2H-thiopyran-4-yl)-3-fluorophenyl]-2-oxo-5-oxazolidinecarboxamide S,S-dioxide;
(5R)-3-[3,5-Difluoro-4-(Tetrahydro-2H-thiopyran-4-yl)phenyl]-2-oxo-5-oxazolidinecarboxamide S,S-dioxide;
(5R)-(−)-3-[3,5-Difluoro-4-(cis-tetrahydro-1-oxido-2H-thiopyran-4-yl)phenyl]-2-oxo-5-oxazolidinecarboxamide;
(5R)-(−)-3-[3,5-Difluoro-4-(trans-tetrahydro-1-oxido-2H-thiopyran-4-yl)phenyl]-2-oxo-5-oxazolidinecarboxamide;
(5R)-N-Methyl-3-[3,5-difluoro-4-(trans-tetrahydro-1-oxido-2H-thiopyran-4-yl)phenyl]-2-oxo-5-oxazolidinecarboxamide;
(5R)-3-[4-(cis-1-(methylimino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(cis-1-imino-1-oxido-1,1,3,4,5,6-hexahydro-2H-thiopyran-4-yl)-3-fluorophenyl]-2-oxo-5-oxazolidinecarboxamide;
(5R)-3-[4-(cis-1-Imino-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(cis-1-(methylimino)-1-oxido-1,1,3,4,5,6-hexahydro-2H-thiopyran-4-yl)-3-fluorophenyl]-2-oxo-5-oxazolidinecarboxamide;
(5R)-3-[4-(trans-1-(imino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(trans-1-(imino)-1-oxido-1,1,3,4,5,6-hexahydro-2H-thiopyran-4-yl)-3-fluorophenyl]-2-oxo5-oxazolidinecarboxamide;
(5R)-3-[4-(trans-1-(methylimino)-1-oxido-1,1,3,4,5,6-hexahydro-2H-thiopyran-4-yl)-3-fluorophenyl]-2-oxo-5-oxazolidinecarboxamide;
(5R)-N-Methyl-3-[4-(trans-1-(methylimino)-1-oxido-1,1,3,4,5,6-hexahydro-2H-thiopyran-4-yl)-3-fluorophenyl]-2-oxo-5-oxazolidinecarboxamide;
(5R)-3-[4-(3,6-Dihydro-2H-thiopyran-4-yl)-3,5-difluorophenyl]-N-methyl-2-oxo-5-oxazolidinecarboxamide S,S-dioxide;
(5R)-3-[4-(3,6-Dihydro-2H-thiopyran-4-yl)-3,5-difluorophenyl]-2-oxo-5-oxazolidinecarboxamide S,S-dioxide; and
(5R)-N-Methyl-3-[3-fluoro-4-(trans-tetrahydro-1-oxido-2H-thiopyran-4-yl)phenyl]-2-oxo-5-oxazolidinecarboxamide.

30. The compound (5R)-(−)-3-[3-Fluoro-4-[4-(hydroxyacetyl)-1-piperazinyl]phenyl]-2-oxo-5-oxazolidinecarboxamide.

31. A compound selected from (5R)-(−)-3-[4-(Thiomorpholin-4-yl)-3,5-difluorophenyl]-2-oxo-5-oxazolidinecarboxamide S,S-dioxide;

(5R)-(−)-3-[4-(Thiomorpholin-4-yl)phenyl]-2-oxo-5-oxazolidinecarboxamide S,S-dioxide;

(5R)-(−)-3-[3-Fluoro-4-(thiomorpholin-4-yl)phenyl]-2-oxo-5-oxazolidinecarboxamide S,S-dioxide;

(5R)-(−)-3-[3-Fluoro-4-(thiomorpholinyl-4-yl)phenyl]-2-oxo-5-oxazolidinecarboxamide S-oxide;

(5R)-3-[3-Fluoro-4-(1-imino-1-oxido-4-thiomorpholinyl)phenyl]-2-oxo-5-oxazolidinecarboxamide;

(5R)-N-Methyl-3-[3-Fluoro-4-(1-imino-1-oxido-4-thiomorpholinyl)phenyl]-2-oxo-5-oxazolidinecarboxamide;

(5R)-3-[3-Fluoro-4-(1-methylimino-1-oxido-4-thiomorpholinyl)phenyl]-2-oxo-5-oxazolidinecarboxamide;

(5R)-N-Methyl-3-[3-Fluoro-4-(1-methylimino-1-oxido-4-thiomorpholinyl)phenyl]-2-oxo-5-oxazolidinecarboxamide;

(5R)-3-[3,5-Difluoro-4-(1-imino-1-oxido-4-thiomorpholinyl)phenyl]-2-oxo-5-oxazolidinecarboxamide;

(5R)-N-Methyl-3-[3,5-Difluoro-4-(1-imino-1-oxido-4-thiomorpholinyl)phenyl]-2-oxo-5-oxazolidinecarboxamide;

(5R)-3-[3,5-Difluoro-4-(1-methylimino-1-oxido-4-thiomorpholinyl)phenyl]-2-oxo-5-oxazolidinecarboxamide;

(5R)-N-Methyl-3-[3,5-Difluoro-4-(1-methylimino-1-oxido-4-thiomorpholinyl)phenyl]-2-oxo-5-oxazolidinecarboxamide;

(5R)-(−)-3-[3,5-Difluoro-4-(Thiomorpholin-4-yl)phenyl]-2-oxo-5-oxazolidinecarboxamide S-oxide;

(5R)-(−)-N-Methyl-3-[3,5-difluoro-4-(thiomorpholin-4-yl)phenyl]-2-oxo-5-oxazolidinecarboxamide S-oxide; and (5R)-(−)-N-Methyl-3-[3,5-difluoro-4-(thiomorpholin-4-yl)phenyl]-2-oxo-5-oxazolidinecarboxamide S,S-dioxide.

32. A compound selected from (5R)-(−)-3-(2,3-Dihydro-3-methyl-2-oxo-6-benzothiazolyl)-2-oxo-5-oxazolidinecarboxamide;

(5R)-(−)-3-(2,3-Dihydro-3-ethyl-2-oxo-6-benzothiazolyl)-2-oxo-5-oxazolidinecarboxamide;

(5R)-(−)-3-(2,3-Dihydro-3-isopropyl-2-oxo-6-benzothiazolyl)-2-oxo-5-oxazolidinecarboxamide;

(5R)-(−)-N-Methyl-3-(2,3-dihydro-3-methyl-2-oxo-6-benzothiazolyl)-2-oxo-5-oxazolidinecarboxamide;

(5R)-(−)-N-Ethyl-3-(2,3-dihydro-3-methyl-2-oxo-6-benzothiazolyl)-2-oxo-5-oxazolidinecarboxamide;

(5R)-(−)-N-(2-Hydroxyethyl)-3-(2,3-dihydro-3-methyl-2-oxo-6-benzothiazolyl)-2-oxo-5-oxazolidinecarboxamide;

(5R)-N-(2-Fluoroethyl)-3-(2,3-dihydro-3-methyl-2-oxo-6-benzothiazolyl)-2-oxo-5-oxazolidinecarboxamide;

(5R)-(−)-N-Methyl-3-(2,3-dihydro-3-ethyl-2-oxo-6-benzothiazolyl)-2-oxo-5-oxazolidinecarboxamide;

(5R)-(−)-N-Methyl-3-(2,3-dihydro-3-isopropyl-2-oxo-6-benzothiazolyl)-2-oxo-5-oxazolidinecarboxamide;

(5R)-3-(2,3-Dihydro-3-methyl-4-fluoro-2-oxo-6-benzothiazolyl)-2-oxo-5-oxazolidinecarboxamide;

(5R)-N-Methyl-3-(2,3-dihydro-3-methyl-4-fluoro-2-oxo-6-benzothiazolyl)-2-oxo-5-oxazolidinecarboxamide;

(5R)-3-(2,3-Dihydro-3-ethyl-4-fluoro-2-oxo-6-benzothiazolyl )-2-oxo-5-oxazolidinecarboxamide;

(5R)-N-Methyl-3-(2,3dihydro-3-ethyl-4-fluoro-2-oxo-6-benzothiazolyl)-2-oxo-5-oxazolidinecarboxamide;

(5R)-3-(2,3-Dihydro-3-isopropyl-4-fluoro-2-oxo-6-benzothiazolyl)-2-oxo-5-oxazolidinecarboxamide; and (5R)-N-Methyl-3-(2,3-dihydro-3-isopropyl-4-fluoro-2-oxo-6-benzothiazolyl)-2-oxo-5-oxazolidinecarboxamide.

33. A compound selected from (5R)-(−)-3-(2,3-dihydro-3-methyl-2-oxo-6-benzoxazolyl)-2-oxo-5-oxazolidinecarboxamide;

(5R)-(−)-3-(2,3-Dihydro-3-ethyl-2-oxo-6-benzoxazolyl)-2-oxo-5-oxazolidinecarboxamide;

(5R)-(−)-3-(2,3-Dihydro-3-isopropyl-2-oxo-6-benzoxazolyl)-2-oxo-5-oxazolidinecarboxamide;

(5R)-(−)-N-Methyl-3-(2,3-dihydro-3-methyl-2-oxo-6-benzoxazolyl)-2-oxo-5-oxazolidinecarboxamide;

(5R)-(−)-N-Methyl-3-(2,3-dihydro-3-ethyl-2-oxo-6-benzoxazolyl)-2-oxo-5-oxazolidinecarboxamide;

(5R)-(−)-N-Methyl-3-(2,3-dihydro-3-isopropyl-2-oxo-6-benzoxazolyl)-2-oxo-5-oxazolidinecarboxamide;

(5R)-3-(2,3-dihydro-3-methyl-4-fluoro-2-oxo-6-benzoxazolyl)-2-oxo-5-oxazolidinecarboxamide;

(5R)-N-Methyl-3-(2,3-dihydro-3-methyl-4-fluoro-2-oxo-6-benzoxazolyl)-2-oxo-5-oxazolidinecarboxamide;

(5R)-3-(2,3-dihydro-3-ethyl-4-fluoro-2-oxo-6-benzoxazolyl)-2-oxo-5-oxazolidinecarboxamide;

(5R)-N-Methyl-3-(2,3-dihydro-3-ethyl-4-fluoro-2-oxo-6-benzoxazolyl)-2-oxo-5-oxazolidinecarboxamide;

(5R)-3-(2,3-Dihydro-3-isopropyl-4-fluoro-2-oxo-6-benzoxazolyl)-2-oxo-5-oxazolidinecarboxamide; and (5R)-N-Methyl-3-(2,3-dihydro-3-isopropyl-4-fluoro-2-oxo-6-benzoxazolyl)-2-oxo-5-oxazolidinecarboxamide.

34. A compound selected from (5R)-3-[(2R)-2,3-Dihydro-1-formyl-2-methyl-1H-indol-5-yl]-2-oxo-5-oxazolidinecarboxamide;

(5R)-3-[(2R)-2,3-Dihydro-1-(hydroxyacetyl)-2-methyl-1H-indol-5-yl]-2-oxo-5-oxazolidinecarboxamide;

(5R)-3-[4-(5,7-Dihydro-6H-pyrrolo[3,4-b]pyridin-6-yl)-3-fluorophenyl]-2-oxo-5-oxazolidinecarboxamide;

(5R)-N-Methyl-3-[4-(5,7-dihydro-6H-pyrrolo[3,4-b]pyridin-6-yl)-3-fluorophenyl]-2-oxo-5-oxazolidinecarboxamide.

35. A compound selected from (5R)-(−)-3-[3,5-Difluoro-4-(1-methoxycarbonyl-3-methylazetidin-3-yl)phenyl]-2-oxo-5-oxazolidinecarboxamide;

(5R)-3-[3,5-Difluoro-4-(1-formyl-3-methylazetidin-3-yl)phenyl]-2-oxo-5-oxazolidinecarboxamide;

(5R)-N-Methyl-3-[3,5-difluoro-4-(1-formyl-3-methylazetidin-3-yl)phenyl]-2-oxo-5-oxazolidinecarboxamide;

(5R)-3-[3-Fluoro-4-(1-formyl-3-methylazetidin-3-yl)phenyl]-2-oxo-5-oxazolidinecarboxamide;

(5R)-N-Methyl-3-[3-fluoro-4-(1-formyl-3-methylazetidin-3-yl)phenyl]-2-oxo-5-oxazolidinecarboxamide; and (5R)-(−)-N-Methyl-3-[3,5-difluoro-4-(1-methoxycarbonyl-3-methylazetidin-3-yl)phenyl]-2-oxo-5-oxazolidinecarboxamide.

36. A compound selected from (5R)-3-(3,4-Dihydro-4-methyl-3-oxo-2H-1,4-benzoxazin-7-yl)-2-oxo-5-oxazolidinecarboxamide;

(5R)-N-Methyl-3-(3,4-dihydro-4-methyl-3-oxo-2H-1,4-benzoxazin-7-yl)-2-oxo-5-oxazolidinecarboxamide;

(5R)-N-(2-Fluoroethyl)-3-[3,4-dihydro-4-methyl-3-oxo-2H-1,4-benzoxazin-7-yl)-2-oxo-5-oxazolidinecarboxamide;

(5R)-3-(3,4-Dihydro-4-methyl-3-oxo-2H-1,4-benzothiazin-7-yl)-2-oxo-5-oxazolidinecarboxamide;

(5R)-3-(1-Methyl-2-oxo-1,2,3,4-tetrahydroquinolin-6-yl)-2-oxo-5-oxazolidinecarboxamide;

(5R)-N-Methyl-3-(1-methyl-2-oxo-1,2,3,4-tetrahydroquinolin-6-yl)-2-oxo-5-oxazolidinecarboxamide;

(5R)-3-(2,2-Difluoro-4-methyl-3,4-dihydro-3-oxo-2H-1,4-benzoxazin-7-yl)-2-oxo-5-oxazolidinecarboxamide;

(5R)-N-Methyl-3-(2,2-difluoro-4-methyl-3,4-dihydro-3-oxo-2H-1,4-benzoxazin-7-yl)-2-oxo-5-oxazolidinecarboxamide;

(5R)-3-(8-Fluoro-1-methyl-2-oxo-1,2,3,4-tetrahydroquinolin-6-yl)-2-oxo-5-oxazolidinecarboxamide;

(5R)-N-Methyl-3-(8-fluoro-1-methyl-2-oxo-1,2,3,4-tetrahydroquinolin-6-yl)-2-oxo-5-oxazolidinecarboxamide;

(5R)-3-(4-Methyl-3-thioxo-3,4-dihydro-2H-1,4-benzothiazin-7-yl)-2-oxo-5-oxazolidinecarboxamide;

(5R)-N-Methyl-3-(3,4-dihydro-4-methyl-3-oxo-2H-1,4-benzothiazin-7-yl)-2-oxo-5-oxazolidinecarboxamide;

(5R)-3-(3,4-Dihydro-5-fluoro-4-methyl-3-oxo-2H-1,4-benzothiazin-7-yl)-2-oxo-5-oxazolidinecarboxamide;

(5R)-N-Methyl-3-(3,4-dihydro-5-fluoro-4-methyl-3-oxo-2H-1,4-benzothiazin-7-yl)-2-oxo-5-oxazolidinecarboxamide;

(5R)-3-(3,4-Dihydro-5-fluoro-4-methyl-3-oxo-2H-1,4-benzoxazin-7-yl)-2-oxo-5-oxazolidinecarboxamide; and (5R)-N-Methyl-3-(3,4-dihydro-5-fluoro-4-methyl-3-oxo-2H-1,4-benzoxazin-7-yl)-2-oxo-5-oxazolidinecarboxamide.

37. A compound selected from (5R)-3-[3-Fluoro-4-(5-oxo-5,6-dihydro-4H-[1,3,4]thiadiazin-2-yl)phenyl]-2-oxo-5-oxazolidinecarboxamide;

(5R)-3-[4-(1,1-dioxido-2,3-dihydro-4H-1,4-thiazin-4-yl)-3,5-difluorophenyl]-2-oxo-5-oxazolidinecarboxamide; and (5R)-3-[4-(2,5-Dihydro-1H-pyrrol-1-yl)-3,5-difluorophenyl]-2-oxo-5-oxazolidinecarboxamide.

38. A compound selected from (5R)-3-[4-(4-oxo-3,4-dihydro-1(2H)-pyridinyl)-3-fluorophenyl]-2-oxo-5-oxazolidinecarboxamide;

(5R)-N-Methyl-3-[4-(4-oxo-3,4-dihydro-1(2H)-pyridinyl)-3-fluorophenyl]-2-oxo-5-oxazolidinecarboxamide;

(5R)-N-Ethyl-3-[4-(4-oxo-3,4-dihydro-1(2H)-pyridinyl)-3-fluorophenyl]-2-oxo-5-oxazolidinecarboxamide;

(5R)-3-[4-(4-oxo-3,4-dihydro-1(2H)-pyridinyl)phenyl]-2-oxo-5-oxazolidinecarboxamide;

(5R)-N-Methyl-3-[4-(4-oxo-3,4-dihydro-1(2H)-pyridinyl)phenyl]-2-oxo-5-oxazolidinecarboxamide;

(5R)-N-Ethyl-3-[4-(4-oxo-3,4-dihydro-1(2H)-pyridinyl)phenyl]-2-oxo-5-oxazolidinecarboxamide;

(5R)-N-(2-Fluoroethyl)-3-[4-(4-oxo-3,4-dihydro-1(2H)-pyridinyl)phenyl]-2-oxo-5-oxazolidinecarboxamide;

(5R)-3-[4-(4-oxo-3,4-dihydro-1(2H)-pyridinyl)-3,5-difluorophenyl]-2-oxo-5-oxazolidinecarboxamide;

(5R)-N-Methyl-3-[4-(4-oxo-3,4-dihydro-1(2H)-pyridinyl)-3,5-difluorophenyl]-2-oxo-5-oxazolidinecarboxamide;

(5R)-N-Ethyl-3-[4-(4-oxo-3,4-dihydro-1(2H)-pyridinyl)-3,5-difluorophenyl]-2-oxo-5-oxazolidinecarboxamide; and (5R)-3-[4-[3,4-Dihydro-4-(hydroxyimino)-1(2H)-pyridinyl]-3-fluorophenyl]-2-oxo-5-oxazolidinecarboxamide.

39. A compound selected from (5R)-3-(2-Formyl-2,3,4,5tetrahydro-1H-2-benzazepin-7-yl)-2-oxo-5-oxazolidinecarboxamide;

(5R)-N-Methyl-3-(2-formyl-2,3,4,5-tetrahydro-1H-2-benzazepin-7-yl)-2-oxo-5-oxazolidinecarboxamide;

(5R)-3-[2-(Hydroxyacetyl)-2,3,4,5-tetrahydro-1H-2-benzazepin-7-yl]-2-oxo-5-oxazolidinecarboxamide;

(5R)-N-Methyl-3-[2-(hydroxyacetyl)-2,3,4,5-tetrahydro-1H-2-benzazepin-7-yl]-2-oxo-5-oxazolidinecarboxamide;

(5R)-3-(3-Formyl-2,3,4,5-tetrahydro-1H-3-benzazepin-7-yl)-2-oxo-5-oxazolidinecarboxamide;

(5R)-N-Methyl-3-(3-formyl-2,3,4,5-tetrahydro-1H-3-benzazepin-7-yl)-2-oxo-5-oxazolidinecarboxamide;

(5R)-3-[3-(Hydroxyacetyl)-2,3,4,5-tetrahydro-1H-3-benzazepin-7-yl]-2-oxo-5-oxazolidinecarboxamide; and (5R)-N-Methyl-3-(3-(hydroxyacetyl)-2,3,4,5-tetrahydro-1H-3-benzazepin-7-yl]-2-oxo-5-oxazolidinecarboxamide.

40. A compound selected from (5R)-3-[4-(1-(2(S)-Hydroxy-3-phosphorylpropanoyl)-1,2,5,6-tetrahydropyrid-4-yl)-3,5-difluorophenyl]-2-oxo-5-oxazolidinecarboxamide;

(5R)-N-Methyl-3-[4-(1-(2(S)-hydroxy-3-phosphorylpropanoyl)-1,2,5,6-tetrahydropyrid-4-yl)-3,5-difluorophenyl]-2-oxo-5-oxazolidinecarboxamide;

(5R)-3-[4-(1-(2(S),3-Dihydroxypropanoyl)-1,2,5,6-tetrahydropyrid-4-yl)-3,5-difluorophenyl]-2-oxo-5-oxazolidinecarboxamide;

(5R)-N-Methyl-3-[4-(1-(2(S),3-dihydroxypropanoyl)-1,2,5,6-tetrahydropyrid-4-yl)-3,5-difluorophenyl]-2-oxo-5-oxazolidinecarboxamide;

(5R)-3-[4-(1-(2(S)-Hydroxy-3-phosphorylpropanoyl)-1,2,5,6-tetrahydropyrid-4-yl)-3-fluorophenyl]-2-oxo-5-oxazolidinecarboxamide;

(5R)-N-Methyl-3-[4-(1-(2(S)-hydroxy-3-phosphorylpropanoyl)-1,2,5,6-tetrahydropyrid-4-yl)-3-fluorophenyl]-2-oxo-5-oxazolidinecarboxamide;

(5R)-3-[4-(1-(2(S),3-Dihydroxypropanoyl)-1,2,5,6-tetrahydropyrid-4-yl)-3-fluorophenyl]-2-oxo-5-oxazolidinecarboxamide; and (5R)-N-Methyl-3-[4-(1-(2(S),3-dihydroxypropanoyl)-1,2,5,6-tetrahydropyrid-4-yl)-3-fluorophenyl]-2-oxo-5-oxazolidinecarboxamide.

41. A method for the treatment of microbial infections in mammals comprising administration of an effective amount of compound of claim 1 or claim 10 to said mammal.

42. The method of claim 41 wherein said compound is administered to the mammal orally, parenterally, transdermally, or topically in a pharmaceutical composition.

43. The method of claim 41 wherein said compound is administered in an amount of from about 0.1 to about 100 mg/kg of body weight/day.

44. The method of claim 41 wherein said compound is administered in an amount of from about 1 to about 50 mg/kg of body weight/day.

45. A pharmaceutical composition comprising a compound of claim 1 or a compound of claim 10 and a pharmaceutically acceptable carrier.

* * * * *